(12) United States Patent
Ring et al.

(10) Patent No.: US 8,399,622 B2
(45) Date of Patent: Mar. 19, 2013

(54) REAGENTS AND METHODS FOR USE IN CANCER DIAGNOSIS, CLASSIFICATION AND THERAPY

(75) Inventors: Brian Z. Ring, Foster City, CA (US); Douglas T. Ross, Burlingame, CA (US); Robert S. Seitz, Hampton Cove, AL (US)

(73) Assignee: Clarient Diagnostic Services, Inc., Aliso Viejo, CA (US)

( * ) Notice: Subject to any disclaimer, the term of this patent is extended or adjusted under 35 U.S.C. 154(b) by 0 days.

(21) Appl. No.: 13/300,134

(22) Filed: Nov. 18, 2011

(65) Prior Publication Data
US 2012/0065107 A1    Mar. 15, 2012

Related U.S. Application Data

(60) Division of application No. 12/879,356, filed on Sep. 10, 2010, which is a division of application No. 12/013,739, filed on Jan. 14, 2008, now Pat. No. 7,811,774, which is a division of application No. 11/061,067, filed on Feb. 18, 2005, now abandoned, which is a continuation-in-part of application No. 10/915,059, filed on Aug. 10, 2004, now abandoned.

(60) Provisional application No. 60/494,334, filed on Aug. 11, 2003, provisional application No. 60/570,206, filed on May 12, 2004.

(51) Int. Cl.
*C07K 16/00* (2006.01)
(52) U.S. Cl. .................. 530/387.1; 530/387.7
(58) Field of Classification Search ........................ None
See application file for complete search history.

(56) References Cited

U.S. PATENT DOCUMENTS

| | | | |
|---|---|---|---|
| 4,383,985 A | 5/1983 | Bartorelli et al. |
| 4,522,918 A | 6/1985 | Schlom et al. |
| 4,579,827 A | 4/1986 | Sakamoto et al. |
| 4,612,282 A | 9/1986 | Schlom et al. |
| 4,657,851 A | 4/1987 | Feller et al. |
| 4,666,845 A | 5/1987 | Mattes et al. |
| 4,707,438 A | 11/1987 | Keydar |
| 4,803,169 A | 2/1989 | Linsley et al. |
| 5,593,847 A | 1/1997 | Barnett et al. |
| 5,741,649 A | 4/1998 | Inazawa |
| 5,790,761 A | 8/1998 | Heseltine et al. |
| 5,840,507 A | 11/1998 | Fruehauf |
| 5,843,684 A | 12/1998 | Levine et al. |
| 5,882,864 A | 3/1999 | An et al. |
| 5,914,238 A | 6/1999 | Keesee et al. |
| 5,983,211 A | 11/1999 | Heseltine et al. |
| 6,063,586 A | 5/2000 | Grandis |
| 6,087,090 A | 7/2000 | Mascarenhas |
| 6,218,131 B1 | 4/2001 | Keesee et al. |
| 6,235,486 B1 | 5/2001 | Young et al. |
| 6,288,039 B1 | 9/2001 | Patierno et al. |
| 6,294,349 B1 | 9/2001 | Streckfus et al. |
| 6,303,324 B1 | 10/2001 | Fruehauf |
| 6,322,989 B1 | 11/2001 | Cohen |
| 6,342,483 B1 | 1/2002 | Holt et al. |
| 6,355,427 B1 | 3/2002 | Jupe et al. |
| 6,358,682 B1 | 3/2002 | Jaffee et al. |
| 6,399,328 B1 | 6/2002 | Vournakis et al. |
| 6,544,742 B1 | 4/2003 | Faris et al. |
| 6,607,894 B1 | 8/2003 | Lopata et al. |
| 6,631,330 B1 | 10/2003 | Poynard |
| 6,638,727 B1 | 10/2003 | Hung et al. |
| 6,649,342 B1 | 11/2003 | Mack et al. |
| 6,670,141 B2 | 12/2003 | Streckfus et al. |
| 6,730,477 B1 | 5/2004 | Sun et al. |
| 6,750,013 B2 | 6/2004 | Gish et al. |
| 6,762,020 B1 | 7/2004 | Mack et al. |
| 6,763,307 B2 | 7/2004 | Berg et al. |
| 6,780,586 B1 | 8/2004 | Gish et al. |
| 6,794,501 B2 | 9/2004 | Chen et al. |
| 6,821,732 B2 | 11/2004 | Fuqua et al. |
| 6,855,554 B2 | 2/2005 | Fritsche et al. |
| 6,905,833 B2 | 6/2005 | Nguyen |
| 6,936,424 B1 | 8/2005 | Watkins et al. |
| 7,056,663 B2 | 6/2006 | Dairkee et al. |
| 7,094,534 B2 | 8/2006 | Pinkel et al. |
| 7,171,311 B2 | 1/2007 | Dai et al. |
| 2002/0006616 A1 | 1/2002 | Gish et al. |
| 2002/0009738 A1 | 1/2002 | Houghton et al. |
| 2002/0068036 A1 | 6/2002 | Hevezi et al. |
| 2002/0068691 A1 | 6/2002 | Salceda et al. |
| 2002/0146727 A1 | 10/2002 | Dillon et al. |
| 2002/0156263 A1 | 10/2002 | Chen |
| 2002/0182621 A1 | 12/2002 | Costa et al. |
| 2003/0039959 A1 | 2/2003 | Love et al. |
| 2003/0049262 A1 | 3/2003 | Love et al. |

(Continued)

FOREIGN PATENT DOCUMENTS

| | | |
|---|---|---|
| WO | WO 91/16632 | 10/1991 |
| WO | WO 98/22139 | 5/1998 |

(Continued)

OTHER PUBLICATIONS

Aas, et al., "Specific P53 Mutations are Associated with de novo Resistance to Doxorubicin in Breast Cancer Patients", *Nature Medicine*, 2(7): 811-814, 1996.
Adam et al., Mol. Cancer Res., Sep. 2003, 826(1): 826-835.
AJCC Cancer Staging Manual, Lippincott, 5th Ed., pp. 171-180, 1997.
Alizadeh, et al., "Distinct Types of Diffuse Large B-Cell Lymphoma Identified by Gene Expression Profiling", Nature, 403: 503-511, 2000.
Alon, et al., "Broad Patterns of Gene Expression Revealed by Clustering Analysis of Tumor and Normal Colon Tissues Probed by Oligonucleotide Arrays", Proc. Natl. Acad. Sci. USA, 96: 6745-6750, 1999.
Anderson, et al., "Prognostic Significance of TP53 Alterations in Breast Carcinoma", Br. J. Cancer, 68: 540-548, 1993.

(Continued)

*Primary Examiner* — Hong Sang
(74) *Attorney, Agent, or Firm* — Charles E. Lyon; Robert N. Sahr; Choate, Hall & Stewart LLP

(57) ABSTRACT

Methods and reagents for classifying tumors and for identifying new tumor classes and subclasses. Methods for correlating tumor class or subclass with therapeutic regimen or outcome, for identifying appropriate (new or known) therapies for particular classes or subclasses, and for predicting outcomes based on class or subclass. New therapeutic agents and methods for the treatment of cancer.

15 Claims, 13 Drawing Sheets

U.S. PATENT DOCUMENTS

| | | | |
|---|---|---|---|
| 2003/0050470 | A1 | 3/2003 | An et al. |
| 2003/0059790 | A1 | 3/2003 | Jaffee et al. |
| 2003/0064385 | A1 | 4/2003 | Dressman et al. |
| 2003/0077832 | A1 | 4/2003 | Fritsche et al. |
| 2003/0087235 | A1 | 5/2003 | Dairkee et al. |
| 2003/0087265 | A1 | 5/2003 | Sauter et al. |
| 2003/0124130 | A1 | 7/2003 | Brown |
| 2003/0124543 | A1 | 7/2003 | Stuart et al. |
| 2003/0125536 | A1 | 7/2003 | Fanger et al. |
| 2003/0152935 | A1 | 8/2003 | Herath |
| 2003/0157544 | A1 | 8/2003 | Gish et al. |
| 2003/0170631 | A1 | 9/2003 | Houghton et al. |
| 2003/0198951 | A1 | 10/2003 | Mack et al. |
| 2003/0198972 | A1 | 10/2003 | Erlander et al. |
| 2003/0211521 | A1 | 11/2003 | Taylor-Papadimitriou |
| 2003/0219767 | A1 | 11/2003 | Ayers et al. |
| 2003/0224374 | A1 | 12/2003 | Dai et al. |
| 2004/0029114 | A1 | 2/2004 | Mack et al. |
| 2004/0058340 | A1 | 3/2004 | Dai et al. |
| 2004/0073016 | A1 | 4/2004 | Frudakis et al. |
| 2004/0091423 | A1 | 5/2004 | Hung et al. |
| 2004/0132118 | A1 | 7/2004 | Furukawa et al. |
| 2004/0142361 | A1 | 7/2004 | Dillion et al. |
| 2004/0146862 | A1 | 7/2004 | Mack et al. |
| 2004/0152144 | A1 | 8/2004 | Sun et al. |
| 2004/0203023 | A1 | 10/2004 | Herath |
| 2004/0209290 | A1 | 10/2004 | Cobleigh et al. |
| 2004/0214179 | A1 | 10/2004 | Wang |
| 2004/0224347 | A1 | 11/2004 | Love et al. |
| 2005/0014208 | A1 | 1/2005 | Krehan et al. |
| 2005/0065333 | A1 | 3/2005 | Seth |
| 2005/0095607 | A1 | 5/2005 | Erlander et al. |
| 2005/0112622 | A1 | 5/2005 | Ring et al. |
| 2005/0164278 | A1 | 7/2005 | Salceda et al. |
| 2005/0176072 | A1 | 8/2005 | Martin et al. |
| 2005/0221398 | A1 | 10/2005 | Jacquemier et al. |
| 2005/0287543 | A1 | 12/2005 | Yu et al. |
| 2006/0003391 | A1 | 1/2006 | Ring et al. |
| 2006/0063190 | A1 | 3/2006 | Fischer et al. |
| 2006/0068418 | A1 | 3/2006 | Godfrey et al. |
| 2006/0083749 | A1 | 4/2006 | Fanger et al. |
| 2006/0141543 | A1 | 6/2006 | Pestlin et al. |
| 2006/0234287 | A1 | 10/2006 | Erlander et al. |
| 2006/0257950 | A1 | 11/2006 | Pestlin et al. |
| 2006/0257951 | A1 | 11/2006 | Pestlin et al. |
| 2006/0257952 | A1 | 11/2006 | Pestlin et al. |
| 2006/0287513 | A1 | 12/2006 | Fanger et al. |
| 2007/0054271 | A1 | 3/2007 | Polyak et al. |
| 2007/0059706 | A1 | 3/2007 | Yu et al. |
| 2008/0131916 | A1 | 6/2008 | Ring et al. |
| 2008/0199891 | A1 | 8/2008 | Ring et al. |

FOREIGN PATENT DOCUMENTS

| | | |
|---|---|---|
| WO | WO 99/44063 | 9/1999 |
| WO | WO 01/51924 | 7/2001 |
| WO | WO 02/064798 | 8/2002 |
| WO | WO 03/010337 | 2/2003 |
| WO | WO 03/015613 | 2/2003 |
| WO | WO 03/087761 | 10/2003 |
| WO | WO 2004/108896 | 12/2004 |
| WO | WO 2005/008213 | 1/2005 |

OTHER PUBLICATIONS

Baxa, et al., "Human Adipocyte Lipid-Binding Protein: Purification of the Protein and Cloning of its Complementary DNA", Biochemistry, 28: 8683-8690, 1989.
Beer, et al., "Gene-Expression Profiles Predict Survival of Patients with Lung Adenocarcinoma", Nature Medicine, 8(8): 816-824, 2002.
Berns, et al., "Prevalence of Amplification of the Oncogenes c-myc, HER2/neu, and Int-2 in One Thousand Human Breast Tumours: Correlation with Steroid Receptors", Eur J. Cancer, 28(2/3): 697-700, 1992.
Bhargava, et al., "Bcl-2 Immunoreactivity in Breast Carcinoma Correlates with Hormone Receptor Positivity", American Journal of Patholo, 145(3): 535-540, 1994.
Bhattacharjee, et al., "Classification of Human Lung Carcinomas by mRNA Expression Profiling Reveals Distinct Adenocarcinoma Subclasses", Proc. Nat. Acad. Sci. USA, 98: 13790-13795, 2001.
Cahill, et al., "Mutations of Mitotic Checkpoint Genes in Human Cancers", Nature, 392: 300-303, 1998.
Cho, et al., "A Genome-Wide Transcriptional Analysis of the Mitotic Cell Cycle", Molecular Cell, 2: 65-73, 1998.
Chu, et al., The Transcriptional Program of Sporulation in Budding Yeast, Science, 282: 699-705, 1998.
Cioffi et al., Lung Cancer, 2001, 33:163-169.
Dairkee, et al., "Expression of Basal and Luminal Epithelium-Specific Keratins in Normal, Benign, and Malignant Breast Tissue", Journal of the National Cancer Institute, 80(9): 691-695, 1988.
DeRisi, et al., "Exploring the Metabolic and Genetic Control of Gene Expression on a Genomic Scale", Science, 278: 680-686, 1997.
Dhanasekaran, et al., "Delineation of Prognosis Biomarkers in Prostate Cancer", Nature, 412: 822-826, 2001.
Di Leo, et al., "Predictive Molecular Markers in the Adjuvant Therapy of Breast Cancer: State of the Art in the Year 2002", Int. J. Clin. Oncol. 7: 245-253, 2002.
Eisen, et al., "Cluster Analysis and Display of Genome-Wide Expression Patterns", Proc. Natl. Acad. Sci. USA, 95: 14863-14868, 1998.
Eisen, et al., "DNA Arrays for Analysis of Gene Expression", Methods of Enzymology, 303: 179-205, 1999.
Fambrough, et al., "Diverse Signaling Pathways Activated by Growth Factor Receptors Induce Broadly Overlapping, Rather than Independent, Sets of Genes", Cell, 97: 727-741, 1999.
Ferrando, et al., "Gene Expression Signatures Define Novel Oncogenic Pathways in T Cell Acute Lymphoblastic Leukemia" Cancer Cell, 1: 75-87, 2002.
Galitski, et al., "Ploidy Regulation of Gene Expression", Science, 285: 251-254, 1999.
Garber, et al., "Diversity of Gene Expression in Adenocarcinoma of the Lung", Proc. Natl. Acad. Sci. USA, 98: 13784-13789, 2001.
Golub, et al., "Molecular Classification of Cancer: Class Discovery and Class Prediction by Gene Expression Monitoring", Science, 286: 531-537, 1999.
Gruvberger, et al., "Estrogen Receptor Status in Breast Cancer is Associated with Remarkably Distinct Gene Expression Patterns", Cancer Res. 61: 5979-5984, 2001.
Guelstein, et al., "Monoclonal Antibody Mapping of Keratins 8 and 17 and of Vimentin in Normal Human Mammary Gland, Benign Tumors, Dysplasias and Breast Cancer", Int. J. Cancer, 42: 147-153, 1988.
Guerin, et al., "Overexpression of Either C-Myc or C-ErbB-2/Neu Proto-Oncogenes in Human Breast Carcinomas: Correlation with Poor Prognosis", Oncogene Research, 3: 21-31, 1988.
Gusterson, et al., "Distribution of Myoepithelial Cells and Basement Membrane Proteins in the Normal Breast and in Benign and Malignant Breast Disease", Cancer Research, 42: 4763-4770, 1982.
Hailey, et al., "Neutralizing Anti-Insulin-Like Growth Factor Receptor 1 Antibodies Inhibit Receptor Function and Induce Receptor Degradation in Tumor Cells", Molecular Cancer Therapeutics, 1: 1349-153, 2002.
Han, et al., "Distinct Cadherin Profiles in Special Variant Carcinomas and Other Tumors of the Breast", Human Pathology, 30(9): 1035-1039, 1999.
Hayes, et al., "Prognosis Factors in Breast Cancer: Current and New Predictors of Metastasis" J. Mamm. Gland Bio. Neo. 6: 375-392, 2001.
Hedenfalk, et al., "Gene-Expression Profiles in Hereditary Breast Cancer", N. Engl. J. Med. 344: 539-548, 2001.
Heintz, et al., "Amplification of the c-erb B-2 Oncogene and Prognosis of Breast Adenocarcinoma", Arch Pathol Lab Med—114: 160-163, 1990.
Heyer, et al., "Exploring Expression Data: Identification and Analysis of Coexpressed Genes", Genome Res. 9: 1106-1115, 1999.
Hippo, et al., "Global Gene Expression Analysis of Gastric Cancer by Oligonucleotide Microarrays", Cancer Res. 62: 233-240, 2002.
Hoch, et al., "Gata-3 is Expressed in Association with Estrogen Receptor in Breast Cancer", Int. J. Cancer (Pred. Oncol). 84: 122-128, 1999.
Hofmann, et al., "Relation Between Resistance of Philadelphia-Chromosome-Positive Acute Lymphoblastic Leukaemia to the Tyrosine Kinase Inhibitor ST1571 and Gene-Expression Profiles: A Gene-Expression Study" Lancet, 359: 481-486, 2002.

International Search Report for PCT application PCT/US2004/026005.

International Search Report for PCT application PCT/US2006/005601.

Iyer, et al., "The Transcriptional Program in the Response of Human Fibroblasts to Serum", Science, 283: 83-87, 1999.

Jazaeri, et al., "Gene Expression Profiles of BRCA I-Linked, BRCA-2-Linked, and Sporadic Ovarian Cancers", J. Natl Cancer Inst. 94: 990-1000, 2002.

Jessen, et al., "Cellular Changes Involved in Conversion of Normal to Malignant Breast: Importance of the Stromal Reaction", Physiological Reviews, 76(1): 69-125, 1996.

Jurcevic, et al., "Expression Profiling of Microdissected Pancreatic Adenocarcinomas", Oncogene, 21: 4587-4594, 2002.

Kakiuchi et al., Mol. Cancer Res., 2003, 1: 485-499.

Kallioniemi, et al., "Tissue Microarray Technology for High-Throughput Molecular Profiling of Cancer", Human Molecular Genetics, 10(7): 657-662, 2001.

Kaplan, et al., "Nonparametric Estimation from Incomplete Observations", J. Am. Stat. Assn. 53: 457-481, 1958.

Khan, et al., "Gene Expression Profiling of Alveolar Rhabdomyosarcoma with cDNA Microarrays", Cancer Research, 58: 5009-5013, 1998.

LaTulippe, et al., "Comprehensive Gene Expression Analysis of Prostate Cancer Reveals Distinct Transcriptional Programs Associated with Metastatic Disease", Cancer Res. 62: 4499-4506, 2002.

Leek, et al., "bcl-2 in Normal Human Breast and Carcinoma, Association with Oestrogen Receptor-Positive, Epidermal Growth Factor Receptor-Negative Tumours and in Situ Cancer", pp. 135-139, 1993.

Levesque et al., Breast Cancer Res. Treat., 1994, 30, 179-195.

Li, et al., "Identification of a Human Mitotic Checkpoint Gene: hsMAD2", Science, 274: 246-248, 1996.

Lin, et al., "Molecular Diagnosis of Colorectal Tumors by Expression Profiles of 50 Genes Expressed Differentially in Adenomas and Carcinomas", Oncogene, 21: 4120-4128, 2002.

Lutz, et al., "MLN64 Exhibits Homology with the Steroidogenic Acute Regulatory Protein(Star) and is Over-Expressed in Human Breast Carcinomas", Int. J. Cancer: 71: 183-191,1997.

MacDonald, et al., "Expression Profiling of Medulloblastoma: PDGFRA and the RAS/MAPK Pathway as Therapeutic Targets for Metastatic Disease" Nature Genet. 29: 143-152, 2001.

Malzahn, et al., "Biological and Prognostic Significance of Stratified Epithelial Cytokeratins in Infiltrating Ductal Breast Carcinomas", Virchows Arch, 433: 119-129, 1998.

Mantel, et al., "Statistical Aspects of the Analysis of Data from Retrospective Studies of Disease", Journal of the National Cancer Institute, 22: 719-748, 1959.

Miettinen, et al., "Endothelial Cell Markers CD31, CD34, and BNH9 Antibody to H- and Y- Antigens—Evaluation of Their Specificity and Sensitivity in the Diagnosis of Vascular Tumors and Comparison with Von Willebrand Factor", Modern Pathology, 7(1): 82-90, 1994.

Nagle, et al., "Characterization of Breast Carcinomas by Two Monoclonal Antibodies Distinguishing Myoepithelial from Luminal Epithelial Cells", The Journal of Histochemistry and Cytochemistry, 34(7): 869-881, 1986.

Nielsen, et al., "Immunohistochemical and Clinical Characterization of the Basal-Like Subtype of Invasive Breast Carcinoma" Clinical Cancer Research, 10: 5367-5374, 2004.

NIH National Institutes of Health Consensus Development Conference Statement: Adjuvant Therapy for Breast Cancer, Nov. 1-3, 2000, 1 Nat. Cancer Inst. Monographs, 30: 5-15, 2001.

Osborne, et al., "The Value of Estrogen and Progesterone Receptors in the Treatment of Breast Cancer", Cancer, 46: 2884-2888, 1980.

Pauletti, et al., "Detection and Quantitation of HER-2/Neu Gene Amplification in Human Breast Cancer Archival Material Using Fluorescence in Situ Hybridization", Oncogene, 13: 63-72, 1996.

Perou, et al., "Distinctive Gene Expression Patterns in Human Mammary Epithelial Cells and Breast Cancers", Proc. Natl Acad. Sci. USA, 96: 9212-9217, 1999.

Pollack, et al., "Genome-Wide Analysis of DNA Copy-Number Changes Using cDNA Microarrays", Nature Genetics, 23: 41-46, 1999.

Prud'Homme, et al., "Cloning of a Gene Expressed in Human Breast Cancer and Regulated by Estrogen in MCF-7 Cells", DNA, 4(1): 11-21, 1985.

Ravdin, et al., "A Demonstration that Breast Cancer Recurrence can be Predicted by Neural Network Analysis", Breast Cancer Res. Treat. 21: 47-53, 1992.

Rhodes, et al., "Large-Scale Meta-Analysis of Cancer Microarray Data Identifies Common Transcriptional Profiles of Neoplastic Transformation and Progression", Proc. Natl. Acad. Sci. USA, 101(25): 9309-9314, 2004.

Ring et al., "Novel prognostic immunohistochemical biomarker panel for estrogen receptor-positive breast cancer", US National Library of Medicine(NLM), Bethesda, MD, US, Jul. 1, 2006. XP002403235, Database accession No. NLM16809728 abstract.

Ring, et al., "Microarrays and Molecular Markers for Tumor Classification", Genome Biology, 3(5): 1-6, 2002.

Ring, et al., "Predictors of Response to Systemic Therapy in Breast Cancer", Forum, 12(1):19-32, 2002.

Rosenwald, et al., "The Use of Molecular Profiling to Predict Survival After Chemotherapy for Diffuse Large-B-Cell Lymphoma", N. Engl. J. Med. 346: 1937, 2002.

Ross, et al., "Systematic Variation in Gene Expression Patterns in Human Cancer Cell Lines", Nature Genetics, 24: 227-235, 2000.

Segal, et al., "A Comparison of Estimated Proportional Hazards Models and Regression Trees", Stat. Med. 8: 539, 550, 1989.

Shimoyama, et al., "Cadherin Cell-Adhesion Molecules in Human Epithelial Tissues and Carcinomas", Cancer Research, 49: 2128-2133, 1989.

Shipp, et al., "Diffuse Large B-Cell Lymphoma Outcome Prediction by Gene-Expression Profiling and Supervised Machine Learning", Nature Med., 8: 68-74, 2002.

Singh, et al., "Gene Expression Correlates of Clinical Prostate Cancer Behavior", Cancer Cell, 1: 203-209, 2002.

Slamon, et al., "Studies of the HER-2/Neu Proto-Oncogene in Human Breast and Ovarian Cancer", Science, 244: 707-712, 1989.

Soler, et al., "P-Cadherin Expression in Breast Carcinoma Indicates Poor Survival", Cancer, 86: 1263-1272, 1999.

Sorlie, et al., "Gene Expression Patterns of Breast Carcinomas Distinguish Tumor Subclasses with Clinical Implications", Proc. Natl. Acad. Sci. USA, 98: 10869-10874, 2001.

Sorlie, et al., "Repeated Observation of Breast Tumor Subtypes in Independent Gene Expression Data Sets", Proc. NatL Acad. Sci. USA, 100(14): 8418-8423, 2003.

Spellman, et al., "Comprehensive Identification of Cell Cycle-Regulated Genes of the Yeast *Saccharomyces cerevisiae* by Microarray Hybridization", Molecular Biology of the Cell, 9: 3273-3297, 1998.

Srinivas, et al., "Proteomics for Cancer Biomarker Discovery", Clinical Chemistry, 48(8): 1160-1169, 2002.

Stein, et al., "The SH2 Domain Protein GRB-7 is Co-Amplified, Overexpressed and in a Tight Complex with HER2 in Breast Cancer", The EMBO Journal, 13(6): 1331-1340, 1994.

Takahashi, et al., "Gene Expression Profiling of Clear Cell Renal Cell Carcinoma: Gene Identification and Prognostic Classification" Proc. Natl. Acad. Sci. USA, 98: 9754-9759, 2001.

Takimoto, et al., "Clinical Applications of the Camptothecins", Biochimica et Biophysica Acta 1400: 107-119, 1998.

Tontonoz, et al., "mPPARy2: Tissue-Specific Regulator of an Adipocyte Enhancer", Genes & Development, 8: 1224-1234, 1994.

Torenbeek, et al., "Value of a Panel of Antibodies to Identify the Primary Origin of Adenocarcinomas Presenting as Bladder Carcinoma", Histopathology, 32: 20-27, 1998.

Torhorst, et al., "Tissue Microarrays for Rapid Linking of Molecular Changes to Clinical Endpoints", American Journal of Pathology, 159(6): 2249-2256, 2001.

Perou, et al., "Molecular Portraits of Human Breast Tumours" Nature, 406: 747-752, 2000.

Pomeroy, et al., "Prediction of Central Nervous System Embryonal Tumour Outcome Based on Gene Expression", Nature, 415: 436-442, 2002.

Van De Rijn, Matt., "Expression of Cytokeratins 17 and 5 Identifies a Group of Breast Carcinomas with Poor Clinical Outcome", American Journal of Patholo , 161(6): 1991-1996, 2002.

Van't Veer, et al., "Gene Expression Profiling Predicts Clinical Outcome of Breast Cancer" Nature, 415: 530-536, 2002.

Wang, et al., "Monitoring Gene Expression Profile Changes in Ovarian Carcinomas Using cDNA Microarray", Gene, 229: 101-108, 1999.

Welsh, et al., "Analysis of Gene Expression Identifies Candidate Markers and Pharmacological Targets in Prostate Cancer", Cancer Res. 61: 5974-5978, 2001.

Welsh, et al., "Analysis of Gene Expression Profiles in Normal and Neoplastic Ovarian Tissue Samples Identifies Candidate Molecular Markers of Epithelial Ovarian Cancer", Proc. Natl. Acad. Sci. USA, 98: 1176-1181, 2001.

West, et al., "Predicting the Clinical Status of Human Breast Cancer by Using Gene Expression Profiles" Proc. Natl. Acad. Sci. USA, 98: 11462-11467, 2001.

Wolf, et al., Prognostic Significance of Polo-Like Kinase (PLK) Expression in Non-Small Cell Lung Cancer, Oncogene, 14: 543-549, 1997.

Yang, et al., "Combining SSH and cDNA Microarrays for Rapid Identification of Differentially Expressed Genes", Nucleic Acids Research, 27(6): 1517-1523, 1999.

Yeoh, et al., "Classification, Subtype Discovery, and Prediction of Outcome in Pediatric Acute Lymphoblastic Leukemia by Gene Expression Profiling", Cancer Cell, 1: 133-143, 2002.

Zhou, et al., "Tumour Amplified Kinase STK15/BTAK Induces Centrosome Amplification, Aneuploidy and Transformation", Nature Genetics, 20: 189-193, 1998.

Zou, et al., "Application of cDNA Microarrays to Generate a Molecular Taxonomy Capable of Distinguishing Between Colon Cancer and Normal Colon", Oncogene, 21: 4855-4862, 2002.

Alizadeh, et al., "Towards a novel classification of human malignancies based on gene expression patterns", *J Pathol*; 195(1): 41-52, 2001.

Bartlett, et al., "Mammostrat as a tool to stratify patients at risk of recurrence during endocrine therapy", *Poster at San Antonio Breast Symposium*, 2008.

Chua, et al., "Overexpression of NDRG1 is an indicator of poor prognosis in hepatocellular carcinoma", *Modern Pathology*, 20: 76-83, 2007.

Finlin, et al., "RERG is a novel ras-related, estrogen-regulated and growth-inhibitory gene in breast cancer", *J Biol Chem*, 276(45): 42259-67, 2001.

Gusterson, et al., "Basal cytokeratins and their relationship to the cellular origin and functional classification of breast cancer", *Breast Cancer Research*, 7: 143-148, 2005.

Hanker, et al., "Tools to study the function of the Ras-related, estrogen-regulated growth inhibitor in breast cancer", *Methods Enzymol*, 439: 53-72, 2008.

Jensen, et al., "Characterization of a novel anti-fatty acid synthase (FASN) antiserum in breast tissue", *Mod Pathol*, 21(12): 1413-20, 2008.

Kennedy et al., Br. J. Cancer, 2003, 88:1077-1083.

Perou, et al., "Distinctive gene expression patterns in human mammary epithelial cells and breast cancers", *Proc Natl Acad Sci USA*, 96(16): 9212-7, 1999.

Ring et al., "Novel prognostic immunohistochemical biomarker panel for estrogen receptor-positive breast cancer", *Journal of Clinical Oncology*, 24(19): 3039-3047, 2006.

Ring, et al., "Gene expression patterns within cell lines are predictive of chemosensitivity", *BMC Genomics*, 9: 74, 2008.

Ring, et al., "Gene expression patterns within cell lines are predictive of chemosensitivity", *Poster at American Association of Cancer Research*, 2006.

Ring, et al., "Microarrays and molecular markers for tumor classification", *Genome Biology*, 3(5): 3-6, 2002.

Ross, et al., "A comparison of gene expression signatures from breast tumors and breast tissue derived cell lines", *Dis Markers*, 17(2): 99-109, 2001.

Ross, et al., "A novel prognostic immunohistochemical biomarker panel for estrogen receptor expressing breast cancer", *Poster at San Antonio Breast Cancer Symposium*, 2005.

Ross, et al., "Chemosensitivity and stratification by a five monoclonal antibody IHC test in the NSABP B20 trial", *Poster at ASCO*, 2007.

Ross, et al., "Chemosensitivity and stratification by a five monoclonal antibody immunohistochemistry test in the NSABP B14 and B20 trials", *Clin Cancer Res*, 14(20): 6602-9, 2008.

Ross, et al., "Prognosis and chemosensitivity using a five monoclonal antibody IHC test in a node negative, tamoxifen-treated, ER + breast cancer—NSABP B14 and B20 trials", *Poster at the ASCO Breast Cancer Symposium*, 2007.

Ross, et al., "Systematic variation in gene expression patterns in human cancer cell lines", *Nat Genet*, 24(3): 227-35, 2000.

Ross, et al., "Translating gene expression patterns into IHC diagnostics for breast cancer: novel IHC reagents predict recurrence in a retrospective cohort at the Comprehensive Cancer Institute of Huntsville", *Poster at San Antonio Breast Cancer Symposium*, 2004.

Ross, et al., "Validation of a five reagent immunohistochemistry assay for prognostication of estrogen-receptor expressing breast cancer", *Poster at American Society of Clinical Oncology*, 2006.

Ross, et al., "Validation of a prognostic algorithm based upon a five monoclonal antibody immunohistochemistry test in Tamoxifen-treated, node negative breast cancer: NSABP B14 and B20 studies", *Poster at San Antonio Breast Cancer Symposium*, 2006.

Russnes, et al., "Translation of breast cancer gene expression profiles into an immunohistochemistry-based classifer", *Poster at the American Association for Cancer Research (AACR) Annual Meeting*, 2007.

Scherf, et al., "A gene expression database for the molecular pharmacology of cancer", *Nat Genet*, 24(3): 236-44, 2000.

Seitz, et al., "A Five Antibody Prognostic IHC Test Identifies Estrogen Receptor Positive Patients Classified as Luminal B at High Risk for Tumor Progression", *Poster at the American Association for Cancer Research (AACR) Annual Meeting*, 2007.

Seitz, et al., "Translation of gene expression patterns into immunohistochemistry biomarkers", *Poster at American Association of Cancer Research*, 2006.

Titus, Karen "Reclassifying cancer, guided by genomics", *College of American Pathologists*, 2001.

van de Rijn, et al., "Expression of cytokeratins 17 and 5 identifies a group of breast carcinomas with poor clinical outcome", *Am J Pathol*, 161(6): 1991-6, 2002.

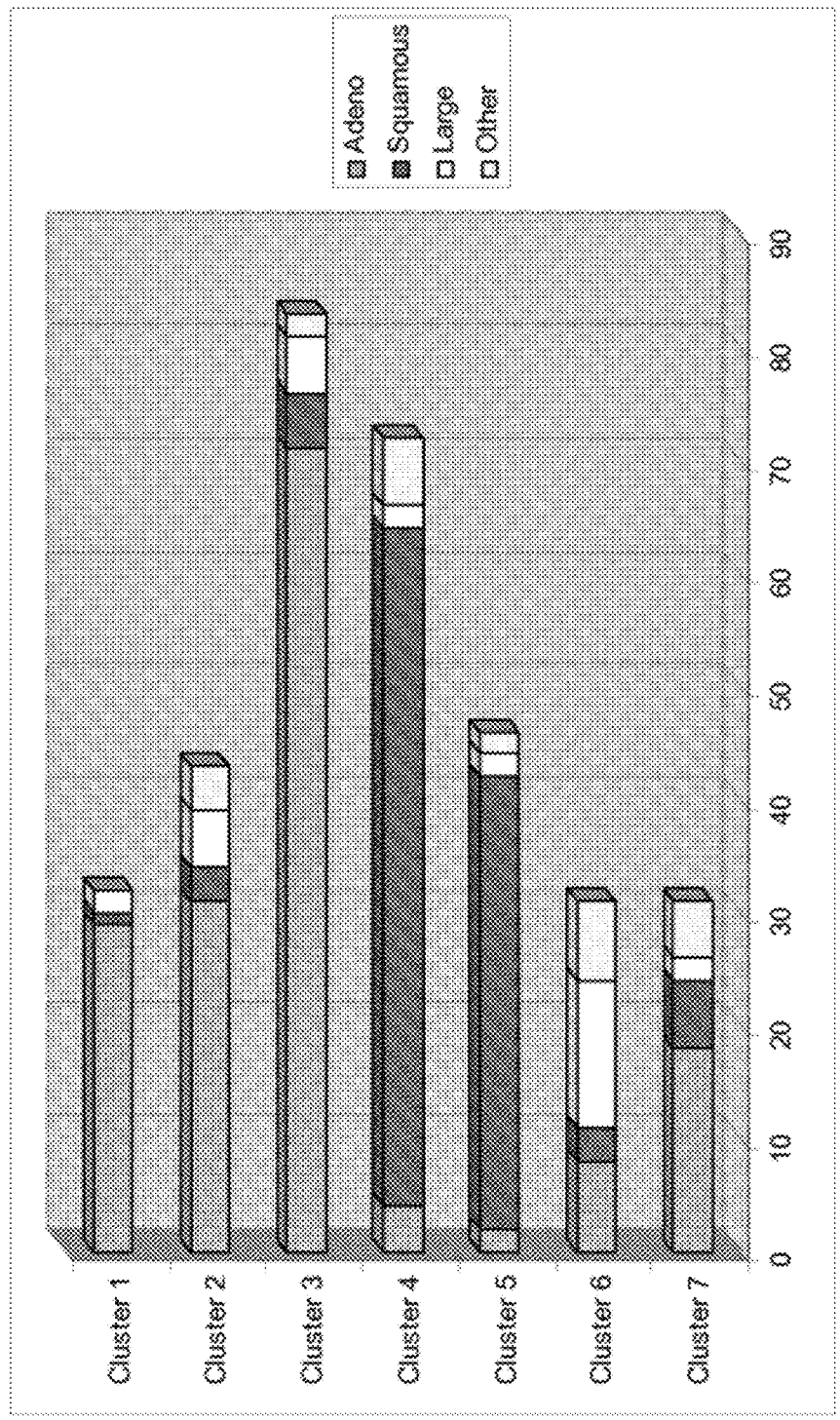

SEQUENCE LISTING

<160> NUMBER OF SEQ ID NOS: 327

<210> SEQ ID NO 1
<211> LENGTH: 13
<212> TYPE: PRT
<213> ORGANISM: Artificial Sequence
<220> FEATURE:
<223> OTHER INFORMATION: Peptide from VAV-3 protein

<400> SEQUENCE: 1

Asp Tyr Ile Ser Lys Ser Lys Glu Asp Val Lys Leu Lys
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Peptide from VAV-3 protein

<400> SEQUENCE: 2

Glu Lys Arg Thr Asn Gly Leu Arg Arg Thr Pro Lys Gln Val Asp
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: Peptide from VAV-3 protein

<400> SEQUENCE: 3

Thr Glu Glu Ser Ile Asn Asp Glu Asp Ile Tyr Lys Gly Leu Pro Asp
1               5                   10                  15

Leu Ile Asp Glu
            20

<210> SEQ ID NO 4
<211> LENGTH: 19
<212> TYPE: PRT
<213> ORGANISM: Artificial Sequence
<220> FEATURE:
<223> OTHER INFORMATION: Peptide from mammoglobin

<400> SEQUENCE: 4

Ser Lys Thr Ile Asn Pro Gln Val Ser Lys Thr Glu Tyr Lys Glu Leu
1               5                   10                  15

-continued

Leu Gln Glu

<210> SEQ ID NO 5
<211> LENGTH: 15
<212> TYPE: PRT
<213> ORGANISM: Artificial Sequence
<220> FEATURE:
<223> OTHER INFORMATION: Peptide from mammoglobin

<400> SEQUENCE: 5

Asp Asp Asn Ala Thr Thr Asn Ala Ile Asp Glu Leu Lys Glu Cys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Peptide from mammoglobin

<400> SEQUENCE: 6

Asn Gln Thr Asp Glu Thr Leu Ser Asn Val Glu Val Phe Met Gln
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Peptide from RB18A (P53 binding)

<400> SEQUENCE: 7

Ser Ser Asp Asp Gly Ile Arg Pro Leu Pro Glu Tyr Ser Thr Glu Lys
1               5                   10                  15

His Lys Lys

<210> SEQ ID NO 8
<211> LENGTH: 15
<212> TYPE: PRT
<213> ORGANISM: Artificial Sequence
<220> FEATURE:
<223> OTHER INFORMATION: Peptide from RB18A (P53 binding)

<400> SEQUENCE: 8

Asn Lys Thr Lys Lys Lys Lys Ser Ser Arg Leu Pro Pro Glu Lys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Peptide from RB18A (P53 binding)

<400> SEQUENCE: 9

Asp Gly Lys Ser Lys Asp Lys Pro Pro Lys Arg Lys Lys Ala Asp Thr
1               5                   10                  15

Glu

<210> SEQ ID NO 10
<211> LENGTH: 18
<212> TYPE: PRT
<213> ORGANISM: Artificial Sequence
<220> FEATURE:
<223> OTHER INFORMATION: Peptide from Putative cadherin-like protein -continued

```
<400> SEQUENCE: 10

Lys Asn Lys Glu Pro Leu Thr Lys Lys Gly Glu Thr Lys Thr Ala Glu
1               5                   10                  15

Arg Asp

<210> SEQ ID NO 11
<211> LENGTH: 17
<212> TYPE: PRT
<213> ORGANISM: Artificial Sequence
<220> FEATURE:
<223> OTHER INFORMATION: Peptide from Putative cadherin-like protein

<400> SEQUENCE: 11

Lys Leu Thr Cys Thr Asp Leu Asp Ser Ser Pro Arg Ser Phe Arg Tyr
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: Peptide from Putative cadherin-like protein

<400> SEQUENCE: 12

Glu Val Asp Tyr Glu Asn Pro Ser Asn Leu Ala Ala Gly Asn Lys Tyr
1               5                   10                  15

Thr

<210> SEQ ID NO 13
<211> LENGTH: 20
<212> TYPE: PRT
<213> ORGANISM: Artificial Sequence
<220> FEATURE:
<223> OTHER INFORMATION: Peptide from Sim to Cyto p450

<400> SEQUENCE: 13

Lys Thr Leu Gln Val Phe Asn Pro Leu Arg Phe Ser Arg Glu Asn Ser
1               5                   10                  15

Glu Lys Ile His
            20

<210> SEQ ID NO 14
<211> LENGTH: 15
<212> TYPE: PRT
<213> ORGANISM: Artificial Sequence
<220> FEATURE:
<223> OTHER INFORMATION: Peptide from Sim to Cyto p450

<400> SEQUENCE: 14

Gln His Phe Ala Ile Ile Glu Cys Lys Val Ala Val Ala Leu Thr
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Peptide from Sim to Cyto p450

<400> SEQUENCE: 15

Arg Lys Phe Leu Ala Pro Asp His Ser Arg Pro Pro Gln Pro Val Arg
1               5                   10                  15

Gln
```

```
<210> SEQ ID NO 16
<211> LENGTH: 16
<212> TYPE: PRT
<213> ORGANISM: Artificial Sequence
<220> FEATURE:
<223> OTHER INFORMATION: Peptide from Chuck Ras

<400> SEQUENCE: 16

Val Leu Pro Leu Lys Asn Ile Leu Asp Glu Ile Lys Lys Pro Lys Asn
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: Peptide from Chuck Ras

<400> SEQUENCE: 17

Tyr Glu Leu Cys Arg Glu Val Arg Arg Arg Met Val Gln Gly Lys
1               5                   10                  15

Thr

<210> SEQ ID NO 18
<211> LENGTH: 19
<212> TYPE: PRT
<213> ORGANISM: Artificial Sequence
<220> FEATURE:
<223> OTHER INFORMATION: Peptide from Chuck Ras

<400> SEQUENCE: 18

Met Ala Lys Ser Ala Glu Val Lys Leu Ala Ile Phe Gly Arg Ala Gly
1               5                   10                  15

Val Gly Lys

<210> SEQ ID NO 19
<211> LENGTH: 15
<212> TYPE: PRT
<213> ORGANISM: Artificial Sequence
<220> FEATURE:
<223> OTHER INFORMATION: Peptide from MDGI

<400> SEQUENCE: 19

Lys Asn Thr Glu Ile Ser Phe Lys Leu Gly Val Glu Phe Asp Glu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Peptide from MDGI

<400> SEQUENCE: 20

His Leu Gln Lys Trp Asp Gly Gln Glu Thr Thr Leu Val Arg Glu
1               5                   10                  15

<210> SEQ ID NO 21
<211> LENGTH: 19
<212> TYPE: PRT
<213> ORGANISM: Artificial Sequence
<220> FEATURE:
<223> OTHER INFORMATION: Peptide from MDGI

<400> SEQUENCE: 21
```

-continued

```
Thr Lys Pro Thr Thr Ile Ile Glu Lys Asn Gly Asp Ile Leu Thr Leu
1               5                   10                  15

Lys Thr His

<210> SEQ ID NO 22
<211> LENGTH: 19
<212> TYPE: PRT
<213> ORGANISM: Artificial Sequence
<220> FEATURE:
<223> OTHER INFORMATION: Peptide from Human GABA-A receptor pi subunit

<400> SEQUENCE: 22

Leu Gln Gln Met Ala Ala Lys Asp Arg Gly Thr Thr Lys Glu Val Glu
1               5                   10                  15

Glu Val Ser

<210> SEQ ID NO 23
<211> LENGTH: 20
<212> TYPE: PRT
<213> ORGANISM: Artificial Sequence
<220> FEATURE:
<223> OTHER INFORMATION: Peptide from Human GABA-A receptor pi subunit

<400> SEQUENCE: 23

Lys Arg Lys Ile Ser Phe Ala Ser Ile Glu Ile Ser Ser Asp Asn Val
1               5                   10                  15

Asp Tyr Ser Asp
            20

<210> SEQ ID NO 24
<211> LENGTH: 21
<212> TYPE: PRT
<213> ORGANISM: Artificial Sequence
<220> FEATURE:
<223> OTHER INFORMATION: Peptide from Human GABA-A receptor pi subunit

<400> SEQUENCE: 24

Asp Gly Asn Asp Val Glu Phe Thr Trp Leu Arg Gly Asn Asp Ser Val
1               5                   10                  15

Arg Gly Leu Glu His
            20

<210> SEQ ID NO 25
<211> LENGTH: 19
<212> TYPE: PRT
<213> ORGANISM: Artificial Sequence
<220> FEATURE:
<223> OTHER INFORMATION: Peptide from Annexin VIII

<400> SEQUENCE: 25

Gln Arg Gln Gln Ile Ala Lys Ser Phe Lys Ala Gln Phe Gly Lys Asp
1               5                   10                  15

Leu Thr Glu

<210> SEQ ID NO 26
<211> LENGTH: 20
<212> TYPE: PRT
<213> ORGANISM: Artificial Sequence
<220> FEATURE:
<223> OTHER INFORMATION: Peptide from Annexin VIII

<400> SEQUENCE: 26

Arg Glu Ile Met Lys Ala Tyr Glu Glu Asp Tyr Gly Ser Ser Leu Glu
1               5                   10                  15
```

```
Glu Asp Ile Gln
            20

<210> SEQ ID NO 27
<211> LENGTH: 18
<212> TYPE: PRT
<213> ORGANISM: Artificial Sequence
<220> FEATURE:
<223> OTHER INFORMATION: Peptide from Annexin VIII

<400> SEQUENCE: 27

Glu Glu Tyr Glu Lys Ile Ala Asn Lys Ser Ile Glu Asp Ser Ile Lys
1               5                  10                  15

Ser Glu

<210> SEQ ID NO 28
<211> LENGTH: 21
<212> TYPE: PRT
<213> ORGANISM: Artificial Sequence
<220> FEATURE:
<223> OTHER INFORMATION: Peptide from hypothetical UBCc containing
      protein

<400> SEQUENCE: 28

Glu Gly Gly Ser Leu Val Pro Ala Ala Arg Gln Gln His Cys Thr Gln
1               5                  10                  15

Val Arg Ser Arg Arg
            20

<210> SEQ ID NO 29
<211> LENGTH: 16
<212> TYPE: PRT
<213> ORGANISM: Artificial Sequence
<220> FEATURE:
<223> OTHER INFORMATION: Peptide from hypothetical UBCc containing
      protein

<400> SEQUENCE: 29

Arg Lys Ala Gly Lys Ser Lys Ser Phe Ser Arg Lys Glu Ala Glu
1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Peptide from hypothetical UBCc containing
      protein

<400> SEQUENCE: 30

Lys Thr His Glu Lys Tyr Gly Trp Val Thr Pro Pro Val Ser Asp Gly
1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: Peptide from MDR1

<400> SEQUENCE: 31

Met Asp Leu Glu Gly Asp Arg Asn Gly Gly Ala Lys Lys Lys Asn
1               5                  10                  15

<210> SEQ ID NO 32
<211> LENGTH: 19
<212> TYPE: PRT
```

```
<213> ORGANISM: Artificial Sequence
<220> FEATURE:
<223> OTHER INFORMATION: Peptide from MDR1

<400> SEQUENCE: 32

Asn Leu Glu Asp Leu Met Ser Asn Ile Thr Asn Arg Ser Asp Ile Asn
1               5                   10                  15

Asp Thr Gly

<210> SEQ ID NO 33
<211> LENGTH: 15
<212> TYPE: PRT
<213> ORGANISM: Artificial Sequence
<220> FEATURE:
<223> OTHER INFORMATION: Peptide from MDR1

<400> SEQUENCE: 33

Arg Gly Ser Gln Ala Gln Asp Arg Lys Leu Ser Thr Lys Glu Ala
1               5                   10                  15

<210> SEQ ID NO 34
<211> LENGTH: 18
<212> TYPE: PRT
<213> ORGANISM: Artificial Sequence
<220> FEATURE:
<223> OTHER INFORMATION: Peptide from MDR3

<400> SEQUENCE: 34

Met Asp Leu Glu Ala Ala Lys Asn Gly Thr Ala Trp Arg Pro Thr Ser
1               5                   10                  15

Ala Glu

<210> SEQ ID NO 35
<211> LENGTH: 17
<212> TYPE: PRT
<213> ORGANISM: Artificial Sequence
<220> FEATURE:
<223> OTHER INFORMATION: Peptide from MDR3

<400> SEQUENCE: 35

Asn Phe Ser Phe Pro Val Asn Phe Ser Leu Ser Leu Leu Asn Pro Gly
1               5                   10                  15

Lys

<210> SEQ ID NO 36
<211> LENGTH: 16
<212> TYPE: PRT
<213> ORGANISM: Artificial Sequence
<220> FEATURE:
<223> OTHER INFORMATION: Peptide from MDR3

<400> SEQUENCE: 36

Lys Asn Ser Gln Met Cys Gln Lys Ser Leu Asp Val Glu Thr Asp Gly
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Peptide from MRP-1

<400> SEQUENCE: 37

Met Ala Leu Arg Gly Phe Cys Ser Ala Asp Gly Ser Asp
1               5                   10
```

```
<210> SEQ ID NO 38
<211> LENGTH: 16
<212> TYPE: PRT
<213> ORGANISM: Artificial Sequence
<220> FEATURE:
<223> OTHER INFORMATION: Peptide from MRP-1

<400> SEQUENCE: 38

Lys Asn Trp Lys Lys Glu Cys Ala Lys Thr Arg Lys Gln Pro Val Lys
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Peptide from MRP-1

<400> SEQUENCE: 39

Asp Ser Ile Glu Arg Arg Pro Val Lys Asp Gly Gly Gly Thr Asn Ser
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Peptide from MRP2/CMOAT

<400> SEQUENCE: 40

Met Leu Glu Lys Phe Cys Asn Ser Thr Phe Trp Asn Ser Ser Phe Leu
1               5                   10                  15

Asp Ser Pro Glu
            20

<210> SEQ ID NO 41
<211> LENGTH: 15
<212> TYPE: PRT
<213> ORGANISM: Artificial Sequence
<220> FEATURE:
<223> OTHER INFORMATION: Peptide from MRP2/CMOAT

<400> SEQUENCE: 41

Ser Ile Leu Cys Gly Thr Phe Gln Phe Gln Thr Leu Ile Arg Thr
1               5                   10                  15

<210> SEQ ID NO 42
<211> LENGTH: 14
<212> TYPE: PRT
<213> ORGANISM: Artificial Sequence
<220> FEATURE:
<223> OTHER INFORMATION: Peptide from MRP2/CMOAT

<400> SEQUENCE: 42

Glu Asn Asn Glu Ser Ser Asn Asn Pro Ser Ser Ile Ala Ser
1               5                   10

<210> SEQ ID NO 43
<211> LENGTH: 16
<212> TYPE: PRT
<213> ORGANISM: Artificial Sequence
<220> FEATURE:
<223> OTHER INFORMATION: Peptide from MRP4

<400> SEQUENCE: 43

Gln Glu Val Lys Pro Asn Pro Leu Gln Asp Ala Asn Ile Cys Ser Arg
1               5                   10                  15
```

<210> SEQ ID NO 44
<211> LENGTH: 16
<212> TYPE: PRT
<213> ORGANISM: Artificial Sequence
<220> FEATURE:
<223> OTHER INFORMATION: Peptide from MRP4

<400> SEQUENCE: 44

Asp Glu Ile Ser Gln Arg Asn Arg Gln Leu Pro Ser Asp Gly Lys Lys
1               5                   10                  15

<210> SEQ ID NO 45
<211> LENGTH: 18
<212> TYPE: PRT
<213> ORGANISM: Artificial Sequence
<220> FEATURE:
<223> OTHER INFORMATION: Peptide from MRP4

<400> SEQUENCE: 45

Val Gln Asp Phe Thr Ala Phe Trp Asp Lys Ala Ser Glu Thr Pro Thr
1               5                   10                  15

Leu Gln

<210> SEQ ID NO 46
<211> LENGTH: 18
<212> TYPE: PRT
<213> ORGANISM: Artificial Sequence
<220> FEATURE:
<223> OTHER INFORMATION: Peptide from MRP3/ CMOAT2

<400> SEQUENCE: 46

Met Asp Ala Leu Cys Gly Ser Gly Glu Leu Gly Ser Lys Phe Trp Asp
1               5                   10                  15

Ser Asn

<210> SEQ ID NO 47
<211> LENGTH: 15
<212> TYPE: PRT
<213> ORGANISM: Artificial Sequence
<220> FEATURE:
<223> OTHER INFORMATION: Peptide from MRP3/ CMOAT2

<400> SEQUENCE: 47

Arg Lys Gln Glu Lys Gln Thr Ala Arg His Lys Ala Ser Ala Ala
1               5                   10                  15

<210> SEQ ID NO 48
<211> LENGTH: 13
<212> TYPE: PRT
<213> ORGANISM: Artificial Sequence
<220> FEATURE:
<223> OTHER INFORMATION: Peptide from MRP3/ CMOAT2

<400> SEQUENCE: 48

Asp Pro Gln Ser Val Glu Arg Lys Thr Ile Ser Pro Gly
1               5                   10

<210> SEQ ID NO 49
<211> LENGTH: 19
<212> TYPE: PRT
<213> ORGANISM: Artificial Sequence
<220> FEATURE:
<223> OTHER INFORMATION: Peptide from MRP5/ MOAT-C

<400> SEQUENCE: 49

```
Met Lys Asp Ile Asp Ile Gly Lys Glu Tyr Ile Ile Pro Ser Pro Gly
1               5                   10                  15

Tyr Arg Ser

<210> SEQ ID NO 50
<211> LENGTH: 18
<212> TYPE: PRT
<213> ORGANISM: Artificial Sequence
<220> FEATURE:
<223> OTHER INFORMATION: Peptide from MRP5/ MOAT-C

<400> SEQUENCE: 50

Arg Asp Arg Glu Asp Ser Lys Phe Arg Arg Thr Arg Pro Leu Glu Cys
1               5                   10                  15

Gln Asp

<210> SEQ ID NO 51
<211> LENGTH: 15
<212> TYPE: PRT
<213> ORGANISM: Artificial Sequence
<220> FEATURE:
<223> OTHER INFORMATION: Peptide from MRP5/ MOAT-C

<400> SEQUENCE: 51

Ser Lys His Glu Ser Ser Asp Val Asn Cys Arg Arg Leu Glu Arg
1               5                   10                  15

<210> SEQ ID NO 52
<211> LENGTH: 20
<212> TYPE: PRT
<213> ORGANISM: Artificial Sequence
<220> FEATURE:
<223> OTHER INFORMATION: Peptide from MRP6

<400> SEQUENCE: 52

Met Ala Ala Pro Ala Glu Pro Cys Ala Gly Gln Gly Val Trp Asn Gln
1               5                   10                  15

Thr Glu Pro Glu
            20

<210> SEQ ID NO 53
<211> LENGTH: 17
<212> TYPE: PRT
<213> ORGANISM: Artificial Sequence
<220> FEATURE:
<223> OTHER INFORMATION: Peptide from MRP6

<400> SEQUENCE: 53

Asp Pro Gly Val Val Asp Ser Ser Ser Gly Ser Ala Ala Gly Lys
1               5                   10                  15

Asp

<210> SEQ ID NO 54
<211> LENGTH: 13
<212> TYPE: PRT
<213> ORGANISM: Artificial Sequence
<220> FEATURE:
<223> OTHER INFORMATION: Peptide from MRP6

<400> SEQUENCE: 54

His Thr Leu Val Ala Glu Asn Ala Met Asn Ala Glu Lys
1               5                   10

<210> SEQ ID NO 55
<211> LENGTH: 15
```

```
<212> TYPE: PRT
<213> ORGANISM: Artificial Sequence
<220> FEATURE:
<223> OTHER INFORMATION: Peptide from BSEP

<400> SEQUENCE: 55

Gln Glu Val Leu Ser Lys Ile Gln His Gly His Thr Ile Ile Ser
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: Peptide from BSEP

<400> SEQUENCE: 56

Thr Asn Ser Ser Leu Asn Gln Asn Met Thr Asn Gly Thr Arg
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Peptide from BSEP

<400> SEQUENCE: 57

Met Ser Asp Ser Val Ile Leu Arg Ser Ile Lys Lys Phe Gly Glu Glu
1               5                   10                  15

Asn Asp

<210> SEQ ID NO 58
<211> LENGTH: 15
<212> TYPE: PRT
<213> ORGANISM: Artificial Sequence
<220> FEATURE:
<223> OTHER INFORMATION: Peptide from ATP-binding cassette, sub-family
      B, member 10

<400> SEQUENCE: 58

Gly Ala Asp Asp Pro Ser Ser Val Thr Ala Glu Glu Ile Gln Arg
1               5                   10                  15

<210> SEQ ID NO 59
<211> LENGTH: 14
<212> TYPE: PRT
<213> ORGANISM: Artificial Sequence
<220> FEATURE:
<223> OTHER INFORMATION: Peptide from ATP-binding cassette, sub-family
      B, member 10

<400> SEQUENCE: 59

Asn Ala Val Ala Ser Pro Glu Phe Pro Pro Arg Phe Asn Thr
1               5                   10

<210> SEQ ID NO 60
<211> LENGTH: 18
<212> TYPE: PRT
<213> ORGANISM: Artificial Sequence
<220> FEATURE:
<223> OTHER INFORMATION: Peptide from ATP-binding cassette, sub-family
      B, member 10

<400> SEQUENCE: 60

Lys Pro Asn Gly Ile Tyr Arg Lys Leu Met Asn Lys Gln Ser Phe Ile
1               5                   10                  15
```

Ser Ala

<210> SEQ ID NO 61
<211> LENGTH: 13
<212> TYPE: PRT
<213> ORGANISM: Artificial Sequence
<220> FEATURE:
<223> OTHER INFORMATION: Peptide from TAP1

<400> SEQUENCE: 61

Met Ala Ser Ser Arg Cys Pro Ala Pro Arg Gly Cys Arg
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Peptide from TAP1

<400> SEQUENCE: 62

Gln Gly Gly Ser Gly Asn Pro Val Arg Arg
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Peptide from TAP1

<400> SEQUENCE: 63

Glu Phe Val Gly Asp Gly Ile Tyr Asn Asn Thr Met Gly His Val His
1               5                   10                  15

Ser

<210> SEQ ID NO 64
<211> LENGTH: 16
<212> TYPE: PRT
<213> ORGANISM: Artificial Sequence
<220> FEATURE:
<223> OTHER INFORMATION: Peptide from SUR1

<400> SEQUENCE: 64

Met Pro Leu Ala Phe Cys Gly Ser Glu Asn His Ser Ala Ala Tyr Arg
1               5                   10                  15

<210> SEQ ID NO 65
<211> LENGTH: 18
<212> TYPE: PRT
<213> ORGANISM: Artificial Sequence
<220> FEATURE:
<223> OTHER INFORMATION: Peptide from SUR1

<400> SEQUENCE: 65

Asp His Leu Gly Lys Glu Asn Asp Val Phe Gln Pro Lys Thr Gln Phe
1               5                   10                  15

Leu Gly

<210> SEQ ID NO 66
<211> LENGTH: 16
<212> TYPE: PRT
<213> ORGANISM: Artificial Sequence
<220> FEATURE:
<223> OTHER INFORMATION: Peptide from SUR1

<400> SEQUENCE: 66

```
Glu Ile Arg Glu Glu Gln Cys Ala Pro His Glu Pro Thr Pro Gln Gly
1               5                   10                  15

<210> SEQ ID NO 67
<211> LENGTH: 12
<212> TYPE: PRT
<213> ORGANISM: Artificial Sequence
<220> FEATURE:
<223> OTHER INFORMATION: Peptide from SUR2

<400> SEQUENCE: 67

Met Ser Leu Ser Phe Cys Gly Asn Asn Ile Ser Ser
1               5                   10

<210> SEQ ID NO 68
<211> LENGTH: 18
<212> TYPE: PRT
<213> ORGANISM: Artificial Sequence
<220> FEATURE:
<223> OTHER INFORMATION: Peptide from SUR2

<400> SEQUENCE: 68

Gln Arg Val Asn Glu Thr Gln Asn Gly Thr Asn Asn Thr Thr Gly Ile
1               5                   10                  15

Ser Glu

<210> SEQ ID NO 69
<211> LENGTH: 19
<212> TYPE: PRT
<213> ORGANISM: Artificial Sequence
<220> FEATURE:
<223> OTHER INFORMATION: Peptide from SUR2

<400> SEQUENCE: 69

Asp Glu Ile Gly Asp Asp Ser Trp Arg Thr Gly Glu Ser Ser Leu Pro
1               5                   10                  15

Phe Glu Ser

<210> SEQ ID NO 70
<211> LENGTH: 21
<212> TYPE: PRT
<213> ORGANISM: Artificial Sequence
<220> FEATURE:
<223> OTHER INFORMATION: Peptide from INTEGRAL MEMBRANE PROTEIN 2B

<400> SEQUENCE: 70

Met Val Lys Val Thr Phe Asn Ser Ala Leu Ala Gln Lys Glu Ala Lys
1               5                   10                  15

Lys Asp Glu Pro Lys
                20

<210> SEQ ID NO 71
<211> LENGTH: 16
<212> TYPE: PRT
<213> ORGANISM: Artificial Sequence
<220> FEATURE:
<223> OTHER INFORMATION: Peptide from INTEGRAL MEMBRANE PROTEIN 2B

<400> SEQUENCE: 71

Gln Thr Ile Glu Glu Asn Ile Lys Ile Phe Glu Glu Glu Val Glu
1               5                   10                  15

<210> SEQ ID NO 72
<211> LENGTH: 21
<212> TYPE: PRT
```

```
<213> ORGANISM: Artificial Sequence
<220> FEATURE:
<223> OTHER INFORMATION: Peptide from INTEGRAL MEMBRANE PROTEIN 2B

<400> SEQUENCE: 72

His Asp Lys Glu Thr Tyr Lys Leu Gln Arg Arg Glu Thr Ile Lys Gly
1               5                   10                  15

Ile Gln Lys Arg Glu
            20

<210> SEQ ID NO 73
<211> LENGTH: 20
<212> TYPE: PRT
<213> ORGANISM: Artificial Sequence
<220> FEATURE:
<223> OTHER INFORMATION: Peptide from ANK-3

<400> SEQUENCE: 73

His Lys Lys Glu Thr Glu Ser Asp Gln Asp Asp Glu Ile Glu Lys Thr
1               5                   10                  15

Asp Arg Arg Gln
            20

<210> SEQ ID NO 74
<211> LENGTH: 20
<212> TYPE: PRT
<213> ORGANISM: Artificial Sequence
<220> FEATURE:
<223> OTHER INFORMATION: Peptide from ANK-3

<400> SEQUENCE: 74

Glu Gly Phe Lys Val Lys Thr Lys Lys Glu Ile Arg His Val Glu Lys
1               5                   10                  15

Lys Ser His Ser
            20

<210> SEQ ID NO 75
<211> LENGTH: 20
<212> TYPE: PRT
<213> ORGANISM: Artificial Sequence
<220> FEATURE:
<223> OTHER INFORMATION: Peptide from ANK-3

<400> SEQUENCE: 75

Met Ala His Ala Ala Ser Gln Leu Lys Lys Asn Arg Asp Leu Glu Ile
1               5                   10                  15

Asn Ala Glu Glu
            20

<210> SEQ ID NO 76
<211> LENGTH: 18
<212> TYPE: PRT
<213> ORGANISM: Artificial Sequence
<220> FEATURE:
<223> OTHER INFORMATION: Peptide from hypothetical protein FLJ21918

<400> SEQUENCE: 76

Glu Arg Ala Leu Ala Ala Ala Gln Arg Cys His Lys Lys Val Met Lys
1               5                   10                  15

Glu Arg

<210> SEQ ID NO 77
<211> LENGTH: 15
<212> TYPE: PRT
<213> ORGANISM: Artificial Sequence
```

```
<220> FEATURE:
<223> OTHER INFORMATION: Peptide from hypothetical protein FLJ21918

<400> SEQUENCE: 77

Thr Ala Gly Met Lys Asp Leu Leu Ser Val Phe Gln Ala Tyr Gln
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Peptide from hypothetical protein FLJ21918

<400> SEQUENCE: 78

Asp Pro Pro Arg Thr Val Leu Gln Ala Pro Lys Glu Trp Val Cys Leu
1               5                   10                  15

<210> SEQ ID NO 79
<211> LENGTH: 20
<212> TYPE: PRT
<213> ORGANISM: Artificial Sequence
<220> FEATURE:
<223> OTHER INFORMATION: Peptide from ataxia-telangiectasia group D-
      associated protein

<400> SEQUENCE: 79

Met Glu Ala Ala Asp Ala Ser Arg Ser Asn Gly Ser Ser Pro Glu Ala
1               5                   10                  15

Arg Asp Ala Arg
            20

<210> SEQ ID NO 80
<211> LENGTH: 17
<212> TYPE: PRT
<213> ORGANISM: Artificial Sequence
<220> FEATURE:
<223> OTHER INFORMATION: Peptide from ataxia-telangiectasia group D-
      associated protein

<400> SEQUENCE: 80

Glu Leu His Leu Lys Pro His Leu Glu Gly Ala Ala Phe Arg Asp His
1               5                   10                  15

Gln

<210> SEQ ID NO 81
<211> LENGTH: 18
<212> TYPE: PRT
<213> ORGANISM: Artificial Sequence
<220> FEATURE:
<223> OTHER INFORMATION: Peptide from ataxia-telangiectasia group D-
      associated protein

<400> SEQUENCE: 81

Glu Gly Glu Gly Leu Gly Gln Ser Leu Gly Asn Phe Lys Asp Asp Leu
1               5                   10                  15

Leu Asn

<210> SEQ ID NO 82
<211> LENGTH: 17
<212> TYPE: PRT
<213> ORGANISM: Artificial Sequence
<220> FEATURE:
<223> OTHER INFORMATION: Peptide from ataxia-telangiectasia group D-
      associated protein

<400> SEQUENCE: 82
```

```
Glu Leu His Leu Lys Pro His Leu Glu Gly Ala Ala Phe Arg Asp His
1               5                   10                  15

Gln

<210> SEQ ID NO 83
<211> LENGTH: 17
<212> TYPE: PRT
<213> ORGANISM: Artificial Sequence
<220> FEATURE:
<223> OTHER INFORMATION: Peptide from iroquois related homeobox 3

<400> SEQUENCE: 83

Gly Ser Glu Glu Arg Gly Ala Gly Arg Gly Ser Ser Gly Gly Arg Glu
1               5                   10                  15

Glu

<210> SEQ ID NO 84
<211> LENGTH: 18
<212> TYPE: PRT
<213> ORGANISM: Artificial Sequence
<220> FEATURE:
<223> OTHER INFORMATION: Peptide from iroquois related homeobox 3

<400> SEQUENCE: 84

Lys Ile Trp Ser Leu Ala Glu Thr Ala Thr Ser Pro Asp Asn Pro Arg
1               5                   10                  15

Arg Ser

<210> SEQ ID NO 85
<211> LENGTH: 20
<212> TYPE: PRT
<213> ORGANISM: Artificial Sequence
<220> FEATURE:
<223> OTHER INFORMATION: Peptide from iroquois related homeobox 3

<400> SEQUENCE: 85

Lys Lys Leu Leu Lys Thr Ala Phe Gln Pro Val Pro Arg Arg Pro Gln
1               5                   10                  15

Asn His Leu Asp
            20

<210> SEQ ID NO 86
<211> LENGTH: 21
<212> TYPE: PRT
<213> ORGANISM: Artificial Sequence
<220> FEATURE:
<223> OTHER INFORMATION: Peptide from Chuck Ras C-term

<400> SEQUENCE: 86

Arg Arg Ser Ser Thr Thr His Val Lys Gln Ala Ile Asn Lys Met Leu
1               5                   10                  15

Thr Lys Ile Ser Ser
            20

<210> SEQ ID NO 87
<211> LENGTH: 20
<212> TYPE: PRT
<213> ORGANISM: Artificial Sequence
<220> FEATURE:
<223> OTHER INFORMATION: Peptide from putative G protein-coupled
      receptor (NP_055188.1|)

<400> SEQUENCE: 87

Met Arg Arg Lys Asn Thr Cys Gln Asn Phe Met Glu Tyr Phe Cys Ile
```

```
                    1               5              10              15

Ser Leu Ala Phe
            20

<210> SEQ ID NO 88
<211> LENGTH: 21
<212> TYPE: PRT
<213> ORGANISM: Artificial Sequence
<220> FEATURE:
<223> OTHER INFORMATION: Peptide from putative G protein-coupled
      receptor (NP_055188.1|)

<400> SEQUENCE: 88

Asn Glu Thr Ile Leu Tyr Phe Pro Phe Ser Ser His Ser Ser Tyr Thr
1               5                  10                  15

Val Arg Ser Lys Lys
            20

<210> SEQ ID NO 89
<211> LENGTH: 19
<212> TYPE: PRT
<213> ORGANISM: Artificial Sequence
<220> FEATURE:
<223> OTHER INFORMATION: Peptide from putative G protein-coupled
      receptor (NP_055188.1|)

<400> SEQUENCE: 89

Lys Val Gln Ile Pro Ala Tyr Ile Glu Met Asn Ile Pro Leu Val Ile
1               5                  10                  15

Leu Cys Gln

<210> SEQ ID NO 90
<211> LENGTH: 18
<212> TYPE: PRT
<213> ORGANISM: Artificial Sequence
<220> FEATURE:
<223> OTHER INFORMATION: Peptide from Calgranulin A

<400> SEQUENCE: 90

Met Leu Thr Glu Leu Glu Lys Ala Leu Asn Ser Ile Ile Asp Val Tyr
1               5                  10                  15

His Lys

<210> SEQ ID NO 91
<211> LENGTH: 22
<212> TYPE: PRT
<213> ORGANISM: Artificial Sequence
<220> FEATURE:
<223> OTHER INFORMATION: Peptide from Calgranulin A

<400> SEQUENCE: 91

Arg Asp Asp Leu Lys Lys Leu Leu Glu Thr Glu Cys Pro Gln Tyr Ile
1               5                  10                  15

Arg Lys Lys Gly Ala Asp
            20

<210> SEQ ID NO 92
<211> LENGTH: 17
<212> TYPE: PRT
<213> ORGANISM: Artificial Sequence
<220> FEATURE:
<223> OTHER INFORMATION: Peptide from Calgranulin A

<400> SEQUENCE: 92

Lys Met Gly Val Ala Ala His Lys Lys Ser His Glu Glu Ser His Lys
```

-continued

```
1               5                   10                  15
Glu

<210> SEQ ID NO 93
<211> LENGTH: 17
<212> TYPE: PRT
<213> ORGANISM: Artificial Sequence
<220> FEATURE:
<223> OTHER INFORMATION: Peptide from hepatocyte nuclear protein 3,
      alpha

<400> SEQUENCE: 93

Pro Glu Ser Arg Lys Asp Pro Ser Gly Ala Ser Asn Pro Ser Ala Asp
1               5                   10                  15

Ser

<210> SEQ ID NO 94
<211> LENGTH: 15
<212> TYPE: PRT
<213> ORGANISM: Artificial Sequence
<220> FEATURE:
<223> OTHER INFORMATION: Peptide from hepatocyte nuclear protein 3,
      alpha

<400> SEQUENCE: 94

His Gly Leu Ala Pro His Glu Ser Gln Leu His Leu Lys Gly Asp
1               5                   10                  15

<210> SEQ ID NO 95
<211> LENGTH: 18
<212> TYPE: PRT
<213> ORGANISM: Artificial Sequence
<220> FEATURE:
<223> OTHER INFORMATION: Peptide from hepatocyte nuclear protein 3,
      alpha

<400> SEQUENCE: 95

Glu Gln Gln His Lys Leu Asp Phe Lys Ala Tyr Glu Gln Ala Leu Gln
1               5                   10                  15

Tyr Ser

<210> SEQ ID NO 96
<211> LENGTH: 17
<212> TYPE: PRT
<213> ORGANISM: Artificial Sequence
<220> FEATURE:
<223> OTHER INFORMATION: Peptide from hepatocyte nuclear protein 3,
      alpha

<400> SEQUENCE: 96

Pro Glu Ser Arg Lys Asp Pro Ser Gly Ala Ser Asn Pro Ser Ala Asp
1               5                   10                  15

Ser

<210> SEQ ID NO 97
<211> LENGTH: 15
<212> TYPE: PRT
<213> ORGANISM: Artificial Sequence
<220> FEATURE:
<223> OTHER INFORMATION: Peptide from hepatocyte nuclear protein 3,
      alpha

<400> SEQUENCE: 97

His Gly Leu Ala Pro His Glu Ser Gln Leu His Leu Lys Gly Asp
1               5                   10                  15
```

```
<210> SEQ ID NO 98
<211> LENGTH: 18
<212> TYPE: PRT
<213> ORGANISM: Artificial Sequence
<220> FEATURE:
<223> OTHER INFORMATION: Peptide from hepatocyte nuclear protein 3,
      alpha

<400> SEQUENCE: 98

Glu Gln Gln His Lys Leu Asp Phe Lys Ala Tyr Glu Gln Ala Leu Gln
1               5                   10                  15

Tyr Ser

<210> SEQ ID NO 99
<211> LENGTH: 20
<212> TYPE: PRT
<213> ORGANISM: Artificial Sequence
<220> FEATURE:
<223> OTHER INFORMATION: Peptide from intestinal trefoil precursor

<400> SEQUENCE: 99

Glu Glu Tyr Val Gly Leu Ser Ala Asn Gln Cys Ala Val Pro Ala Lys
1               5                   10                  15

Asp Arg Val Asp
            20

<210> SEQ ID NO 100
<211> LENGTH: 15
<212> TYPE: PRT
<213> ORGANISM: Artificial Sequence
<220> FEATURE:
<223> OTHER INFORMATION: Peptide from intestinal trefoil precursor

<400> SEQUENCE: 100

Arg Val Asp Cys Gly Tyr Pro His Val Thr Pro Lys Glu Cys Asn
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Peptide from intestinal trefoil precursor

<400> SEQUENCE: 101

Val Pro Trp Cys Phe Lys Pro Leu Gln Glu Ala Glu Cys Thr Phe
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Peptide from intestinal trefoil precursor

<400> SEQUENCE: 102

Val Pro Trp Cys Phe Lys Pro Leu Gln Glu Ala Glu Cys Thr Phe
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Peptide from Keratin 17

<400> SEQUENCE: 103
```

Lys Lys Glu Pro Val Thr Thr Arg Gln Val Arg Thr Ile Val Glu Glu
1               5                   10                  15

<210> SEQ ID NO 104
<211> LENGTH: 17
<212> TYPE: PRT
<213> ORGANISM: Artificial Sequence
<220> FEATURE:
<223> OTHER INFORMATION: Peptide from Keratin 17

<400> SEQUENCE: 104

Gln Asp Gly Lys Val Ile Ser Ser Arg Glu Gln Val His Gln Thr Thr
1               5                   10                  15

Arg

<210> SEQ ID NO 105
<211> LENGTH: 15
<212> TYPE: PRT
<213> ORGANISM: Artificial Sequence
<220> FEATURE:
<223> OTHER INFORMATION: Peptide from Keratin 17

<400> SEQUENCE: 105

Ser Ser Ser Ile Lys Gly Ser Ser Gly Leu Gly Gly Gly Ser Ser
1               5                   10                  15

<210> SEQ ID NO 106
<211> LENGTH: 20
<212> TYPE: PRT
<213> ORGANISM: Artificial Sequence
<220> FEATURE:
<223> OTHER INFORMATION: Peptide from LIV-1

<400> SEQUENCE: 106

Asp His Asn His Ala Ala Ser Gly Lys Asn Lys Arg Lys Ala Leu Cys
1               5                   10                  15

Pro Asp His Asp
        20

<210> SEQ ID NO 107
<211> LENGTH: 21
<212> TYPE: PRT
<213> ORGANISM: Artificial Sequence
<220> FEATURE:
<223> OTHER INFORMATION: Peptide from LIV-1

<400> SEQUENCE: 107

Glu Glu Pro Ala Met Glu Met Lys Arg Gly Pro Leu Phe Ser His Leu
1               5                   10                  15

Ser Ser Gln Asn Ile
        20

<210> SEQ ID NO 108
<211> LENGTH: 16
<212> TYPE: PRT
<213> ORGANISM: Artificial Sequence
<220> FEATURE:
<223> OTHER INFORMATION: Peptide from LIV-1

<400> SEQUENCE: 108

Gln Arg Tyr Ser Arg Glu Glu Leu Lys Asp Ala Gly Val Ala Thr Leu
1               5                   10                  15

<210> SEQ ID NO 109
<211> LENGTH: 22

```
<212> TYPE: PRT
<213> ORGANISM: Artificial Sequence
<220> FEATURE:
<223> OTHER INFORMATION: Peptide from NAT1

<400> SEQUENCE: 109

Met Asp Ile Glu Ala Tyr Leu Glu Arg Ile Gly Tyr Lys Lys Ser Arg
1               5                   10                  15

Asn Lys Leu Asp Leu Glu
            20

<210> SEQ ID NO 110
<211> LENGTH: 22
<212> TYPE: PRT
<213> ORGANISM: Artificial Sequence
<220> FEATURE:
<223> OTHER INFORMATION: Peptide from NAT1

<400> SEQUENCE: 110

Gln Met Trp Gln Pro Leu Glu Leu Ile Ser Gly Lys Asp Gln Pro Gln
1               5                   10                  15

Val Pro Cys Val Phe Arg
            20

<210> SEQ ID NO 111
<211> LENGTH: 20
<212> TYPE: PRT
<213> ORGANISM: Artificial Sequence
<220> FEATURE:
<223> OTHER INFORMATION: Peptide from NAT1

<400> SEQUENCE: 111

Phe Asn Ile Ser Leu Gln Arg Lys Leu Val Pro Lys His Gly Asp Arg
1               5                   10                  15

Phe Phe Thr Ile
            20

<210> SEQ ID NO 112
<211> LENGTH: 20
<212> TYPE: PRT
<213> ORGANISM: Artificial Sequence
<220> FEATURE:
<223> OTHER INFORMATION: Peptide from x-box binding

<400> SEQUENCE: 112

Gln Pro Pro Phe Leu Cys Gln Trp Gly Arg His Gln Pro Ser Trp Lys
1               5                   10                  15

Pro Leu Met Asn
            20

<210> SEQ ID NO 113
<211> LENGTH: 20
<212> TYPE: PRT
<213> ORGANISM: Artificial Sequence
<220> FEATURE:
<223> OTHER INFORMATION: Peptide from x-box binding

<400> SEQUENCE: 113

Glu Lys Thr His Gly Leu Val Val Glu Asn Gln Glu Leu Arg Gln Arg
1               5                   10                  15

Leu Gly Met Asp
            20

<210> SEQ ID NO 114
<211> LENGTH: 21
```

```
<212> TYPE: PRT
<213> ORGANISM: Artificial Sequence
<220> FEATURE:
<223> OTHER INFORMATION: Peptide from x-box binding

<400> SEQUENCE: 114

Arg Gln Arg Leu Thr His Leu Ser Pro Glu Glu Lys Ala Leu Arg Arg
1               5                   10                  15

Lys Leu Lys Asn Arg
            20

<210> SEQ ID NO 115
<211> LENGTH: 16
<212> TYPE: PRT
<213> ORGANISM: Artificial Sequence
<220> FEATURE:
<223> OTHER INFORMATION: Peptide from ATPase, H+ transporting, lysosomal
      (vacuolar proton pump), beta polypeptide, 56/58kD, isoform 1R7340

<400> SEQUENCE: 115

Arg Glu His Met Gln Ala Val Thr Arg Asn Tyr Ile Thr His Pro Arg
1               5                   10                  15

<210> SEQ ID NO 116
<211> LENGTH: 13
<212> TYPE: PRT
<213> ORGANISM: Artificial Sequence
<220> FEATURE:
<223> OTHER INFORMATION: Peptide from ATPase, H+ transporting, lysosomal
      (vacuolar proton pump), beta polypeptide, 56/58kD, isoform 1R7340

<400> SEQUENCE: 116

Lys Lys Ser Lys Ala Val Leu Asp Tyr His Asp Asp Asn
1               5                   10

<210> SEQ ID NO 117
<211> LENGTH: 19
<212> TYPE: PRT
<213> ORGANISM: Artificial Sequence
<220> FEATURE:
<223> OTHER INFORMATION: Peptide from ATPase, H+ transporting, lysosomal
      (vacuolar proton pump), beta polypeptide, 56/58kD, isoform 1R7340

<400> SEQUENCE: 117

Asp Glu Phe Tyr Ser Arg Glu Gly Arg Leu Gln Asp Leu Ala Pro Asp
1               5                   10                  15

Thr Ala Leu

<210> SEQ ID NO 118
<211> LENGTH: 18
<212> TYPE: PRT
<213> ORGANISM: Artificial Sequence
<220> FEATURE:
<223> OTHER INFORMATION: Peptide from hypothetical protein MGC2714 (in
      part)

<400> SEQUENCE: 118

Arg Tyr Ala Phe Asp Phe Ala Arg Asp Lys Asp Gln Arg Ser Leu Asp
1               5                   10                  15

Ile Asp

<210> SEQ ID NO 119
<211> LENGTH: 19
<212> TYPE: PRT
<213> ORGANISM: Artificial Sequence
<220> FEATURE:
<223> OTHER INFORMATION: Peptide from hypothetical protein MGC2714 (in
```

```
                  part)

<400> SEQUENCE: 119

Ser Val Phe Tyr Gln Tyr Leu Glu Gln Ser Lys Tyr Arg Val Met Asn
1               5                   10                  15

Lys Asp Gln

<210> SEQ ID NO 120
<211> LENGTH: 22
<212> TYPE: PRT
<213> ORGANISM: Artificial Sequence
<220> FEATURE:
<223> OTHER INFORMATION: Peptide from hypothetical protein MGC2714 (in
      part)

<400> SEQUENCE: 120

Glu Asp Gly Ala Trp Pro Val Leu Leu Asp Glu Phe Val Glu Trp Gln
1               5                   10                  15

Lys Val Arg Gln Thr Ser
            20

<210> SEQ ID NO 121
<211> LENGTH: 19
<212> TYPE: PRT
<213> ORGANISM: Artificial Sequence
<220> FEATURE:
<223> OTHER INFORMATION: Peptide from Reproduction 8

<400> SEQUENCE: 121

Ser Phe Lys Ser Pro Gln Val Tyr Leu Lys Glu Glu Glu Lys Asn
1               5                   10                  15

Glu Lys Arg

<210> SEQ ID NO 122
<211> LENGTH: 17
<212> TYPE: PRT
<213> ORGANISM: Artificial Sequence
<220> FEATURE:
<223> OTHER INFORMATION: Peptide from Reproduction 8

<400> SEQUENCE: 122

Arg Lys Lys Gln Gln Glu Ala Gln Gly Glu Lys Ala Ser Arg Tyr Ile
1               5                   10                  15

Glu

<210> SEQ ID NO 123
<211> LENGTH: 20
<212> TYPE: PRT
<213> ORGANISM: Artificial Sequence
<220> FEATURE:
<223> OTHER INFORMATION: Peptide from Reproduction 8

<400> SEQUENCE: 123

Glu Asp Ile Gly Ile Thr Val Asp Thr Val Leu Ile Leu Glu Glu Lys
1               5                   10                  15

Glu Gln Thr Asn
            20

<210> SEQ ID NO 124
<211> LENGTH: 18
<212> TYPE: PRT
<213> ORGANISM: Artificial Sequence
<220> FEATURE:
<223> OTHER INFORMATION: Peptide from slit1
```

```
<400> SEQUENCE: 124

Asp Phe Arg Cys Glu Glu Gly Gln Glu Gly Gly Cys Leu Pro Arg
1               5                   10                  15

Pro Gln

<210> SEQ ID NO 125
<211> LENGTH: 21
<212> TYPE: PRT
<213> ORGANISM: Artificial Sequence
<220> FEATURE:
<223> OTHER INFORMATION: Peptide from slit1

<400> SEQUENCE: 125

Asp Gly Thr Ser Phe Ala Glu Glu Val Glu Lys Pro Thr Lys Cys Gly
1               5                   10                  15

Cys Ala Leu Cys Ala
            20

<210> SEQ ID NO 126
<211> LENGTH: 18
<212> TYPE: PRT
<213> ORGANISM: Artificial Sequence
<220> FEATURE:
<223> OTHER INFORMATION: Peptide from slit1

<400> SEQUENCE: 126

Lys Ala Phe Arg Gly Ala Thr Asp Leu Lys Asn Leu Arg Leu Asp Lys
1               5                   10                  15

Asn Gln

<210> SEQ ID NO 127
<211> LENGTH: 19
<212> TYPE: PRT
<213> ORGANISM: Artificial Sequence
<220> FEATURE:
<223> OTHER INFORMATION: Peptide from sry-box9

<400> SEQUENCE: 127

Met Asn Leu Leu Asp Pro Phe Met Lys Met Thr Asp Glu Gln Glu Lys
1               5                   10                  15

Gly Leu Ser

<210> SEQ ID NO 128
<211> LENGTH: 18
<212> TYPE: PRT
<213> ORGANISM: Artificial Sequence
<220> FEATURE:
<223> OTHER INFORMATION: Peptide from sry-box9

<400> SEQUENCE: 128

Asn Thr Phe Pro Lys Gly Glu Pro Asp Leu Lys Lys Glu Ser Glu Glu
1               5                   10                  15

Asp Lys

<210> SEQ ID NO 129
<211> LENGTH: 19
<212> TYPE: PRT
<213> ORGANISM: Artificial Sequence
<220> FEATURE:
<223> OTHER INFORMATION: Peptide from sry-box9

<400> SEQUENCE: 129

Lys Asn Gly Gln Ala Glu Ala Glu Glu Ala Thr Glu Gln Thr His Ile
1               5                   10                  15
```

Ser Pro Asn

<210> SEQ ID NO 130
<211> LENGTH: 18
<212> TYPE: PRT
<213> ORGANISM: Artificial Sequence
<220> FEATURE:
<223> OTHER INFORMATION: Peptide from EGF-Like Domain, Multiple 2

<400> SEQUENCE: 130

Gln Ala Ser Ser Leu Arg Leu Glu Pro Gly Arg Ala Asn Asp Gly Asp
1               5                   10                  15

Trp His

<210> SEQ ID NO 131
<211> LENGTH: 20
<212> TYPE: PRT
<213> ORGANISM: Artificial Sequence
<220> FEATURE:
<223> OTHER INFORMATION: Peptide from EGF-Like Domain, Multiple 2

<400> SEQUENCE: 131

Glu Leu Lys Gly Phe Ala Glu Arg Leu Gln Arg Asn Glu Ser Gly Leu
1               5                   10                  15

Asp Ser Gly Arg
            20

<210> SEQ ID NO 132
<211> LENGTH: 17
<212> TYPE: PRT
<213> ORGANISM: Artificial Sequence
<220> FEATURE:
<223> OTHER INFORMATION: Peptide from EGF-Like Domain, Multiple 2

<400> SEQUENCE: 132

Arg Ser Gly Lys Ser Gln Pro Ser Tyr Ile Pro Phe Leu Leu Arg Glu
1               5                   10                  15

Glu

<210> SEQ ID NO 133
<211> LENGTH: 22
<212> TYPE: PRT
<213> ORGANISM: Artificial Sequence
<220> FEATURE:
<223> OTHER INFORMATION: Peptide from Gamma-glytamyl hydrolase

<400> SEQUENCE: 133

Arg Arg Ser Asp Tyr Ala Lys Val Ala Lys Ile Phe Tyr Asn Leu Ser
1               5                   10                  15

Ile Gln Ser Phe Asp Asp
            20

<210> SEQ ID NO 134
<211> LENGTH: 19
<212> TYPE: PRT
<213> ORGANISM: Artificial Sequence
<220> FEATURE:
<223> OTHER INFORMATION: Peptide from Gamma-glytamyl hydrolase

<400> SEQUENCE: 134

Lys Asn Phe Thr Met Asn Glu Lys Leu Lys Lys Phe Phe Asn Val Leu
1               5                   10                  15

Thr Thr Asn

-continued

<210> SEQ ID NO 135
<211> LENGTH: 20
<212> TYPE: PRT
<213> ORGANISM: Artificial Sequence
<220> FEATURE:
<223> OTHER INFORMATION: Peptide from Gamma-glytamyl hydrolase

<400> SEQUENCE: 135

Glu Phe Phe Val Asn Glu Ala Arg Lys Asn Asn His His Phe Lys Ser
1               5                   10                  15

Glu Ser Glu Glu
            20

<210> SEQ ID NO 136
<211> LENGTH: 19
<212> TYPE: PRT
<213> ORGANISM: Artificial Sequence
<220> FEATURE:
<223> OTHER INFORMATION: Peptide from Bullous Pemphigoid Antigen 1

<400> SEQUENCE: 136

Lys Asn Thr Gln Ala Ala Glu Ala Leu Val Lys Leu Tyr Glu Thr Lys
1               5                   10                  15

Leu Cys Glu

<210> SEQ ID NO 137
<211> LENGTH: 17
<212> TYPE: PRT
<213> ORGANISM: Artificial Sequence
<220> FEATURE:
<223> OTHER INFORMATION: Peptide from Bullous Pemphigoid Antigen 1

<400> SEQUENCE: 137

Gln Glu Asn Gln Pro Glu Asn Ser Lys Thr Leu Ala Thr Gln Leu Asn
1               5                   10                  15

Gln

<210> SEQ ID NO 138
<211> LENGTH: 19
<212> TYPE: PRT
<213> ORGANISM: Artificial Sequence
<220> FEATURE:
<223> OTHER INFORMATION: Peptide from Bullous Pemphigoid Antigen 1

<400> SEQUENCE: 138

Lys Gln Met Glu Lys Asp Leu Ala Phe Gln Lys Gln Val Ala Glu Lys
1               5                   10                  15

Gln Leu Lys

<210> SEQ ID NO 139
<211> LENGTH: 17
<212> TYPE: PRT
<213> ORGANISM: Artificial Sequence
<220> FEATURE:
<223> OTHER INFORMATION: Peptide from fasn

<400> SEQUENCE: 139

Glu Phe Val Glu Gln Leu Arg Lys Glu Gly Val Phe Ala Lys Glu Val
1               5                   10                  15

Arg

<210> SEQ ID NO 140
<211> LENGTH: 18
<212> TYPE: PRT

-continued

```
<213> ORGANISM: Artificial Sequence
<220> FEATURE:
<223> OTHER INFORMATION: Peptide from fasn

<400> SEQUENCE: 140

Asp Arg His Pro Gln Ala Leu Glu Ala Ala Gln Ala Glu Leu Gln Gln
1               5                   10                  15

His Asp

<210> SEQ ID NO 141
<211> LENGTH: 20
<212> TYPE: PRT
<213> ORGANISM: Artificial Sequence
<220> FEATURE:
<223> OTHER INFORMATION: Peptide from fasn

<400> SEQUENCE: 141

Arg Glu Val Arg Gln Leu Thr Leu Arg Lys Leu Gln Glu Leu Ser Ser
1               5                   10                  15

Lys Ala Asp Glu
            20

<210> SEQ ID NO 142
<211> LENGTH: 19
<212> TYPE: PRT
<213> ORGANISM: Artificial Sequence
<220> FEATURE:
<223> OTHER INFORMATION: Peptide from Matrix Metalloproteinase 14

<400> SEQUENCE: 142

Ala Tyr Ile Arg Glu Gly His Glu Lys Gln Ala Asp Ile Met Ile Phe
1               5                   10                  15

Phe Ala Glu

<210> SEQ ID NO 143
<211> LENGTH: 18
<212> TYPE: PRT
<213> ORGANISM: Artificial Sequence
<220> FEATURE:
<223> OTHER INFORMATION: Peptide from Matrix Metalloproteinase 14

<400> SEQUENCE: 143

Asp Glu Ala Ser Leu Glu Pro Gly Tyr Pro Lys His Ile Lys Glu Leu
1               5                   10                  15

Gly Arg

<210> SEQ ID NO 144
<211> LENGTH: 16
<212> TYPE: PRT
<213> ORGANISM: Artificial Sequence
<220> FEATURE:
<223> OTHER INFORMATION: Peptide from Matrix Metalloproteinase 14

<400> SEQUENCE: 144

Arg Gly Ser Phe Met Gly Ser Asp Glu Val Phe Thr Tyr Phe Tyr Lys
1               5                   10                  15

<210> SEQ ID NO 145
<211> LENGTH: 20
<212> TYPE: PRT
<213> ORGANISM: Artificial Sequence
<220> FEATURE:
<223> OTHER INFORMATION: Peptide from ABP/ZF

<400> SEQUENCE: 145
```

```
Arg Gln Glu His Cys Met Ser Glu His Phe Lys Asn Arg Pro Ala Cys
1               5                   10                  15

Leu Gly Ala Arg
            20

<210> SEQ ID NO 146
<211> LENGTH: 19
<212> TYPE: PRT
<213> ORGANISM: Artificial Sequence
<220> FEATURE:
<223> OTHER INFORMATION: Peptide from ABP/ZF

<400> SEQUENCE: 146

Gln Gly His Lys Trp Gly Glu Ser Pro Ser Gln Gly Thr Gln Ala Gly
1               5                   10                  15

Ala Gly Lys

<210> SEQ ID NO 147
<211> LENGTH: 21
<212> TYPE: PRT
<213> ORGANISM: Artificial Sequence
<220> FEATURE:
<223> OTHER INFORMATION: Peptide from ABP/ZF

<400> SEQUENCE: 147

Arg Ala Cys Gly Lys Arg Val Ser Glu Gly Asp Arg Asn Gly Ser Gly
1               5                   10                  15

Gly Gly Lys Trp Gly
            20

<210> SEQ ID NO 148
<211> LENGTH: 16
<212> TYPE: PRT
<213> ORGANISM: Artificial Sequence
<220> FEATURE:
<223> OTHER INFORMATION: Peptide from fatty acid binding protein 7,
      FABP7

<400> SEQUENCE: 148

Met Val Glu Ala Phe Cys Ala Thr Trp Lys Leu Thr Asn Ser Gln Asn
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Peptide from fatty acid binding protein 7,
      FABP7

<400> SEQUENCE: 149

Gln Val Gly Asn Val Thr Lys Pro Thr Val Ile Ile Ser Gln Glu
1               5                   10                  15

<210> SEQ ID NO 150
<211> LENGTH: 14
<212> TYPE: PRT
<213> ORGANISM: Artificial Sequence
<220> FEATURE:
<223> OTHER INFORMATION: Peptide from fatty acid binding protein 7,
      FABP7

<400> SEQUENCE: 150

Lys Val Val Ile Arg Thr Leu Ser Thr Phe Lys Asn Thr Glu
1               5                   10
```

```
<210> SEQ ID NO 151
<211> LENGTH: 19
<212> TYPE: PRT
<213> ORGANISM: Artificial Sequence
<220> FEATURE:
<223> OTHER INFORMATION: Peptide from Cadherin 3

<400> SEQUENCE: 151

Arg Ala Val Phe Arg Glu Ala Glu Val Thr Leu Glu Ala Gly Gly Ala
1               5                   10                  15

Glu Gln Glu

<210> SEQ ID NO 152
<211> LENGTH: 17
<212> TYPE: PRT
<213> ORGANISM: Artificial Sequence
<220> FEATURE:
<223> OTHER INFORMATION: Peptide from Cadherin 3

<400> SEQUENCE: 152

Gln Glu Pro Ala Leu Phe Ser Thr Asp Asn Asp Phe Thr Val Arg
1               5                   10                  15

Asn

<210> SEQ ID NO 153
<211> LENGTH: 15
<212> TYPE: PRT
<213> ORGANISM: Artificial Sequence
<220> FEATURE:
<223> OTHER INFORMATION: Peptide from Cadherin 3

<400> SEQUENCE: 153

Gln Lys Tyr Glu Ala His Val Pro Glu Asn Ala Val Gly His Glu
1               5                   10                  15

<210> SEQ ID NO 154
<211> LENGTH: 14
<212> TYPE: PRT
<213> ORGANISM: Artificial Sequence
<220> FEATURE:
<223> OTHER INFORMATION: Peptide from GRO1 Oncogene

<400> SEQUENCE: 154

Lys Lys Ile Ile Glu Lys Met Leu Asn Ser Asp Lys Ser Asn
1               5                   10

<210> SEQ ID NO 155
<211> LENGTH: 20
<212> TYPE: PRT
<213> ORGANISM: Artificial Sequence
<220> FEATURE:
<223> OTHER INFORMATION: Peptide from Effector cell protease receptor 1

<400> SEQUENCE: 155

Gly Lys Pro Gly Asn Gln Asn Ser Lys Asn Glu Pro Pro Lys Lys Arg
1               5                   10                  15

Glu Arg Glu Arg
            20

<210> SEQ ID NO 156
<211> LENGTH: 14
<212> TYPE: PRT
<213> ORGANISM: Artificial Sequence
<220> FEATURE:
<223> OTHER INFORMATION: Peptide from Effector cell protease receptor 1

<400> SEQUENCE: 156
```

-continued

Gln Ala Glu Ala Pro Leu Val Pro Leu Ser Arg Gln Asn Lys
1               5                   10

<210> SEQ ID NO 157
<211> LENGTH: 13
<212> TYPE: PRT
<213> ORGANISM: Artificial Sequence
<220> FEATURE:
<223> OTHER INFORMATION: Peptide from Effector cell protease receptor 1

<400> SEQUENCE: 157

Asn Cys Phe Leu Thr Glu Arg Lys Ala Gln Pro Asp Glu
1               5                   10

<210> SEQ ID NO 158
<211> LENGTH: 15
<212> TYPE: PRT
<213> ORGANISM: Artificial Sequence
<220> FEATURE:
<223> OTHER INFORMATION: Peptide from PLOD2

<400> SEQUENCE: 158

Lys Gln Val Asp Leu Glu Asn Val Trp Leu Asp Phe Ile Arg Glu
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Peptide from PLOD2

<400> SEQUENCE: 159

Glu Phe Asp Thr Val Asp Leu Ser Ala Val Asp Val His Pro Asn
1               5                   10                  15

<210> SEQ ID NO 160
<211> LENGTH: 18
<212> TYPE: PRT
<213> ORGANISM: Artificial Sequence
<220> FEATURE:
<223> OTHER INFORMATION: Peptide from PLOD2

<400> SEQUENCE: 160

Asn Lys Glu Val Tyr His Glu Lys Asp Ile Lys Val Phe Phe Asp Lys
1               5                   10                  15

Ala Lys

<210> SEQ ID NO 161
<211> LENGTH: 17
<212> TYPE: PRT
<213> ORGANISM: Artificial Sequence
<220> FEATURE:
<223> OTHER INFORMATION: Peptide from Cytochrome p450, subfamily IIa

<400> SEQUENCE: 161

Lys Arg Gly Ile Glu Glu Arg Ile Gln Glu Glu Ser Gly Phe Leu Ile
1               5                   10                  15

Glu

<210> SEQ ID NO 162
<211> LENGTH: 17
<212> TYPE: PRT
<213> ORGANISM: Artificial Sequence
<220> FEATURE:
<223> OTHER INFORMATION: Peptide from Cytochrome p450, subfamily IIa

<400> SEQUENCE: 162

Asp Arg Val Ile Gly Lys Asn Arg Gln Pro Lys Phe Glu Asp Arg Thr
1               5                   10                  15
Lys

<210> SEQ ID NO 163
<211> LENGTH: 16
<212> TYPE: PRT
<213> ORGANISM: Artificial Sequence
<220> FEATURE:
<223> OTHER INFORMATION: Peptide from Cytochrome p450, subfamily IIa

<400> SEQUENCE: 163

Asn Pro Gln His Phe Leu Asp Asp Lys Gly Gln Phe Lys Lys Ser Asp
1               5                   10                  15

<210> SEQ ID NO 164
<211> LENGTH: 18
<212> TYPE: PRT
<213> ORGANISM: Artificial Sequence
<220> FEATURE:
<223> OTHER INFORMATION: Peptide from Putative nucleoside
      transporter-like protein

<400> SEQUENCE: 164

Arg His Cys Ile Leu Gly Glu Trp Leu Pro Ile Leu Ile Met Ala Val
1               5                   10                  15
Phe Asn

<210> SEQ ID NO 165
<211> LENGTH: 16
<212> TYPE: PRT
<213> ORGANISM: Artificial Sequence
<220> FEATURE:
<223> OTHER INFORMATION: Peptide from Putative nucleoside
      transporter-like protein

<400> SEQUENCE: 165

Lys Gln Arg Glu Leu Ala Gly Asn Thr Met Thr Val Ser Tyr Met Ser
1               5                   10                  15

<210> SEQ ID NO 166
<211> LENGTH: 21
<212> TYPE: PRT
<213> ORGANISM: Artificial Sequence
<220> FEATURE:
<223> OTHER INFORMATION: Peptide from Putative nucleoside
      transporter-like protein

<400> SEQUENCE: 166

Arg Asn Ala His Gly Ser Cys Leu His Ala Ser Thr Ala Asn Gly Ser
1               5                   10                  15
Ile Leu Ala Gly Leu
            20

<210> SEQ ID NO 167
<211> LENGTH: 16
<212> TYPE: PRT
<213> ORGANISM: Artificial Sequence
<220> FEATURE:
<223> OTHER INFORMATION: Peptide from Solute Carrier Family 28
      (sodium-coupled nucleoside transporter), member 2"

<400> SEQUENCE: 167

Glu Leu Met Glu Lys Glu Val Glu Pro Glu Gly Ser Lys Arg Thr Asp

-continued

```
<210> SEQ ID NO 168
<211> LENGTH: 15
<212> TYPE: PRT
<213> ORGANISM: Artificial Sequence
<220> FEATURE:
<223> OTHER INFORMATION: Peptide from Solute Carrier Family 28
      (sodium-coupled nucleoside transporter), member 2"

<400> SEQUENCE: 168

Lys Ala Arg Ser Phe Cys Lys Thr His Ala Arg Leu Phe Lys Lys
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Peptide from Solute Carrier Family 28
      (sodium-coupled nucleoside transporter), member 2

<400> SEQUENCE: 169

Lys Asn Lys Arg Leu Ser Gly Met Glu Glu Trp Ile Glu Gly Glu Lys
1               5                   10                  15

<210> SEQ ID NO 170
<211> LENGTH: 17
<212> TYPE: PRT
<213> ORGANISM: Artificial Sequence
<220> FEATURE:
<223> OTHER INFORMATION: Peptide from Hepatic angiopoietin-related
      protein

<400> SEQUENCE: 170

Glu Gly Ser Thr Asp Leu Pro Leu Ala Pro Glu Ser Arg Val Asp Pro
1               5                   10                  15
Glu

<210> SEQ ID NO 171
<211> LENGTH: 15
<212> TYPE: PRT
<213> ORGANISM: Artificial Sequence
<220> FEATURE:
<223> OTHER INFORMATION: Peptide from Hepatic angiopoietin-related
      protein

<400> SEQUENCE: 171

Lys Val Ala Gln Gln Gln Arg His Leu Glu Lys Gln His Leu Arg
1               5                   10                  15

<210> SEQ ID NO 172
<211> LENGTH: 20
<212> TYPE: PRT
<213> ORGANISM: Artificial Sequence
<220> FEATURE:
<223> OTHER INFORMATION: Peptide from Hepatic angiopoietin-related
      protein

<400> SEQUENCE: 172

Asp His Lys His Leu Asp His Glu Val Ala Lys Pro Ala Arg Arg Lys
1               5                   10                  15
Arg Leu Pro Glu
            20

<210> SEQ ID NO 173
<211> LENGTH: 17
```

```
<212> TYPE: PRT
<213> ORGANISM: Artificial Sequence
<220> FEATURE:
<223> OTHER INFORMATION: Peptide from Carcinoembryonic antigen-related
      cell adhesion molecule 5

<400> SEQUENCE: 173

Lys Leu Thr Ile Glu Ser Thr Pro Phe Asn Val Ala Glu Gly Lys Glu
1               5                   10                  15

Cys

<210> SEQ ID NO 174
<211> LENGTH: 21
<212> TYPE: PRT
<213> ORGANISM: Artificial Sequence
<220> FEATURE:
<223> OTHER INFORMATION: Peptide from Carcinoembryonic antigen-related
      cell adhesion molecule 5

<400> SEQUENCE: 174

Lys Ser Asp Leu Val Asn Glu Glu Ala Thr Gly Gln Phe Arg Val Tyr
1               5                   10                  15

Pro Glu Leu Pro Lys
            20

<210> SEQ ID NO 175
<211> LENGTH: 18
<212> TYPE: PRT
<213> ORGANISM: Artificial Sequence
<220> FEATURE:
<223> OTHER INFORMATION: Peptide from Carcinoembryonic antigen-related
      cell adhesion molecule 5

<400> SEQUENCE: 175

Lys Pro Val Glu Asp Lys Asp Ala Val Ala Phe Thr Cys Glu Pro Glu
1               5                   10                  15

Ala Gln

<210> SEQ ID NO 176
<211> LENGTH: 22
<212> TYPE: PRT
<213> ORGANISM: Artificial Sequence
<220> FEATURE:
<223> OTHER INFORMATION: Peptide from podocalyxin-like protein 1

<400> SEQUENCE: 176

Asp Glu Lys Leu Ile Ser Leu Ile Cys Arg Ala Val Lys Ala Thr Phe
1               5                   10                  15

Asn Pro Ala Gln Asp Lys
            20

<210> SEQ ID NO 177
<211> LENGTH: 19
<212> TYPE: PRT
<213> ORGANISM: Artificial Sequence
<220> FEATURE:
<223> OTHER INFORMATION: Peptide from podocalyxin-like protein 1

<400> SEQUENCE: 177

Lys Asp Lys Trp Asp Glu Leu Lys Glu Ala Gly Val Ser Asp Met Lys
1               5                   10                  15

Leu Gly Asp

<210> SEQ ID NO 178
<211> LENGTH: 23
```

```
<212> TYPE: PRT
<213> ORGANISM: Artificial Sequence
<220> FEATURE:
<223> OTHER INFORMATION: Peptide from podocalyxin-like protein 1

<400> SEQUENCE: 178

Asp Ser Trp Ile Val Pro Leu Asp Asn Leu Thr Lys Asp Asp Leu Asp
1               5                   10                  15

Glu Glu Glu Asp Thr His Leu
            20

<210> SEQ ID NO 179
<211> LENGTH: 20
<212> TYPE: PRT
<213> ORGANISM: Artificial Sequence
<220> FEATURE:
<223> OTHER INFORMATION: Peptide from glycyl-tRNA synthetase

<400> SEQUENCE: 179

Arg Lys Arg Val Leu Glu Ala Lys Glu Leu Ala Leu Gln Pro Lys Asp
1               5                   10                  15

Asp Ile Val Asp
            20

<210> SEQ ID NO 180
<211> LENGTH: 21
<212> TYPE: PRT
<213> ORGANISM: Artificial Sequence
<220> FEATURE:
<223> OTHER INFORMATION: Peptide from glycyl-tRNA synthetase

<400> SEQUENCE: 180

Arg His Gly Val Ser His Lys Val Asp Asp Ser Ser Gly Ser Ile Gly
1               5                   10                  15

Arg Arg Tyr Ala Arg
            20

<210> SEQ ID NO 181
<211> LENGTH: 20
<212> TYPE: PRT
<213> ORGANISM: Artificial Sequence
<220> FEATURE:
<223> OTHER INFORMATION: Peptide from glycyl-tRNA synthetase

<400> SEQUENCE: 181

Glu Ala Arg Tyr Pro Leu Phe Glu Gly Gln Glu Thr Gly Lys Lys Glu
1               5                   10                  15

Thr Ile Glu Glu
            20

<210> SEQ ID NO 182
<211> LENGTH: 18
<212> TYPE: PRT
<213> ORGANISM: Artificial Sequence
<220> FEATURE:
<223> OTHER INFORMATION: Peptide from LBP protein 32

<400> SEQUENCE: 182

Glu Ala Leu Tyr Pro Gln Arg Arg Ser Tyr Thr Ser Glu Asp Glu Ala
1               5                   10                  15

Trp Lys

<210> SEQ ID NO 183
<211> LENGTH: 19
<212> TYPE: PRT
```

```
<213> ORGANISM: Artificial Sequence
<220> FEATURE:
<223> OTHER INFORMATION: Peptide from LBP protein 32

<400> SEQUENCE: 183

Asp Tyr Tyr Lys Val Pro Arg Glu Arg Arg Ser Ser Thr Ala Lys Pro
1               5                   10                  15

Glu Val Glu

<210> SEQ ID NO 184
<211> LENGTH: 19
<212> TYPE: PRT
<213> ORGANISM: Artificial Sequence
<220> FEATURE:
<223> OTHER INFORMATION: Peptide from LBP protein 32

<400> SEQUENCE: 184

Asp Lys Tyr Asp Val Pro His Asp Lys Ile Gly Lys Ile Phe Lys Lys
1               5                   10                  15

Cys Lys Lys

<210> SEQ ID NO 185
<211> LENGTH: 21
<212> TYPE: PRT
<213> ORGANISM: Artificial Sequence
<220> FEATURE:
<223> OTHER INFORMATION: Peptide from Putative Integral Membrane
      Transporter (LC27)

<400> SEQUENCE: 185

Asp Pro Asp Gln Tyr Asn Phe Ser Ser Ser Glu Leu Gly Gly Asp Phe
1               5                   10                  15

Glu Phe Met Asp Asp
            20

<210> SEQ ID NO 186
<211> LENGTH: 15
<212> TYPE: PRT
<213> ORGANISM: Artificial Sequence
<220> FEATURE:
<223> OTHER INFORMATION: Peptide from Putative Integral Membrane
      Transporter (LC27)

<400> SEQUENCE: 186

Glu Tyr Ile Arg Gln Leu Pro Pro Asn Phe Pro Tyr Arg Asp Asp
1               5                   10                  15

<210> SEQ ID NO 187
<211> LENGTH: 20
<212> TYPE: PRT
<213> ORGANISM: Artificial Sequence
<220> FEATURE:
<223> OTHER INFORMATION: Peptide from Putative Integral Membrane
      Transporter (LC27)

<400> SEQUENCE: 187

Asp Thr Thr Val Leu Leu Pro Pro Tyr Asp Asp Ala Thr Val Asn Gly
1               5                   10                  15

Ala Ala Lys Glu
            20

<210> SEQ ID NO 188
<211> LENGTH: 14
<212> TYPE: PRT
<213> ORGANISM: Artificial Sequence
<220> FEATURE:
```

```
<223> OTHER INFORMATION: Peptide from Cyclin E2

<400> SEQUENCE: 188

Arg Arg Glu Glu Val Thr Lys Lys His Gln Tyr Glu Ile Arg
1               5                   10

<210> SEQ ID NO 189
<211> LENGTH: 19
<212> TYPE: PRT
<213> ORGANISM: Artificial Sequence
<220> FEATURE:
<223> OTHER INFORMATION: Peptide from Cyclin E2

<400> SEQUENCE: 189

Lys Glu Ser Arg Tyr Val His Asp Lys His Phe Glu Val Leu His Ser
1               5                   10                  15

Asp Leu Glu

<210> SEQ ID NO 190
<211> LENGTH: 15
<212> TYPE: PRT
<213> ORGANISM: Artificial Sequence
<220> FEATURE:
<223> OTHER INFORMATION: Peptide from Cyclin E2

<400> SEQUENCE: 190

Asp Phe Phe Asp Arg Phe Met Leu Thr Gln Lys Asp Ile Asn Lys
1               5                   10                  15

<210> SEQ ID NO 191
<211> LENGTH: 19
<212> TYPE: PRT
<213> ORGANISM: Artificial Sequence
<220> FEATURE:
<223> OTHER INFORMATION: Peptide from KIAA0253

<400> SEQUENCE: 191

Glu Ser Lys His Phe Thr Arg Asp Leu Met Glu Lys Leu Lys Gly Arg
1               5                   10                  15

Thr Ser Arg

<210> SEQ ID NO 192
<211> LENGTH: 17
<212> TYPE: PRT
<213> ORGANISM: Artificial Sequence
<220> FEATURE:
<223> OTHER INFORMATION: Peptide from KIAA0253

<400> SEQUENCE: 192

Glu Thr Asp Arg Leu Pro Arg Cys Val Arg Ser Thr Ala Arg Leu Ala
1               5                   10                  15

Arg

<210> SEQ ID NO 193
<211> LENGTH: 20
<212> TYPE: PRT
<213> ORGANISM: Artificial Sequence
<220> FEATURE:
<223> OTHER INFORMATION: Peptide from KIAA0253

<400> SEQUENCE: 193

Glu Ser Arg Trp Lys Asp Ile Arg Ala Arg Ile Phe Leu Ile Ala Ser
1               5                   10                  15

Lys Glu Leu Glu
            20
```

<210> SEQ ID NO 194
<211> LENGTH: 12
<212> TYPE: PRT
<213> ORGANISM: Artificial Sequence
<220> FEATURE:
<223> OTHER INFORMATION: Peptide from FXYD domain-containing ion
      transport regulator 3

<400> SEQUENCE: 194

Ser Glu Trp Arg Ser Ser Gly Glu Gln Ala Gly Arg
1               5                   10

<210> SEQ ID NO 195
<211> LENGTH: 16
<212> TYPE: PRT
<213> ORGANISM: Artificial Sequence
<220> FEATURE:
<223> OTHER INFORMATION: Peptide from FXYD domain-containing ion
      transport regulator 3

<400> SEQUENCE: 195

Lys Cys Lys Cys Lys Phe Gly Gln Lys Ser Gly His His Pro Gly Glu
1               5                   10                  15

<210> SEQ ID NO 196
<211> LENGTH: 23
<212> TYPE: PRT
<213> ORGANISM: Artificial Sequence
<220> FEATURE:
<223> OTHER INFORMATION: Peptide from FXYD domain-containing ion
      transport regulator 3

<400> SEQUENCE: 196

Lys Val Thr Leu Gly Leu Leu Val Phe Leu Ala Gly Phe Pro Val Leu
1               5                   10                  15

Asp Ala Asn Asp Leu Glu Asp
            20

<210> SEQ ID NO 197
<211> LENGTH: 21
<212> TYPE: PRT
<213> ORGANISM: Artificial Sequence
<220> FEATURE:
<223> OTHER INFORMATION: Peptide from Immunoglobulin Superfamily, Member
      3

<400> SEQUENCE: 197

Lys Val Ala Lys Glu Ser Asp Ser Val Phe Val Leu Lys Ile Tyr His
1               5                   10                  15

Leu Arg Gln Glu Asp
            20

<210> SEQ ID NO 198
<211> LENGTH: 19
<212> TYPE: PRT
<213> ORGANISM: Artificial Sequence
<220> FEATURE:
<223> OTHER INFORMATION: Peptide from Immunoglobulin Superfamily, Member
      3

<400> SEQUENCE: 198

Glu Arg Glu Lys Thr Val Thr Gly Glu Phe Ile Asp Lys Glu Ser Lys
1               5                   10                  15

Arg Pro Lys

```
<210> SEQ ID NO 199
<211> LENGTH: 18
<212> TYPE: PRT
<213> ORGANISM: Artificial Sequence
<220> FEATURE:
<223> OTHER INFORMATION: Peptide from Immunoglobulin Superfamily, Member
      3

<400> SEQUENCE: 199

Lys Arg Ala Glu Asp Thr Ala Gly Gln Thr Ala Leu Thr Val Met Arg
1               5                   10                  15

Pro Asp

<210> SEQ ID NO 200
<211> LENGTH: 19
<212> TYPE: PRT
<213> ORGANISM: Artificial Sequence
<220> FEATURE:
<223> OTHER INFORMATION: Peptide from STAM2

<400> SEQUENCE: 200

Lys Val Ala Arg Lys Val Arg Ala Leu Tyr Asp Phe Glu Ala Val Glu
1               5                   10                  15

Asp Asn Glu

<210> SEQ ID NO 201
<211> LENGTH: 18
<212> TYPE: PRT
<213> ORGANISM: Artificial Sequence
<220> FEATURE:
<223> OTHER INFORMATION: Peptide from STAM2

<400> SEQUENCE: 201

Glu Thr Glu Val Ala Ala Val Asp Lys Leu Asn Val Ile Asp Asp
1               5                   10                  15

Val Glu

<210> SEQ ID NO 202
<211> LENGTH: 19
<212> TYPE: PRT
<213> ORGANISM: Artificial Sequence
<220> FEATURE:
<223> OTHER INFORMATION: Peptide from STAM2

<400> SEQUENCE: 202

Glu Ile Lys Lys Ser Glu Pro Glu Pro Val Tyr Ile Asp Glu Asp Lys
1               5                   10                  15

Met Asp Arg

<210> SEQ ID NO 203
<211> LENGTH: 18
<212> TYPE: PRT
<213> ORGANISM: Artificial Sequence
<220> FEATURE:
<223> OTHER INFORMATION: Peptide from Dickkopf Homolog 1

<400> SEQUENCE: 203

Asp Glu Glu Cys Gly Thr Asp Glu Tyr Cys Ala Ser Pro Thr Arg Gly
1               5                   10                  15

Gly Asp

<210> SEQ ID NO 204
<211> LENGTH: 20
<212> TYPE: PRT
<213> ORGANISM: Artificial Sequence
```

```
<220> FEATURE:
<223> OTHER INFORMATION: Peptide from Dickkopf Homolog 1

<400> SEQUENCE: 204

Arg Gly Glu Ile Glu Glu Thr Ile Thr Glu Ser Phe Gly Asn Asp His
1               5                   10                  15

Ser Thr Leu Asp
            20

<210> SEQ ID NO 205
<211> LENGTH: 22
<212> TYPE: PRT
<213> ORGANISM: Artificial Sequence
<220> FEATURE:
<223> OTHER INFORMATION: Peptide from Putative Anion Transporter 1

<400> SEQUENCE: 205

Met Asp Leu Arg Arg Arg Asp Tyr His Met Glu Arg Pro Leu Leu Asn
1               5                   10                  15

Gln Glu His Leu Glu Glu
            20

<210> SEQ ID NO 206
<211> LENGTH: 16
<212> TYPE: PRT
<213> ORGANISM: Artificial Sequence
<220> FEATURE:
<223> OTHER INFORMATION: Peptide from Putative Anion Transporter 1

<400> SEQUENCE: 206

Asp Thr Asp Ile Tyr Arg Asp Val Ala Glu Tyr Ser Glu Ala Lys Glu
1               5                   10                  15

<210> SEQ ID NO 207
<211> LENGTH: 24
<212> TYPE: PRT
<213> ORGANISM: Artificial Sequence
<220> FEATURE:
<223> OTHER INFORMATION: Peptide from Putative Anion Transporter 1

<400> SEQUENCE: 207

Glu Phe Tyr Ser Asp Ala Leu Lys Gln Arg Cys Gly Val Asp Val Asp
1               5                   10                  15

Phe Leu Ile Ser Gln Lys Lys Lys
            20

<210> SEQ ID NO 208
<211> LENGTH: 20
<212> TYPE: PRT
<213> ORGANISM: Artificial Sequence
<220> FEATURE:
<223> OTHER INFORMATION: Peptide from Wnt Inhibitory Factor 1

<400> SEQUENCE: 208

Asp Ala His Gln Ala Arg Val Leu Ile Gly Phe Glu Glu Asp Ile Leu
1               5                   10                  15

Ile Val Ser Glu
            20

<210> SEQ ID NO 209
<211> LENGTH: 18
<212> TYPE: PRT
<213> ORGANISM: Artificial Sequence
<220> FEATURE:
<223> OTHER INFORMATION: Peptide from Wnt Inhibitory Factor 1
```

```
<400> SEQUENCE: 209

Glu Arg Arg Ile Cys Glu Cys Pro Asp Gly Phe His Gly Pro His Cys
1               5                   10                  15

Glu Lys

<210> SEQ ID NO 210
<211> LENGTH: 18
<212> TYPE: PRT
<213> ORGANISM: Artificial Sequence
<220> FEATURE:
<223> OTHER INFORMATION: Peptide from PRAME

<400> SEQUENCE: 210

Asp Ile Lys Met Ile Leu Lys Met Val Gln Leu Asp Ser Ile Glu Asp
1               5                   10                  15

Leu Glu

<210> SEQ ID NO 211
<211> LENGTH: 19
<212> TYPE: PRT
<213> ORGANISM: Artificial Sequence
<220> FEATURE:
<223> OTHER INFORMATION: Peptide from PRAME

<400> SEQUENCE: 211

Lys Arg Lys Val Asp Gly Leu Ser Thr Glu Ala Glu Gln Pro Phe Ile
1               5                   10                  15

Pro Val Glu

<210> SEQ ID NO 212
<211> LENGTH: 20
<212> TYPE: PRT
<213> ORGANISM: Artificial Sequence
<220> FEATURE:
<223> OTHER INFORMATION: Peptide from PRAME

<400> SEQUENCE: 212

Lys Glu Gly Ala Cys Asp Glu Leu Phe Ser Tyr Leu Ile Glu Lys Val
1               5                   10                  15

Lys Arg Lys Lys
            20

<210> SEQ ID NO 213
<211> LENGTH: 15
<212> TYPE: PRT
<213> ORGANISM: Artificial Sequence
<220> FEATURE:
<223> OTHER INFORMATION: Peptide from Prostaglandin E Synthase

<400> SEQUENCE: 213

Arg Leu Arg Lys Lys Ala Phe Ala Asn Pro Glu Asp Ala Leu Arg
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Peptide from Prostaglandin E Synthase

<400> SEQUENCE: 214

Arg Ser Asp Pro Asp Val Glu Arg Cys Leu Arg Ala His Arg Asn Asp
1               5                   10                  15
```

```
<210> SEQ ID NO 215
<211> LENGTH: 17
<212> TYPE: PRT
<213> ORGANISM: Artificial Sequence
<220> FEATURE:
<223> OTHER INFORMATION: Peptide from Prostaglandin E Synthase

<400> SEQUENCE: 215

Arg Val Ala His Thr Val Ala Tyr Leu Gly Lys Leu Arg Ala Pro Ile
1               5                   10                  15

Arg

<210> SEQ ID NO 216
<211> LENGTH: 17
<212> TYPE: PRT
<213> ORGANISM: Artificial Sequence
<220> FEATURE:
<223> OTHER INFORMATION: Peptide from Solute Carrier Family 7, member
      5/LAT1 protein

<400> SEQUENCE: 216

Lys Arg Arg Ala Leu Ala Ala Pro Ala Ala Glu Glu Lys Glu Glu Ala
1               5                   10                  15

Arg

<210> SEQ ID NO 217
<211> LENGTH: 20
<212> TYPE: PRT
<213> ORGANISM: Artificial Sequence
<220> FEATURE:
<223> OTHER INFORMATION: Peptide from Solute Carrier Family 7, member
      5/LAT1 protein

<400> SEQUENCE: 217

Glu Ala Arg Glu Lys Met Leu Ala Ala Lys Ser Ala Asp Gly Ser Ala
1               5                   10                  15

Pro Ala Gly Glu
            20

<210> SEQ ID NO 218
<211> LENGTH: 16
<212> TYPE: PRT
<213> ORGANISM: Artificial Sequence
<220> FEATURE:
<223> OTHER INFORMATION: Peptide from Solute Carrier Family 7, member
      5/LAT1 protein

<400> SEQUENCE: 218

Met Ile Trp Leu Arg His Arg Lys Pro Glu Leu Glu Arg Pro Ile Lys
1               5                   10                  15

<210> SEQ ID NO 219
<211> LENGTH: 14
<212> TYPE: PRT
<213> ORGANISM: Artificial Sequence
<220> FEATURE:
<223> OTHER INFORMATION: Peptide from v-maf musculoaponeurotic
      fibrosarcoma (avian) oncogene family, protein K or NF-E2p18"

<400> SEQUENCE: 219

Lys Pro Asn Lys Ala Leu Lys Val Lys Lys Glu Ala Gly Glu
1               5                   10

<210> SEQ ID NO 220
<211> LENGTH: 22
<212> TYPE: PRT
<213> ORGANISM: Artificial Sequence
```

-continued

```
<220> FEATURE:
<223> OTHER INFORMATION: Peptide from v-maf musculoaponeurotic
      fibrosarcoma (avian) oncogene family, protein K or NF-E2p18"

<400> SEQUENCE: 220

Lys Arg Val Thr Gln Lys Glu Glu Leu Glu Arg Gln Arg Val Glu Leu
1               5                   10                  15

Gln Gln Glu Val Glu Lys
            20

<210> SEQ ID NO 221
<211> LENGTH: 12
<212> TYPE: PRT
<213> ORGANISM: Artificial Sequence
<220> FEATURE:
<223> OTHER INFORMATION: Peptide from v-maf musculoaponeurotic
      fibrosarcoma (avian) oncogene family, protein K or NF-E2p18"

<400> SEQUENCE: 221

Arg Leu Glu Leu Asp Ala Leu Arg Ser Lys Tyr Glu
1               5                   10

<210> SEQ ID NO 222
<211> LENGTH: 21
<212> TYPE: PRT
<213> ORGANISM: Artificial Sequence
<220> FEATURE:
<223> OTHER INFORMATION: Peptide from CEGP1

<400> SEQUENCE: 222

Lys Met His Thr Asp Gly Arg Ser Cys Leu Glu Arg Glu Asp Thr Val
1               5                   10                  15

Leu Glu Val Thr Glu
            20

<210> SEQ ID NO 223
<211> LENGTH: 18
<212> TYPE: PRT
<213> ORGANISM: Artificial Sequence
<220> FEATURE:
<223> OTHER INFORMATION: Peptide from CEGP1

<400> SEQUENCE: 223

Lys Lys Gly Phe Lys Leu Leu Thr Asp Glu Lys Ser Cys Gln Asp Val
1               5                   10                  15

Asp Glu

<210> SEQ ID NO 224
<211> LENGTH: 21
<212> TYPE: PRT
<213> ORGANISM: Artificial Sequence
<220> FEATURE:
<223> OTHER INFORMATION: Peptide from CEGP1

<400> SEQUENCE: 224

Lys Arg Thr Glu Lys Arg Leu Arg Lys Ala Ile Arg Thr Leu Arg Lys
1               5                   10                  15

Ala Val His Arg Glu
            20

<210> SEQ ID NO 225
<211> LENGTH: 17
<212> TYPE: PRT
<213> ORGANISM: Artificial Sequence
<220> FEATURE:
<223> OTHER INFORMATION: Peptide from GABRE gamma-aminobutyric acid
```

(GABA) A receptor, epsilon

<400> SEQUENCE: 225

Arg Val Glu Gly Pro Gln Thr Glu Ser Lys Asn Glu Ala Ser Ser Arg
1               5                   10                  15

Asp

<210> SEQ ID NO 226
<211> LENGTH: 19
<212> TYPE: PRT
<213> ORGANISM: Artificial Sequence
<220> FEATURE:
<223> OTHER INFORMATION: Peptide from GABRE gamma-aminobutyric acid
      (GABA) A receptor, epsilon

<400> SEQUENCE: 226

Glu Glu Thr Lys Ser Thr Glu Thr Glu Thr Gly Ser Arg Val Gly Lys
1               5                   10                  15

Leu Pro Glu

<210> SEQ ID NO 227
<211> LENGTH: 17
<212> TYPE: PRT
<213> ORGANISM: Artificial Sequence
<220> FEATURE:
<223> OTHER INFORMATION: Peptide from S100 calcium-binding protein A10

<400> SEQUENCE: 227

Asp Lys Gly Tyr Leu Thr Lys Glu Asp Leu Arg Val Leu Met Glu Lys
1               5                   10                  15

Glu

<210> SEQ ID NO 228
<211> LENGTH: 20
<212> TYPE: PRT
<213> ORGANISM: Artificial Sequence
<220> FEATURE:
<223> OTHER INFORMATION: Peptide from S100 calcium-binding protein A10

<400> SEQUENCE: 228

Lys Asp Pro Leu Ala Val Asp Lys Ile Met Lys Asp Leu Asp Gln Cys
1               5                   10                  15

Arg Asp Gly Lys
            20

<210> SEQ ID NO 229
<211> LENGTH: 23
<212> TYPE: PRT
<213> ORGANISM: Artificial Sequence
<220> FEATURE:
<223> OTHER INFORMATION: Peptide from v-myb avian myeloblastosis viral
      oncogene homolog-like 2

<400> SEQUENCE: 229

Glu Glu Asp Leu Lys Glu Val Leu Arg Ser Glu Ala Gly Ile Glu Leu
1               5                   10                  15

Ile Ile Glu Asp Asp Ile Arg
            20

<210> SEQ ID NO 230
<211> LENGTH: 21
<212> TYPE: PRT
<213> ORGANISM: Artificial Sequence
<220> FEATURE:
<223> OTHER INFORMATION: Peptide from v-myb avian myeloblastosis viral oncogene homolog-like 2

<400> SEQUENCE: 230

Met Ser Arg Arg Thr Arg Cys Glu Asp Leu Asp Glu Leu His Tyr Gln
1               5                   10                  15

Asp Thr Asp Ser Asp
            20

<210> SEQ ID NO 231
<211> LENGTH: 20
<212> TYPE: PRT
<213> ORGANISM: Artificial Sequence
<220> FEATURE:
<223> OTHER INFORMATION: Peptide from v-myb avian myeloblastosis viral
      oncogene homolog-like 2

<400> SEQUENCE: 231

Arg Arg Ser Pro Ile Lys Lys Val Arg Lys Ser Leu Ala Leu Asp Ile
1               5                   10                  15

Val Asp Glu Asp
            20

<210> SEQ ID NO 232
<211> LENGTH: 17
<212> TYPE: PRT
<213> ORGANISM: Artificial Sequence
<220> FEATURE:
<223> OTHER INFORMATION: Peptide from nucleoside phosphorylase

<400> SEQUENCE: 232

Glu Asp Tyr Lys Asn Thr Ala Glu Trp Leu Leu Ser His Thr Lys His
1               5                   10                  15

Arg

<210> SEQ ID NO 233
<211> LENGTH: 22
<212> TYPE: PRT
<213> ORGANISM: Artificial Sequence
<220> FEATURE:
<223> OTHER INFORMATION: Peptide from nucleoside phosphorylase

<400> SEQUENCE: 233

Asp Glu Arg Phe Gly Asp Arg Phe Pro Ala Met Ser Asp Ala Tyr Asp
1               5                   10                  15

Arg Thr Met Arg Gln Arg
            20

<210> SEQ ID NO 234
<211> LENGTH: 16
<212> TYPE: PRT
<213> ORGANISM: Artificial Sequence
<220> FEATURE:
<223> OTHER INFORMATION: Peptide from nucleoside phosphorylase

<400> SEQUENCE: 234

Lys Val Ile Met Asp Tyr Glu Ser Leu Glu Lys Ala Asn His Glu Glu
1               5                   10                  15

<210> SEQ ID NO 235
<211> LENGTH: 22
<212> TYPE: PRT
<213> ORGANISM: Artificial Sequence
<220> FEATURE:
<223> OTHER INFORMATION: Peptide from aldo-keto reductase family 1,
      member C4

```
<400> SEQUENCE: 235

Asp Gln Asp Arg Lys Ser Arg Leu Met Gly Leu Glu Ala Leu Lys Ser
1               5                   10                  15

His Ile Met Ala Ala Lys
            20

<210> SEQ ID NO 236
<211> LENGTH: 20
<212> TYPE: PRT
<213> ORGANISM: Artificial Sequence
<220> FEATURE:
<223> OTHER INFORMATION: Peptide from aldo-keto reductase family 1,
      member C4

<400> SEQUENCE: 236

Lys Gly Val Ile Val Asp Lys Asp Phe Ser His Pro Gln Met Pro Lys
1               5                   10                  15

Lys Val Glu Asp
            20

<210> SEQ ID NO 237
<211> LENGTH: 17
<212> TYPE: PRT
<213> ORGANISM: Artificial Sequence
<220> FEATURE:
<223> OTHER INFORMATION: Peptide from aldo-keto reductase family 1,
      member C4

<400> SEQUENCE: 237

Arg Met Ile Leu Lys Ile Asp Asp Ile Arg Lys Pro Gly Glu Ser Glu
1               5                   10                  15

Glu

<210> SEQ ID NO 238
<211> LENGTH: 20
<212> TYPE: PRT
<213> ORGANISM: Artificial Sequence
<220> FEATURE:
<223> OTHER INFORMATION: Peptide from Non-metastatic cells 1, protein
      (NM23A)

<400> SEQUENCE: 238

Arg Leu Gln Pro Glu Phe Lys Pro Lys Gln Leu Glu Gly Thr Met Ala
1               5                   10                  15

Asn Cys Glu Arg
            20

<210> SEQ ID NO 239
<211> LENGTH: 20
<212> TYPE: PRT
<213> ORGANISM: Artificial Sequence
<220> FEATURE:
<223> OTHER INFORMATION: Peptide from Non-metastatic cells 1, protein
      (NM23A)

<400> SEQUENCE: 239

Lys Phe Met Gln Ala Ser Glu Asp Leu Leu Lys Glu His Tyr Val Asp
1               5                   10                  15

Leu Lys Asp Arg
            20

<210> SEQ ID NO 240
<211> LENGTH: 21
<212> TYPE: PRT
<213> ORGANISM: Artificial Sequence
```

```
<220> FEATURE:
<223> OTHER INFORMATION: Peptide from Non-metastatic cells 1, protein
      (NM23A)

<400> SEQUENCE: 240

Asp Ser Val Glu Ser Ala Glu Lys Glu Ile Gly Leu Trp Phe His Pro
1               5                   10                  15

Glu Glu Leu Val Asp
            20

<210> SEQ ID NO 241
<211> LENGTH: 18
<212> TYPE: PRT
<213> ORGANISM: Artificial Sequence
<220> FEATURE:
<223> OTHER INFORMATION: Peptide from Squalene epoxidase

<400> SEQUENCE: 241

Lys Ser Pro Pro Glu Ser Glu Asn Lys Glu Gln Leu Glu Ala Arg Arg
1               5                   10                  15

Arg Arg

<210> SEQ ID NO 242
<211> LENGTH: 18
<212> TYPE: PRT
<213> ORGANISM: Artificial Sequence
<220> FEATURE:
<223> OTHER INFORMATION: Peptide from Squalene epoxidase

<400> SEQUENCE: 242

Arg Asp Gly Arg Lys Val Thr Val Ile Glu Arg Asp Leu Lys Glu Pro
1               5                   10                  15

Asp Arg

<210> SEQ ID NO 243
<211> LENGTH: 17
<212> TYPE: PRT
<213> ORGANISM: Artificial Sequence
<220> FEATURE:
<223> OTHER INFORMATION: Peptide from Squalene epoxidase

<400> SEQUENCE: 243

Asp His Leu Lys Glu Pro Phe Leu Glu Ala Thr Asp Asn Ser His Leu
1               5                   10                  15

Arg

<210> SEQ ID NO 244
<211> LENGTH: 19
<212> TYPE: PRT
<213> ORGANISM: Artificial Sequence
<220> FEATURE:
<223> OTHER INFORMATION: Peptide from Pregnancy-induced growth inhibitor

<400> SEQUENCE: 244

Asp Leu Glu Val Lys Asp Trp Met Gln Lys Lys Arg Arg Gly Leu Arg
1               5                   10                  15

Asn Ser Arg

<210> SEQ ID NO 245
<211> LENGTH: 24
<212> TYPE: PRT
<213> ORGANISM: Artificial Sequence
<220> FEATURE:
<223> OTHER INFORMATION: Peptide from Pregnancy-induced growth inhibitor
```

<400> SEQUENCE: 245

Glu Tyr His Lys Val His Gln Met Met Arg Glu Gln Ser Ile Leu Ser
1               5                   10                  15

Pro Ser Pro Tyr Glu Gly Tyr Arg
            20

<210> SEQ ID NO 246
<211> LENGTH: 23
<212> TYPE: PRT
<213> ORGANISM: Artificial Sequence
<220> FEATURE:
<223> OTHER INFORMATION: Peptide from Pregnancy-induced growth inhibitor

<400> SEQUENCE: 246

Arg His Gln Leu Leu Cys Phe Lys Glu Asp Cys Gln Ala Val Phe Gln
1               5                   10                  15

Asp Leu Glu Gly Val Glu Lys
            20

<210> SEQ ID NO 247
<211> LENGTH: 16
<212> TYPE: PRT
<213> ORGANISM: Artificial Sequence
<220> FEATURE:
<223> OTHER INFORMATION: Peptide from Putative 4TM Mal-like protein

<400> SEQUENCE: 247

Gly Pro Asp Ile Leu Arg Thr Tyr Ser Gly Ala Phe Val Cys Leu Glu
1               5                   10                  15

<210> SEQ ID NO 248
<211> LENGTH: 12
<212> TYPE: PRT
<213> ORGANISM: Artificial Sequence
<220> FEATURE:
<223> OTHER INFORMATION: Peptide from Putative 4TM Mal-like protein

<400> SEQUENCE: 248

Cys Ser Leu Gly Leu Ala Leu Arg Arg Trp Arg Pro
1               5                   10

<210> SEQ ID NO 249
<211> LENGTH: 20
<212> TYPE: PRT
<213> ORGANISM: Artificial Sequence
<220> FEATURE:
<223> OTHER INFORMATION: Peptide from aldo-keto reductase family 1,
      member C1/C2

<400> SEQUENCE: 249

Arg Tyr Leu Thr Leu Asp Ile Phe Ala Gly Pro Pro Asn Tyr Pro Phe
1               5                   10                  15

Ser Asp Glu Tyr
            20

<210> SEQ ID NO 250
<211> LENGTH: 20
<212> TYPE: PRT
<213> ORGANISM: Artificial Sequence
<220> FEATURE:
<223> OTHER INFORMATION: Peptide from aldo-keto reductase family 1,
      member C4

<400> SEQUENCE: 250

His Tyr Phe Asn Ser Asp Ser Phe Ala Ser His Pro Asn Tyr Pro Tyr
1               5                   10                  15

```
<210> SEQ ID NO 251
<211> LENGTH: 20
<212> TYPE: PRT
<213> ORGANISM: Artificial Sequence
<220> FEATURE:
<223> OTHER INFORMATION: Peptide from aldo-keto reductase family 1,
      member C4

<400> SEQUENCE: 251

Arg Tyr Val Val Met Asp Phe Leu Met Asp His Pro Asp Tyr Pro Phe
1               5                   10                  15

Ser Asp Glu Tyr
            20

<210> SEQ ID NO 252
<211> LENGTH: 17
<212> TYPE: PRT
<213> ORGANISM: Artificial Sequence
<220> FEATURE:
<223> OTHER INFORMATION: Peptide from Putative ParB-like nuclease domain
      containing protein

<400> SEQUENCE: 252

Asp Pro Ala Lys Val Gln Ser Leu Val Asp Thr Ile Arg Glu Asp Pro
1               5                   10                  15

Asp

<210> SEQ ID NO 253
<211> LENGTH: 17
<212> TYPE: PRT
<213> ORGANISM: Artificial Sequence
<220> FEATURE:
<223> OTHER INFORMATION: Peptide from Putative ParB-like nuclease domain
      containing protein

<400> SEQUENCE: 253

Arg Glu Thr Ile Pro Ala Lys Leu Val Gln Ser Thr Leu Ser Asp Leu
1               5                   10                  15

Arg

<210> SEQ ID NO 254
<211> LENGTH: 17
<212> TYPE: PRT
<213> ORGANISM: Artificial Sequence
<220> FEATURE:
<223> OTHER INFORMATION: Peptide from Putative glucose transporter-like
      protein

<400> SEQUENCE: 254

Ser Asp Thr Thr Glu Glu Leu Thr Val Ile Lys Ser Ser Leu Lys Asp
1               5                   10                  15

Glu

<210> SEQ ID NO 255
<211> LENGTH: 16
<212> TYPE: PRT
<213> ORGANISM: Artificial Sequence
<220> FEATURE:
<223> OTHER INFORMATION: Peptide from Putative glucose transporter-like
      protein

<400> SEQUENCE: 255
```

His Ser Arg Ser Ser Leu Met Pro Leu Arg Asn Asp Val Asp Lys Arg
1               5                   10                  15

<210> SEQ ID NO 256
<211> LENGTH: 20
<212> TYPE: PRT
<213> ORGANISM: Artificial Sequence
<220> FEATURE:
<223> OTHER INFORMATION: Peptide from CLIC5

<400> SEQUENCE: 256

Asp Ala Asn Thr Cys Gly Glu Asp Lys Gly Ser Arg Arg Lys Phe Leu
1               5                   10                  15

Asp Gly Asp Glu
            20

<210> SEQ ID NO 257
<211> LENGTH: 20
<212> TYPE: PRT
<213> ORGANISM: Artificial Sequence
<220> FEATURE:
<223> OTHER INFORMATION: Peptide from AX119005

<400> SEQUENCE: 257

Gln Leu Glu Glu Met Thr Glu Leu Glu Ser Pro Lys Cys Lys Arg Gln
1               5                   10                  15

Glu Asn Glu Gln
            20

<210> SEQ ID NO 258
<211> LENGTH: 20
<212> TYPE: PRT
<213> ORGANISM: Artificial Sequence
<220> FEATURE:
<223> OTHER INFORMATION: Peptide from FARP1

<400> SEQUENCE: 258

Gln Ala Asp Gly Ala Ala Ser Ala Pro Thr Glu Glu Glu Glu Glu Val
1               5                   10                  15

Val Lys Asp Arg
            20

<210> SEQ ID NO 259
<211> LENGTH: 20
<212> TYPE: PRT
<213> ORGANISM: Artificial Sequence
<220> FEATURE:
<223> OTHER INFORMATION: Peptide from TRPS1

<400> SEQUENCE: 259

Ser Gly Asp Ser Leu Glu Thr Lys Glu Asp Gln Lys Met Ser Pro Lys
1               5                   10                  15

Ala Thr Glu Glu
            20

<210> SEQ ID NO 260
<211> LENGTH: 20
<212> TYPE: PRT
<213> ORGANISM: Artificial Sequence
<220> FEATURE:
<223> OTHER INFORMATION: Peptide from FAT

<400> SEQUENCE: 260

Lys Ile Arg Leu Pro Glu Arg Glu Lys Pro Asp Arg Glu Arg Asn Ala
1               5                   10                  15

Arg Arg Glu Pro
            20

<210> SEQ ID NO 261
<211> LENGTH: 20
<212> TYPE: PRT
<213> ORGANISM: Artificial Sequence
<220> FEATURE:
<223> OTHER INFORMATION: Peptide from GRN

<400> SEQUENCE: 261

Arg Gly Thr Lys Cys Leu Arg Arg Glu Ala Pro Arg Trp Asp Ala Pro
1               5                   10                  15

Leu Arg Asp Pro
            20

<210> SEQ ID NO 262
<211> LENGTH: 20
<212> TYPE: PRT
<213> ORGANISM: Artificial Sequence
<220> FEATURE:
<223> OTHER INFORMATION: Peptide from NDRG1

<400> SEQUENCE: 262

Gly Thr Arg Ser Arg Ser His Thr Ser Glu Gly Thr Arg Ser Arg Ser
1               5                   10                  15

His Thr Ser Glu
            20

<210> SEQ ID NO 263
<211> LENGTH: 18
<212> TYPE: PRT
<213> ORGANISM: Artificial Sequence
<220> FEATURE:
<223> OTHER INFORMATION: Peptide from FABP5

<400> SEQUENCE: 263

Glu Glu Thr Thr Ala Asp Gly Arg Lys Thr Gln Thr Val Cys Asn Phe
1               5                   10                  15

Thr Asp

<210> SEQ ID NO 264
<211> LENGTH: 16
<212> TYPE: PRT
<213> ORGANISM: Artificial Sequence
<220> FEATURE:
<223> OTHER INFORMATION: Peptide from CDKN1C

<400> SEQUENCE: 264

Ala Lys Arg Lys Arg Ser Ala Pro Glu Lys Ser Ser Gly Asp Val Pro
1               5                   10                  15

<210> SEQ ID NO 265
<211> LENGTH: 20
<212> TYPE: PRT
<213> ORGANISM: Artificial Sequence
<220> FEATURE:
<223> OTHER INFORMATION: Peptide from AMACR

<400> SEQUENCE: 265

Arg Val Asp Arg Pro Gly Ser Arg Tyr Asp Val Ser Arg Leu Gly Arg
1               5                   10                  15

Gly Lys Arg Ser
            20

```
<210> SEQ ID NO 266
<211> LENGTH: 17
<212> TYPE: PRT
<213> ORGANISM: Artificial Sequence
<220> FEATURE:
<223> OTHER INFORMATION: Peptide from GABRB3

<400> SEQUENCE: 266

Glu Thr Val Asp Lys Leu Leu Lys Gly Tyr Asp Ile Arg Leu Arg Pro
1               5                   10                  15

Asp

<210> SEQ ID NO 267
<211> LENGTH: 20
<212> TYPE: PRT
<213> ORGANISM: Artificial Sequence
<220> FEATURE:
<223> OTHER INFORMATION: Peptide from KIAA0872 protein

<400> SEQUENCE: 267

Ala Pro Gly Gly Ala Glu Asp Leu Glu Asp Thr Gln Phe Pro Ser Glu
1               5                   10                  15

Glu Ala Arg Glu
            20

<210> SEQ ID NO 268
<211> LENGTH: 20
<212> TYPE: PRT
<213> ORGANISM: Artificial Sequence
<220> FEATURE:
<223> OTHER INFORMATION: Peptide from TNFRSF21

<400> SEQUENCE: 268

Arg Lys Ser Ser Arg Thr Leu Lys Lys Gly Pro Arg Gln Asp Pro Ser
1               5                   10                  15

Ala Ile Val Glu
            20

<210> SEQ ID NO 269
<211> LENGTH: 20
<212> TYPE: PRT
<213> ORGANISM: Artificial Sequence
<220> FEATURE:
<223> OTHER INFORMATION: Peptide from TRIP8

<400> SEQUENCE: 269

Gly Ser Glu Ser Gly Asp Ser Asp Glu Ser Glu Ser Lys Ser Glu Gln
1               5                   10                  15

Arg Thr Lys Arg
            20

<210> SEQ ID NO 270
<211> LENGTH: 20
<212> TYPE: PRT
<213> ORGANISM: Artificial Sequence
<220> FEATURE:
<223> OTHER INFORMATION: Peptide from BSTP5

<400> SEQUENCE: 270

Glu Ala Asp Ser Gly Asp Ala Arg Arg Leu Pro Arg Ala Arg Gly Glu
1               5                   10                  15

Arg Arg Arg His
            20

<210> SEQ ID NO 271
```

```
<211> LENGTH: 19
<212> TYPE: PRT
<213> ORGANISM: Artificial Sequence
<220> FEATURE:
<223> OTHER INFORMATION: Peptide from cdc25b

<400> SEQUENCE: 271

Arg Leu Glu Arg Pro Gln Asp Arg Asp Thr Pro Val Gln Asn Lys Arg
1               5                   10                  15

Arg Arg Ser

<210> SEQ ID NO 272
<211> LENGTH: 19
<212> TYPE: PRT
<213> ORGANISM: Artificial Sequence
<220> FEATURE:
<223> OTHER INFORMATION: Peptide from laminin, beta 1 (lamb1)

<400> SEQUENCE: 272

Asp Arg Val Glu Asp Val Met Met Glu Arg Glu Ser Gln Phe Lys Glu
1               5                   10                  15

Lys Gln Glu

<210> SEQ ID NO 273
<211> LENGTH: 17
<212> TYPE: PRT
<213> ORGANISM: Artificial Sequence
<220> FEATURE:
<223> OTHER INFORMATION: Peptide from papillary renal cell carcinoma
      (translocation-associated) (prcc)

<400> SEQUENCE: 273

Asp Glu Ala Phe Lys Arg Leu Gln Gly Lys Arg Asn Arg Gly Arg Glu
1               5                   10                  15

Glu

<210> SEQ ID NO 274
<211> LENGTH: 15
<212> TYPE: PRT
<213> ORGANISM: Artificial Sequence
<220> FEATURE:
<223> OTHER INFORMATION: Peptide from TNFSF10

<400> SEQUENCE: 274

Arg Phe Gln Glu Glu Ile Lys Glu Asn Thr Lys Asn Asp Lys Gln
1               5                   10                  15

<210> SEQ ID NO 275
<211> LENGTH: 19
<212> TYPE: PRT
<213> ORGANISM: Artificial Sequence
<220> FEATURE:
<223> OTHER INFORMATION: Peptide from titin

<400> SEQUENCE: 275

Lys Arg Asp Lys Glu Gly Val Arg Trp Thr Lys Cys Asn Lys Lys Thr
1               5                   10                  15

Leu Thr Asp

<210> SEQ ID NO 276
<211> LENGTH: 19
<212> TYPE: PRT
<213> ORGANISM: Artificial Sequence
<220> FEATURE:
<223> OTHER INFORMATION: Peptide from DNA fragmentation factor, 45 kD,
      alpha polypeptide
```

<400> SEQUENCE: 276

Lys Glu Gly Ser Leu Leu Ser Lys Gln Glu Ser Lys Ala Ala Phe
1               5                   10                  15

Gly Glu Glu

<210> SEQ ID NO 277
<211> LENGTH: 19
<212> TYPE: PRT
<213> ORGANISM: Artificial Sequence
<220> FEATURE:
<223> OTHER INFORMATION: Peptide from Caspase 2

<400> SEQUENCE: 277

Glu Ser Asp Ala Gly Lys Glu Lys Leu Pro Lys Met Arg Leu Pro
1               5                   10                  15

Arg Ser Asp

<210> SEQ ID NO 278
<211> LENGTH: 19
<212> TYPE: PRT
<213> ORGANISM: Artificial Sequence
<220> FEATURE:
<223> OTHER INFORMATION: Peptide from GSPT1

<400> SEQUENCE: 278

Glu Arg Asp Lys Gly Lys Thr Val Glu Val Gly Arg Ala Tyr Phe Glu
1               5                   10                  15

Thr Glu Lys

<210> SEQ ID NO 279
<211> LENGTH: 15
<212> TYPE: PRT
<213> ORGANISM: Artificial Sequence
<220> FEATURE:
<223> OTHER INFORMATION: Peptide from GCN5L2

<400> SEQUENCE: 279

Glu Lys Phe Arg Val Glu Lys Asp Lys Leu Val Pro Glu Lys Arg
1               5                   10                  15

<210> SEQ ID NO 280
<211> LENGTH: 18
<212> TYPE: PRT
<213> ORGANISM: Artificial Sequence
<220> FEATURE:
<223> OTHER INFORMATION: Peptide from FLJ23293

<400> SEQUENCE: 280

Glu Asn Tyr Glu Asp Asp Asp Leu Val Asn Ser Asp Glu Val Met Lys
1               5                   10                  15

Lys Pro

<210> SEQ ID NO 281
<211> LENGTH: 17
<212> TYPE: PRT
<213> ORGANISM: Artificial Sequence
<220> FEATURE:
<223> OTHER INFORMATION: Peptide from HSPC037 protein

<400> SEQUENCE: 281

Pro Lys Ala Asp Glu Ile Arg Thr Leu Val Lys Asp Met Trp Asp Thr
1               5                   10                  15

Arg

<210> SEQ ID NO 282
<211> LENGTH: 19
<212> TYPE: PRT
<213> ORGANISM: Artificial Sequence
<220> FEATURE:
<223> OTHER INFORMATION: Peptide from FLJ20093

<400> SEQUENCE: 282

Arg Lys Arg Cys Leu Glu Asp Ser Glu Asp Phe Gly Val Lys Lys Ala
1               5                   10                  15

Arg Thr Glu

<210> SEQ ID NO 283
<211> LENGTH: 19
<212> TYPE: PRT
<213> ORGANISM: Artificial Sequence
<220> FEATURE:
<223> OTHER INFORMATION: Peptide from KIAA0176

<400> SEQUENCE: 283

Glu Pro Lys Ser Phe Leu Cys Arg Leu Cys Cys Gln Glu Asp Pro Glu
1               5                   10                  15

Leu Asp Ser

<210> SEQ ID NO 284
<211> LENGTH: 18
<212> TYPE: PRT
<213> ORGANISM: Artificial Sequence
<220> FEATURE:
<223> OTHER INFORMATION: Peptide from KIAA0856

<400> SEQUENCE: 284

Glu Glu Tyr Asp Arg Glu Ser Lys Ser Ser Asp Asp Val Asp Tyr Arg
1               5                   10                  15

Gly Ser

<210> SEQ ID NO 285
<211> LENGTH: 16
<212> TYPE: PRT
<213> ORGANISM: Artificial Sequence
<220> FEATURE:
<223> OTHER INFORMATION: Peptide from FLJ14642

<400> SEQUENCE: 285

Glu Gln Arg Ala Arg Trp Glu Arg Lys Arg Ala Cys Thr Ala Arg Glu
1               5                   10                  15

<210> SEQ ID NO 286
<211> LENGTH: 17
<212> TYPE: PRT
<213> ORGANISM: Artificial Sequence
<220> FEATURE:
<223> OTHER INFORMATION: Peptide from RNA methyltransferase (HpaII tiny
      fragments locus 9C)

<400> SEQUENCE: 286

Glu Arg Lys Gln Leu Glu Cys Glu Gln Val Leu Gln Lys Leu Ala Lys
1               5                   10                  15

Glu

<210> SEQ ID NO 287
<211> LENGTH: 19
<212> TYPE: PRT
<213> ORGANISM: Artificial Sequence

```
<220> FEATURE:
<223> OTHER INFORMATION: Peptide from Serine rich hypothetical protein

<400> SEQUENCE: 287

Arg Asn Ser Glu Thr Lys Val Arg Arg Ser Thr Arg Leu Gln Lys Asp
1               5                   10                  15

Leu Glu Asn

<210> SEQ ID NO 288
<211> LENGTH: 16
<212> TYPE: PRT
<213> ORGANISM: Artificial Sequence
<220> FEATURE:
<223> OTHER INFORMATION: Peptide from Similar to mitotic phosphoprotein
      44 [Xenopus laevis]

<400> SEQUENCE: 288

Ser Asp Tyr Gln Val Ile Ser Asp Arg Gln Thr Pro Lys Lys Asp Glu
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: Peptide from SMC4

<400> SEQUENCE: 289

Asp Ile Glu Gly Lys Leu Pro Gln Thr Glu Gln Glu Leu Lys Glu
1               5                   10                  15

<210> SEQ ID NO 290
<211> LENGTH: 19
<212> TYPE: PRT
<213> ORGANISM: Artificial Sequence
<220> FEATURE:
<223> OTHER INFORMATION: Peptide from phosphatidylserine synthase

<400> SEQUENCE: 290

Asp Asp Val Asn Tyr Lys Met His Phe Arg Met Ile Asn Glu Gln Gln
1               5                   10                  15

Val Glu Asp

<210> SEQ ID NO 291
<211> LENGTH: 17
<212> TYPE: PRT
<213> ORGANISM: Artificial Sequence
<220> FEATURE:
<223> OTHER INFORMATION: Peptide from polo (Drosophia)-like kinase

<400> SEQUENCE: 291

Glu Asn Pro Leu Pro Glu Arg Pro Arg Glu Lys Glu Glu Pro Val Val
1               5                   10                  15

Arg

<210> SEQ ID NO 292
<211> LENGTH: 19
<212> TYPE: PRT
<213> ORGANISM: Artificial Sequence
<220> FEATURE:
<223> OTHER INFORMATION: Peptide from Pirin

<400> SEQUENCE: 292

Arg Glu Gln Ser Glu Gly Val Gly Ala Arg Val Arg Arg Ser Ile Gly
1               5                   10                  15
```

```
Arg Pro Glu

<210> SEQ ID NO 293
<211> LENGTH: 19
<212> TYPE: PRT
<213> ORGANISM: Artificial Sequence
<220> FEATURE:
<223> OTHER INFORMATION: Peptide from ABCA3

<400> SEQUENCE: 293

Pro Arg Ala Val Ala Gly Lys Glu Glu Glu Asp Ser Asp Pro Glu Lys
1               5                   10                  15

Ala Leu Arg

<210> SEQ ID NO 294
<211> LENGTH: 17
<212> TYPE: PRT
<213> ORGANISM: Artificial Sequence
<220> FEATURE:
<223> OTHER INFORMATION: Peptide from ABCA7

<400> SEQUENCE: 294

Glu Lys Ala Asp Thr Asp Met Glu Gly Ser Val Asp Thr Arg Gln Glu
1               5                   10                  15

Lys

<210> SEQ ID NO 295
<211> LENGTH: 19
<212> TYPE: PRT
<213> ORGANISM: Artificial Sequence
<220> FEATURE:
<223> OTHER INFORMATION: Peptide from ABCB7

<400> SEQUENCE: 295

Arg Val Gln Asn His Asp Asn Pro Lys Trp Glu Ala Lys Lys Glu Asn
1               5                   10                  15

Ile Ser Lys

<210> SEQ ID NO 296
<211> LENGTH: 19
<212> TYPE: PRT
<213> ORGANISM: Artificial Sequence
<220> FEATURE:
<223> OTHER INFORMATION: Peptide from ABCC12

<400> SEQUENCE: 296

Arg Ser Pro Pro Ala Lys Gly Ala Thr Gly Pro Glu Glu Gln Ser Asp
1               5                   10                  15

Ser Leu Lys

<210> SEQ ID NO 297
<211> LENGTH: 19
<212> TYPE: PRT
<213> ORGANISM: Artificial Sequence
<220> FEATURE:
<223> OTHER INFORMATION: Peptide from ABCG2

<400> SEQUENCE: 297

Arg Glu Glu Asp Phe Lys Ala Thr Glu Ile Ile Glu Pro Ser Lys Gln
1               5                   10                  15

Asp Lys Pro

<210> SEQ ID NO 298
<211> LENGTH: 15
```

```
<212> TYPE: PRT
<213> ORGANISM: Artificial Sequence
<220> FEATURE:
<223> OTHER INFORMATION: Peptide from SLC21A8

<400> SEQUENCE: 298

Asp Lys Thr Cys Met Lys Trp Ser Thr Asn Ser Cys Gly Ala Gln
1               5                   10                  15

<210> SEQ ID NO 299
<211> LENGTH: 14
<212> TYPE: PRT
<213> ORGANISM: Artificial Sequence
<220> FEATURE:
<223> OTHER INFORMATION: Peptide from SLC22A6

<400> SEQUENCE: 299

Asp Ala Asn Leu Ser Lys Asn Gly Gly Leu Glu Val Trp Leu
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Peptide from SLC35A2

<400> SEQUENCE: 300

Glu Pro Phe Leu Pro Lys Leu Leu Thr Lys
1               5                   10

<210> SEQ ID NO 301
<211> LENGTH: 19
<212> TYPE: PRT
<213> ORGANISM: Artificial Sequence
<220> FEATURE:
<223> OTHER INFORMATION: Peptide from cdc25b isoforms 1,3

<400> SEQUENCE: 301

Arg Lys Ser Glu Ala Gly Ser Gly Ala Ala Ser Ser Ser Gly Glu Asp
1               5                   10                  15

Lys Glu Asn

<210> SEQ ID NO 302
<211> LENGTH: 19
<212> TYPE: PRT
<213> ORGANISM: Artificial Sequence
<220> FEATURE:
<223> OTHER INFORMATION: Peptide from SCD stearoyl-CoA desaturase
      delta-9-desaturase

<400> SEQUENCE: 302

Asp Asp Ile Tyr Asp Pro Thr Tyr Lys Asp Lys Glu Gly Pro Ser Pro
1               5                   10                  15

Lys Val Glu

<210> SEQ ID NO 303
<211> LENGTH: 19
<212> TYPE: PRT
<213> ORGANISM: Artificial Sequence
<220> FEATURE:
<223> OTHER INFORMATION: Peptide from MAPK12 mitogen-activated protein
      kinase 12

<400> SEQUENCE: 303

Gln Ser Asp Glu Ala Lys Asn Asn Met Lys Gly Leu Pro Glu Leu Glu
1               5                   10                  15
```

Lys Lys Asp

<210> SEQ ID NO 304
<211> LENGTH: 19
<212> TYPE: PRT
<213> ORGANISM: Artificial Sequence
<220> FEATURE:
<223> OTHER INFORMATION: Peptide from NFKB2 nuclear factor of kappa
      light 2 (p49/p100)

<400> SEQUENCE: 304

Ser Arg Pro Gln Gly Leu Thr Glu Ala Glu Gln Arg Glu Leu Glu Gln
1               5                   10                  15

Glu Ala Lys

<210> SEQ ID NO 305
<211> LENGTH: 14
<212> TYPE: PRT
<213> ORGANISM: Artificial Sequence
<220> FEATURE:
<223> OTHER INFORMATION: Peptide from TNFRSF5

<400> SEQUENCE: 305

Arg Val Gln Gln Lys Gly Thr Ser Glu Thr Asp Thr Ile Cys
1               5                   10

<210> SEQ ID NO 306
<211> LENGTH: 16
<212> TYPE: PRT
<213> ORGANISM: Artificial Sequence
<220> FEATURE:
<223> OTHER INFORMATION: Peptide from EBI3 Epstein-Barr virus induced
      gene 3

<400> SEQUENCE: 306

Val Arg Leu Ser Pro Leu Ala Glu Arg Gln Leu Gln Val Gln Trp Glu
1               5                   10                  15

<210> SEQ ID NO 307
<211> LENGTH: 19
<212> TYPE: PRT
<213> ORGANISM: Artificial Sequence
<220> FEATURE:
<223> OTHER INFORMATION: Peptide from ZNF339

<400> SEQUENCE: 307

Arg Arg Ser Leu Gly Val Ser Val Arg Ser Trp Asp Glu Leu Pro Asp
1               5                   10                  15

Glu Lys Arg

<210> SEQ ID NO 308
<211> LENGTH: 17
<212> TYPE: PRT
<213> ORGANISM: Artificial Sequence
<220> FEATURE:
<223> OTHER INFORMATION: Peptide from DAB2IP

<400> SEQUENCE: 308

Asp Glu Gly Leu Gly Pro Asp Pro Pro His Arg Asp Arg Leu Arg Ser
1               5                   10                  15

Lys

<210> SEQ ID NO 309
<211> LENGTH: 18
<212> TYPE: PRT

```
<213> ORGANISM: Artificial Sequence
<220> FEATURE:
<223> OTHER INFORMATION: Peptide from PPFIA1

<400> SEQUENCE: 309

Ser Gly Lys Arg Ser Ser Asp Gly Ser Leu Ser His Glu Glu Asp Leu
1               5                   10                  15

Ala Lys

<210> SEQ ID NO 310
<211> LENGTH: 19
<212> TYPE: PRT
<213> ORGANISM: Artificial Sequence
<220> FEATURE:
<223> OTHER INFORMATION: Peptide from CAB66760

<400> SEQUENCE: 310

Ser Gln Glu Arg Ser Asp Ser Pro Glu Ile Cys His Tyr Glu Lys Ser
1               5                   10                  15

Phe His Lys

<210> SEQ ID NO 311
<211> LENGTH: 17
<212> TYPE: PRT
<213> ORGANISM: Artificial Sequence
<220> FEATURE:
<223> OTHER INFORMATION: Peptide from novel hypothetical protein

<400> SEQUENCE: 311

Lys Val Asn Pro Glu Pro Thr His Glu Ile Arg Cys Asn Ser Glu Val
1               5                   10                  15

Lys

<210> SEQ ID NO 312
<211> LENGTH: 16
<212> TYPE: PRT
<213> ORGANISM: Artificial Sequence
<220> FEATURE:
<223> OTHER INFORMATION: Peptide from frizzled homolog 7 FZD7

<400> SEQUENCE: 312

Ser Asp Gly Arg Gly Arg Pro Ala Phe Pro Phe Ser Cys Pro Arg Gln
1               5                   10                  15

<210> SEQ ID NO 313
<211> LENGTH: 15
<212> TYPE: PRT
<213> ORGANISM: Artificial Sequence
<220> FEATURE:
<223> OTHER INFORMATION: Peptide from SLC3A2

<400> SEQUENCE: 313

Gly Ser Lys Glu Asp Phe Asp Ser Leu Leu Gln Ser Ala Lys Lys
1               5                   10                  15

<210> SEQ ID NO 314
<211> LENGTH: 18
<212> TYPE: PRT
<213> ORGANISM: Artificial Sequence
<220> FEATURE:
<223> OTHER INFORMATION: Peptide from PLA2R1 phospholipase A2 receptor 1

<400> SEQUENCE: 314

Gln Lys Glu Glu Lys Thr Trp His Glu Ala Leu Arg Ser Cys Gln Ala
1               5                   10                  15
```

-continued

Asp Asn

<210> SEQ ID NO 315
<211> LENGTH: 17
<212> TYPE: PRT
<213> ORGANISM: Artificial Sequence
<220> FEATURE:
<223> OTHER INFORMATION: Peptide from KIAA0182

<400> SEQUENCE: 315

Glu Lys Ala Glu Glu Gly Pro Arg Lys Arg Glu Pro Ala Pro Leu Asp
1               5                   10                  15

Lys

<210> SEQ ID NO 316
<211> LENGTH: 14
<212> TYPE: PRT
<213> ORGANISM: Artificial Sequence
<220> FEATURE:
<223> OTHER INFORMATION: Peptide from thymidine kinase 2, mitochondrial

<400> SEQUENCE: 316

Glu Gln Asn Arg Asp Arg Ile Leu Thr Pro Glu Asn Arg Lys
1               5                   10

<210> SEQ ID NO 317
<211> LENGTH: 14
<212> TYPE: PRT
<213> ORGANISM: Artificial Sequence
<220> FEATURE:
<223> OTHER INFORMATION: Peptide from FLJ12799

<400> SEQUENCE: 317

Arg Asp Trp Tyr Ile Gly Leu Val Ser Asp Glu Lys Trp Lys
1               5                   10

<210> SEQ ID NO 318
<211> LENGTH: 17
<212> TYPE: PRT
<213> ORGANISM: Artificial Sequence
<220> FEATURE:
<223> OTHER INFORMATION: Peptide from KIAA1007

<400> SEQUENCE: 318

Asp Ser Tyr Leu Lys Thr Arg Ser Pro Val Thr Phe Leu Ser Asp Leu
1               5                   10                  15

Arg

<210> SEQ ID NO 319
<211> LENGTH: 17
<212> TYPE: PRT
<213> ORGANISM: Artificial Sequence
<220> FEATURE:
<223> OTHER INFORMATION: Peptide from DKFZP566O1646

<400> SEQUENCE: 319

Lys Cys Arg Gly Glu Thr Val Ala Lys Glu Ile Ser Glu Ala Met Lys
1               5                   10                  15

Ser

<210> SEQ ID NO 320
<211> LENGTH: 17
<212> TYPE: PRT
<213> ORGANISM: Artificial Sequence
<220> FEATURE:
<223> OTHER INFORMATION: Peptide from ART-4

-continued

<400> SEQUENCE: 320

Lys Pro Pro Gln Glu Thr Glu Lys Gly His Ser Ala Cys Glu Pro Glu
1               5                   10                  15

Asn

<210> SEQ ID NO 321
<211> LENGTH: 14
<212> TYPE: PRT
<213> ORGANISM: Artificial Sequence
<220> FEATURE:
<223> OTHER INFORMATION: Peptide from GNA12

<400> SEQUENCE: 321

Glu Arg Arg Ala Gly Ser Gly Ala Arg Asp Ala Glu Arg Glu
1               5                   10

<210> SEQ ID NO 322
<211> LENGTH: 16
<212> TYPE: PRT
<213> ORGANISM: Artificial Sequence
<220> FEATURE:
<223> OTHER INFORMATION: Peptide from GrpE-like protein cochaperone
      (HMGE)

<400> SEQUENCE: 322

Ser Glu Gln Lys Ala Asp Pro Pro Ala Thr Glu Lys Thr Leu Leu Glu
1               5                   10                  15

<210> SEQ ID NO 323
<211> LENGTH: 19
<212> TYPE: PRT
<213> ORGANISM: Artificial Sequence
<220> FEATURE:
<223> OTHER INFORMATION: Peptide from FLJ34922

<400> SEQUENCE: 323

Glu Ala Glu Trp Ser Gln Gly Val Gln Gly Thr Leu Arg Ile Lys Lys
1               5                   10                  15

Tyr Leu Thr

<210> SEQ ID NO 324
<211> LENGTH: 17
<212> TYPE: PRT
<213> ORGANISM: Artificial Sequence
<220> FEATURE:
<223> OTHER INFORMATION: Peptide from FLJ20457

<400> SEQUENCE: 324

Glu Glu Ser Lys Ser Ile Thr Glu Gly Leu Leu Thr Gln Lys Gln Tyr
1               5                   10                  15

Glu

<210> SEQ ID NO 325
<211> LENGTH: 16
<212> TYPE: PRT
<213> ORGANISM: Artificial Sequence
<220> FEATURE:
<223> OTHER INFORMATION: Peptide from solute carrier family 7, (cationic
      amino acid transporter, y+ system) member 11

<400> SEQUENCE: 325

Gln Asn Phe Lys Asp Ala Phe Ser Gly Arg Asp Ser Ser Ile Thr Arg
1               5                   10                  15

```
-continued

<210> SEQ ID NO 326
<211> LENGTH: 15
<212> TYPE: PRT
<213> ORGANISM: Artificial Sequence
<220> FEATURE:
<223> OTHER INFORMATION: Peptide from Integrin, beta 4

<400> SEQUENCE: 326

Thr Glu Asp Val Asp Glu Phe Arg Asn Lys Leu Gln Gly Glu Arg
1               5                   10                  15

<210> SEQ ID NO 327
<211> LENGTH: 20
<212> TYPE: PRT
<213> ORGANISM: Artificial Sequence
<220> FEATURE:
<223> OTHER INFORMATION: Peptide from Solute Carrier Family 7, member
      5/LAT1 protein

<400> SEQUENCE: 327

Lys Gly Asp Val Ser Asn Leu Asp Pro Asn Phe Ser Phe Glu Gly Thr
1               5                   10                  15

Lys Leu Asp Val
            20
```

REAGENTS AND METHODS FOR USE IN CANCER DIAGNOSIS, CLASSIFICATION AND THERAPY

PRIORITY INFORMATION

This application is a divisional application of U.S. Ser. No. 12/879,356 filed Sep. 10, 2010, which is a divisional application of U.S. Ser. No. 12/013,739 filed Jan. 14, 2008, (now U.S. Pat. No. 7,811,774),which is a divisional application of U.S. Ser. No. 11/061,067 filed Feb. 18, 2005 now abandoned, which is a continuation-in-part of U.S. Ser. No. 10/915,059 filed Aug. 10, 2004 now abandoned which claimed priority to U.S. Ser. No. 60/494,334 filed Aug. 11, 2003 and U.S. Ser. No. 60/570,206 filed May 12, 2004. The entire contents of each of these applications are hereby incorporated by reference.

SEQUENCE LISTING

In accordance with 37 CFR 1.52(e)(5), a Sequence Listing in the form of a text file (entitled "Sequence Listing.txt," created on Sep. 7, 2010, and 93 kilobytes) is incorporated herein by reference in its entirety.

BACKGROUND OF THE INVENTION

A major challenge of cancer treatment is the selection of therapeutic regimens that maximize efficacy and minimize toxicity for a given patient. A related challenge lies in the attempt to provide accurate diagnostic, prognostic and predictive information. At present, tumors are generally classified under the tumor-node-metastasis (TNM) system. This system, which uses the size of the tumor, the presence or absence of tumor in regional lymph nodes, and the presence or absence of distant metastases, to assign a stage to the tumor is described in the *AJCC Cancer Staging Manual*, Lippincott, 5th ed., pp. 171-180 (1997). The assigned stage is used as a basis for selection of appropriate therapy and for prognostic purposes. In addition to the TNM parameters, morphologic appearance is used to further classify tumors into tumor types and thereby aid in selection of appropriate therapy. However, this approach has serious limitations. Tumors with similar histopathologic appearance can exhibit significant variability in terms of clinical course and response to therapy. For example, some tumors are rapidly progressive while others are not. Some tumors respond readily to hormonal therapy or chemotherapy while others are resistant.

Assays for cell surface markers, e.g., using immunohistochemistry, have provided means for dividing certain tumor types into subclasses. For example, one factor considered in prognosis and treatment decisions for breast cancer is the presence or absence of the estrogen receptor (ER) in tumor samples. ER-positive breast cancers typically respond much more readily to hormonal therapies such as tamoxifen, which acts as an anti-estrogen in breast tissue, than ER-negative tumors. Though useful, these analyses only in part predict the clinical behavior of breast tumors. There is phenotypic diversity present in cancers that current diagnostic tools fail to detect. As a consequence, there is still much controversy over how to stratify patients amongst potential treatments in order to optimize outcome (e.g., for breast cancer see "NIH Consensus Development Conference Statement: Adjuvant Therapy for Breast Cancer, Nov. 1-3, 2000", *J. Nat. Cancer Inst. Monographs,* 30:5-15, 2001 and Di Leo et al., *Int. J. Clin. Oncol.* 7:245-253, 2002).

There clearly exists a need for improved methods and reagents for classifying tumors. Once these methods and reagents are available, clinical studies can be performed that will allow the identification of classes or subclasses of patients having different prognosis and/or responses to therapy. Such prognostic tools will allow more rationally based choices governing the aggressiveness of therapeutic interventions; such predictive tools will also be useful for directing patients into appropriate treatment protocols.

SUMMARY OF THE INVENTION

The invention encompasses the realization that particular panels of tumor sample binding agents ("interaction partners") can be used to provide new insights into the biology of cancer. Among other things, the present invention provides methods and reagents for classifying tumors and for identifying new tumor classes and subclasses. The invention further provides methods for correlating tumor class or subclass with therapeutic regimen or outcome, for identifying appropriate (new or known) therapies for particular classes or subclasses, and for predicting outcomes based on class or subclass. The invention further provides new therapeutic agents and methods for the treatment of cancer.

For example, the present invention provides methods for identifying suitable panels of interaction partners (e.g., without limitation antibodies) whose binding is correlated with any of a variety of desirable aspects such as tumor class or subclass, tumor source (e.g., primary tumor versus metastases), likely prognosis, responsiveness to therapy, etc. Specifically, collections of interaction partners are selected and their activity in binding to a variety of different tumors, normal tissues and/or cell lines is assessed. Data are collected for multiple interaction partners to multiple samples and correlations with interesting or desirable features are assessed. As described herein, the detection of individual interaction partners or panels thereof that bind differentially with different tumors provides new methods of use in cancer prognosis and treatment selection. In addition, these interaction partners provide new therapies for treating cancer.

As described in further detail below, the invention employs methods for grouping interaction partners within a panel into subsets by determining their binding patterns across a collection of samples obtained from different tumor tissues, normal tissues and/or cell lines. The invention also groups the tumor samples into classes or subclasses based on similarities in their binding to a panel of interaction partners. This two-dimensional grouping approach permits the association of particular classes of tumors with particular subsets of interaction partners that, for example, show relatively high binding to tumors within that class. Correlation with clinical information indicates that the tumor classes have clinical significance in terms of prognosis or response to chemotherapy.

BRIEF DESCRIPTION OF APPENDICES A-F

This patent application refers to material comprising tables and data presented as appendices.

Appendix A is a table that lists the antibodies included in the breast, lung and/or colon panels that are discussed in the Examples. The table includes the antibody ID, parent gene name, NCBI LocusLink ID, UniGene ID, known aliases for the parent gene, peptides that were used in preparing antibodies, antibody titer and a link to any relevant IHC images of Appendix B. Using the parent gene name, NCBI LocusLink ID, UniGene ID, and/or known aliases for the parent gene, a skilled person can readily obtain the nucleotide (and corresponding amino acid) sequences for each and every one of the parent genes that are listed in Appendix A from a public database (e.g., GenBank, Swiss-Prot or any future derivative of these). The nucleotide and corresponding amino acid sequences for each and every one of the parent genes that are listed in Appendix A are hereby incorporated by reference from these public databases. Antibodies with AGI IDs that begin with s5 or s6 were obtained from commercial sources as indicated. The third and fourth columns of Appendix A indicate whether the antibodies of the breast cancer classification panel were identified by staining with the Russian breast cohort (Example 2) and/or the HH breast cohort (Example 3). The fifth and sixth columns indicate whether the antibodies of the lung cancer classification panel were identified by staining with the Russian lung cohort (Example 4) and/or the HH lung cohort (Example 5). The seventh column indicates the antibodies of the colon cancer classification panel. These were all identified by staining with the Russian colon cohort (Example 6).

Appendix B includes breast IHC images, colon IHC images and lung IHC images. The IHC images of Appendix B are referenced in the right hand column of Appendix A. An actual copy of Appendix B is not included with this continuation-in-part but can be found in parent case U.S. Ser. No. 10/915,059 filed Aug. 10, 2004 (published as US 2005/0112662 on May 26, 2005), the entire contents of which are hereby incorporated by reference.

Appendix C is a table that lists exemplary antibodies whose binding patterns have been shown to correlate with tumor prognosis in breast cancer patients. The results are grouped into four categories that have been clinically recognized to be of significance: all patients, ER+ patients, ER− patients, and ER+/lymph node metastases negative (ER+/node−) patients. Scoring methods 1-3 use the following schemes: method 1 (0=negative; 1=weak; 2=strong); method 2 (0=negative; 1=weak or strong); and method 3 (0=negative or weak; 1=strong). This table was prepared using samples from the HH breast cohort as described in Example 10.

Appendix D is a table that lists exemplary antibodies whose binding patterns have been shown to correlate with tumor prognosis in lung cancer patients. The results are grouped into three categories that have been clinically recognized to be of significance: all patients, adenocarcinoma patients, and squamous cell carcinoma patients. Scoring methods 1-3 use the following schemes: method 1 (0=negative; 1=weak; 2=strong); method 2 (0=negative; 1=weak or strong); and method 3 (0=negative or weak; 1=strong).

Appendix E is a table that lists exemplary antibodies whose binding patterns have been shown to correlate with tumor prognosis in breast cancer patients. The results are grouped into four categories that have been clinically recognized to be of significance: all patients, ER+ patients, ER− patients, and ER+/lymph node metastases negative (ER+/node−) patients. Scoring methods 1-3 use the following schemes: method 1 (0=negative; 1=weak; 2=strong); method 2 (0=negative; 1=weak or strong); and method 3 (0=negative or weak; 1=strong). This table was prepared using samples from the HH breast cohort as described in Example 12. Appendix E differs from Appendix C because of further analysis.

Appendix F is a table that lists exemplary antibodies whose binding patterns have been shown to correlate with tumor prognosis in lung cancer patients. The results are grouped into two categories that have been clinically recognized to be of significance: all patients and adenocarcinoma patients. Scoring methods 1-3 use the following schemes: method 1 (0=negative; 1=weak; 2=strong); method 2 (0=negative; 1=weak or strong); and method 3 (0=negative or weak; 1=strong). This table was prepared using samples from the HH and UAB lung cohorts as described in Example 13. The p-values and hazard ratios that were obtained with each cohort are shown. The antibodies listed have a prognostic p-value of less than 0.2 in both cohorts.

BRIEF DESCRIPTION OF THE DRAWING

FIG. 18 shows the relative proportions of different lung cancer morphologies that were identified in seven sub-classes of patients in the HH lung cohort.

DEFINITIONS

Figure 1:
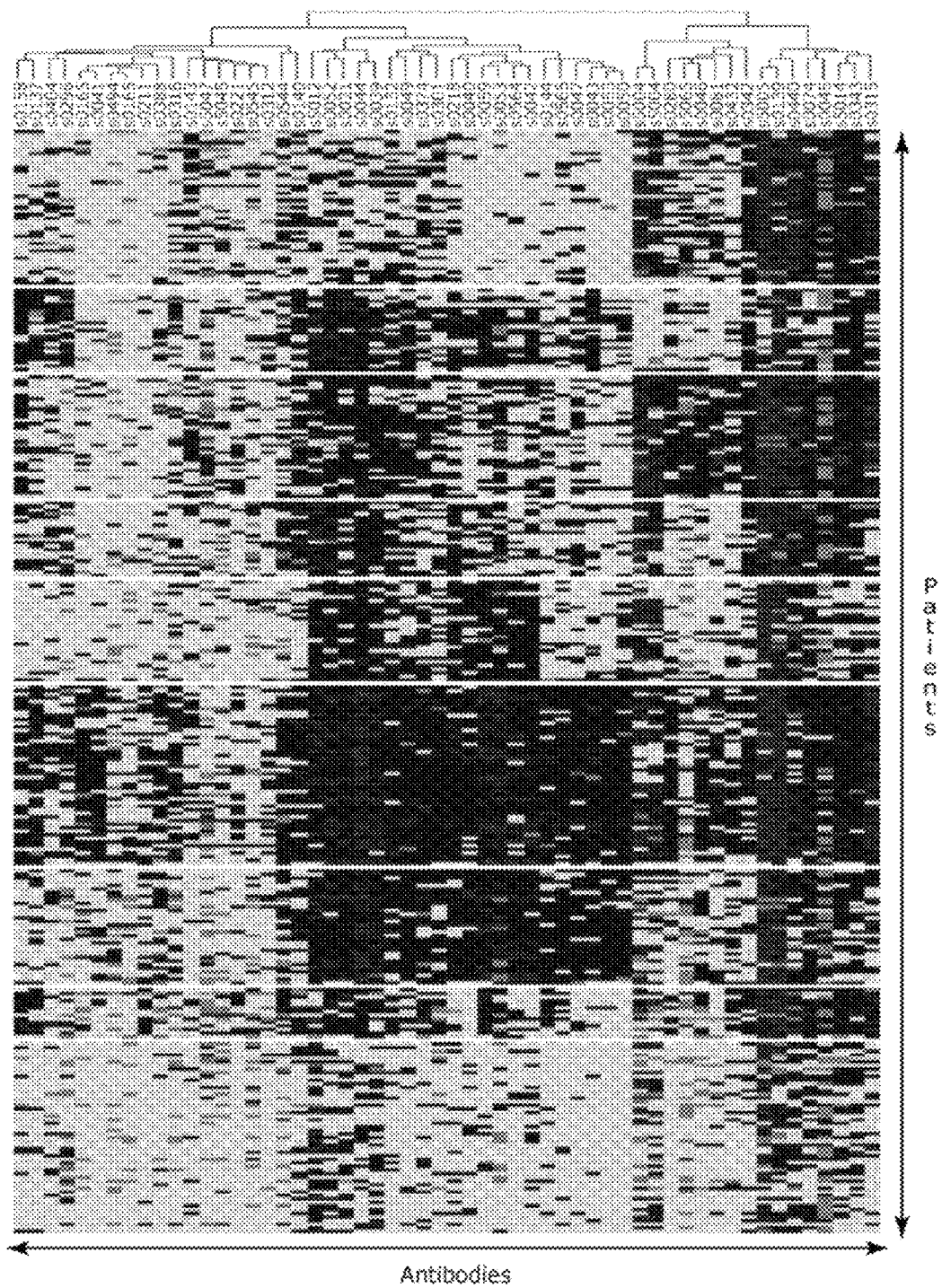
FIG. 1 depicts semi-quantitative immunohistochemistry (IHC) scoring of a 298 breast cancer patient cohort with an inventive breast cancer classification panel. The panel was prepared as described in Example 2—antibodies were used as interaction partners. The patients (rows) were classified using k-means clustering while the antibodies (columns) were organized using hierarchical clustering. Dark gray represents strong positive staining, black represents weak positive staining, while light gray represents the absence of staining and medium gray represents a lack of data. As illustrated in the Figure, nine groups of patients were identified by their consensus pattern of staining with the panel of antibodies.

Associated—When an interaction partner and a tumor marker are physically "associated" with one another as described herein, they are linked by direct non-covalent interactions. Desirable non-covalent interactions include those of the type which occur between an immunoglobulin molecule and an antigen for which the immunoglobulin is specific, for example, ionic interactions, hydrogen bonds, van der Waals interactions, hydrophobic interactions, etc. The strength, or affinity of the physical association can be expressed in terms of the dissociation constant ($K_d$) of the interaction, wherein a smaller $K_d$ represents a greater affinity. The association properties of selected interaction partners and tumor markers can be quantified using methods well known in the art (e.g., see Davies et al., *Annual Rev. Biochem.* 59:439, 1990).

Classification panel—A "classification panel" of interaction partners is a set of interaction partners whose collective pattern of binding or lack of binding to a tumor sample, when taken together, is sufficient to classify the tumor sample as a member of a particular class or subclass of tumor, or as not a member of a particular class or subclass of tumor.

Correlation—"Correlation" refers to the degree to which one variable can be predicted from another variable, e.g., the degree to which a patient's therapeutic response can be predicted from the pattern of binding between a set of interaction partners and a tumor sample taken from that patient. A variety of statistical methods may be used to measure correlation between two variables, e.g., without limitation the student t-test, the Fisher exact test, the Pearson correlation coefficient, the Spearman correlation coefficient, the Chi squared test, etc. Results are traditionally given as a measured correlation coefficient with a p-value that provides a measure of the likelihood that the correlation arose by chance. A correlation with a p-value that is less than 0.05 is generally considered to be statistically significant. Preferred correlations have p-values that are less than 0.01, especially less than 0.001.

Interaction partner—An "interaction partner" is an entity that physically associates with a tumor marker. For example and without limitation, an interaction partner may be an antibody or a fragment thereof that physically associates with a tumor marker. In general, an interaction partner is said to "associate specifically" with a tumor marker if it associates at a detectable level with the tumor marker and does not associate detectably with unrelated molecular entities (e.g., other tumor markers) under similar conditions. Specific association between a tumor marker and an interaction partner will typically be dependent upon the presence of a particular structural feature of the target tumor marker such as an antigenic determinant or epitope recognized by the interaction partner. Generally, if an interaction partner is specific for epitope A, the presence of a molecular entity (e.g., a protein) containing epitope A or the presence of free unlabeled A in a reaction containing both free labeled A and the interaction partner thereto, will reduce the amount of labeled A that binds to the interaction partner. In general, it is to be understood that specificity need not be absolute. For example, it is well known in the art that antibodies frequently cross-react with other epitopes in addition to the target epitope. Such cross-reactivity may be acceptable depending upon the application for which the interaction partner is to be used. Thus the degree of specificity of an interaction partner will depend on the context in which it is being used. In general, an interaction partner exhibits specificity for a particular tumor marker if it favors binding with that partner above binding with other potential partners, e.g., other tumor markers. One of ordinary skill in the art will be able to select interaction partners having a sufficient degree of specificity to perform appropriately in any given application (e.g., for detection of a target tumor marker, for therapeutic purposes, etc.). It is also to be understood that specificity may be evaluated in the context of additional factors such as the affinity of the interaction partner for the target tumor marker versus the affinity of the interaction partner for other potential partners, e.g., other tumor markers. If an interaction partner exhibits a high affinity for a target tumor marker and low affinity for non-target molecules, the interaction partner will likely be an acceptable reagent for diagnostic purposes even if it lacks specificity. It will be appreciated that once the specificity of an interaction partner is established in one or more contexts, it may be employed in other, preferably similar, contexts without necessarily re-evaluating its specificity.

Predictive panel—A "predictive panel" of interaction partners is a set of interaction partners whose collective pattern of binding or lack of binding to a tumor sample, when taken together, has sufficient correlation to classify the tumor sample as being from a patient who is likely (or not) to respond to a given therapeutic regimen.

Prognostic panel—A "prognostic panel" of interaction partners is a set of interaction partners whose collective pattern of binding or lack of binding to a tumor sample, when taken together, has sufficient correlation to classify the tumor sample as being from a patient who is likely to have a given outcome. Generally, "outcome" may include, but is not limited to, the average life expectancy of the patient, the likelihood that the patient will survive for a given amount of time (e.g., 6 months, 1 year, 5 years, etc.), the likelihood of recurrence, the likelihood that the patient will be disease-free for a specified prolonged period of time, or the likelihood that the patient will be cured of the disease.

Response—The "response" of a tumor or a cancer to therapy may represent any detectable change, for example at the molecular, cellular, organellar, or organismal level. For instance, tumor size, patient life expectancy, recurrence, or the length of time the patient survives, etc., are all responses. Responses can be measured in any of a variety of ways, including for example non-invasive measuring of tumor size (e.g., CT scan, image-enhanced visualization, etc.), invasive measuring of tumor size (e.g., residual tumor resection, etc.), surrogate marker measurement (e.g., serum PSA, etc.), clinical course variance (e.g., measurement of patient quality of life, time to relapse, survival time, etc.).

Small molecule—A "small molecule" is a non-polymeric molecule. A small molecule can be synthesized in a laboratory (e.g., by combinatorial synthesis) or found in nature (e.g., a natural product). A small molecule is typically characterized in that it contains several carbon-carbon bonds and has a molecular weight of less than about 1500 Da, although this characterization is not intended to be limiting for the purposes of the present invention.

Tumor markers—"Tumor markers" are molecular entities that are detectable in tumor samples. Generally, tumor markers will be proteins that are present within the tumor sample, e.g., within the cytoplasm or membranes of tumor cells and/or secreted from such cells. According to the present invention, sets of tumor markers that correlate with tumor class or subclass are identified. Thus, subsequent tumor samples may be classified or subclassified based on the presence of these sets of tumor markers.

Tumor sample—As used herein the term "tumor sample" is taken broadly to include cell or tissue samples removed from a tumor, cells (or their progeny) derived from a tumor that may be located elsewhere in the body (e.g., cells in the bloodstream or at a site of metastasis), or any material derived by processing such a sample. Derived tumor samples may include, for example, nucleic acids or proteins extracted from the sample.

DETAILED DESCRIPTION OF CERTAIN PREFERRED EMBODIMENTS OF THE INVENTION

As noted above, the present invention provides techniques and reagents for the classification and subclassification, of tumors. Such classification (or subclassification) has many beneficial applications. For example, a particular tumor class or subclass may correlate with prognosis and/or susceptibility to a particular therapeutic regimen. As such, the classification or subclassification may be used as the basis for a prognostic or predictive kit and may also be used as the basis for identifying previously unappreciated therapies. Therapies that are effective against only a particular class or subclass of tumor may have been lost in studies whose data were not stratified by subclass; the present invention allows such data to be re-stratified, and allows additional studies to be performed, so that class- or subclass-specific therapies may be identified and/or implemented. Alternatively or additionally, the present invention allows identification and/or implementation of therapies that are targeted to genes identified as class- or subclass-specific.

Classification and Subclassification of Tumors

In general, according to the present invention, tumors are classified or subclassified on the basis of tumor markers whose presence is correlated with a particular class or subclass. In preferred embodiments, the tumor markers are detected via their physical association with an interaction partner. Included in the present invention are kits comprising sets of interaction partners that together can be used to identify or classify a particular tumor sample; such sets are generally referred to as "classification panels".

The present invention provides systems of identifying classification panels. In general, tumor samples are contacted with individual interaction partners, and binding between the interaction partners and their cognate tumor markers is detected. For example, panels of interaction partners that identify a particular class or subclass of tumor within tumor samples of a selected tissue of origin may be defined by contacting individual interaction partners with a variety of different tumor samples (e.g., from different patients) all of the same tissue of origin. Individual interaction partners may be selected for inclusion in the ultimate classification panel based on their binding to only a subset of the tumor samples (e.g., see Examples 1-4). Those of ordinary skill in the art, however, will appreciate that all that is required for a collection of interaction partners to operate effectively as a classification panel is that the combined binding characteristics of member interaction partners together are sufficient to classify a particular tumor sample.

The inventive process of identifying useful panels of interaction partners as described herein may itself result in the identification of new tumor classes or subclasses. That is, through the process of analyzing interaction partner binding patterns, investigators will often discover new tumor classes or subclasses to which sets of interaction partners bind. Thus, the processes (a) of defining classification panels of interaction partners for given tumor classes or subclasses; and (b) identifying new tumor classes or subclasses may well be experimentally interrelated. In general, the greater the number of tumor samples tested, the greater the likelihood that new classes or subclasses will be defined.

Often, when identifying sets of interaction partners that can act as a classification (or subclassification) panel, it will be desirable to obtain the largest set of tumor samples possible, and also to collect the largest amount of information possible about the individual samples. For example, the origin of the tumor, the gender of the patient, the age of the patient, the staging of the tumor (e.g., according to the TNM system), any microscopic or submicroscopic characteristics of the tumor that may have been determined, may be recorded. Those of ordinary skill in the art will appreciate that the more information that is known about a tumor sample, the more aspects of that sample are available for correlation with interaction partner binding.

The systems of the present invention have particular utility in classifying or subclassifying tumor samples that are not otherwise distinguishable from one another. Thus, in some embodiments, it will be desirable to analyze the largest collection of tumor samples that are most similar to one another.

When obtaining tumor samples for testing according to the present invention, it is generally preferred that the samples represent or reflect characteristics of a population of patients or samples. It may also be useful to handle and process the samples under conditions and according to techniques common to clinical laboratories. Although the present invention is not intended to be limited to the strategies used for processing tumor samples, we note that, in the field of pathology, it is often common to fix samples in buffered formalin, and then to dehydrate them by immersion in increasing concentrations of ethanol followed by xylene. Samples are then embedded into paraffin, which is then molded into a "paraffin block" that is a standard intermediate in histologic processing of tissue samples. The present inventors have found that many useful interaction partners display comparable binding regardless of the method of preparation of tumor samples; those of ordinary skill in the art can readily adjust observations to account for differences in preparation procedure.

In preferred embodiments of the invention, large numbers of tissue samples are analyzed simultaneously. In some embodiments, a tissue array is prepared. Tissue arrays may be constructed according to a variety of techniques. According to one procedure, a commercially-available mechanical device (e.g., the manual tissue arrayer MTA1 from Beecher Instruments of Sun Prairie, Wis.) is used to remove an 0.6-micron-diameter, full thickness "core" from a paraffin block (the donor block) prepared from each patient, and to insert the core into a separate paraffin block (the recipient block) in a designated location on a grid. In preferred embodiments, cores from as many as about 400 patients can be inserted into a single recipient block; preferably, core-to-core spacing is approximately 1 mm. The resulting tissue array may be processed into thin sections for staining with interaction partners according to standard methods applicable to paraffin embedded material. Depending upon the thickness of the donor blocks, as well as the dimensions of the clinical material, a single tissue array can yield about 50-150 slides containing >75% relevant tumor material for assessment with interaction partners. Construction of two or more parallel tissue arrays of cores from the same cohort of patient samples can provide relevant tumor material from the same set of patients in duplicate or more. Of course, in some cases, additional samples will be present in one array and not another.

The present inventors have found that it is often desirable to evaluate some aspects of the binding characteristics of potential interaction partners before or while assessing the desirability of including them in an interaction panel. For example, the inventors have found that it is often desirable to perform a titration study in which different concentrations of the interaction partner are contacted with a diverse set of tissue samples derived from a variety of different tissues (e.g., normal and/or tumor) in order to identify a concentration or titer at which differential binding is observed. This titer is referred to herein as a "discriminating titer". Such differential staining may be observed between different tissue samples and/or between different cell types within a given tissue sample.

In general, any tissue sample may be used for this purpose (e.g., samples obtained from the epididymis, esophagus, gall bladder, kidneys, liver, lungs, lymph nodes, muscles, ovaries, pancreas, parathyroid glands, placenta, prostate, saliva, skin, spleen, stomach, testis, thymus, thyroid, tonsils, uterus, etc.). For such titration studies, greater diversity among samples is often preferred. Without intending to limit the present invention, the inventors observe that useful titers for particular interaction partners can typically be defined in a study of approximately 40-70 different tissue samples from about 20-40 different tissues.

Binding studies (for titration, for assessment of inclusion in a panel, or during use of a panel) may be performed in any format that allows specific interaction to be detected. Where large numbers of samples are to be handled, it may be desirable to utilize arrayed and/or automated formats. Particularly preferred formats include tissue arrays as discussed above. The staining of large numbers of samples derived from a variety of tumors in a tissue array format allows excellent comparative assessment of differential staining between or among samples under identical conditions. According to the present invention, staining patterns that identify at least about 10% of samples as binding with a particular interaction partner, or at least about 20, 30, 40, 50% or more of samples, are likely to represent "real" differential staining patterns (i.e., real variations in binding with interaction partner and not experimental variations, for example, due to sample processing or day to day variation in staining techniques).

Any available technique may be used to detect binding between an interaction partner and a tumor sample. One powerful and commonly used technique is to have a detectable label associated (directly or indirectly) with the interaction partner. For example, commonly-used labels that often are associated with antibodies used in binding studies include fluorochromes, enzymes, gold, iodine, etc. Tissue staining by bound interaction partners is then assessed, preferably by a trained pathologist or cytotechnologist. For example, a scoring system may be utilized to designate whether the interaction partner does or does not bind to (e.g., stain) the sample, whether it stains the sample strongly or weakly and/or whether useful information could not be obtained (e.g., because the sample was lost, there was no tumor in the sample or the result was otherwise ambiguous). Those of ordinary skill in the art will recognize that the precise characteristics of the scoring system are not critical to the invention. For example, staining may be assessed qualitatively or quantitatively; more or less subtle gradations of staining may be defined; etc.

Whatever the format, and whatever the detection strategy, identification of a discriminating titer can simplify binding studies to assess the desirability of including a given interaction partner in a panel. In such studies, the interaction partner is contacted with a plurality of different tumor samples that preferably have at least one common trait (e.g., tissue of origin), and often have multiple common traits (e.g., tissue of origin, stage, microscopic characteristics, etc.). In some cases, it will be desirable to select a group of samples with at least one common trait and at least one different trait, so that a panel of interaction partners is defined that distinguishes the different trait. In other cases, it will be desirable to select a group of samples with no detectable different traits, so that a panel of interaction partners is defined that distinguishes among previously indistinguishable samples. Those of ordinary skill in the art will understand, however, that the present invention often will allow both of these goals to be accomplished even in studies of sample collections with varying degrees of similarity and difference.

According to the present invention, interaction partners that bind to tumor samples may be characterized by their ability to discriminate among tumor samples. Any of a variety of techniques may be used to identify discriminating interaction partners. To give but one example, the present inventors have found it useful to define a "consensus panel" of tissue samples for tumors of a particular tissue of origin (see Examples 2-6). Those of ordinary skill in the art will again appreciate that the precise parameters used to designate a particular sample as interpretable and reproducible are not critical to the invention. Interaction partners may then be classified based on their ability to discriminate among tissue samples in the consensus panel (see Examples 2-6).

Assessing Prognosis or Therapeutic Regimen

The present invention further provides systems for identifying panels of interaction partners whose binding correlates with factors beyond tumor class or subclass, such as likelihood of a particular favorable or unfavorable outcome, susceptibility (or lack thereof) to a particular therapeutic regimen, etc.

As mentioned in the background, current approaches to assigning prognostic probabilities and/or selecting appropriate therapeutic regimens for particular tumors generally utilize the tumor-node-metastasis (TNM) system. This system uses the size of the tumor, the presence or absence of tumor in regional lymph nodes and the presence or absence of distant metastases, to assign a stage to the tumor. The assigned stage is used as a basis for selection of appropriate therapy and for prognostic purposes.

The present invention provides new methods and systems for evaluating tumor prognosis and/or recommended therapeutic approaches. In particular, the present invention provides systems for identifying panels of interaction partners whose binding correlates with tumor prognosis or therapeutic outcome.

For example, interaction partners whose binding correlates with prognosis can be identified by evaluating their binding to a collection of tumor samples for which prognosis is known or knowable. That is, the strategies of the invention may be employed either to identify collections of interaction partners whose binding correlates with a known outcome, or may be employed to identify a differential staining pattern that is then correlated with outcome (which outcome may either be known in advance or determined over time).

In general, it is preferred that inventive binding analyses be performed on human tumor samples. However, it is not necessary that the human tumors grow in a human host. Particularly for studies in which long-term outcome data are of interest (especially prognostic or predictive studies), it can be particularly useful to analyze samples grown in vitro (e.g., cell lines) or, more preferably, in a non-human host (e.g., a rodent, a dog, a sheep, a pig, or other animal). For instance, Example 9 provides a description of an assay in which inventive techniques employing human tumor cells growing in a non-human host are employed to define and/or utilize a panel of interaction partners whose binding to tumor samples correlates with prognosis and/or responsiveness to therapy.

It will often be desirable, when identifying interaction partners whose binding correlates with prognosis, to collect information about treatment regimens that may have been applied to the tumor whose sample is being assessed, in order to control for effects attributable to tumor therapy. Prognostic panel binding may correlate with outcome independent of treatment (Hayes et al., *J. Mamm. Gland Bio. Neo.* 6:375, 2001). Many prognostic markers, however, have both prognostic and predictive character (e.g., Her2/Neu status). Many of the individual interaction partners that comprise a prognostic panel may likewise have predictive capability and/or be members of a predictive panel.

Those of ordinary skill in the art will appreciate that prognostic panels (or individual interaction partners) have greater clinical utility if their binding/lack thereof correlates with positive/negative outcomes that are well separated statistically.

The inventive strategies may also be applied to the identification of predictive panels of interaction partners (i.e., panels whose binding correlates with susceptibility to a particular therapy). As noted above, some prognostic panels may also have predictive capabilities.

Interaction partners to be included in predictive panels are identified in binding studies performed on tumor samples that do or do not respond to a particular therapy. As with the prognostic panels, predictive panels may be assembled based on tests of tumor samples whose responsiveness is already known, or on samples whose responsiveness is not known in advance. As with the prognostic studies discussed above, the source of the tumor samples is not essential and can include, for example, tumor cell lines whose responsiveness to particular chemical agents has been determined, tumor samples from animal models in which tumors have been artificially introduced and therapeutic responsiveness has been determined and/or samples from naturally-occurring (human or other animal) tumors for which outcome data (e.g., time of survival, responsiveness to therapy, etc.) are available. Panels of interaction partners whose binding to tumor samples correlates with any prognostic or therapeutic trend can be defined and utilized as described herein.

Once correlations between interaction partner binding and tumor behavior have been established, the defined prognostic or predictive panels can be used to evaluate and classify tumor samples from patients and can be relied upon, for example to guide selection of an effective therapeutic regimen. As with the tumor classification studies described above, the process of identifying interaction partner panels whose binding correlates with outcome may itself identify particular outcomes not previously appreciated as distinct.

Those of ordinary skill in the art will appreciate that it is likely that, in at least some instances, tumor class or subclass identity will itself correlate with prognosis or responsiveness. In such circumstances, it is possible that the same set of interaction partners can act as both a classification panel and a prognosis or predictive panel.

Tumor Elements Bound By Interaction Partners

The inventive strategies for identifying and utilizing interaction partner panels in classifying or analyzing tumor samples do not rely on any assumptions about the identity or characteristics of the tumor components bound by the interaction partners. So long as interaction partner binding within the relevant panel correlates with some feature of interest, the inventive teachings apply. In many if not most, cases, however, it is expected that binding will be with a protein expressed by tumor cells.

In some preferred embodiments of the invention, interaction partners bind to tumor markers that (a) are differentially expressed in tumor cells; (b) are members of protein families whose activities contribute to relevant biological events (e.g., gene families that have been implicated in cancer such as oncogenes, tumor suppressor genes, and genes that regulate apoptosis; gene families that have been implicated in drug resistance; etc.); (c) are present on or in the plasma membrane of the tumor cells; and/or (d) are the products of degradation of tumor components, which degradation products might be detectable in patient serum.

In fact, according to the present invention, interaction partners for analysis and use in inventive panels may sometimes be identified by first identifying a tumor-associated protein of interest, and then finding a potential interaction partner that binds with the protein. Binding by this potential interaction partner to tumor samples may then be assessed and utilized as described herein.

For example, as described in the Examples, the present inventors have successfully assembled classification panels comprised of antibodies that bind to tumor protein antigens. Candidate antigens were identified both through literature reviews of proteins that play a biological role in tumor initiation or progression, or that are known to be differentially expressed in tumors, and through gene expression studies that identified additional differentially expressed proteins.

Work by the present inventors, as well as by others, has already demonstrated that studies of gene expression patterns in large tumor cohorts can identify novel tumor classes (see, for example, Perou et al., *Nature* 406:747, 2000; Sorlie et al., *Proc Natl Acad. Sci. USA* 98:10869, 2001; van't Veer et al., *Nature* 415:530, 2002; West et al., *Proc Natl. Acad. Sci. USA* 98:11462, 2001; Hedenfalk et al., *N. Engl. J. Med.* 344:539, 2001; Gruvberger et al., *Cancer Res.* 61:5979, 2001; MacDonald et al., *Nature Genet.* 29:143, 2001; Pomeroy et al., *Nature* 415:436, 2002; Jazaeri et al., *J. Natl Cancer Inst* 94:990, 2002; Welsh et al., *Proc. Natl. Acad. Sci. USA* 98:1176, 2001; Wang et al., *Gene* 229:101, 1999; Beer et al., *Nature Med.* 8:816, 2002; Garber et al., *Proc Natl Acad Sci USA* 98:13784, 2001; Bhattacharjee et al., *Proc Natl Acad Sci USA* 98:13790, 2001; Zou et al., *Oncogene* 21:4855, 2002; Lin et al., *Oncogene* 21:4120, 2002; Alon et al., *Proc Natl Acad Sci USA* 96:6745, 1999; Takahashi et al., *Proc Natl Acad Sci USA* 98:9754, 2001; Singh et al., *Cancer Cell* 1:203, 2002; LaTulippe et al., *Cancer Res.* 62:4499, 2002; Welsh et al., *Cancer Res.* 61:5974, 2001; Dhanasekaran et al., *Nature* 412:822, 2001; Hippo et al., *Cancer Res.* 62:233, 2002; Yeoh et al., *Cancer Cell* 1:133, 2002; Hofmann et al., *Lancet* 359:481, 2002; Ferrando et al., *Cancer Cell* 1:75, 2002; Shipp et al., *Nature Med* 8:68, 2002; Rosenwald et al., *N. Engl. J. Med.* 346:1937, 2002; and Alizadeh et al., *Nature* 403:503, 2000, each of which is incorporated herein by reference).

The gene sets described in these publications are promising candidates for genes that are likely to encode tumor markers whose interaction partners are useful in tumor classification and subclassification according to the present invention. Of particular interest are gene sets differentially expressed in solid tumors.

Furthermore, in general, given that differentially expressed genes are likely to be responsible for the different phenotypic characteristics of tumors, the present invention recognizes that such genes will often encode tumor markers for which a useful interaction partner, that discriminates among tumor classes or subclasses, can likely be prepared. A differentially expressed gene is a gene whose transcript abundance varies between different samples, e.g., between different tumor samples, between normal versus tumor samples, etc. In general, the amount by which the expression varies and the number of samples in which the expression varies by that amount will depend upon the number of samples and the particular characteristics of the samples. One skilled in the art will be able to determine, based on knowledge of the samples, what constitutes a significant degree of differential expression. Such genes can be identified by any of a variety of techniques including, for instance, in situ hybridization, Northern blot, nucleic acid amplification techniques (e.g., PCR, quantitative PCR, the ligase chain reaction, etc.), and, most commonly, microarray analysis.

Furthermore, those of ordinary skill in the art will readily appreciate, reading the present disclosure, that the inventive processes described herein of identifying and/or using sets of interaction partners whose binding (or lack thereof) correlates with an interesting tumor feature (e.g., tumor type or subtype, patient outcome, responsiveness of tumor or patient to therapy, etc.) inherently identifies both interaction partners of interest and the tumor markers to which they bind. Thus, one important aspect of the present invention is the identification of tumor markers whose ability (or lack thereof) to associate with an interaction partner correlates with a tumor characteristic of interest. Such tumor markers are useful as targets for identification of new therapeutic reagents, as well as of additional interaction partners useful in the practice of the present invention. Thus, it is to be understood that discussions of interaction partners presented herein are typically not limited to a particular interaction partner compound or entity, but may be generalized to include any compound or entity that binds to the relevant tumor marker(s) with requisite specificity and affinity.

Preparation of Interaction Partners

In general, interaction partners are entities that physically associate with selected tumor markers. Thus, any entity that binds detectably to a tumor marker may be utilized as an interaction partner in accordance with the present invention, so long as it binds with an appropriate combination of affinity and specificity.

Particularly preferred interaction partners are antibodies, or fragments (e.g., F(ab) fragments, F(ab')$_2$ fragments, Fv fragments, or sFv fragments, etc.; see, for example, Inbar et al., *Proc. Nat. Acad. Sci. USA* 69:2659, 1972; Hochman et al., *Biochem.* 15:2706, 1976; and Ehrlich et al., *Biochem.* 19:4091, 1980; Huston et al., *Proc. Nat. Acad. Sci. USA* 85:5879, 1998; U.S. Pat. Nos. 5,091,513 and 5,132,405 to Huston et al.; and U.S. Pat. No. 4,946,778 to Ladner et al., each of which is incorporated herein by reference). In certain embodiments, interaction partners may be selected from libraries of mutant antibodies (or fragments thereof). For example, collections of antibodies that each include different point mutations may be screened for their association with a tumor marker of interest. Yet further, chimeric antibodies may be used as interaction partners, e.g., "humanized" or "veneered" antibodies as described in greater detail below.

It is to be understood that the present invention is not limited to using antibodies or antibody fragments as interaction partners of inventive tumor markers. In particular, the present invention also encompasses the use of synthetic interaction partners that mimic the functions of antibodies. Several approaches to designing and/or identifying antibody mimics have been proposed and demonstrated (e.g., see the reviews by Hsieh-Wilson et al., *Acc. Chem. Res.* 29:164, 2000 and Peczuh and Hamilton, *Chem. Rev.* 100:2479, 2000). For example, small molecules that bind protein surfaces in a fashion similar to that of natural proteins have been identified by screening synthetic libraries of small molecules or natural product isolates (e.g., see Gallop et al., *J. Med. Chem.* 37:1233, 1994; Gordon et al., *J. Med. Chem.* 37:1385, 1994; DeWitt et al., *Proc. Natl. Acad. Sci. U.S.A.* 90:6909, 1993; Bunin et al., *Proc. Natl. Acad. Sci. U.S.A.* 91:4708, 1994; Virgilio and Ellman, *J. Am. Chem. Soc.* 116:11580, 1994; Wang et al., *J. Med. Chem.* 38:2995, 1995; and Kick and Ellman, *J. Med. Chem.* 38:1427, 1995). Similarly, combinatorial approaches have been successfully applied to screen libraries of peptides and polypeptides for their ability to bind a range of proteins (e.g., see Cull et al., *Proc. Natl. Acad. Sci. U.S.A.* 89:1865, 1992; Mattheakis et al., *Proc. Natl. Acad. Sci. U.S.A.* 91:9022, 1994; Scott and Smith, *Science* 249:386, 1990; Devlin et al., *Science* 249:404, 1990; Corey et al., *Gene* 128:129, 1993; Bray et al., *Tetrahedron Lett.* 31:5811, 1990; Fodor et al., *Science* 251:767, 1991; Houghten et al., *Nature* 354:84, 1991; Lam et al., *Nature* 354:82, 1991; Blake and Litzi-Davis, *Bioconjugate Chem.* 3:510, 1992; Needels et al., *Proc. Natl. Acad. Sci. U.S.A.* 90:10700, 1993; and Ohlmeyer et al., *Proc. Natl. Acad. Sci. U.S.A.* 90:10922, 1993). Similar approaches have also been used to study carbohydrate-protein interactions (e.g., see Oldenburg et al., *Proc. Natl. Acad. Sci. U.S.A.* 89:5393, 1992) and polynucleotide-protein interactions (e.g., see Ellington and Szostak, *Nature* 346:818, 1990 and Tuerk and Gold, *Science* 249:505, 1990). These approaches have also been extended to study interactions between proteins and unnatural biopolymers such as oligocarbamates, oligoureas, oligosulfones, etc. (e.g., see Zuckermann et al., *J. Am. Chem. Soc.* 114:10646, 1992; Simon et al., *Proc. Natl. Acad. Sci. U.S.A.* 89:9367, 1992; Zuckermann et al., *J. Med. Chem.* 37:2678, 1994; Burgess et al., *Angew. Chem., Int. Ed. Engi.* 34:907, 1995; and Cho et al., *Science* 261:1303, 1993). Yet further, alternative protein scaffolds that are loosely based around the basic fold of antibody molecules have been suggested and may be used in the preparation of inventive interaction partners (e.g., see Ku and Schultz *Proc. Natl. Acad. Sci. U.S.A.* 92:6552, 1995). Antibody mimics comprising a scaffold of a small molecule such as 3-aminomethylbenzoic acid and a substituent consisting of a single peptide loop have also been constructed. The peptide loop performs the binding function in these mimics (e.g., see Smythe et al., *J. Am. Chem. Soc.* 116:2725, 1994). A synthetic antibody mimic comprising multiple peptide loops built around a calixarene unit has also been described (e.g., see U.S. Pat. No. 5,770,380 to Hamilton et al.).

Detecting Association of Interaction Partners and Tumor Markers

Any available strategy or system may be utilized to detect association between an interaction partner and its cognate tumor marker. In certain embodiments, association can be detected by adding a detectable label to the interaction partner. In other embodiments, association can be detected by using a labeled secondary interaction partner that associates specifically with the primary interaction partner, e.g., as is well known in the art of antigen/antibody detection. The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Examples of indirectly detectable include chemiluminescent labels, e.g., enzymes that are capable of converting a substrate to a chromogenic product such as alkaline phosphatase, horseradish peroxidase and the like.

Once a labeled interaction partner has bound a tumor marker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In general, association between an interaction partner and its cognate tumor marker may be assayed by contacting the interaction partner with a tumor sample that includes the marker. Depending upon the nature of the sample, appropriate methods include, but are not limited to, immunohistochemistry (IHC), radioimmunoassay, ELISA, immunoblotting and fluorescence activates cell sorting (FACS). In the case where the polypeptide is to be detected in a tissue sample, e.g., a biopsy sample, IHC is a particularly appropriate detection method. Techniques for obtaining tissue and cell samples and performing IHC and FACS are well known in the art.

The inventive strategies for classifying and/or subclassifying tumor samples may be applied to samples of any type and of any tissue of origin. In certain preferred embodiments of the invention, the strategies are applied to solid tumors. Historically, researchers have encountered difficulty in defining solid tumor subtypes, given the challenges associated with defining their molecular characteristics. As demonstrated in the Examples, the present invention is particularly beneficial in this area. Particularly preferred solid tumors include, for example, breast, lung, colon, and ovarian tumors. The invention also encompasses the recognition that tumor markers that are secreted from the cells in which they are produced may be present in serum, enabling their detection through a blood test rather than requiring a biopsy specimen. An interaction partner that binds to such tumor markers represents a particularly preferred embodiment of the invention.

In general, the results of such an assay can be presented in any of a variety of formats. The results can be presented in a qualitative fashion. For example, the test report may indicate only whether or not a particular tumor marker was detected, perhaps also with an indication of the limits of detection. Additionally the test report may indicate the subcellular location of binding, e.g., nuclear versus cytoplasmic and/or the relative levels of binding in these different subcellular locations. The results may be presented in a semi-quantitative fashion. For example, various ranges may be defined and the ranges may be assigned a score (e.g., 0 to 5) that provides a certain degree of quantitative information. Such a score may reflect various factors, e.g., the number of cells in which the tumor marker is detected, the intensity of the signal (which may indicate the level of expression of the tumor marker), etc. The results may be presented in a quantitative fashion, e.g., as a percentage of cells in which the tumor marker is detected, as a concentration, etc. As will be appreciated by one of ordinary skill in the art, the type of output provided by a test will vary depending upon the technical limitations of the test and the biological significance associated with detection of the tumor marker. For example, in the case of certain tumor markers a purely qualitative output (e.g., whether or not the tumor marker is detected at a certain detection level) provides significant information. In other cases a more quantitative output (e.g., a ratio of the level of expression of the tumor marker in two samples) is necessary.

Identification of Novel Therapies

Predictive panels of interaction agents are useful according to the present invention not only to classify tumor samples obtained from cancer sufferers with respect to their likely responsiveness to known therapies, but also to identify potential new therapies or therapeutic agents that could be useful in the treatment of cancer.

For example, as noted above, the process of identifying or using inventive panels according to the present invention simultaneously identifies and/or characterizes tumor markers in or on the tumor cells that correlate with one or more selected tumor characteristics (e.g., tumor type or subtype, patient prognosis, and/or responsiveness of tumor or patient to therapy). Such tumor markers are attractive candidates for identification of new therapeutic agents (e.g., via screens to detect compounds or entities that bind to the tumor markers, preferably with at least a specified affinity and/or specificity, and/or via screens to detect compounds or entities that modulate (i.e., increase or decrease) expression, localization, modification, or activity of the tumor markers. In many instances, interaction partners themselves may prove to be useful therapeutics.

Thus the present invention provides interaction partners that are themselves useful therapeutic agents. For example, binding by an interaction partner, or a collection of interaction partners, to a cancer cell, might inhibit growth of that cell. Alternatively or additionally, interaction partners defined or prepared according to the present invention could be used to deliver a therapeutic agent to a cancer cell. In particular, interaction partners may be coupled to one or more therapeutic agents. Suitable agents in this regard include radionuclides and drugs. Preferred radionuclides include $^{90}$Y, $^{123}$I, $^{125}$I, $^{131}$I, $^{186}$Re, $^{188}$Re, $^{211}$At and $^{212}$Bi. Preferred drugs include chlorambucil, ifosphamide, meclorethamine, cyclophosphamide, carboplatin, cisplatin, procarbazine, decarbazine, carmustine, cytarabine, hydroxyurea, mercaptopurine, methotrexate, thioguanine, 5-fluorouracil, actinomycin D, bleomycin, daunorubicin, doxorubicin, etoposide, vinblastine, vincristine, L-asparginase, adrenocorticosteroids, canciclovir triphosphate, adenine arabinonucleoside triphosphate, 5-aziridinyl-4-hydroxylamino-2-nitrobenzamide, acrolein, phosphoramide mustard, 6-methylpurine, etoposide, methotrexate, benzoic acid mustard, cyanide and nitrogen mustard.

According to such embodiments, the therapeutic agent may be coupled with an interaction partner by direct or indirect covalent or non-covalent interactions. A direct interaction between a therapeutic agent and an interaction partner is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Indirect interactions might involve a linker group that is itself associated with both the therapeutic agent and the interaction partner. A linker group can function as a spacer to distance an interaction partner from an agent in order to avoid interference with association capabilities. A linker group can also serve to increase the chemical reactivity of a substituent on an agent or an interaction partner and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfydryl groups or oxidized carbohydrate residues. There are numerous references describing such methodology, e.g., U.S. Pat. No. 4,671,958, to Rodwell et al. It will further be appreciated that a therapeutic agent and an interaction partner may be coupled via non-covalent interactions, e.g., ligand/receptor type interactions. Any ligand/receptor pair with a sufficient stability and specificity to operate in the context of the invention may be employed to couple a therapeutic agent and an interaction partner. To give but an example, a therapeutic agent may be covalently linked with biotin and an interaction partner with avidin. The strong non-covalent binding of biotin to avidin would then allow for coupling of the therapeutic agent and the interaction partner. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and maltose binding protein (MBP) and further those described in Kessler pp. 105-152 of *Advances in Mutagenesis"* Ed. by Kessler, Springer-Verlag, 1990; *"Affinity Chromatography: Methods and Protocols (Methods in Molecular Biology)"* Ed. by Pascal Baillon, Humana Press, 2000; and *"Immobilized Affinity Ligand Techniques"* by Hermanson et al., Academic Press, 1992.

Where a therapeutic agent is more potent when free from the interaction partner, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710 to Spitler), by irradiation of a photolabile bond (e.g., U.S. Pat. No. 4,625,014 to Senter et al.), by hydrolysis of derivatized amino acid side chains (e.g., U.S. Pat. No. 4,638,045 to Kohn et al.), by serum complement-mediated hydrolysis (e.g., U.S. Pat. No. 4,671,958 to Rodwell et al.) and by acid-catalyzed hydrolysis (e.g., U.S. Pat. No. 4,569,789 to Blattler et al.).

In certain embodiments, it may be desirable to couple more than one therapeutic agent to an interaction partner. In one embodiment, multiple molecules of an agent are coupled to one interaction partner molecule. In another embodiment, more than one type of therapeutic agent may be coupled to one interaction partner molecule. Regardless of the particular embodiment, preparations with more than one agent may be prepared in a variety of ways. For example, more than one agent may be coupled directly to an interaction partner molecule, or linkers that provide multiple sites for attachment can be used.

Alternatively, a carrier can be used. A carrier may bear the agents in a variety of ways, including covalent bonding either directly or via a linker group. Suitable carriers include proteins such as albumins (e.g., U.S. Pat. No. 4,507,234 to Kato et al.), peptides, and polysaccharides such as aminodextran (e.g., U.S. Pat. No. 4,699,784 to Shih et al.). A carrier may also bear an agent by non-covalent bonding or by encapsulation, such as within a liposome vesicle (e.g., U.S. Pat. Nos. 4,429,008 to Martin et al. and 4,873,088 to Mayhew et al.). Carriers specific for radionuclide agents include radiohalogenated small molecules and chelating compounds. For example, U.S. Pat. No. 4,735,792 to Srivastava discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562 to Davison et al. discloses representative chelating compounds and their synthesis.

When interaction partners are themselves therapeutics, it will be understood that, in many cases, any interaction partner that binds with the same tumor marker may be so used.

In one preferred embodiment of the invention, the therapeutic agents (whether interaction partners or otherwise) are antibodies. As is well known in the art, when using an antibody or fragment thereof for therapeutic purposes it may prove advantageous to use a "humanized" or "veneered" version of an antibody of interest to reduce any potential immunogenic reaction. In general, "humanized" or "veneered" antibody molecules and fragments thereof minimize unwanted immunological responses toward antihuman antibody molecules which can limit the duration and effectiveness of therapeutic applications of those moieties in human recipients.

A number of "humanized" antibody molecules comprising an antigen binding portion derived from a non-human immunoglobulin have been described in the art, including chimeric antibodies having rodent variable regions and their associated complementarity-determining regions (CDRs) fused to human constant domains (e.g., see Winter et al., *Nature* 349: 293, 1991; Lobuglio et al., *Proc. Nat. Acad. Sci. USA* 86:4220, 1989; Shaw et al., *J. Immunol.* 138:4534, 1987; and Brown et al., *Cancer Res.* 47:3577, 1987), rodent CDRs grafted into a human supporting framework region (FR) prior to fusion with an appropriate human antibody constant domain (e.g., see Riechmann et al., *Nature* 332:323, 1988; Verhoeyen et al., *Science* 239:1534, 1988; and Jones et al. *Nature* 321:522, 1986) and rodent CDRs supported by recombinantly veneered rodent FRs (e.g., see European Patent Publication No. 519,596, published Dec. 23, 1992). It is to be understood that the invention also encompasses "fully human" antibodies produced using the XenoMouse™ technology (AbGenix Corp., Fremont, Calif.) according to the techniques described in U.S. Pat. No. 6,075,181.

Yet further, so-called "veneered" antibodies may be used that include "veneered FRs". The process of veneering involves selectively replacing FR residues from, e.g., a murine heavy or light chain variable region, with human FR residues in order to provide a xenogeneic molecule comprising an antigen binding portion which retains substantially all of the native FR polypeptide folding structure. Veneering techniques are based on the understanding that the antigen binding characteristics of an antigen binding portion are determined primarily by the structure and relative disposition of the heavy and light chain CDR sets within the antigen-association surface (e.g., see Davies et al., *Ann. Rev. Biochem.* 59:439, 1990). Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

Preferably, interaction partners suitable for use as therapeutics (or therapeutic agent carriers) exhibit high specificity for the target tumor marker and low background binding to other tumor markers. In certain embodiments, monoclonal antibodies are preferred for therapeutic purposes.

Tumor markers that are expressed on the cell surface represent preferred targets for the development of therapeutic agents, particularly therapeutic antibodies. For example, cell surface proteins can be tentatively identified using sequence analysis based on the presence of a predicted transmembrane domain. Their presence on the cell surface can ultimately be confirmed using IHC.

Kits

Useful sets or panels of interaction partners according to the present invention may be prepared and packaged together in kits for use in classifying, diagnosing, or otherwise characterizing tumor samples, or for inhibiting tumor cell growth or otherwise treating cancer.

Any available technique may be utilized in the preparation of individual interaction partners for inclusion in kits. For example, protein or polypeptide interaction partners may be produced by cells (e.g., recombinantly or otherwise), may be chemically synthesized, or may be otherwise generated in vitro (e.g., via in vitro transcription and/or translation). Non-protein or polypeptide interaction partners (e.g., small molecules, etc.) may be synthesized, may be isolated from within or around cells that produce them, or may be otherwise generated.

When antibodies are used as interaction partners, these may be prepared by any of a variety of techniques known to those of ordinary skill in the art (e.g., see Harlow and Lane, *Antibodies: A Laboratory Manual*, Cold Spring Harbor Laboratory, 1988). For example, antibodies can be produced by cell culture techniques, including the generation of monoclonal antibodies, or via transfection of antibody genes into suitable bacterial or mammalian cell hosts, in order to allow for the production of recombinant antibodies. In one technique, an "immunogen" comprising an antigenic portion of a tumor marker of interest (or the tumor marker itself) is initially injected into any of a wide variety of mammals (e.g., mice, rats, rabbits, sheep or goats). In this step, a tumor marker (or an antigenic portion thereof) may serve as the immunogen without modification. Alternatively, particularly for relatively short tumor markers, a superior immune response may be elicited if the tumor marker is joined to a carrier protein, such as bovine serum albumin or keyhole limpet hemocyanin (KLH). The immunogen is injected into the animal host, preferably according to a predetermined schedule incorporating one or more booster immunizations and the animals are bled periodically. Polyclonal antibodies specific for the tumor marker may then be purified from such antisera by, for example, affinity chromatography using the tumor marker (or an antigenic portion thereof) coupled to a suitable solid support. An exemplary method is described in Example 7.

If desired for diagnostic or therapeutic kits, monoclonal antibodies specific for a tumor marker of interest may be prepared, for example, using the technique of Kohler and Milstein, *Eur. J. Immunol.* 6:511, 1976 and improvements thereto. Briefly, these methods involve the preparation of immortal cell lines capable of producing antibodies having the desired specificity (i.e., reactivity with the tumor marker of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the tumor marker. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation and extraction. The tumor marker of interest may be used in the purification process in, for example, an affinity chromatography step.

In addition to inventive interaction partners, preferred kits for use in accordance with the present invention may include, a reference sample, instructions for processing samples, performing the test, instructions for interpreting the results, buffers and/or other reagents necessary for performing the test. In certain embodiments the kit can comprise a panel of antibodies.

Pharmaceutical Compositions

As mentioned above, the present invention provides new therapies and methods for identifying these. In certain embodiments, an interaction partner may be a useful therapeutic agent. Alternatively or additionally, interaction partners defined or prepared according to the present invention bind to tumor markers that serve as targets for therapeutic agents. Also, inventive interaction partners may be used to deliver a therapeutic agent to a cancer cell. For example, interaction partners provided in accordance with the present invention may be coupled to one or more therapeutic agents.

In addition, as mentioned above, to the extent that a particular predictive panel correlates with responsiveness to a particular therapy because it detects changes that reflect inhibition (or inhibitability) of cancer cell growth, that panel could be used to evaluate therapeutic candidates (e.g., small molecule drugs) for their ability to induce the same or similar changes in different cells. In particular, binding by the panel could be assessed on cancer cells before and after exposure to candidate therapeutics; those candidates that induce expression of the tumor markers to which the panel binds are then identified.

The invention includes pharmaceutical compositions comprising these inventive therapeutic agents. In general, a pharmaceutical composition will include a therapeutic agent in addition to one or more inactive agents such as a sterile, biocompatible carrier including, but not limited to, sterile water, saline, buffered saline, or dextrose solution. The pharmaceutical compositions may be administered either alone or in combination with other therapeutic agents including other chemotherapeutic agents, hormones, vaccines and/or radiation therapy. By "in combination with", it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the inventive pharmaceutical compositions in combination with agents that may improve their bioavailability, reduce or modify their metabolism, inhibit their excretion, or modify their distribution within the body. The invention encompasses treating cancer by administering the pharmaceutical compositions of the invention. Although the pharmaceutical compositions of the present invention can be used for treatment of any subject (e.g., any animal) in need thereof, they are most preferably used in the treatment of humans.

The pharmaceutical compositions of this invention can be administered to humans and other animals by a variety of routes including oral, intravenous, intramuscular, intra-arterial, subcutaneous, intraventricular, transdermal, rectal, intravaginal, intraperitoneal, topical (as by powders, ointments, or drops), bucal, or as an oral or nasal spray or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc. At present the intravenous route is most commonly used to deliver therapeutic antibodies. However, the invention encompasses the delivery of the inventive pharmaceutical composition by any appropriate route taking into consideration likely advances in the sciences of drug delivery.

General considerations in the formulation and manufacture of pharmaceutical agents may be found, for example, in *Remington's Pharmaceutical Sciences*, 19$^{th}$ ed., Mack Publishing Co., Easton, Pa., 1995.

According to the methods of treatment of the present invention, cancer is treated or prevented in a patient such as a human or other mammal by administering to the patient a therapeutically effective amount of a therapeutic agent of the invention, in such amounts and for such time as is necessary to achieve the desired result. By a "therapeutically effective amount" of a therapeutic agent of the invention is meant a sufficient amount of the therapeutic agent to treat (e.g., to ameliorate the symptoms of, delay progression of, prevent recurrence of, cure, etc.) cancer at a reasonable benefit/risk ratio, which involves a balancing of the efficacy and toxicity of the therapeutic agent. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the agent. Although in general therapeutic agents having a large therapeutic index are preferred, as is well known in the art, a smaller therapeutic index may be acceptable in the case of a serious disease, particularly in the absence of alternative therapeutic options. Ultimate selection of an appropriate range of doses for administration to humans is determined in the course of clinical trials.

It will be understood that the total daily usage of the therapeutic agents and compositions of the present invention for any given patient will be decided by the attending physician within the scope of sound medical judgment. The specific therapeutically effective dose level for any particular patient will depend upon a variety of factors including the disorder being treated and the severity of the disorder; the activity of the specific therapeutic agent employed; the specific composition employed; the age, body weight, general health, sex and diet of the patient; the time of administration, route of administration and rate of excretion of the specific therapeutic agent employed; the duration of the treatment; drugs used in combination or coincidental with the specific therapeutic agent employed; and like factors well known in the medical arts.

The total daily dose of the therapeutic agents of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 0.1 µg to about 2000 mg of the therapeutic agent(s) of the invention per day in single or multiple doses.

EXEMPLIFICATION

Example 1

Selection of Candidate Genes and Identification of Potential Interaction Partners for Tumor Classification Panels The present inventors identified a collection of candidate genes that (a) were differentially expressed across a set of tumor samples in a manner that suggested they distinguish biologically distinct classes of tumors; (b) were members of a gene functional class that has been linked to cellular pathways implicated in tumor prognosis or drug resistance; (c) were known or thought to display an expression, localization, modification, or activity pattern that correlates with a relevant tumor feature; etc.

For example, differentially expressed genes were identified using microarrays as described in co-pending U.S. patent application Ser. No. 09/916,722, filed Jul. 26, 2001 entitled "REAGENTS AND METHODS FOR USE IN MANAGING BREAST CANCER", the entire contents of which are incorporated herein by reference. Other genes were typically selected on the basis of published data suggesting their possible implication in drug resistance, cancer prognosis, etc. A total of 730 candidate genes were identified as encoding proteins against which antibodies should be raised.

Rabbit polyclonal affinity-purified antibodies were then raised against 661 of these proteins as described in Example 7. Each antibody was initially tested over a range of dilutions on tissue arrays that included a set of normal tissues, tumor tissues and cell lines, so that, for each antibody, a discriminating titer was established at which differential staining across the diverse set was observed. The preparation and staining of tissue arrays is described in greater detail in Example 8. Of the 661 antibodies subjected to this analysis, 460 showed differential staining and were considered of sufficient interest for further analysis.

Example 2

Breast Cancer Classification Panel (Russian Breast Cohort)

The present inventors prepared an exemplary panel of antibodies for use in classifying breast tumors. 272 of the 460 differentially staining antibodies of Example 1 exhibited a reproducibly robust staining pattern on tissues relevant for this application. These antibodies were therefore applied (at appropriate titers) to a tissue array comprised of approximately 400 independent breast tumor samples from a cohort of breast cancer patients (the Russian breast cohort). Stained tissue samples were scored by a trained cytotechnologist or pathologist on a semi-quantitative scale in which 0=no stain on tumor cells; 1=no information; 2=weak staining of tumor cells; and 3=strong staining of tumor cells. Antibodies were included in a breast cancer classification panel if they stained greater than 10% and less than 90% of a defined "consensus panel" of the breast tumor tissue samples on at least two independent tissue arrays.

A given tissue sample was included in this "consensus panel" if at least 80% of the antibodies tested gave interpretable scores (i.e., a non-zero score) with that sample. Of the 400 breast tumor samples in the tissue array about 320 were included in the consensus panel. Also, in scoring antibody binding to the consensus panel, all scores represented a consensus score of replicate tissue arrays comprised of independent samples from the same sources. The consensus score was determined by computing the median (rounded down to an integer, where applicable) of all scores associated with a given antibody applied under identical conditions to the particular patient sample. In cases where the variance of the scores was greater than 2, the score was changed to 1 (i.e., no information). The data for each antibody was stored in an Oracle-based database that contained the semi-quantitative scores of tumor tissue staining and also contained links to both patient clinical information and stored images of the stained patient samples.

Through this analysis 90 of the 272 tested antibodies were selected for inclusion in an exemplary breast cancer classification panel (see Appendix A, e.g., S0021, S0022, S0039, etc.). It is to be understood that any sub-combination of these 90 antibodies may be used in constructing an inventive breast cancer classification panel. It will also be appreciated that additional antibodies may be added to or removed from an inventive breast cancer classification panel as more tumor markers are identified and/or more samples are tested (e.g., see Example 3).

FIG. 1 shows the pattern of reactivity observed with certain members of this panel of antibodies across samples from the Russian breast cohort. Dark gray represents strong positive staining, black represents weak positive staining, while light gray represents the absence of staining and medium gray represents a lack of data. Images of stained samples can be found in Appendix B (see right hand column of Appendix A for cross-references to corresponding antibodies).

The patients (rows) were classified using k-means clustering (as described, for example, in MacQueen in *Proceedings of the Fifth Berkeley Symposium on Mathematical Statistics and Probability* (Le Cam et al., Eds.; University of California Press, Berkeley, Calif.) 1:281, 1967; Heyer et al., *Genome Res.* 9:1106, 1999, each of which is incorporated herein by reference) while the antibodies (columns) were organized using hierarchical clustering (as described in, for example, Sokal et al., *Principles of Numerical Taxonomy* (Freeman & Co., San Francisco, Calif.), 1963; Eisen et al., *Proc. Natl. Acad. Sci. USA* 95:14863, 1998, each of which is incorporated herein by reference). As shown in FIG. 1, nine subclasses of breast cancer patients were identified by their consensus pattern of staining with this breast cancer classification panel.

Example 3

Breast Cancer Classification Panel (HH Breast Cohort)

In order to refine and expand the breast cancer classification panel of Example 2, the present inventors tested 109 of the 460 differentially staining antibodies of Example 1 on samples from a new cohort of 550 breast cancer patients (the Huntsville Hospital breast cohort or "HH breast" cohort, the characteristics of which are described in Example 10).

Antibodies were included in an updated breast cancer classification panel if they stained more than 10% and less than 90% of the particular consensus panel of tissue samples tested. Through this analysis 87 of the 109 tested antibodies were selected (see Appendix A, e.g., S0011, S0018, S0020, etc.).

Example 4

Lung Cancer Classification Panel (Russian Lung Cohort)

The present inventors also prepared an exemplary panel of antibodies for use in classifying lung tumors. 417 of the 460 differentially staining antibodies of Example 1 exhibited a reproducibly robust staining pattern on tissues relevant for this application. These antibodies were therefore applied (at the titers determined in Example 1) to a tissue array comprised of approximately 400 independent lung tumor tissues from a cohort of lung cancer patients (the Russian lung cohort). Stained tissue samples were scored by a trained cytotechnologist or pathologist as before and again antibodies were included in the classification panel if they stained greater than 10% and less than 90% of a defined "consensus panel" of tissue samples on at least two independent tissue arrays.

Through this analysis an exemplary lung cancer classification panel was generated that was made up of 106 of the 417 tested antibodies (see Appendix A, e.g., s0021, s0022, s0024, etc.). It is to be understood that any sub-combination of these 106 antibodies may be used in constructing an inventive lung cancer classification panel. It will also be appreciated that additional antibodies may be added to or removed from an inventive lung cancer classification panel as more tumor markers are identified and/or more samples are tested (e.g., see Example 5).

Figure 2:
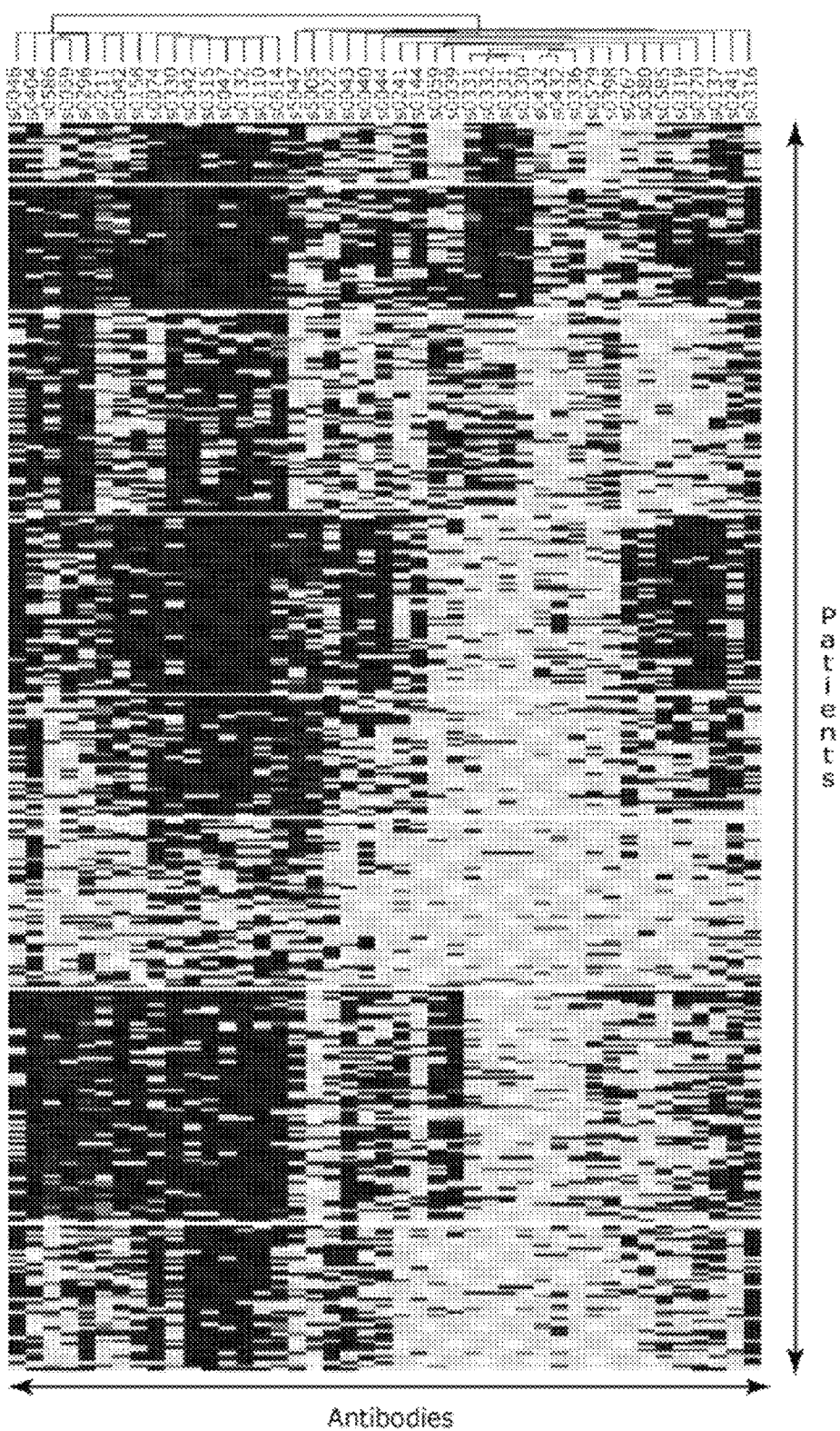
FIG. 2 depicts semi-quantitative immunohistochemistry (IHC) scoring of a 387 lung cancer patient cohort with an inventive lung cancer classification panel. The panel was prepared as described in Example 4—antibodies were used as interaction partners. The patients (rows) were classified using k-means clustering while the antibodies (columns) were organized using hierarchical clustering. Dark gray represents strong positive staining, black represents weak positive staining, while light gray represents the absence of staining and medium gray represents a lack of data. As illustrated in the Figure, eight groups of patients were identified by their consensus pattern of staining with the panel of antibodies.

FIG. 2 shows the pattern of reactivity observed with certain members of this panel of antibodies across samples from the Russian lung cohort. Dark gray represents strong positive staining, black represents weak positive staining, while light gray represents the absence of staining and medium gray represents a lack of data. Images of stained samples can be found in Appendix B (see right hand column of Appendix A for cross-references to corresponding antibodies).

The patients (rows) were again classified using k-means clustering while the antibodies (columns) were organized using hierarchical clustering. As shown in FIG. 2, eight sub-classes of lung cancer patients were identified by their consensus pattern of staining with this lung cancer classification panel.

Example 5

Lung Cancer Classification Panel (HH Lung Cohort)

In order to refine and expand the lung cancer classification panel of Example 4, the present inventors tested 54 of the 460 differentially staining antibodies of Example 1 on samples from a new cohort of 379 lung cancer patients (the Huntsville Hospital lung cohort or "HH lung" cohort, the characteristics of which are described in Example 11).

Antibodies were included in an updated colon cancer classification panel if they stained more than 10% and less than 90% of the particular consensus panel of tissue samples tested. Through this analysis 39 of the 54 tested antibodies were selected (see Appendix A, e.g., S0021, S0022, S0046, etc.).

Example 6

Colon Cancer Classification Panel (Russian Colon Cohort)

The present inventors also prepared an exemplary panel of antibodies for use in classifying colon tumors. 382 of the 460 differentially staining antibodies of Example 1 exhibited a reproducibly robust staining pattern on tissues relevant for this application. These antibodies were therefore applied (at the titers determined in Example 1) to a tissue array comprised of approximately 400 independent colon tumor tissues from a cohort of colon cancer patients (the Russian colon cohort). Stained tissue samples were scored by a trained cytotechnologist or pathologist as before and again antibodies were included in the classification panel if they stained greater than 10% and less than 90% of a defined "consensus panel" of tissue samples on at least two independent tissue arrays.

Through this analysis a colon antibody classification panel was generated that was made up of 86 of the 382 tested antibodies (see Appendix A, e.g., S0022, S0036, S0039, etc.). It will be appreciated that any sub-combination of these 86 antibodies may be used in constructing an inventive colon cancer classification panel. It will also be appreciated that additional antibodies may be added to or removed from an inventive colon cancer classification panel as more tumor markers are identified and/or more samples are tested.

Figure 3:
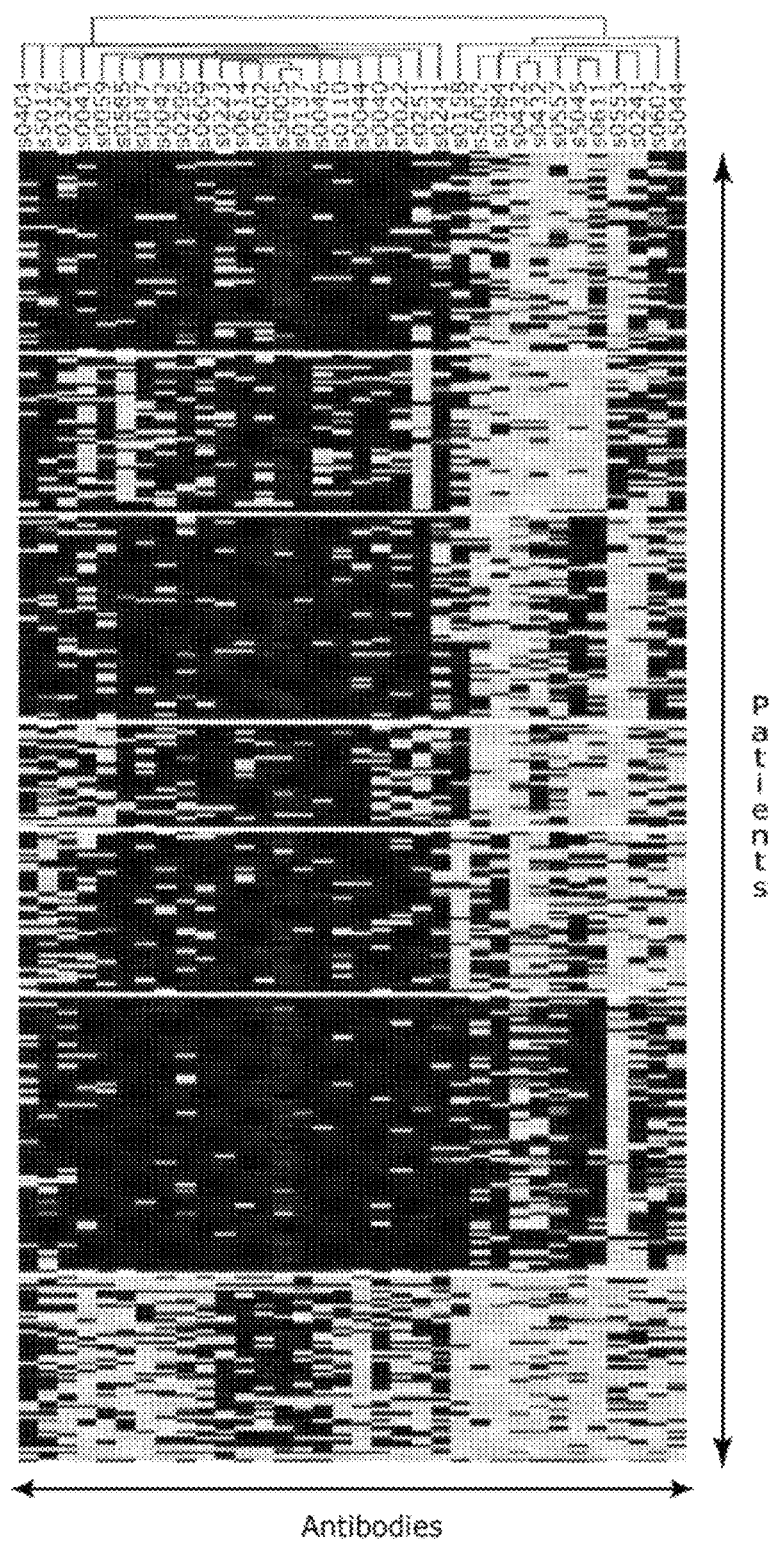
FIG. 3 depicts semi-quantitative immunohistochemistry (IHC) scoring of a 359 colon cancer patient cohort with an inventive colon cancer classification panel. The panel was prepared as described in Example 6—antibodies were used as interaction partners. The patients (rows) were classified using k-means clustering while the antibodies (columns) were organized using hierarchical clustering. Dark gray represents strong positive staining, black represents weak positive staining, while light gray represents the absence of staining and medium gray represents a lack of data. As illustrated in the Figure, seven groups of patients were identified by their consensus pattern of staining with the panel of antibodies.

FIG. 3 shows the pattern of reactivity observed with certain members of this panel of antibodies across samples from the Russian colon cohort. Dark gray represents strong positive staining, black represents weak positive staining, while light gray represents the absence of staining and medium gray represents a lack of data. Images of the stained samples can be found in Appendix B (see right hand column of Appendix A for cross-references to corresponding antibodies).

The patients (rows) were again classified using k-means clustering while the antibodies (columns) were organized using hierarchical clustering. As shown in FIG. 3, seven sub-classes of patients were identified by their consensus pattern of staining with this exemplary colon cancer classification panel.

Example 7

Raising Antibodies

This example describes a method that was employed to generate the majority of the antibodies that were used in Examples 1-6. Similar methods may be used to generate an antibody that binds to any polypeptide of interest (e.g., to polypeptides that are or are derived from other tumor markers). In some cases, antibodies may be obtained from commercial sources (e.g., Chemicon, Dako, Oncogene Research Products, NeoMarkers, etc.) or other publicly available sources (e.g., Imperial Cancer Research Technology, etc.).

Materials and Solutions

Anisole (Cat. No. A4405, Sigma, St. Louis, Mo.)

2,2'-azino-di-(3-ethyl-benzthiazoline-sulfonic acid) (ABTS) (Cat. No. A6499, Molecular Probes, Eugene, Oreg.)

Activated maleimide Keyhole Limpet Hemocyanin (Cat. No. 77106, Pierce, Rockford, Ill.)

Keyhole Limpet Hemocyanin (Cat. No. 77600, Pierce, Rockford, Ill.)

Phosphoric Acid ($H_3PO_4$) (Cat. No. P6560, Sigma)

Glacial Acetic Acid (Cat No. BP1185-500, Fisher)

EDC (EDAC) (Cat No. 341006, Calbiochem)
25% Glutaraldehyde (Cat No. G-5882, Sigma)
Glycine (Cat No. G-8898, Sigma)
Biotin (Cat. No. B2643, Sigma)
Boric acid (Cat. No. B0252, Sigma)
Sepharose 4B (Cat. No. 17-0120-01, LKB/Pharmacia, Uppsala, Sweden)
Bovine Serum Albumin (LP) (Cat. No. 100 350, Boehringer Mannheim, Indianapolis, Ind.)
Cyanogen bromide (Cat. No. C6388, Sigma)
Dialysis tubing Spectra/Por Membrane MWCO: 6-8,000 (Cat. No. 132 665, Spectrum Industries, Laguna Hills, Calif.)
Dimethyl formamide (DMF) (Cat. No. 22705-6, Aldrich, Milwaukee, Wis.)
DIC (Cat. No. BP 592-500, Fisher)
Ethanedithiol (Cat. No. 39, 802-0, Aldrich)
Ether (Cat. No. TX 1275-3, EM Sciences)
Ethylenediaminetetraacetatic acid (EDTA) (Cat. No. BP 120-1, Fisher, Springfield, N.J.)
1-ethyl-3-(3' dimethylaminopropyl)-carbodiimide, HCL (EDC) (Cat. no. 341-006, Calbiochem, San Diego, Calif.)
Freund's Adjuvant, complete (Cat. No. M-0638-50B, Lee Laboratories, Grayson, Ga.)
Freund's Adjuvant, incomplete (Cat. No. M-0639-50B, Lee Laboratories)
Fritted chromatography columns (Column part No. 12131011; Frit Part No. 12131029, Varian Sample Preparation Products, Harbor City, Calif.)
Gelatin from Bovine Skin (Cat. No. G9382, Sigma)
Goat anti-rabbit IgG, biotinylated (Cat. No. A 0418, Sigma)
HOBt (Cat. No. 01-62-0008, Calbiochem)
Horseradish peroxidase (HRP) (Cat. No. 814 393, Boehringer Mannheim)
HRP-Streptavidin (Cat. No. S 5512, Sigma)
Hydrochloric Acid (Cat. No. 71445-500, Fisher)
Hydrogen Peroxide 30% w/w (Cat. No. H1009, Sigma)
Methanol (Cat. No. A412-20, Fisher)
Microtiter plates, 96 well (Cat. No. 2595, Corning-Costar, Pleasanton, Calif.)
N-α-Fmoc protected amino acids from Calbiochem. See '97-'98 Catalog pp. 1-45.
N-α-Fmoc protected amino acids attached to Wang Resin from Calbiochem. See '97-'98 Catalog pp. 161-164.
NMP (Cat. No. CAS 872-50-4, Burdick and Jackson, Muskegon, Mich.)
Peptide (Synthesized by Research Genetics. Details given below)
Piperidine (Cat. No. 80640, Fluka, available through Sigma)
Sodium Bicarbonate (Cat. No. BP328-1, Fisher)
Sodium Borate (Cat. No. B9876, Sigma)
Sodium Carbonate (Cat. No. BP357-1, Fisher)
Sodium Chloride (Cat. No. BP 358-10, Fisher)
Sodium Hydroxide (Cat. No. SS 255-1, Fisher)
Streptavidin (Cat. No. 1 520, Boehringer Mannheim)
Thioanisole (Cat. No. T-2765, Sigma)
Trifluoroacetic acid (Cat. No. TX 1275-3, EM Sciences)
Tween-20 (Cat. No. BP 337-500, Fisher)
Wetbox (Rectangular Servin' Saver™ Part No. 3862, Rubbermaid, Wooster, Ohio)
BBS—Borate Buffered Saline with EDTA dissolved in distilled water (pH 8.2 to 8.4 with HCl or NaOH), 25 mM Sodium borate (Borax), 100 mM Boric Acid, 75 mM NaCl and 5 mM EDTA.
0.1 N HCl in saline as follows: concentrated HCl (8.3 ml/0.917 liter distilled water) and 0.154 M NaCl
Glycine (pH 2.0 and pH 3.0) dissolved in distilled water and adjusted to the desired pH, 0.1 M glycine and 0.154 M NaCl.
5× Borate 1× Sodium Chloride dissolved in distilled water, 0.11 M NaCl, 60 mM Sodium Borate and 250 mM Boric Acid.
Substrate Buffer in distilled water adjusted to pH 4.0 with sodium hydroxide, 50 to 100 mM Citric Acid.
AA solution: HOBt is dissolved in NMP (8.8 grams HOBt to 1 liter NMP). Fmoc-N-a-amino at a concentration at 0.53 M.
DIC solution: 1 part DIC to 3 parts NMP.
Deprotecting solution: 1 part Piperidine to 3 parts DMF.
Reagent R: 2 parts anisole, 3 parts ethanedithiol, 5 parts thioanisole and 90 parts trifluoroacetic acid.

Equipment

MRX Plate Reader (Dynatech, Chantilly, Va.)
Hamilton Eclipse (Hamilton Instruments, Reno, Nev.)
Beckman TJ-6 Centrifuge (Model No. TJ-6, Beckman Instruments, Fullerton, Calif.)
Chart Recorder (Recorder 1 Part No. 18-1001-40, Pharmacia LKB Biotechnology)
UV Monitor (Uvicord SU Part No. 18-1004-50, Pharmacia LKB Biotechnology)
Amicon Stirred Cell Concentrator (Model 8400, Amicon, Beverly, Mass.)
30 kD MW cut-off filter (Cat. No. YM-30 Membranes Cat. No. 13742, Amicon)
Multi-channel Automated Pipettor (Cat. No. 4880, Corning Costar, Cambridge, Mass.)
pH Meter Corning 240 (Corning Science Products, Corning Glassworks, Corning, N.Y.)
ACT396 peptide synthesizer (Advanced ChemTech, Louisville, Ky.)
Vacuum dryer (Box from Labconco, Kansas City, Mo. and Pump from Alcatel, Laurel, Md.).
Lyophilizer (Unitop 600s1 in tandem with Freezemobile 12, both from Virtis, Gardiner, N.Y.)

Peptide Selection

Peptides against which antibodies would be raised were selected from within the polypeptide sequence of interest using a program that uses the Hopp/Woods method (described in Hopp and Woods, *Mol. Immunol.* 20:483, 1983 and Hopp and Woods, *Proc. Nat. Acad. Sci. U.S.A.* 78:3824, 1981). The program uses a scanning window that identifies peptide sequences of 15-20 amino acids containing several putative antigenic epitopes as predicted by low solvent accessibility. This is in contrast to most implementations of the Hopp/Woods method, which identify single short (~6 amino acids) presumptive antigenic epitopes. Occasionally the predicted solvent accessibility was further assessed by PHD prediction of loop structures (described in Rost and Sander, *Proteins* 20:216, 1994). Preferred peptide sequences display minimal similarity with additional known human proteins. Similarity was determined by performing BLASTP alignments, using a wordsize of 2 (described in Altschul et al., *J. Mol. Biol.* 215:403, 1990). All alignments given an EXPECT value less than 1000 were examined and alignments with similarities of greater than 60% or more than four residues in an exact contiguous non-gapped alignment forced those peptides to be rejected. When it was desired to target regions of proteins exposed outside the cell membrane, extracellular regions of the protein of interest were determined from the literature or as defined by predicted transmembrane domains using a hidden Markov model (described in Krogh et al., *J.*

*Mol. Biol.* 305:567, 2001). When the peptide sequence was in an extracellular domain, peptides were rejected if they contained N-linked glycosylation sites. As shown in Appendix A, one to three peptide sequences were selected for each polypeptide using this procedure.

Peptide Synthesis

The sequence of the desired peptide was provided to the peptide synthesizer. The C-terminal residue was determined and the appropriate Wang Resin was attached to the reaction vessel. The peptides were synthesized C-terminus to N-terminus by adding one amino acid at a time using a synthesis cycle. Which amino acid is added was controlled by the peptide synthesizer, which looks to the sequence of the peptide that was entered into its database. The synthesis steps were performed as follows:

Step 1—Resin Swelling: Added 2 ml DMF, incubated 30 minutes, drained DMF.

Step 2—Synthesis cycle (repeated over the length of the peptide)
- 2a—Deprotection: 1 ml deprotecting solution was added to the reaction vessel and incubated for 20 minutes.
- 2b—Wash Cycle
- 2c—Coupling: 750 ml of amino acid solution (changed as the sequence listed in the peptide synthesizer dictated) and 250 ml of DIC solution were added to the reaction vessel. The reaction vessel was incubated for thirty minutes and washed once. The coupling step was repeated once.
- 2d—Wash Cycle Step 3—Final Deprotection: Steps 2a and 2b were performed one last time.

Resins were deswelled in methanol (rinsed twice in 5 ml methanol, incubated 5 minutes in 5 ml methanol, rinsed in 5 ml methanol) and then vacuum dried.

Peptide was removed from the resin by incubating 2 hours in reagent R and then precipitated into ether. Peptide was washed in ether and then vacuum dried. Peptide was resolubilized in diH$_2$O, frozen and lyophilized overnight.

Conjugation of Peptide with Keyhole Limpet Hemocyanin

Peptide (6 mg) was conjugated with Keyhole Limpet Hemocyanin (KLH). When the selected peptide included at least one cysteine, three aliquots (2 mg) were dissolved in PBS (2 ml) and coupled to KLH via glutaraldehyde, EDC or maleimide activated KLH (2 mg) in 2 ml of PBS for a total volume of 4 ml. When the peptide lacked cysteine, two aliquots (3 mg) were coupled via glutaraldehyde and EDC methods.

Maleimide coupling is accomplished by mixing 2 mg of peptide with 2 mg of maleimide-activated KLH dissolved in PBS (4 ml) and incubating 4 hr.

EDC coupling is accomplished by mixing 2 mg of peptide, 2 mg unmodified KLH, and 20 mg of EDC in 4 ml PBS (lowered to pH 5 by the addition of phosphoric acid), and incubating for 4 hours. The reaction is stopped by the slow addition of 1.33 ml acetic acid (pH 4.2). When using EDC to couple 3 mg of peptide, the amounts listed above are increased by a factor of 1.5.

Glutaraldehyde coupling occurs when 2 mg of peptide are mixed with 2 mg of KLH in 0.9 ml of PBS. 0.9 ml of 0.2% glutaraldehyde in PBS is added and mixed for one hour. 0.46 ml of 1 M glycine in PBS is added and mixed for one hour. When using glutaraldehyde to couple 3 mg of peptide, the above amounts are increased by a factor of 1.5.

The conjugated aliquots were subsequently repooled, mixed for two hours, dialyzed in 1 liter PBS and lyophilized.

Immunization of Rabbits

Two New Zealand White Rabbits were injected with 250 μg (total) KLH conjugated peptide in an equal volume of complete Freund's adjuvant and saline in a total volume of 1 ml. 100 μg KLH conjugated peptide in an equal volume of incomplete Freund's Adjuvant and saline were then injected into three to four subcutaneous dorsal sites for a total volume of 1 ml two, six, eight and twelve weeks after the first immunization. The immunization schedule was as follows:

| Day 0 | Pre-immune bleed, primary immunization |
| Day 15 | 1st boost |
| Day 27 | 1st bleed |
| Day 44 | 2nd boost |
| Day 57 | 2nd bleed and 3rd boost |
| Day 69 | 3rd bleed |
| Day 84 | 4th boost |
| Day 98 | 4th bleed |

Collection of Rabbit Serum

The rabbits were bled (30 to 50 ml) from the auricular artery. The blood was allowed to clot at room temperature for 15 minutes and the serum was separated from the clot using an IEC DPR-6000 centrifuge at 5000 g. Cell-free serum was decanted gently into a clean test tube and stored at −20° C. for affinity purification.

Determination of Antibody Titer

All solutions with the exception of wash solution were added by the Hamilton Eclipse, a liquid handling dispenser. The antibody titer was determined in the rabbits using an ELISA assay with peptide on the solid phase. Flexible high binding ELISA plates were passively coated with peptide diluted in BBS (100 μl, 1 μg/well) and the plate was incubated at 4° C. in a wetbox overnight (air-tight container with moistened cotton balls). The plates were emptied and then washed three times with BBS containing 0.1% Tween-20 (BBS-TW) by repeated filling and emptying using a semi-automated plate washer. The plates were blocked by completely filling each well with BBS-TW containing 1% BSA and 0.1% gelatin (BBS-TW-BG) and incubating for 2 hours at room temperature. The plates were emptied and sera of both pre- and post-immune serum were added to wells. The first well contained sera at 1:50 in BBS. The sera were then serially titrated eleven more times across the plate at a ratio of 1:1 for a final (twelfth) dilution of 1:204,800. The plates were incubated overnight at 4° C. The plates were emptied and washed three times as described.

Biotinylated goat anti-rabbit IgG (100 μl) was added to each microtiter plate test well and incubated for four hours at room temperature. The plates were emptied and washed three times. Horseradish peroxidase-conjugated Streptavidin (100 μl diluted 1:10,000 in BBS-TW-BG) was added to each well and incubated for two hours at room temperature. The plates were emptied and washed three times. The ABTS was prepared fresh from stock by combining 10 ml of citrate buffer (0.1 M at pH 4.0), 0.2 ml of the stock solution (15 mg/ml in water) and 10 μl of 30% hydrogen peroxide. The ABTS solution (100 μl) was added to each well and incubated at room temperature. The plates were read at 414 nm, 20 minutes following the addition of substrate.

Preparation of Peptide Affinity Purification Column:

The affinity column was prepared by conjugating 5 mg of peptide to 10 ml of cyanogen bromide-activated Sepharose 4B and 5 mg of peptide to hydrazine-Sepharose 4B. Briefly, 100 μl of DMF was added to peptide (5 mg) and the mixture was vortexed until the contents were completely wetted. Water was then added (900 μl) and the contents were vortexed until the peptide dissolved. Half of the dissolved peptide (500 µl) was added to separate tubes containing 10 ml of cyanogen-bromide activated Sepharose 4B in 0.1 ml of borate buffered saline at pH 8.4 (BBS) and 10 ml of hydrazine-Sepharose 4B in 0.1 M carbonate buffer adjusted to pH 4.5 using excess EDC in citrate buffer pH 6.0. The conjugation reactions were allowed to proceed overnight at room temperature. The conjugated Sepharose was pooled and loaded onto fritted columns, washed with 10 ml of BBS, blocked with 10 ml of 1 M glycine and washed with 10 ml 0.1 M glycine adjusted to pH 2.5 with HCl and re-neutralized in BBS. The column was washed with enough volume for the optical density at 280 nm to reach baseline.

Affinity Purification of Antibodies

The peptide affinity column was attached to a UV monitor and chart recorder. The titered rabbit antiserum was thawed and pooled. The serum was diluted with one volume of BBS and allowed to flow through the columns at 10 ml per minute. The non-peptide immunoglobulins and other proteins were washed from the column with excess BBS until the optical density at 280 nm reached baseline. The columns were disconnected and the affinity purified column was eluted using a stepwise pH gradient from pH 7.0 to 1.0. The elution was monitored at 280 nm and fractions containing antibody (pH 3.0 to 1.0) were collected directly into excess 0.5 M BBS. Excess buffer (0.5 M BBS) in the collection tubes served to neutralize the antibodies collected in the acidic fractions of the pH gradient.

The entire procedure was repeated with "depleted" serum to ensure maximal recovery of antibodies. The eluted material was concentrated using a stirred cell apparatus and a membrane with a molecular weight cutoff of 30 kD. The concentration of the final preparation was determined using an optical density reading at 280 nm. The concentration was determined using the following formula: mg/ml=$OD_{280}$/1.4.

It will be appreciated that in certain embodiments, additional steps may be used to purify antibodies of the invention. In particular, it may prove advantageous to repurify antibodies, e.g., against one of the peptides that was used in generating the antibodies. It is to be understood that the present invention encompasses antibodies that have been prepared with such additional purification or repurification steps. It will also be appreciated that the purification process may affect the binding between samples and the inventive antibodies.

Example 8

Preparing and Staining Tissue Arrays

This example describes a method that was employed to prepare the tissue arrays that were used in Examples 1-6. This example also describes how the antibody staining was performed.

Tissue arrays were prepared by inserting full-thickness cores from a large number of paraffin blocks (donor blocks) that contain fragments of tissue derived from many different patients and/or different tissues or fragments of tissues from a single patient, into a virgin paraffin block (recipient block) in a grid pattern at designated locations in a grid. A standard slide of the paraffin embedded tissue (donor block) was then made which contained a thin section of the specimen amenable to H & E staining A trained pathologist, or the equivalent versed in evaluating tumor and normal tissue, designated the region of interest for sampling on the tissue array (e.g., a tumor area as opposed to stroma). A commercially available tissue arrayer from Beecher Instruments was then used to remove a core from the donor block which was then inserted into the recipient block at a designated location. The process was repeated until all donor blocks had been inserted into the recipient block. The recipient block was then thin-sectioned to yield 50-300 slides containing cores from all cases inserted into the block.

The selected antibodies were then used to perform immunohistochemical staining using the DAKO Envision+, Peroxidase IHC kit (DAKO Corp., Carpenteria, Calif.) with DAB substrate according to the manufacturer's instructions.

Example 9

Correlating Interaction Partner Binding with Outcome/Responsiveness of Xenograft Tumors According to the present invention, panels of useful interaction partners may be defined through analysis of human tumor cells grown in a non-human host. In particular, such analyses may define interaction partner panels whose binding correlates with prognosis and/or with responsiveness to therapy.

Cells derived from human tumors may be transplanted into a host animal (e.g., a mouse), preferably into an immunocompromised host animal. In preferred embodiments of the invention, cells (e.g., cell lines, tumor samples obtained from human patients, etc.) from a variety of different human tumors (e.g., at least 10, 20, 30, 40, 50, 60 or more different tumors) are transplanted into host animals. The animals are then treated with different (e.g., increasing) concentrations of a chemical compound known or thought to be selectively toxic to tumors with a predetermined common characteristic (e.g., class or subclass). Relative growth or regression of the tumors may then be assessed using standard techniques.

In certain embodiments of the invention, a dataset of sensitivity of the transplanted cells to a given compound or set of compounds may optionally be created. For example, a dataset might consist of the concentration of compound administered to the host animal that inhibited tumor growth 50% at 96 hr (i.e., the $LD_{50}$) for each of the cell samples or cell lines tested. Such a dataset, for example across at least 10, 20, 30, 40, 50, 60 or more cell lines, could then be correlated with the relative staining of the binding partners across the same cell lines. Those binding partners whose interaction (or lack thereof) with cells was highly correlated with either sensitivity to or resistance to a given compound would be useful members of a predictive panel.

Example 10

Correlating Interaction Partner Binding with Clinical Prognostic Data in Breast Cancer According to the present invention, panels of useful interaction partners may be defined through analysis of correlations between binding patterns and clinical prognostic data. In particular, such analyses may define interaction partner panels whose binding correlates with prognosis.

The following describes the identification of exemplary panels of antibodies whose binding has been shown to correlate with the prognosis of breast cancer patients. The data was obtained using samples from the Huntsville Hospital breast cohort (the "HH breast" cohort) that was referred to in Example 3.

The HH breast cohort was generated from 1082 breast cancer patients that were treated by the Comprehensive Cancer Institute (Huntsville, Ala.) between 1990 and 2000. This larger group was filtered to a study group of 550 patients by eliminating patients according to the following criteria: 249 that had no chart which could be found; 103 that had no clinical follow up; and 180 that did not have sufficient clinical material in the paraffin block to sample. For the remaining 550 patients, clinical data through Dec. 31, 2002 was available. Every patient in the cohort therefore had between 2 and 13 years of follow-up. The average time of follow-up among patients who did not recur was 5.6 years. Of the 550 patients, 140 had a recurrence of cancer within the study period; 353 patients were estrogen receptor positive (ER+); 154 were estrogen receptor negative (ER−); and 43 were undetermined. Some patients within these groups received adjuvant hormone therapy as shown in Table 1:

TABLE 1

|  | Total | Hormone | No hormone | Unknown |
|---|---|---|---|---|
| ER+ | 353 | 278 | 68 | 7 |
| ER− | 154 | 70 | 83 | 1 |
| Undetermined | 43 | 28 | 15 | 0 |

In addition, 263 patients received chemotherapy. Up to 16 different regimens were used, however, most were variants of cyclophosphamide, doxorubicin (with and without 5-fluorouracil and/or cyclophosphamide), methotrexate and 5-fluorouracil. Finally, 333 of the patients received radiation. Clinical information regarding age, stage, node status, tumor size, and grade was obtained.

The clinical information for the patients in the cohort is summarized in Table 2.

TABLE 2

|  | All (550) | ER+ (353) | ER− (154) |
|---|---|---|---|
| Stage = 1 | 236 | 162 | 49 |
| Stage = 2 | 269 | 167 | 87 |
| Stage = 3 | 44 | 23 | 18 |
| Undetermined | 1 | 0 | 0 |
| Mean Age @ Dx | 58 | 59 | 55 |
| Tumor status = 0 | 1 | 0 | 1 |
| Tumor status = 1 | 295 | 203 | 63 |
| Tumor status = 2 | 195 | 122 | 62 |
| Tumor status = 3 | 26 | 14 | 11 |
| Tumor status = 4 | 14 | 6 | 8 |
| Undetermined | 21 | 8 | 9 |
| Node status = 0 | 326 | 215 | 76 |
| Node status = 1 | 205 | 127 | 71 |
| Node status = 2 | 10 | 6 | 3 |
| Undetermined | 10 | 5 | 4 |
| Metastasis = 0 | 527 | 338 | 147 |
| Metastasis = 1 | 5 | 4 | 1 |
| Undetermined | 19 | 11 | 6 |

Where each category is defined in Table 3. These rules are not fixed and staging is typically done by an oncologist based on TNM status and other factors. These definitions for staging will not necessarily match with the stage that each patient was actually given. Node status is the primary tool for staging purposes.

TABLE 3

| | |
|---|---|
| Tumor status = 0 | No evidence of tumor |
| Tumor status = 1 | <2 cm |
| Tumor status = 2 | 2-5 cm |
| Tumor status = 3 | >5 cm |
| Tumor status = 4 | Any size but extends to chest wall |
| Node status = 0 | No regional LN metastasis |
| Node status = 1 | Ancillary LN metastasis but nodes still moveable |
| Node status = 2 | Ancillary LN metastasis with nodes fixed to each other OR internal mammary node metastasis |
| Metastasis = 0 | No distant metastasis |
| Metastasis = 1 | Distant metastasis |
| Stage = 1 | T1, N0, M0 |
| Stage = 2 | T0, N1, M0    T1, N1, M0    T2, N0, M0    T2, N1, M0    T3, N0, M0 |
| Stage = 3 | T(0-3), N2, M0    T3, N1, M0    T4, NX, M0 |
| Stage = 4 | TX, NX, M1 |

Samples from patients in the cohort were stained with antibodies from the breast cancer classification panel identified in Appendix A (as previously described in Examples 2 and 3). The stained samples were then scored in a semi-quantitative fashion, with 0=negative, 1=weak staining, and 2=strong staining When appropriate, alternative scoring systems were used (i.e., 0=negative, 1=weak or strong; or 0=negative or weak and 1=strong staining) For each antibody, the scoring system used was selected to produce the most significant prognostication of the patients, as determined by a log-rank test (e.g., see Mantel and Haenszel, *Journal of the National Cancer Institute* 22:719-748, 1959). The results are presented in Appendix C and are grouped into four categories that have been clinically recognized to be of significance: all patients, ER+ patients, ER− patients, and ER+/node− patients. As shown, the antibodies were found to have differing significances for each of these categories of breast cancer patients.

It is to be understood that exclusion of a particular antibody from any prognostic panel based on these experiments is not determinative. Indeed, it is anticipated that additional data with other samples may lead to the identification of other antibodies (from Appendix A and beyond) that may have prognostic value for these and other classes of patients.

The expected relationship between the staining of patient samples with each antibody and the recurrence of tumors was measured using the Kaplan-Meier estimate of expected recurrence (e.g., see Kaplan and Meier, *J. Am. Stat. Assn.* 53:457-81, 1958). The log-rank test was used to determine the significance of different expected recurrences for each antibody (e.g., see Mantel and Haenszel, *Journal of the National Cancer Institute*, 22:719-748, 1959). This produces the p-value that is listed for each antibody in Appendix C. Preferred antibodies are those that produce a p-value of less than 0.10.

The degree to which these antibodies predicted recurrence was determined using a Cox univariate proportional hazard model (e.g., see Cox and Oakes, "Analysis of Survival Data", Chapman & Hall, 1984). The "hazard ratio" listed in Appendix C for each antibody reflects the predicted increase in risk of recurrence for each increase in the staining score. Scores greater than 1.0 indicate that staining predicts an increased risk of recurrence compared to an average individual, scores less than 1.0 indicate that staining predicts a decreased risk.

It will be appreciated that these antibodies can be used alone or in combinations to predict recurrence (e.g., in combinations of 2, 3, 4, 5, 6, 7, 8, 9, 10 or more antibodies). It will also be appreciated that while a given antibody may not predict recurrence when used alone the same antibody may predict recurrence when used in combination with others. It will also be understood that while a given antibody or combination of antibodies may not predict recurrence in a given set of patients (e.g., ER+ patients), the same antibody or combination of antibodies may predict recurrence in a different set of patients (e.g., ER− patients). Similarly, it is to be understood that while a given antibody or combination of antibodies may not predict recurrence in a given set of patients (e.g., ER+ patients), the same antibody or combination of antibodies may predict recurrence in a subset of these patients (e.g., ER+/node negative patients).

These prognostic panels could be constructed using any method. Without limitation these include simple empirically derived rules, Cox multivariate proportional hazard models (e.g., see Cox and Oakes, "Analysis of Survival Data", Chapman & Hall, 1984), regression trees (e.g., see Segal and Bloch, *Stat. Med.* 8:539-50, 1989), and/or neural networks (e.g., see Ravdin et al., *Breast Cancer Res. Treat.* 21:47-53, 1992). In certain embodiments a prognostic panel might include between 2-10 antibodies, for example 3-9 or 5-7 antibodies. It will be appreciated that these ranges are exemplary and non-limiting.

The prognostic value of exemplary panels of antibodies were also assessed by generating Kaplan-Meier recurrence curves for ER+ and ER+/node− patients and then comparing these with curves produced for these same patients with the standard Nottingham Prognostic Index (NPI).

Figure 4A:
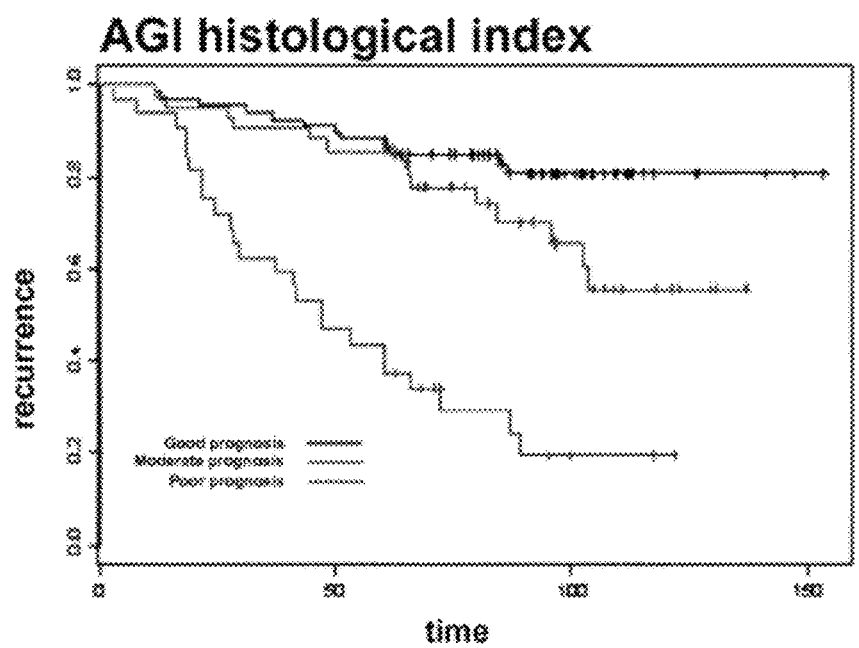
FIG. 4 shows Kaplan-Meier curves that were generated for ER+ patients after prognostic classification based on (A) staining with a prognostic panel of antibodies from Appendix C and (B) the Nottingham Prognostic Index (NPI). In each case the patients were placed into one of three prognostic groups, namely "poor" (bottom curve), "moderate" (middle curve) and "good" (top curve).
Figure 5A:
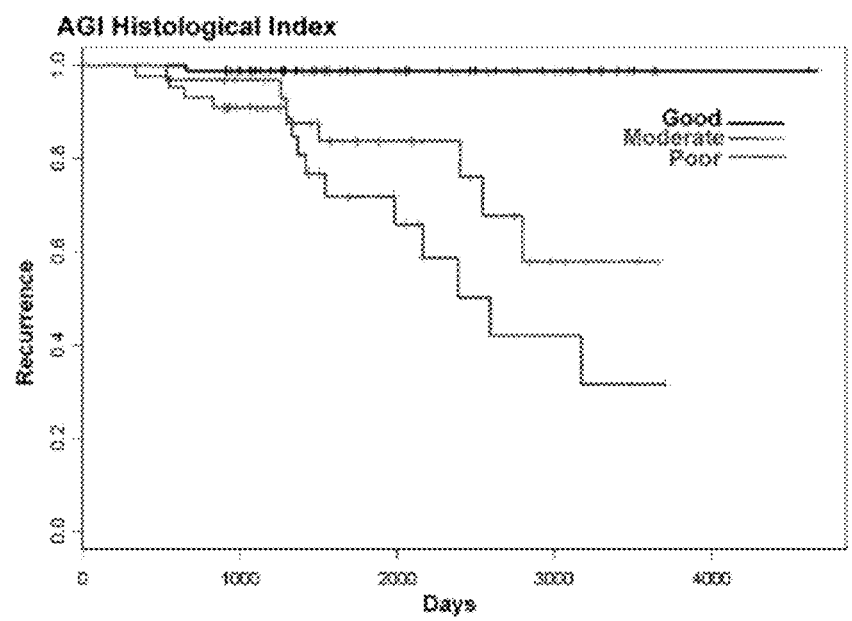
FIG. 5 shows Kaplan-Meier curves that were generated for ER+/node− patients after prognostic classification based on (A) staining with a prognostic panel of antibodies from Appendix C and (B) the Nottingham Prognostic Index (NPI). In each case the patients were placed into one of three prognostic groups, namely "poor" (bottom curve), "moderate" (middle curve) and "good" (top curve). Note that under the NPI scheme ER+/node− patients are never categorized as having a "poor" prognosis. For this reason, FIG. 5B only includes curves for patients with a "moderate" or "good" prognosis.

In order to generate Kaplan-Meier curves based on antibody panels, Cox univariate proportional hazard regression models were first run with all antibodies from Appendix C utilizing all three scoring procedures. The antibodies and scoring systems best able to predict recurrence were then used in a regression tree model and pruned to maintain predictive power while reducing complexity. Patients whom the panel predicted as being strongly likely to recur were placed in the "poor" prognosis group. Patients whom the panel predicted as being strongly unlikely to recur were given the prediction of "good". Patients whom the panel predicted as neither being strongly likely to recur or not recur were placed in the "moderate" prognosis group. Kaplan-Meier curves were then calculated based on recurrence data for patients within each group. FIG. 4A show the curves that were obtained for ER+ patients in each of these prognostic groups. FIG. 5A show the curves that were obtained for ER+/node− patients in each of these prognostic groups.

The antibodies from Appendix C that were used to predict recurrence for ER+ patients (FIG. 4A) were: s0296P1 (1:225 dilution, scoring method 3), s6006 (1:1 dilution, scoring method 2), s0545 (1:900 dilution, scoring method 2), s0063 (1:300 dilution, scoring method 2), s6002 (1:1 dilution, scoring method 3), s0081 (1:20 dilution, scoring method 2), s0255 (1:1000 dilution, scoring method 3), and s0039 (1:100 dilution, scoring method 2).

The antibodies from Appendix C that were used to predict recurrence for ER+/node− patients (FIG. 5A) were: s0143P3 (1:630 dilution, scoring method 1), s0137 (1:2500 dilution, scoring method 2), s0260 (1:5400 dilution, scoring method 2), s0702 (1:178200 dilution, scoring method 2), s0545 (1:900 dilution, scoring method 2), s6002 (1:1 dilution, scoring method 1), and s6007 (1:1 dilution, scoring method 1).

Kaplan-Meier recurrence curves were then generated for the same patients based on their standard NPI scores. NPI scores were calculated for patients according to the standard formula NPI=(0.2×tumor diameter in cm)+lymph node stage+tumor grade. As is well known in the art, lymph node stage is either 1 (if there are no nodes affected), 2 (if 1-3 glands are affected) or 3 (if more than 3 glands are affected). The tumor grade was scored according to the Bloom-Richardson Grade system (Bloom and Richardson, *Br. J. Cancer* 11:359-377, 1957). According to this system, tumors were examined histologically and given a score for the frequency of cell mitosis (rate of cell division), tubule formation (percentage of cancer composed of tubular structures), and nuclear pleomorphism (change in cell size and uniformity). Each of these features was assigned a score ranging from 1 to 3 as shown in Table 4. The scores for each feature were then added together for a final sum that ranged between 3 to 9. A tumor with a final sum of 3, 4, or 5 was considered a Grade 1 tumor (less aggressive appearance); a sum of 6 or 7 a Grade 2 tumor (intermediate appearance); and a sum of 8 or 9 a Grade 3 tumor (more aggressive appearance).

TABLE 4

|  | Score |
|---|---|
| Tubule formation (% of carcinoma composed of tubular structures) | |
| >75% | 1 |
| 10-75% | 2 |
| <10% | 3 |
| Nuclear pleomorphism (Change in Cells) | |
| Small, uniform cells | 1 |
| Moderate increase in size and variation | 2 |
| Marked variation | 3 |
| Mitosis Count (Cell Division) | |
| Up to 7 | 1 |
| 8 to 14 | 2 |
| 15 or more | 3 |

Figure 4B:
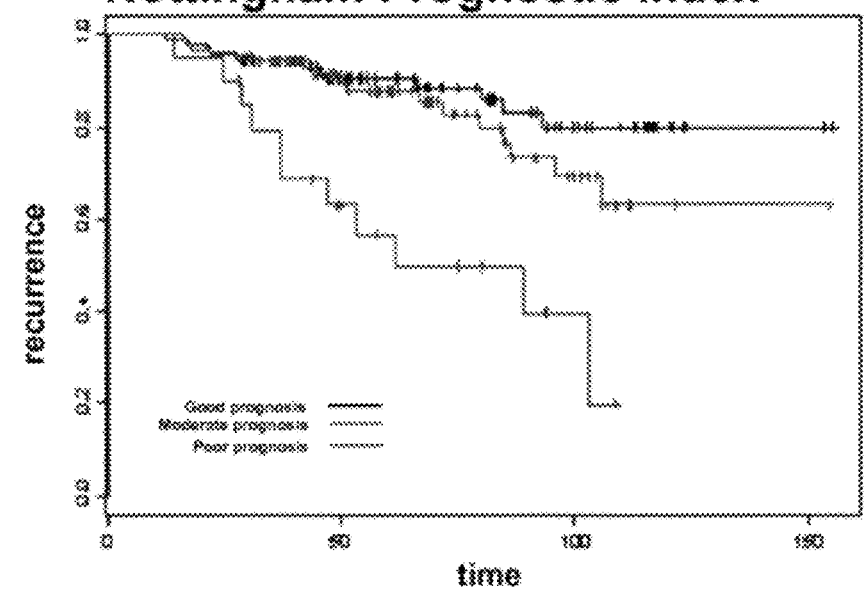
Figure 5B:
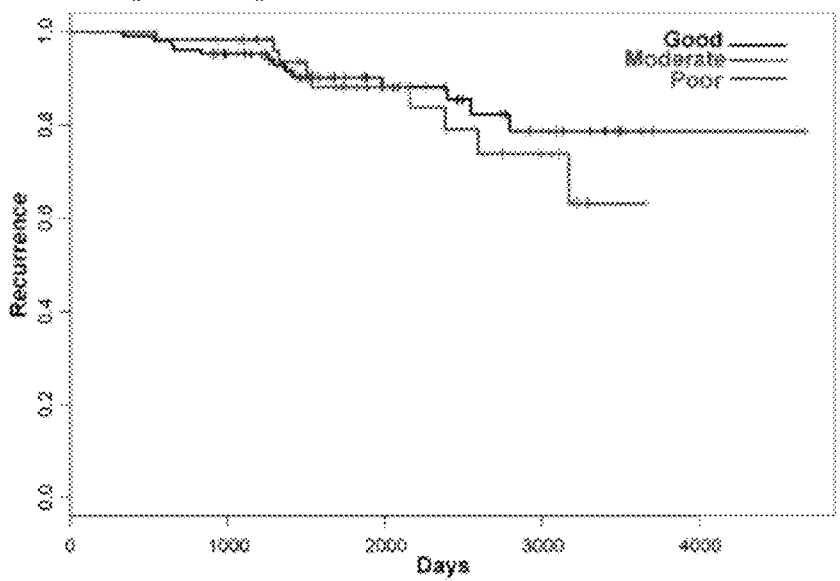

Patients with tumors having an overall NPI score of less than 3.4 were placed in the "good" prognosis group. Those with an NPI score of between 3.4 and 5.4 were placed in the "moderate" prognosis group and patients with an NPI score of more than 5.4 were placed in the "poor" prognosis group. Kaplan-Meier curves were then calculated based on recurrence data for patients within each group. FIG. 4B show the curves that were obtained for ER+ patients in each of these NPI prognostic groups. FIG. 5B show the curves that were obtained for ER+/node− patients in each of these NPI prognostic groups. By definition ER+/node− patients have an NPI score that is less than 5.4. This explains why there is no "poor" prognosis curve in FIG. 5B. Example 12 describes other exemplary prognostic panels for breast cancer patients.

Example 11

Correlating Interaction Partner Binding with Clinical Prognostic Data in Lung Cancer This Example describes the identification of exemplary panels of antibodies whose binding has been shown to correlate with the prognosis of lung cancer patients. The data was obtained using samples from the Huntsville Hospital lung cohort (the "HH lung" cohort) that was referred to in Example 5.

The HH lung cohort was generated from 544 lung cancer patients that were treated by the Comprehensive Cancer Institute (Huntsville, Ala.) between 1987 and 2002. This larger group was filtered to a study group of 379 patients by eliminating patients that had insufficient clinical follow up or that did not have sufficient clinical material in the paraffin block to sample. For the remaining patients, clinical data through Sep. 30, 2003 was available. This set of patients consisted of 232 males and 147 females. The average time of follow-up among patients who did not recur was 3.5 years. Of the 379 patients, 103 had a recurrence of cancer within the study period. All patients in this study were diagnosed at a pathological stage of 1 or 2, with 305 patients at stage 1, 1A, or 1B, and 74 patients at stage 2, 2A, or 2B.

Samples from patients in the cohort were stained with antibodies from the lung cancer classification panel identified in Appendix A (as previously described in Examples 4 and 5). The stained samples were then scored in a semi-quantitative fashion; scoring methods 1-3 use the following schemes: method 1 (0=negative; 1=weak; 2=strong); method 2 (0=negative; 1=weak or strong); and method 3 (0=negative or weak; 1=strong). For each antibody, the scoring system used was selected to produce the most significant prognostication of the patients, as determined by a log-rank test (e.g., see Mantel and Haenszel, *Journal of the National Cancer Institute* 22:719-748, 1959). The results are presented in Appendix D and are grouped into three categories that have been clinically recognized to be of significance: all patients, adenocarcinoma patients, and squamous cell carcinoma patients. As shown, the antibodies were found to have differing significances for each of these categories of lung cancer patients.

It is to be understood that exclusion of a particular antibody from any prognostic panel based on these experiments is not determinative. Indeed, it is anticipated that additional data with other samples may lead to the identification of other antibodies (from Appendix A and beyond) that may have prognostic value for these and other classes of patients.

As for the breast study of Example 10, the expected relationship between the staining of patient samples with each antibody and the recurrence of tumors was measured using the Kaplan-Meier estimate of expected recurrence and a log-rank test was used to determine the significance of different expected recurrences. This produces the p-value that is listed for each antibody in Appendix D. Preferred antibodies are those that produce a p-value of less than 0.10.

The degree to which these antibodies predicted recurrence was determined using a Cox univariate proportional hazard model. The "hazard ratio" listed in Appendix D for each antibody reflects the predicted increase in risk of recurrence for each increase in the staining score. Scores greater than 1.0 indicate that staining predicts an increased risk of recurrence compared to an average individual, scores less than 1.0 indicate that staining predicts a decreased risk.

As a number of patients had information regarding whether or not the cancer recurred but lacked information on time to recurrence, a chi-square test was also performed. This standard statistical test shows the degree of divergence between observed and expected frequencies and does not employ time to recurrence, as does the log-rank test. Preferred antibodies are those that produce a p-value of less than 0.10.

It will be appreciated that these prognostic antibodies can be used alone or in combinations to predict recurrence (e.g., in combinations of 2, 3, 4, 5, 6, 7, 8, 9, 10 or more antibodies). It will also be appreciated that while a given antibody may not predict recurrence when used alone, the same antibody may predict recurrence when used in combination with others. It will also be understood that while a given antibody or combination of antibodies may not predict recurrence in a given set of patients (e.g., adenocarcinoma patients), the same antibody or combination of antibodies may predict recurrence in a different set of patients (e.g., squamous cell carcinoma patients).

As for the breast study of Example 10, these prognostic panels could be constructed using any method. Without limitation these include simple empirically derived rules, Cox multivariate proportional hazard models, regression trees, and/or neural networks. In certain embodiments a prognostic panel might include between 2-10 antibodies, for example 3-9 or 5-7 antibodies. It will be appreciated that these ranges are exemplary and non-limiting. The construction of exemplary prognostic panels for lung cancer patients is described in Example 13.

Example 12

Prognostic Breast Cancer Panels

This Example builds on the results of Example 10 and describes the identification of additional exemplary panels of antibodies whose binding has been shown to correlate with the prognosis of breast cancer patients.

First, the individual prognostic ability of the antibodies of Appendix C was refined using samples from the HH breast cohort that was described in Example 2. In particular, certain antibodies were excluded based on subjective assessment of specificity and scoreability. The methodology paralleled that used in Example 10 and the updated antibody data is presented in Appendix E.

Second, prognostic panels in two currently identified clinically important subclasses of breast cancer patients were generated, namely ER+/node- patients and ER- patients. To minimize the chance of identifying spurious associations, only those antibodies from Appendix E that showed sufficient significance (p-value of less than 0.10) in either the ER+ or ER+/node- patient classes were used in creating prognostic panels for the ER+/node- patients, and only the similarly significant markers from the ER- patient set for creating a prognostic panel for the ER- patients. Using Cox proportional hazard analysis and regression tree analysis (as described in Example 10) candidate panels (and dendrograms for regression tree analysis) were derived for prediction of early recurrence. For both ER+/node- patients and ER- patients, panels and dendrograms were chosen that identified patients with significantly increased risks of recurrence.

Prognostic Panels Generated by Cox Analysis

Cox proportional hazard analysis treats the component antibodies of a panel as additive risk factors. The panels for the specified patient classes were created by initially using all applicable antibodies, and then iteratively removing antibodies from the panel. If the removal of an antibody increased or did not affect the significance and prognostic ability of the panel as a whole, it was excluded, otherwise it was retained. In this manner preferred panels with minimal numbers of antibodies were created. The preferred panels for ER+/node- and ER- patients are presented in Tables 5 and 6, respectively. Antibodies within the preferred panels are ranked based on their relative contributions to the overall prediction function.

TABLE 5

| Panel | Analysis | P value[1] | Hazard ratio[2] |
|---|---|---|---|
| Breast ER+/node− | Cox | 8.17E−05 | 5.68 |
| AGI ID | Rank | P value[3] | Terms[4] |
| S0702/s0296P1 | 1 | 0.00015 | −0.213, 1.330 |
| s6006 | 2 | 0.00660 | −0.325, 0.799 |
| s0404 | 3 | 0.06200 | −0.099, 0.958 |
| s0545 | 4 | 0.10000 | −0.112, 0.604 |
| s0235 | 5 | 0.25000 | −0.114, 0.390 |

[1] P value of overall panel
[2] Hazard ratio of overall panel
[3] P value of the contribution of a given antibody to the overall panel
[4] Contribution of given antibody to overall panel prediction function depending on IHC score (e.g., scores of 0 or 1 for s6006 which uses scoring method 2 [see Appendix E] result in its term in the model equaling −0.325 or 0.799, respectively).

TABLE 6

| Panel | Analysis | P value[1] | Hazard ratio[2] |
|---|---|---|---|
| Breast ER− | Cox | 3.10E−03 | 2.25 |
| AGI ID | Rank | P value[3] | Terms[4] |
| s0691 | 1 | 0.04700 | −0.163, 0.436, 0.640 |
| s0545 | 2 | 0.08900 | −0.339, 0.259 |
| s0330x1 | 3 | 0.57000 | 0.510, −5.560 |

[1,2,3,4] See Table 5

Figure 6:
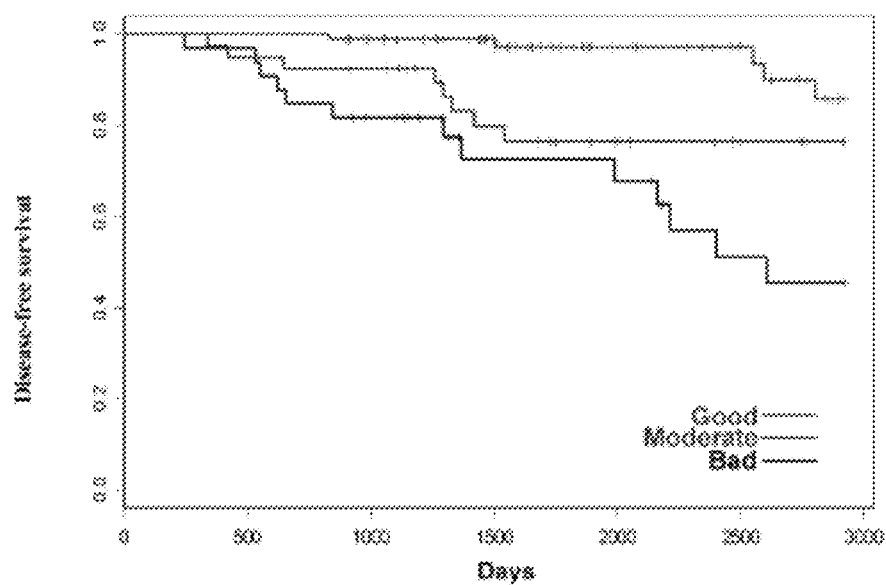
FIG. 6 shows Kaplan-Meier curves that were generated for ER+/node− patients after prognostic classification based on staining with the exemplary prognostic panel of antibodies from Table 5. In each case the patients were placed into one of three prognostic groups, namely "bad" (bottom curve), "moderate" (middle curve) and "good" (top curve).
Figure 7:
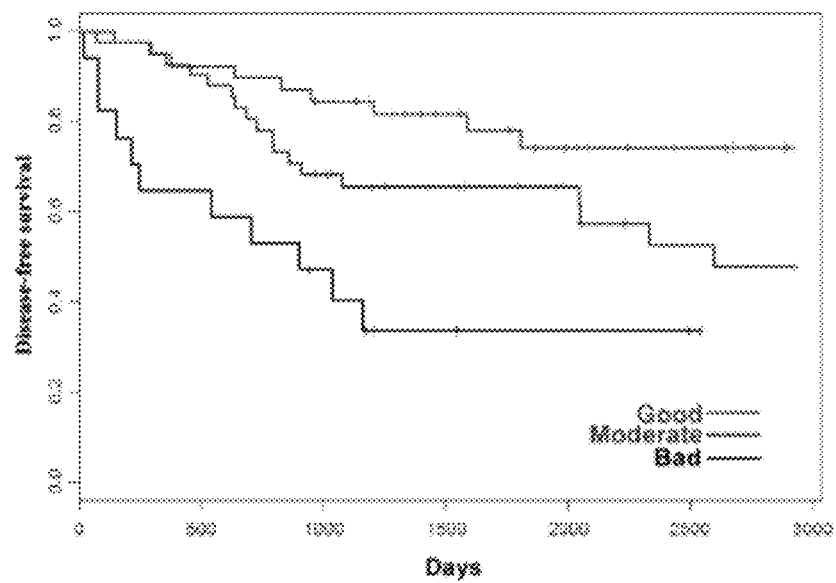
FIG. 7 shows Kaplan-Meier curves that were generated for ER− patients after prognostic classification based on staining with the exemplary prognostic panel of antibodies from Table 6. In each case the patients were placed into one of three prognostic groups, namely "bad" (bottom curve), "moderate" (middle curve) and "good" (top curve).

The prognostic value of these exemplary panels were assessed by generating Kaplan-Meier recurrence curves for ER+/node− and ER− patients. Patients whom the panels predicted as being strongly likely to recur were placed in the "bad" prognosis group. Patients whom the panels predicted as being strongly unlikely to recur were given the prediction of "good". Patients whom the panels predicted as neither being strongly likely to recur or not recur were placed in the "moderate" prognosis group. Kaplan-Meier curves were then calculated based on recurrence data for patients within each group. FIG. 6 shows the curves that were obtained for ER+/node− patients in each of these prognostic groups. FIG. 7 shows the curves that were obtained for ER− patients in each of these prognostic groups.

When lymph node status was included as an additional variable for the ER− patient set the preferred panel was as shown in Table 7.

TABLE 7

| Panel | Type | P value[1] | Hazard ratio[2] |
|---|---|---|---|
| Breast ER− | Cox plus node | 3.70E−05 | 3.93 |
| AGI ID | Rank | P value[3] | Terms[4] |
| s6007 | 1 | 0.05000 | −0.460, 0.280 |
| s0545 | 2 | 0.06400 | −0.400, 0.290 |
| s0068 | 3 | 0.18000 | −0.350, 0.160 |
| s0330x1 | 4 | 0.62000 | −5.820, 0.450 |

[1,2,3,4] See Table 5

Figure 8:
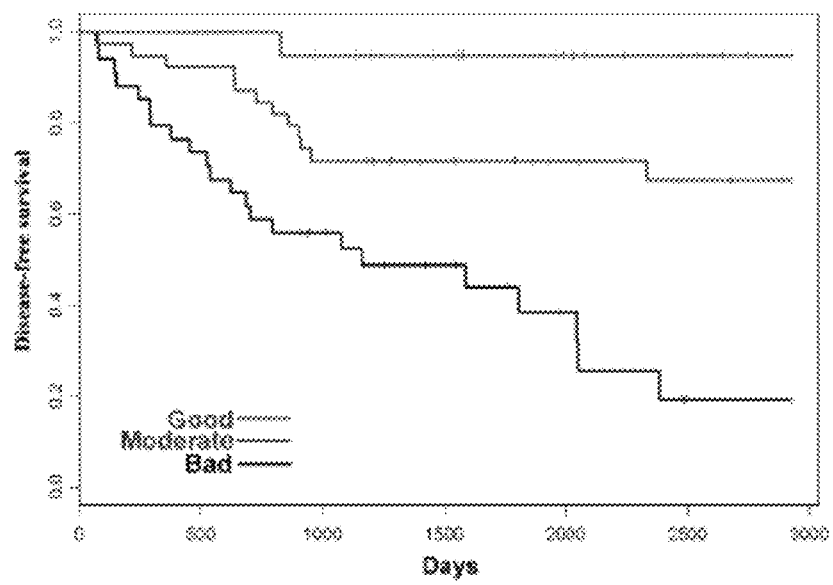
FIG. 8 shows Kaplan-Meier curves that were generated for ER− patients after prognostic classification based on staining with the exemplary prognostic panel of antibodies from Table 7. In each case the patients were placed into one of three prognostic groups, namely "bad" (bottom curve), "moderate" (middle curve) and "good" (top curve).

The prognostic value of this exemplary panel was also assessed by generating Kaplan-Meier recurrence curves for ER− patients. Patients whom the panel predicted as being strongly likely to recur were placed in the "bad" prognosis group. Patients whom the model predicted as being strongly unlikely to recur were given the prediction of "good". Patients whom the model predicted as neither being strongly likely to recur or not recur were placed in the "moderate" prognosis group. Kaplan-Meier curves were then calculated based on recurrence data for patients within each group. FIG. 8 shows the curves that were obtained for ER− patients in each of these prognostic groups.

While the preferred Cox panels of the invention for ER+/node− and ER− patients include each of the listed antibodies, it is to be understood that other related panels are encompassed by the present invention. In particular, it will be appreciated that the present invention is in no way limited to the specific antibodies listed. For example, other antibodies directed to the same biomarker(s) may be used (e.g., taking the Cox ER+/node− panel, it can be readily seen from Appendix A that antibodies s0702 or s0296P1 can be replaced with other antibodies directed to biomarker Hs.184601; antibody s6006 can be replaced with other antibodies directed to biomarker Hs.1846, etc.). As noted, addition of certain antibodies from Appendix E had no effect on the significance and prognostic ability of the panel as a whole. Thus, antibodies may be added to any given panel without necessarily diminishing the utility of a panel for patient prognosis. The inclusion of antibodies beyond those listed in Appendix E is also within the scope of the invention. In certain embodiments less than all of the listed antibodies may be used in a prognostic panel.

Generally, a Cox panel for ER+/node− patients will include at least two antibodies selected from the group consisting of antibodies directed to biomarkers Hs.184601, Hs.1846, Hs.75789, Hs.63609 and Hs.220529 (e.g., s0702 and/or s0296P1, s6006, s0404, s0545 and s0235, see Table 5 and Appendix A). Preferably, the panel will include an antibody directed to biomarker Hs.184601 and at least one antibody directed to a biomarker selected from the group consisting of Hs.1846, Hs.75789, Hs.63609 and Hs.220529. All permutations of these antibodies are encompassed. In one embodiment an antibody to biomarker Hs.184601 (e.g., s0702 and/or s0296P1) is used with an antibody to biomarker Hs.1846 (e.g., s6006). In another embodiment an antibody to biomarker Hs.184601 is used with antibodies to biomarkers Hs.1846 and Hs.75789 (e.g., s6006 and s0404). In other embodiments an antibody to biomarker Hs.184601 is used with antibodies to biomarkers Hs.1846, Hs.75789, Hs.63609 and optionally Hs.220529 (e.g., s6006, s0404, s0545 and optionally s0235). In preferred embodiments an antibody to Hs.184601 is used with antibodies to biomarkers Hs.1846, Hs.75789, Hs.63609 and Hs.220529.

Similarly, a Cox panel for ER− patients will include at least two antibodies selected from the group consisting of antibodies directed to biomarkers Hs.6682, Hs.63609 and Hs.306098 (e.g., s0691, s0545 and s0330×1, see Table 6 and Appendix A). Preferably, the panel will include an antibody directed to biomarker Hs.6682 and antibodies to one or both of biomarkers Hs.63609 and Hs.306098. In preferred embodiments an antibody to biomarker Hs.6682 is used with antibodies to biomarkers Hs.63609 and Hs.306098.

When lymph node status is used as an additional variable, an inventive prognostic Cox panel for ER− patients will include at least two antibodies selected from the group consisting of antibodies directed to biomarkers Hs.80976, Hs.63609, Hs.416854 and Hs.306098 (e.g., s6007, s0545, s0068 and s0330×1, see Table 7 and Appendix A). Preferably, the panel will include an antibody directed to biomarker Hs.80976 and antibodies to one or more of biomarkers Hs.63609, Hs.416854 and Hs.306098. All permutations of these antibodies are encompassed. In one embodiment an antibody to biomarker Hs.80976 is used with an antibody to biomarker Hs.63609. In another embodiment an antibody to biomarker Hs.80976 is used with antibodies to biomarkers Hs.63609 and Hs.416854 and optionally with a biomarker to Hs.306098. In preferred embodiments an antibody to biomarker Hs.80976 is used with antibodies to biomarkers Hs.63609, Hs.416854 and Hs.306098.

The present invention also encompasses methods of assessing the prognosis of a patient having a breast tumor using these exemplary panels. After obtaining a tumor sample from a patient with unknown prognosis the sample is contacted with two or more antibodies from the panels of Tables 5, 6 and/or 7. The patient's likely prognosis is then assessed based upon the pattern of positive and negative binding of the two or more antibodies to the tumor sample.

Prognostic Panels Generated by Regression Tree Analysis

Figure 9:
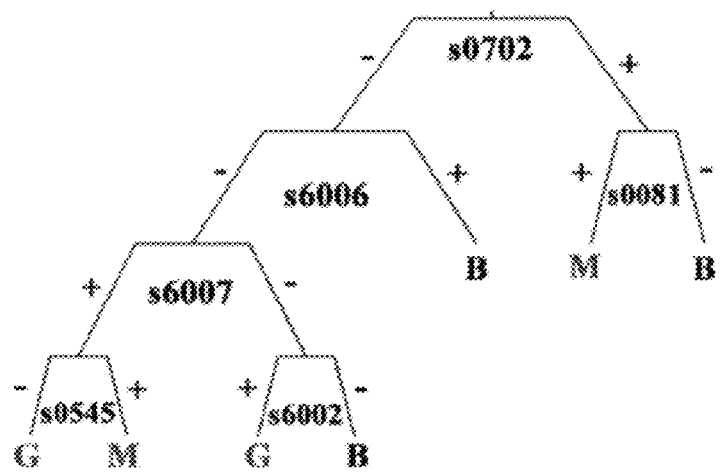
FIG. 9 shows a dendrogram for the tree panel of Table 8 that may be used for the prognostic classification of ER+/node− patients. If a patient is positive for staining at a given node his or her prognosis decision tree follows the branch marked with a "+". Conversely if a patient is negative for staining at a given node his or her prognosis decision tree follows the branch marked "−". This is done until a terminus is reached.

Regression trees classify the patients into a number of subclasses each defined by their pattern of binding to a unique set of antibodies from within a panel. An exemplary tree (or "dendrogram") for ER+/node− patients is shown in FIG. 9 which is discussed below. Regression trees were initially created with all applicable antibodies, and then "pruned" to a minimal complexity (least number of terminal nodes without losing too much prognostic ability) using a cross validation procedure. This cross validation procedure involved building panels and dendrograms using a series of patient groups that were picked from the total patient set using a series of increasingly pruned trees. The results over the tested groups were summed and the minimally complex least error-prone panel and dendrogram were chosen. The resulting dendrogram was further simplified by placing nodes with a range of response values into the classes "good" or "poor" (or alternatively "good", "moderate" or "poor"). Table 8 lists the antibodies of an exemplary ER+/node− tree panel that was constructed as described above. The dendrograms for this panel is illustrated in FIG. 9.

TABLE 8

| Panel | Analysis | P value[1] | Hazard ratio[2] |
|---|---|---|---|
| Breast ER+/node− | Tree | 2.82E−05 | 6.06 |

| AGI ID | Rank |
|---|---|
| s0702/s0296P1 | 1 |
| s0081 | 2 |
| s6006 | 2 |
| s6007 | 3 |
| s0545 | 4 |
| s6002 | 4 |

[1]P value of overall panel
[2]Hazard ratio of overall panel

As illustrated in FIG. 9, if a patient is positive for staining at a given node his or her prognosis decision tree follows the branch marked with a "+". Conversely if a patient is negative for staining at a given node his or her prognosis decision tree follows the branch marked "−". This is done until a terminus is reached.

For example, if patient A is positive for staining with s0702 and negative for staining with s0081 then, based on the dendrogram, his or her prognosis is "bad". In contrast, if patient B is negative for staining with s0702, negative for staining with s6006, positive for staining with s6007 and negative for staining with s0545 then his or her prognosis is "good". It will be appreciated from the foregoing and FIG. 9 that the number of stains required in order to yield a prognosis will vary from patient to patient. However, from a practical standpoint (and without limitation), it may prove advantageous to complete all the stains for a given panel in one sitting rather than adopting an iterative approach with each individual antibody.

Figure 10:
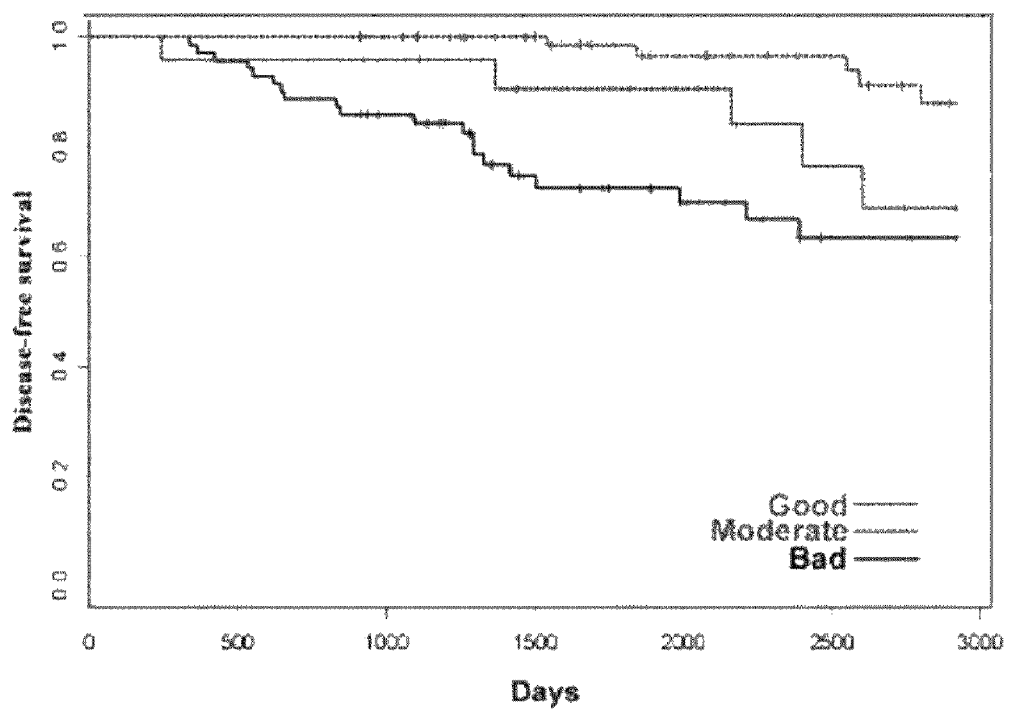
FIG. 10 shows Kaplan-Meier curves that were generated for ER+/node− patients after prognostic classification based on staining with the exemplary prognostic panel of antibodies from Table 8. In each case the patients were placed into one of three prognostic groups, namely "bad" (bottom curve), "moderate" (middle curve) and "good" (top curve).

The prognostic value of the exemplary panel of Table 8 was also assessed by generating Kaplan-Meier recurrence curves for ER+/node− patients. Patients whom the panel predicted as being strongly likely to recur were placed in the "bad" prognosis group. Patients whom the panel predicted as being strongly unlikely to recur were given the prediction of "good". Patients whom the panel predicted as neither being strongly likely to recur or not recur were placed in the "moderate" prognosis group. Kaplan-Meier curves were then calculated based on recurrence data for patients within each group. FIG. 10 shows the curves that were obtained for ER+/node− patients in each of these prognostic groups.

Generally, a tree panel for ER+/node− patients will include an antibody to biomarker Hs.184601 (e.g., s0702 or s0296P1) with antibodies to one or both of biomarkers Hs.155956 and Hs.1846 (e.g., s0081 and s6006, see Table 8 and Appendix A). In certain embodiments an antibody to biomarker Hs.80976 (e.g., s6007) may be added, optionally with antibodies to one or both of biomarkers Hs.63609 and Hs.2905 (e.g., s0545 and s6002). In preferred embodiments, the tree panel includes an antibody to biomarker Hs.184601 and antibodies to biomarkers Hs.155956, Hs.1846, Hs.80976, Hs.63609 and Hs.2905.

Figure 11:
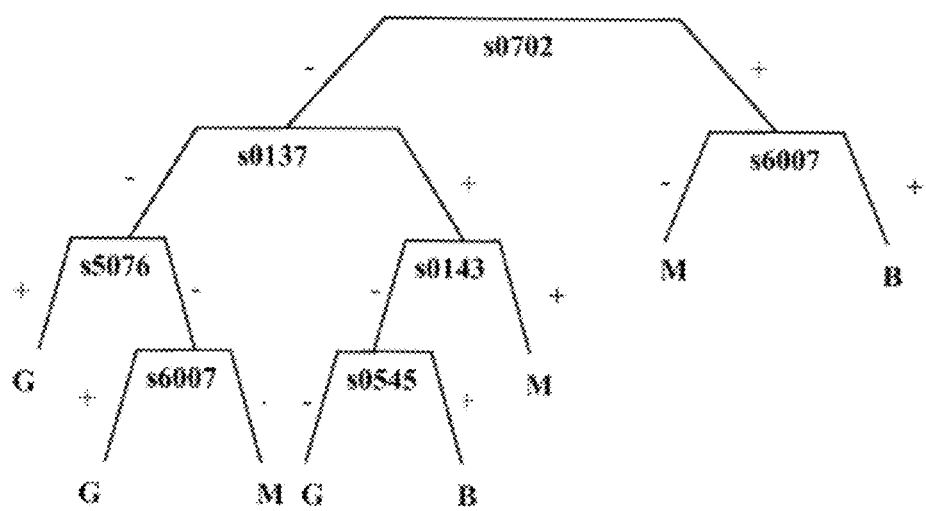
FIG. 11 shows a dendrogram for the tree panels of Table 9 that may be used for the prognostic classification of ER+ and ER− patients. If a patient is positive for staining at a given node his or her prognosis decision tree follows the branch marked with a "+". Conversely if a patient is negative for staining at a given node his or her prognosis decision tree follows the branch marked "−". This is done until a terminus is reached.
Figure 11:
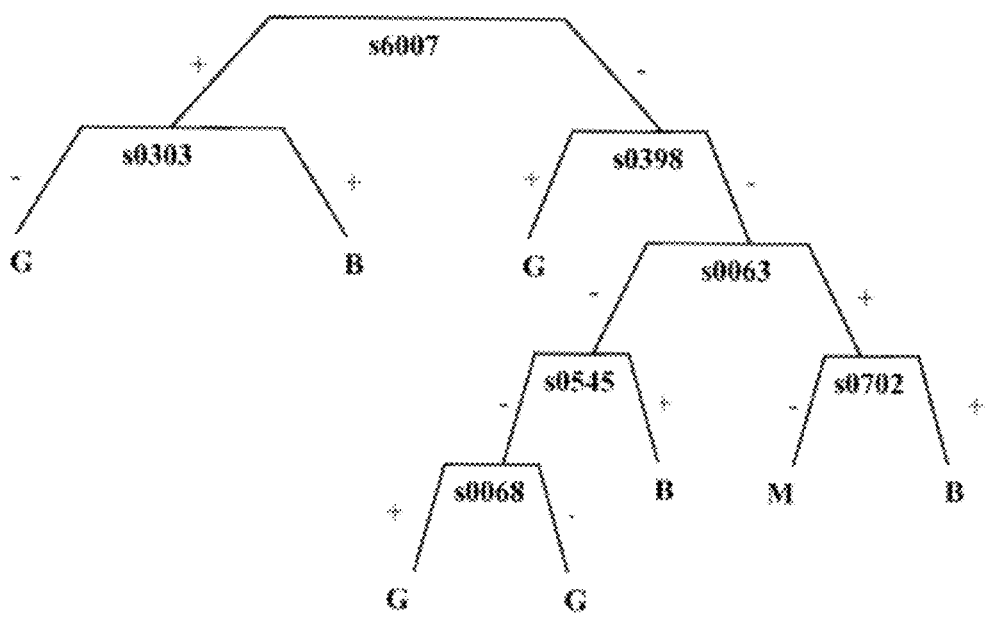

Table 9 lists the antibodies of exemplary ER+ and ER− tree panels that were constructed as described above for the ER+/node− tree panel of Table 8. The dendrograms for theses panels are illustrated in FIG. 11.

TABLE 9

| Panel | Analysis | Panel | Analysis |
|---|---|---|---|
| Breast ER+ | Tree | Breast ER− | Tree |
| AGI ID | Rank | AGI ID | Rank |
| s0702/s0296P1 | 1 | s6007 | 1 |
| s0137 | 2 | s0303 | 2 |
| s6007 | 2 | s0398 | 2 |
| s5076 | 3 | s0063 | 3 |
| s0143 | 3 | s0545 | 4 |
| s6007 | 4 | s0702/s0296P1 | 4 |
| s0545 | 4 | s0068 | 5 |

The present invention also encompasses methods of assessing the prognosis of a patient having a breast tumor using an inventive tree panel. For example, after obtaining a tumor sample from a patient with unknown prognosis the sample is contacted with two or more antibodies from the panel of Table 8 (or one of the panels in Table 9). The patient's likely prognosis is then assessed based upon the positive or negative binding of the two or more antibodies to the tumor sample using the dendrogram of FIG. 9 (or FIG. 11). Taking the ER+/node− panel of Table 8 as an example, the method generally includes a step of contacting the tumor sample with an antibody to biomarker Hs.184601 (e.g., s0702 or s0296P1) and antibodies to one or both of biomarkers Hs.155956 and Hs.1846 (e.g., s0081 and/or s6006). In other embodiments the tumor sample is further contacted with an antibody to biomarker Hs.80976 (e.g., s6007) and optionally with antibodies to biomarkers Hs.63609 and/or Hs.2905 (e.g., s0545 and/or s6002). As mentioned above, the tumor sample may be contacted with these antibodies in a single sitting or sequentially based on the binding results of a previous stain. Obviously the tumor sample may be divided and different antibodies contacted with different fractions. Alternatively different original tumor samples may be contacted with different antibodies.

Whether created by Cox or regression tree analysis, the exemplary prognostic panels were determined to be independent of age, stage, and grade. To ensure that the panels were not identifying classes of patients unlikely to be found to be significant in an independent cohort, cross validation was used to estimate the error inherent in each panel. Ten-fold cross-validation was performed by sequentially "leaving-out" 10% of patients and building panels on the remaining patients ten times such that all patients were ultimately classified. This included re-determining the set of antibodies sufficiently significant to be employed in the panel building process (p-value <0.10). Cross validated p-values reflect the confidence calculated for the sum of the ten independent panels and confirmed the statistical significance of these panels. For the ER+/node– patient set, both the Cox (Table 5) and regression tree (Table 8) panels showed significance after cross-validation (p-value/hazard ratio of 1.12E-02/2.36 and 3.40E-03/2.91, respectively). For the ER– patient set, the Cox panels (Tables 6-7) were also shown to be able to retain significance (p-value/hazard ratios of 6.40E-02/1.37 and 1.80E-03/1.79 for the panels of Table 6 and 7, respectively).

It is to be understood that each of the exemplary Cox and tree panels described herein may be used alone, in combination with one another (e.g., the Cox panel of Table 5 and the tree panel of Table 8 for ER+/node– patients) or in conjunction with other panels and/or independent prognostic factors.

Example 13

Prognostic Lung Cancer Panels

This Example builds on the results of Example 11 and describes the identification of exemplary panels of antibodies whose binding has been shown to correlate with the prognosis of lung cancer patients.

Prognostic panels in two currently identified clinically important subclasses of lung cancer patients were generated, namely adenocarcinoma and squamous cell carcinoma patients. Consistent with the known clinical significance of diagnoses of these two subclasses of lung cancer patients it was found that the most robust models were derived when patients were first classified in this manner, and then the separate patient groups modeled independently. It will be appreciated that this approach is non-limiting and that models could be generated using all lung cancer patients or using other subclasses of patients. To minimize the chance of identifying spurious associations, only those antibodies from Appendix D that showed sufficient significance (p-value of less than 0.10) in the adenocarcinoma patient class were used in creating prognostic panels for the adenocarcinoma patients, and only the similarly significant markers from the squamous cell carcinoma patient class for creating a prognostic panel for the squamous cell carcinoma patients. Using Cox proportional hazard analysis (as described in Example 10) candidate panels were derived for prediction of early recurrence. For both adenocarcinoma and squamous cell carcinoma patients, panels were chosen that identified patients with significantly increased risks of recurrence.

As previously noted, Cox proportional hazard analysis treats the component antibodies of a panel as additive risk factors. The panels for the specified patient classes were created by initially using all applicable antibodies, and then iteratively removing antibodies from the panel. If the removal of an antibody increased or did not affect the significance and prognostic ability of the panel as a whole, it was excluded, otherwise it was retained. In this manner preferred panels with minimal numbers of antibodies were created. The preferred panels for squamous cell carcinoma and adenocarcinoma patients are presented in Tables 10 and 11, respectively. Antibodies within the preferred panels are ranked based on their relative contributions to the overall prediction function.

TABLE 10

| Panel | Analysis | P value[1] | Hazard ratio[2] |
|---|---|---|---|
| Lung squamous | Cox | 3.20E-05 | 6.88 |
| AGI ID | Rank | P value[3] | Terms[4] |
| s0022 | 1 | 0.00620 | 0.880, –1.240 |
| s0702/s0296P1 | 2 | 0.12000 | 0.980, –0.150 |
| s0330 | 3 | 0.13000 | 0.870, –0.034 |
| s0586 | 4 | 0.16000 | 0.680, –0.250 |

[1]P value of overall panel
[2]Hazard ratio of overall panel
[3]P value of the contribution of a given antibody to the overall panel
[4]Contribution of given antibody to overall panel prediction function depending on IHC score (e.g., scores of 0 or 1 for s0022 which uses scoring method 2 [see Appendix D] result in its term in the model equaling 0.880 or –1.240, respectively).

TABLE 11

| Panel | Analysis | P value[1] | Hazard ratio[2] |
|---|---|---|---|
| Lung adenocarcinoma | Cox | 1.30E-05 | 3.23 |
| AGI ID | Rank | P value[3] | Terms[4] |
| s6013 | 1 | 0.02000 | –0.430, 0.520 |
| s0545 | 2 | 0.03500 | –0.070, 1.150 |
| s0404 | 3 | 0.04000 | –0.270, 0.550 |
| s0702/s0296P1 | 4 | 0.08800 | –0.230, 0.450 |

[1,2,3,4]See Table 10

Figure 12:
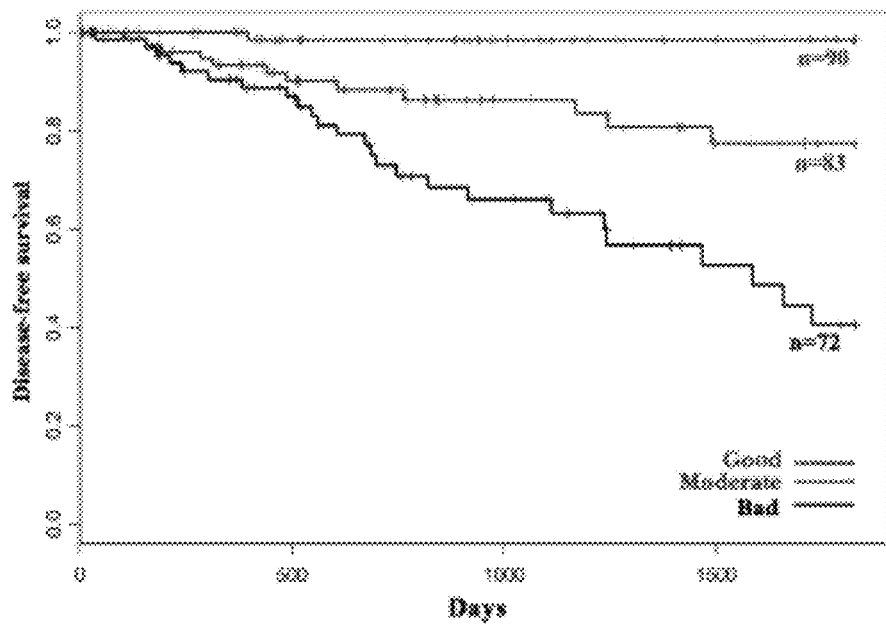
FIG. 12 shows Kaplan-Meier curves that were generated for combined lung cancer patients (HH cohort) after prognostic classification with the exemplary prognostic panels of antibodies from Tables 10 and 11. In each case the patients were placed into one of three prognostic groups, namely "bad" (bottom curve), "moderate" (middle curve) and "good" (top curve).
Figure 13:
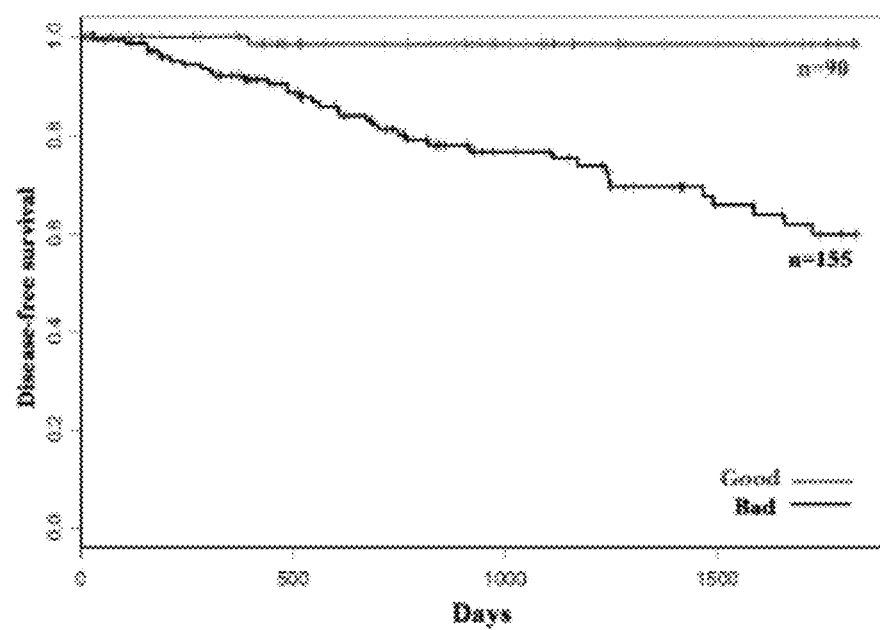
FIG. 13 shows the curves that were obtained when patients in the "moderate" and "bad" groups of FIG. 12 were combined into a single "bad" prognostic group.

The prognostic value of these exemplary panels were assessed by generating Kaplan-Meier recurrence curves for the combined lung cancer patients of the HH lung cohort. Patients were initially classified as adenocarcinoma or squamous cell carcinoma patients. For each patient the pattern of antibody staining with the applicable panel (i.e., Table 10 or 11) was then assessed. Patients whom the panels predicted as being strongly likely to recur were placed in the "bad" prognosis group. Patients whom the panels predicted as being strongly unlikely to recur were given the prediction of "good". Patients whom the panels predicted as neither being strongly likely to recur or not recur were placed in the "moderate" prognosis group. Kaplan-Meier curves were then calculated based on five year recurrence data for patients within each group. FIG. 12 shows the curves that were obtained when the combined lung cancer patients were placed in "good", "moderate" or "bad" prognosis groups. FIG. 13 shows the curves that were obtained when patients in the "moderate" and "bad" groups were combined into a single "bad" prognostic group.

To ensure that the panels were not identifying classes of patients unlikely to be found to be significant in an independent cohort, cross validation was used to estimate the error inherent in each panel. Ten-fold cross-validation was performed by sequentially "leaving-out" 10% of patients and building panels on the remaining patients ten times such that all patients were ultimately classified. This included re-determining the set of antibodies sufficiently significant to be employed in the panel building process (p-value <0.10). Cross validated p-values reflect the confidence calculated for the sum of the ten independent panels and confirmed the statistical significance of these panels. The panels showed significance after cross-validation with the combined lung patients (p-value/hazard ratio of 2.20E-02/1.48 when a "good", "moderate" and "bad" scheme was used and 1.80E-02/2.07 when a "good" and "bad" scheme was used).

While preferred Cox panels of the invention for lung cancer patients include each of the listed antibodies, it is to be understood that other related panels are encompassed by the present invention. In particular, it will be appreciated that the present invention is in no way limited to the specific antibodies listed. For example, other antibodies directed to the same biomarker(s) may be used (e.g., taking the squamous cell carcinoma panel, it can be readily seen from Appendix A that antibody s0022 can be replaced with other antibodies directed to biomarker Hs.176588; s0702 or s0296P1 can be replaced with other antibodies directed to biomarker Hs.184601, etc.). Other antibodies from Appendix D may be added to any given panel without necessarily diminishing the utility of a panel for patient prognosis. The inclusion of antibodies beyond those listed in Appendix D is also within the scope of the invention. In certain embodiments less than all of the listed antibodies may be used in a prognostic panel.

Generally, a Cox panel for squamous cell carcinoma patients will include at least two antibodies selected from the group consisting of antibodies directed to biomarkers Hs.176588, Hs.184601, Hs.306098 and Hs.194720 (e.g., s0022, s0702 or s0296P1, s0330 and s0586, see Table 10 and Appendix A). Preferably, the panel will include an antibody directed to biomarker Hs.176588 and at least one antibody directed to a biomarker selected from the group consisting of Hs.184601, Hs.306098 and Hs.194720. All permutations of these antibodies are encompassed. In one embodiment an antibody to biomarker Hs.176588 (e.g., s0022) is used with an antibody to biomarker Hs.184601 (e.g., s0702 and/or s0296P1). In another embodiment an antibody to biomarker Hs.176588 is used with antibodies to biomarkers Hs.184601 and Hs.306098 (e.g., s0702 or s0296P1 and s0330). In preferred embodiments an antibody to biomarker Hs.176588 is used with antibodies to biomarkers Hs.184601, Hs.306098 and Hs.194720.

Similarly, a Cox panel for adenocarcinoma patients will include at least two antibodies selected from the group consisting of antibodies directed to biomarkers Hs.323910, Hs.63609, Hs.75789 and Hs.184601 (e.g., s6013, s0545, s0404 and s0702 or s0296P1, see Table 11 and Appendix A). Preferably, the panel will include an antibody directed to biomarker Hs.323910 and at least one antibody directed to a biomarker selected from the group consisting of Hs.63609, Hs.75789 and Hs.184601. All permutations of these antibodies are encompassed. In one embodiment an antibody to biomarker Hs.323910 (e.g., s6013) is used with an antibody to biomarker Hs.63609 (e.g., s0545). In another embodiment an antibody to biomarker Hs.323910 is used with antibodies to biomarkers Hs.63609 and Hs.75789 (e.g., s0545 and s0404). In preferred embodiments an antibody to biomarker Hs.323910 is used with antibodies to biomarkers Hs.63609, Hs.75789 and Hs.184601.

It is to be understood that these exemplary Cox panels may be used alone, in combination with one another or in conjunction with other panels and/or independent prognostic factors.

The present invention also encompasses methods of assessing the prognosis of a patient having a lung tumor using these exemplary panels. After obtaining a tumor sample from a patient with unknown prognosis the sample is contacted with two or more antibodies from the panels of Table 10 and/or 11. The patient's likely prognosis is then assessed based upon the positive or negative binding of the two or more antibodies to the tumor sample.

Example 14

Use of Prognostic Lung Cancer Panels with an Independent Cohort

This Example builds on the results of Example 13 by describing how the exemplary prognostic lung cancer panels were used to predict recurrence in an independent cohort of lung cancer patients.

Figure 14:
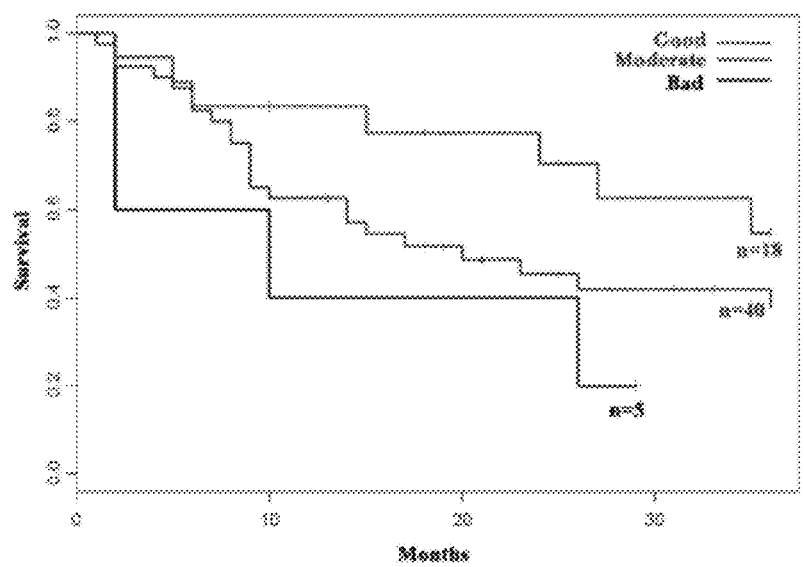
FIG. 14 shows Kaplan-Meier curves that were generated for combined lung cancer patients (UAB cohort) after prognostic classification with the exemplary prognostic panels of antibodies from Tables 10 and 11. In each case the patients were placed into one of three prognostic groups, namely "bad" (bottom curve), "moderate" (middle curve) and "good" (top curve).
Figure 15:
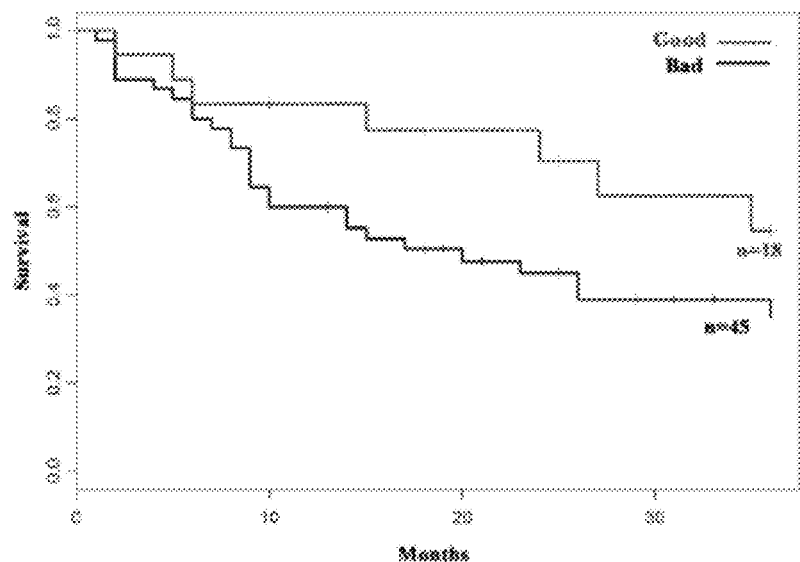
FIG. 15 shows the curves that were obtained when the patients in the "moderate" and "bad" groups of FIG. 14 were combined into a single "bad" prognostic group.
Figure 16:
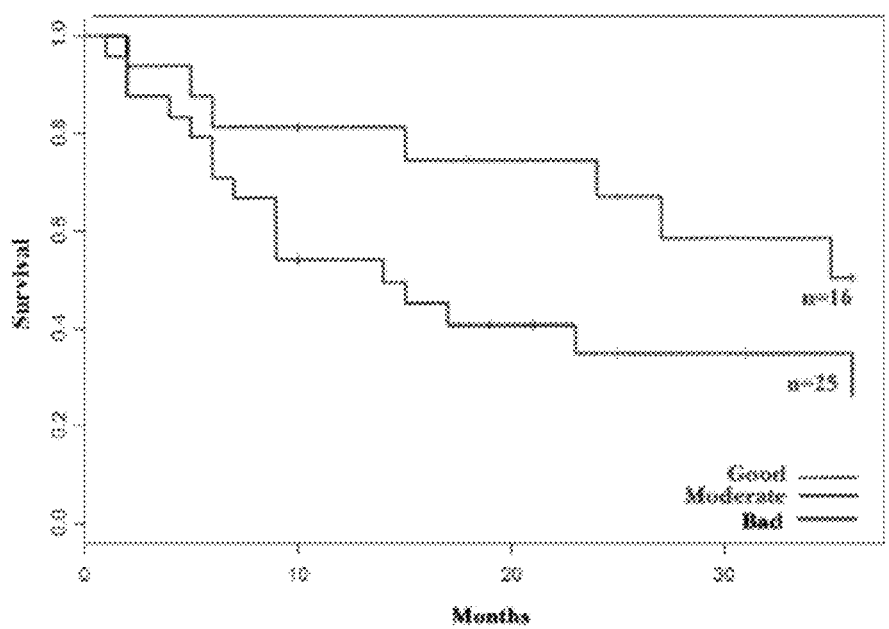
FIG. 16 shows Kaplan-Meier curves that were generated for adenocarcinoma patients (UAB cohort) after prognostic classification with the exemplary prognostic panels of antibodies from Table 11. In each case the patients were placed into one of three prognostic groups, namely "bad" (bottom curve), "moderate" (middle curve) and "good" (top curve).
Figure 17:
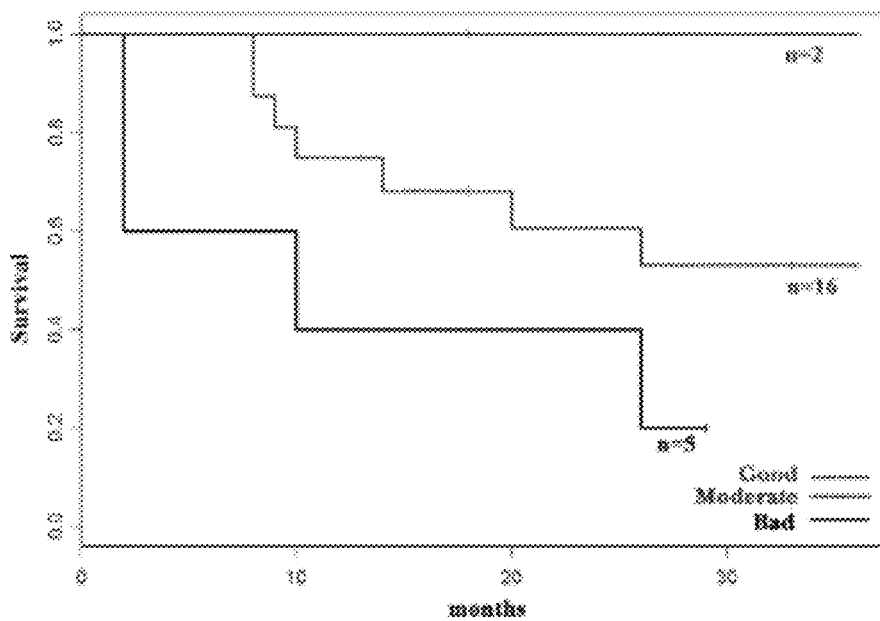
FIG. 17 shows Kaplan-Meier curves that were generated for squamous cell carcinoma patients (UAB cohort) after prognostic classification with the exemplary prognostic panels of antibodies from Table 10. In each case the patients were placed into one of three prognostic groups, namely "bad" (bottom curve), "moderate" (middle curve) and "good" (top curve).

A cohort of 119 lung cancer patients from the University of Alabama-Birmingham (UAB) was used for this purpose. Relatively limited clinical data was available for these patients, in most cases only survival time was available. The average time of follow-up among patients who did not die of disease was 28 months. Of the 119 patients, 54 were noted to have had a recurrence of cancer within the study period, and 74 died of disease. This cohort differed significantly from the HH lung cohort (see Example 11) in that it was not limited to early stage tumors, and therefore the cohort had a greater incidence of death due to disease. Since recurrence data for this cohort was limited, the prognostic panels of Example 13 (designed to predict recurrence) were used to predict survival in this independent cohort. Specifically, the prognostic value of the panels were assessed by generating Kaplan-Meier survival curves for the combined lung cancer patients of the UAB cohort. As in Example 13, patients were initially classified as adenocarcinoma or squamous cell carcinoma patients. For each patient the pattern of antibody staining with the applicable panel (i.e., Table 10 or 11) was then assessed. Patients were placed in "bad", "moderate" and "good" prognosis groups based on their binding patterns with these antibodies. Kaplan-Meier curves were then calculated based on survival data for patients within each group. FIG. 14 shows the curves that were obtained when the combined lung cancer patients were placed in "good", "moderate" or "bad" prognosis groups (p-value/hazard ratio of 5.20E-02/1.98). FIG. 15 shows the curves that were obtained when the patients in the "moderate" and "bad" groups were combined into a single "bad" prognostic group (p-value/hazard ratio of 2.50E-02/3.03). FIG. 16 shows the curves that were obtained when the subclass of adenocarcinoma patients were placed in "good", "moderate" or "bad" prognosis groups (no patients fell within the "bad" group hence there are only two curves, p-value/hazard ratio of 4.00E-02/2.19). FIG. 17 shows the curves that were obtained when the subclass of squamous cell carcinoma patients were placed in "good", "moderate" or "bad" prognosis groups (p-value/hazard ratio of 2.50E-02/3.03).

The prognostic significance of individual antibodies identified in the HH lung cohort (i.e., those listed in Appendix D) were also reassessed using the five year survival data from the UAB cohort. The methodology was as described in Example 11. The prognostic significance of these same antibodies was also recalculated using five year recurrence data from the HH lung cohort (instead of the complete follow-up period as in Example 11 where patients who did not die of disease were followed for a period of up to ten years). Based on these calculations, several antibodies from Appendix D were found to have a relatively significant individual prognostic value (p-value less than 0.2) in both the HH and UAB lung cohorts. These antibodies are presented in Appendix F.

Example 15

Use of a Lung Cancer Classification Panel with an Independent Cohort

The pattern of reactivity with the lung cancer classification panel of Example 5 (see Appendix A) was determined using samples from the HH lung cohort (data not shown). As in Example 4, patients were classified using k-means clustering. Seven sub-classes of lung cancer patients were chosen by their consensus pattern of staining.

The morphology of the lung cancers within each sub-class were determined and are shown graphically in FIG. 18. Interestingly, the sub-classes were found to comprise patients with lung cancers having similar morphological characteristics (i.e., sub-classes 1, 2, 3 and 7 were composed of a majority of patients with adenocarcinomas; sub-classes 4 and 5 were composed of a majority of patients with squamous cell carcinomas and sub-class 6 was composed of a majority of patients with large cell carcinomas). These results suggest that the antibodies in the classification panel are recognizing biological and clinical diversity in lung cancers.

Out of interest, the prognostic value of these seven sub-classes was also assessed. (Note that these sub-classes were constructed based on sample staining patterns across the entire classification panel of Appendix A. This differs from the approach that was described in Example 14 where specific antibodies with predetermined prognostic value were combined into prognostic panels that were then used to classify patients). The average probability of recurrence for the overall HH cohort was first calculated and found to level out at about 38% after six years. Average probabilities within each of the seven HH sub-classes were then calculated and compared with the overall average. Sub-classes with an average probability of recurrence after six years that was greater than 48% (i.e., more than 10% worse than the overall population) were classified as having a "bad" prognosis. Sub-classes with an average probability of recurrence after six years that was less than 28% (i.e., more than 10% better than the overall population) were classified as having a "good" prognosis. Sub-classes with an average probability of recurrence after six years of 28 to 48% were classified as having a "moderate" prognosis. Based on this analysis, HH sub-classes 1, 6 and 7 were classified as "bad"; HH sub-classes 2 and 4 as "moderate"; and HH sub-classes 3 and 5 as "good". When the recurrence data for patients in the "bad", "moderate" and "good" classes were combined and plotted as Kaplan-Meier curves the different outcomes for the three prognostic groups were statistically significant (p-value <0.02, data not shown).

In order to assess whether the sub-classes of FIG. 18 would correlate across lung cancers in general, the k-means clustering criteria that were used in classifying the HH lung cohort were "forced" onto samples from an independent lung cohort (namely the UAB lung cohort that was described in Example 14). Note that while the HH lung cohort was composed of Stage I/II patients, the UAB lung cohort was composed of Stage III/IV patients. Thus, overall the prognosis of UAB patients was worse than the prognosis of HH patients. First, the mean values from the HH k-means analysis were calculated for each of the seven HH sub-classes of FIG. 18. Antibody staining results for each UAB sample were then compared with all seven means and samples were assigned to one of the seven "HH sub-classes" based on the closest match. The seven UAB clusters were then classified as having a "bad", "moderate" and "good" prognosis based simply on the prognoses that had been previously determined for the corresponding seven HH sub-classes (see above). When the recurrence data for patients in the "bad", "moderate" and "good" classes were combined and plotted as Kaplan-Meier curves the different outcomes for the three prognostic groups were again statistically significant (p-value <0.02, data not shown). Examination of the curves and subsequent analysis showed that "good" and "moderate" gave similar outcomes relative to each other while "bad" was clearly divergent from these two.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

APPENDIX A

| AGI ID | GENE NAME | BREAST PANEL? | | LUNG PANEL? | | COLON PANEL? | NCBI LocusLink ID | UniGene ID | ALIASES |
|---|---|---|---|---|---|---|---|---|---|
| | | Russ. | HH | Russ. | HH | Russ. | | | |
| S0011 | VAV-3 protein | | X | | | | 10451 | Hs.267659 | VAV3; VAV3 ONCOGENE; ONCOGENE VAV3; vav 3 oncogene |
| S0018 | mammoglobin | | X | | | | 4250 | Hs.46452 | UGB2; MGB1; mammaglobin 1; MAMMAGLOBIN A PRECURSOR |
| S0020 | RB18A (P53 binding) | | X | | | | 5469 | Hs.15578 | RB18A; TRIP2; PPARGBP; PBP; CRSP1; PPARBP; CRSP200; DRIP230; PPAR-BINDING PROTEIN; PPARG binding protein; PPAR binding protein; CRSP, 200-KD SUBUNIT; PEROXISOME PROLIFERATOR-ACTIVATED RECEPTOR-BINDING PROTEIN; THYROID HORMONE RECEPTOR INTERACTOR 2; RECOGN |
| S0021 | Putative cadherin-like protein | X | X | X | X | | 222256 | Hs.12496 | FLJ23834 |
| S0022 | Sim to Cyto p450 | X | X | X | X | X | 199974 | Hs.176588 | cytochrome P450 4Z1 |
| S0024 | Chuck Ras | | | | X | | 85004 | Hs.21594 | RERG; RAS-like, estrogen-regulated, growth-inhibitor |
| S0032 | MDGI | | X | | | | 2170 | Hs.49881 | MDGI; O-FABP; FABP3; FABP11; H-FABP; FATTY ACID-BINDING PROTEIN, SKELETAL MUSCLE; Fatty acid-binding protein 3, muscle; fatty acid binding protein 11; FATTY ACID-BINDING PROTEIN, MUSCLE AND HEART; fatty acid binding protein 3, muscle and heart (mammary-de |

APPENDIX A-continued

| AGI ID | GENE NAME | BREAST PANEL? Russ. | HH | LUNG PANEL? Russ. | HH | COLON PANEL? Russ. | NCBI LocusLink ID | UniGene ID | ALIASES |
|---|---|---|---|---|---|---|---|---|---|
| S0036 | Human GABA-A receptor pi subunit | | | | | X | 2568 | Hs.70725 | GABRP; GAMMA-AMINOBUTYRIC ACID RECEPTOR, PI; GABA-A RECEPTOR, PI POLYPEPTIDE; gamma-aminobutyric acid (GABA) A receptor, pi |
| S0037 | Annexin VIII | | X | | | | 244 | Hs.87268 | ANX8; ANXA8; annexin VIII; annexin A8 |
| S0039 | hypothetical UBCc containing protein (Ubiquitin-conjugating enzyme E2, catalytic domain homologues) | X | X | X | | X | | Hs.351357 | |
| S0040 | MDR1 | X | X | X | | X | 5243 | Hs.21330 | GP170; PGY1; P-gp; ABCB1; ABC20; MDR1; DOXORUBICIN RESISTANCE; P-GLYCOPROTEIN 1; multidrug resistance 1; P-glycoprotein-1/multiple drug resistance-1; MULTIDRUG RESISTANCE PROTEIN 1; ATP-BINDING CASSETTE, SUBFAMILY B, MEMBER 1; P glycoprotein 1/multiple dr |
| S0041 | MDR3 | X | | | | | 5244 | Hs.73812 | MDR2; MDR3; PGY3; PFIC-3; ABCB4; ABC21; MDR2/3; P-GLYCOPROTEIN 3; MULTIDRUG RESISTANCE 3; P-glycoprotein-3/multiple drug resistance-3; MULTIDRUG RESISTANCE PROTEIN 3; P glycoprotein 3/multiple drug resistance 3; ATP-binding cassette, sub-family B (MDR/TAP |
| S0042 | MRP-1 | X | X | X | | X | 4363 | Hs.89433 | MRP; MRP1; GS-X; ABC29; ABCC1; ABCC; multidrug resistance protein; multiple drug resistance-associated protein; MULTIDRUG RESISTANCE-ASSOCIATED PROTEIN 1; multiple drug resistance protein 1; ATP-BINDING CASSETTE, SUBFAMILY C, MEMBER 1; ATP-binding cassett |
| S0043 | MRP2/CMOAT | X | X | X | | X | 1244 | Hs.193852 | MRP2; cMRP; CMOAT; ABCC2; ABC30; ABC#; CMOAT1; DJS; MULTIDRUG RESISTANCE-ASSOCIATED PROTEIN 2; CANALICULAR MULTIDRUG RESISTANCE PROTEIN; MULTISPECIFIC ORGANIC ANION TRANSPORTER, CANALICULAR; CANALICULAR MULTISPECIFIC ORGANIC ANION TRANSPORTER 1; ATP-BINDI |
| S0044 | MRP4 | X | X | X | | X | 10257 | Hs.139336 | MOAT-B; MRP4; ABCC4; MOATB; EST170205; MRP/CMOAT-RELATED ABC TRANSPORTER; MULTIDRUG RESISTANCE-ASSOCIATED PROTEIN 4; MULTISPECIFIC ORGANIC ANION TRANSPORTER B; ATP-binding cassette, sub-family C, member 4; ATP-BINDING CASSETTE, SUBFAMILY C, MEMBER 4; ATP- |
| S0045 | MRP3/CMOAT2 | X | | | | | 8714 | Hs.90786 | MOAT-D; MRP3; ABCC3; MLP2; ABC31; EST90757; CMOAT2; MULTIDRUG RESISTANCE-ASSOCIATED PROTEIN 3; canicular multispecific organic anion transporter; ATP-BINDING CASSETTE, SUBFAMILY C, MEMBER 3; CANALICULAR MULTISPECIFIC ORGANIC ANION TRANSPORTER 2; ATP-bindi |

APPENDIX A-continued

| AGI ID | GENE NAME | BREAST PANEL? Russ. | HH | LUNG PANEL? Russ. | HH | COLON PANEL? Russ. | NCBI LocusLink ID | UniGene ID | ALIASES |
|---|---|---|---|---|---|---|---|---|---|
| S0046 | MRP5/MOAT-C | X | | X | X | X | 10057 | Hs.108660 | ABCC5; MRP5; EST277145; ABC33; SMRP; pABC11; MOATC; ABC TRANSPORTER MOAT-C; MULTIDRUG RESISTANCE-ASSOCIATED PROTEIN 5; canalicular multispecific organic anion transporter C; ATP-binding cassette, sub-family C, member 5; ATP-BINDING CASSETTE, SUBFAMILY C, |
| S0047 | MRP6 | X | | X | | X | 368 | Hs.274260 | MOAT-E; MRP6; ARA; EST349056; ABCC6; MOATE; PXE; MLP1; ABC34; *pseudoxanthoma elasticum*; ANTHRACYCLINE RESISTANCE-ASSOCIATED PROTEIN; MULTIDRUG RESISTANCE-ASSOCIATED PROTEIN 6; ATP-BINDING CASSETTE, SUBFAMILY C, MEMBER 6; ATP-binding cassette, sub-family C |
| S0048 | BSEP | X | | | | | 8647 | Hs.158316 | BSEP; ABCB11; PFIC-2; SPGP; PGY4; PFIC2; ABC16; SISTER OF P-GLYCOPROTEIN; bile salt export pump; progressive familial intrahepatic cholestasis 2; ABC member 16, MDR/TAP subfamily; ATP-BINDING CASSETTE, SUBFAMILY B, MEMBER 11; ATP-binding cassette, sub-fam |
| S0049 | ATP-binding cassette, sub-family B, member 10 | X | X | | | | 23456 | Hs.1710 | MTABC2; EST20237; MABC2; M-ABC2; ABCB10; MITOCHONDRIAL ABC PROTEIN 2; ATP-BINDING CASSETTE, SUBFAMILY B, MEMBER 10; ATP-binding cassette, sub-family B, member 10; ATP-binding cassette, sub-family B (MDR/TAP), member 10 |
| S0050 | TAP1 | X | X | | | | 6890 | Hs.352018 | |
| S0052 | SUR1 | X | | X | | X | 6833 | Hs.54470 | SUR1; MRP8; ABC36; SUR; HI; ABCC8; HRINS; PHHI; sulfonylurea receptor (hyperinsulinemia); SULFONYLUREA RECEPTOR 1; SULFONYLUREA RECEPTOR, BETA-CELL HIGH-AFFINITY; ATP-binding cassette, sub-family C, member 8; ATP-BINDING CASSETTE, SUBFAMILY C, MEMBER 8; A |
| S0053 | SUR2 | X | X | | | | 10060 | Hs.248960 | SUR2; ABC37; ABCC9; sulfonylurea receptor 2A; ATP-BINDING CASSETTE, SUBFAMILY C, MEMBER 9; ATP-binding cassette, sub-family C (CFTR/MRP), member 9; ATP-binding cassette, sub-family C, member 9, isoform SUR2A-delta-14; ATP-binding cassette, sub-family C, m |
| S0055 | INTEGRAL MEMBRANE PROTEIN 2B (TRANSMEMBRANE PROTEIN BRI) | | X | | | | 9445 | Hs.239625 | E25B; ABRI; E3-16; FBD; BRI2; BRICD2B; ITM2B; BRI GENE; BRICHOS domain containing 2B; integral membrane protein 2B |
| S0057 | ANK-3 | | X | | | | 288 | Hs.75893 | ankyrin-G; ANK3; ankyrin-3, node of Ranvier; ankyrin 3 isoform 1; ankyrin 3 isoform 2; ankyrin 3, node of Ranvier (ankyrin G) |
| S0058 | hypothetical protein FLJ21918 (RNA recognition motif (RRM) containing protein) | | | X | | | 80004 | Hs.282093 | FLJ21918; hypothetical protein FLJ21918 |
| S0059 | ataxia-telangiectasia group D-associated protein | X | X | X | | X | 23650 | Hs.82237 | ATDC; TRIM29; tripartite motif-containing 29; ataxia-telangiectasia group D-associated protein; tripartite motif protein TRIM29 isoform alpha; tripartite motif protein TRIM29 isoform beta |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0059P2 | ataxia-telangiectasia group D-associated protein | | X | | X | | 23650 | Hs.82237 | ATDC; TRIM29; tripartite motif-containing 29; ataxia-telangiectasia group D-associated protein; tripartite motif protein TRIM29 isoform alpha; tripartite motif protein TRIM29 isoform beta |
| S0063 | iroquois related homeobox 3 | | X | X | X | X | 79191 | Hs.3321 | |
| S0068 | Chuck Ras C-term | | X | | | | 85004 | Hs.416854 | RERG; hypothetical protein MGC15754; RAS-like, estrogen-regulated, growth-inhibitor |
| S0070 | putative G protein-coupled receptor (NP_055188.1|) | X | | | | | 26996 | Hs.97101 | GPCR150; GPR160; putative G protein-coupled receptor; G protein-coupled receptor 160 |
| S0072 | Calgranulin A | | X | | X | | 6279 | Hs.100000 | MRP-8; MIF; S100A8; MRP8; CFAG; L1Ag; 60B8AG; P8; CGLA; CAGA; NIF; MA387; CP-10; CYSTIC FIBROSIS ANTIGEN; MIGRATION INHIBITORY FACTOR-RELATED PROTEIN 8; LEUKOCYTE L1 COMPLEX LIGHT CHAIN; S100 calcium-binding protein A8 (calgranulin A) |
| S0073 | hepatocyte nuclear protein 3, alpha | | X | | | | 3169 | Hs.70604 | HNF3A; MGC33105; TCF3A; FOXA1; forkhead box A1; HEPATOCYTE NUCLEAR FACTOR 3-ALPHA; hepatocyte nuclear factor 3, alpha |
| S0073P2 | hepatocyte nuclear protein 3, alpha | | X | | X | | 3169 | Hs.70604 | HNF3A; MGC33105; TCF3A; FOXA1; forkhead box A1; HEPATOCYTE NUCLEAR FACTOR 3-ALPHA; hepatocyte nuclear factor 3, alpha |
| S0074 | intestinal trefoil precursor | X | X | X | | X | 7033 | Hs.82961 | TFF3; trefoil factor 3 (intestinal); trefoil factor 3, HITF, human intestinal trefoil factor |
| S0074P3 | intestinal trefoil precursor | | | | X | | 7033 | Hs.82961 | TFF3; trefoil factor 3 (intestinal); trefoil factor 3, HITF, human intestinal trefoil factor |
| S0076x1 | Keratin 17 | | X | | | | 3872 | Hs.2785 | PCHC1; PC; PC2; 39.1; KRT17; K17; CYTOKERATIN 17; VERSION 1; CK 17; KERATIN, TYPE I CYTOSKELETAL 17 |
| S0079 | LIV-1 | | X | | X | | 25800 | Hs.79136 | LIV-1; LIV-1 protein, estrogen regulated |
| S0081 | NAT1 | X | X | | | | 9 | Hs.155956 | MNAT; NAT-1; AAC1; NAT1; ACETYL-CoA:ARYLAMINE N-ACETYLTRANSFERASE; EC 2.3.1.5; arylamine N-acetyltransferase-1; N-ACETYLTRANSFERASE TYPE 1; ARYLAMINE N-ACETYLTRANSFERASE, MONOMORPHIC; ARYLAMINE N-ACETYLTRANSFERASE 1; N-acetyltransferase 1 (arylamine N-ace |
| S0086 | x-box binding | | X | | | | 7494 | Hs.149923 | XBP2; TREB5; XBP1; X-box-binding protein-1; X BOX-BINDING PROTEIN 1; X BOX-BINDING PROTEIN 2; X-box binding protein 1 |
| S0096 | ATPase, H+ transporting, lysosomal (vacuolar proton pump), beta polypeptide, 56/58 kD, isoform 1R7340 | | X | | X | | 525 | Hs.64173 | ATP6B1; VATB; 3.6.1.34; VPP3; RTA1B; EC 3.6.3.14; V-ATPASE B1 SUBUNIT; VACUOLAR PROTON PUMP B ISOFORM 1; ENDOMEMBRANE PROTON PUMP 58 KDA SUBUNIT; VACUOLAR ATP SYNTHASE SUBUNIT B, KIDNEY ISOFORM; ATPase, H+ TRANSPORTING, LYSOSOMAL, BETA SUBUNIT, ISOFORM 1; |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0110 | hypothetical protein MGC2714 (in part) | X | | X | | X | 84259 | Hs.74284 | hypothetical protein MGC2714 |
| S0117 | Reproduction 8 | | | | | X | 7993 | Hs.153678 | D8S2298E; REP8; reproduction 8; Reproduction/chromosome 8 |
| S0119 | slit1 | | | | | X | 6585 | Hs.133466 | SLIT3; MEGF4; SLIL1; Slit-1; SLIT1; slit homolog 1 (Drosophila); SLIT, DROSOPHILA, HOMOLOG OF, 1; MULTIPLE EPIDERMAL GROWTH FACTOR-LIKE DOMAINS 4 |
| S0132 | sry-box9 | X | | X | | X | 6662 | Hs.2316 | SRA1; CMD1; SOX9; CMPD1; CMPD1 SRY-BOX 9; transcription factor SOX9; TRANSCRIPTION FACTOR SOX-9; ACAMPOMELIC CAMPOMELIC DYSPLASIA; SRY-RELATED HMG-BOX GENE 9; SEX REVERSAL, AUTOSOMAL, 1; SRY (sex-determining region Y)-box 9 protein; SRY (sex-determining r |
| S0137 | EGF-Like Domain, Multiple 2 | X | X | X | X | X | 1952 | Hs.57652 | EGFL2; CDHF10; KIAA0279; CELSR2; MEGF3; EGF-like-domain, multiple 2; epidermal growth factor-like 2; multiple epidermal growth factor-like domains 3; cadherin EGF LAG seven-pass G-type receptor 2; similar to cadherin-related tumor suppressor hFat protein; |
| S0139 | Gamma-glytamyl hydrolase | X | X | | | | 8836 | Hs.78619 | GGH; GH; EC 3.4.19.9; GAMMA-GLU-X CARBOXYPEPTIDASE; GAMMA-GLUTAMYL HYDROLASE PRECURSOR; gamma-glutamyl hydrolase (conjugase, folylpolygammaglutamyl hydrolase) precursor |
| S0140 | Bullous Pemphigoid Antigen 1 | X | X | X | | X | 667 | Hs.198689 | BP240; FLJ13425; FLJ32235; FLJ21489; FLJ30627; CATX-15; KIAA0728; BPAG1; dystonin; hemidesmosomal plaque protein; bullous pemphigoid antigen 1, 230/240 kDa; bullous pemphigoid antigen 1 (230/240 kD); bullous pemphigoid antigen 1 isoform 1eA precursor; bullo |
| S0140P1 | Bullous Pemphigoid Antigen 1 | | X | | | | 667 | Hs.198689 | BP240; FLJ13425; FLJ32235; FLJ21489; FLJ30627; CATX-15; KIAA0728; BPAG1; dystonin; hemidesmosomal plaque protein; bullous pemphigoid antigen 1, 230/240 kDa; bullous pemphigoid antigen 1 (230/240 kD); bullous pemphigoid antigen 1 isoform 1eA precursor; bullo |
| S0143 | fasn | X | X | X | | | 2194 | Hs.83190 | FASN; FAS; EC 2.3.1.85; EC 4.2.1.61; EC 1.3.1.10; EC 1.1.1.100; EC 3.1.2.14; EC 2.3.1.41; EC 2.3.1.38; EC 2.3.1.39; fatty acid synthase |
| S0143P3 | fasn | | X | | X | | 2194 | Hs.83190 | FASN; FAS; EC 2.3.1.85; EC 4.2.1.61; EC 1.3.1.10; EC 1.1.1.100; EC 3.1.2.14; EC 2.3.1.41; EC 2.3.1.38; EC 2.3.1.39; fatty acid synthase |
| S0144 | Matrix Metalloproteinase 14 | X | | X | | | 4323 | Hs.2399 | MMP-14; MMP-X1; MT1MMP; MMP14; MTMMP1; MT1-MMP; EC 3.4.24.—; MT-MMP 1; membrane-type-1 matrix metalloproteinase; MATRIX METALLOPROTEINASE-14 PRECURSOR; matrix metalloproteinase 14 (membrane-inserted); membrane-type matrix metalloproteinase 1; MATRIX METAL |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0149 | ABP/ZF | X | | | | | 55503 | Hs.302740 | TRPV6; ECAC2; CAT1; CATL; CALCIUM TRANSPORTER 1; CALCIUM TRANSPORTER-LIKE PROTEIN; EPITHELIAL CALCIUM CHANNEL 2; transient receptor potential cation channel, subfamily V, member 6 |
| S0156 | fatty acid binding protein 7, FABP7 | X | | X | | X | 2173 | Hs.26770 | B-FABP; FABP7; FABPB; MRG; mammary-derived growth inhibitor-related; FATTY ACID-BINDING PROTEIN 7; FATTY ACID-BINDING PROTEIN, BRAIN; fatty acid binding protein 7, brain |
| S0158 | Cadherin 3 | X | X | X | | X | 1001 | Hs.2877 | CDHP; HJMD; PLACENTAL-CADHERIN; PCAD; CDH3; placental cadherin; CADHERIN-3 PRECURSOR; CADHERIN, PLACENTAL; calcium-dependent adhesion protein, placental; cadherin 3, type 1 preproprotein; cadherin 3, type 1, P-cadherin (placental); cadherin 3, P-cadherin |
| S0165 | GRO1 Oncogene | X | X | | | | 2919 | Hs.789 | GRO1; CXCL1; MGSA; SCYB1; GROA; GRO PROTEIN, ALPHA; GRO1 oncogene (melanoma growth-stimulating activity); MELANOMA GROWTH STIMULATORY ACTIVITY, ALPHA; GRO1 oncogene (melanoma growth stimulating activity, alpha); SMALL INDUCIBLE CYTOKINE SUBFAMILY B, MEMBE |
| S0171 | Effector cell protease receptor 1 | X | | | | | N/A | Hs.1578 | BIRC5; baculoviral IAP repeat-containing 5 (survivin) |
| S0193 | PLOD2 | | X | | | | 5352 | Hs.41270 | PLOD2; LYSYL HYDROXYLASE 2; LYSINE HYDROXYLASE 2; PROCOLLAGEN-LYSINE, 2-OXOGLUTARATE 5-DIOXYGENASE 2; procollagen-lysine, 2-oxoglutarate 5-dioxygenase (lysine hydroxylase 2); procollagen-lysine, 2-oxoglutarate 5-dioxygenase (lysine hydroxylase) 2 isoform |
| S0211 | Cytochrome p450, subfamily IIa | X | | X | | | 1549 | Hs.250615 | CYPIIA7; P450-IIA4; CPAD; CPA7; CYP2A7; EC 1.14.14.1; CYTOCHROME P450 2A7; cytochrome P450, subfamily IIA (phenobarbital-inducible), polypeptide 7, isoform 2; cytochrome P450, subfamily IIA (phenobarbital-inducible), polypeptide 7, isoform 1 |
| S0218 | Putative nucleoside transporter-like protein | X | | | | | 222962 | Hs.4302 | ENT4 |
| S0221 | Solute Carrier Family 28 (sodium-coupled nucleoside transporter), member 2" | X | | X | | | 9153 | Hs.193665 | HCNT2; SLC28A2; CNT2; SPNT1; SPNT; CNT 2; SODIUM/NUCLEOSIDE COTRANSPORTER 2; NA(+)/NUCLEOSIDE COTRANSPORTER 2; SODIUM/PURINE NUCLEOSIDE CO-TRANSPORTER; SODIUM-COUPLED NUCLEOSIDE TRANSPORTER 2; CONCENTRATIVE NUCLEOSIDE TRANSPORTER 2; SODIUM-DEPENDENT PURIN |
| S0223 | Hepatic angiopoietin-related protein | X | | X | | X | 51129 | Hs.9613 | HFARP; FIAF; ANGPTL4; PGAR; angiopoietin-like 4; FASTING-INDUCED ADIPOSE FACTOR; PPARG ANGIOPOIETIN-RELATED PROTEIN; HEPATIC FIBRINOGEN/ANGIOPOIETIN-RELATED PROTEIN; PPAR(gamma) angiopoietin related protein; PPAR(gamma) angiopoietin related gene; angiopoi |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0235 | Carcinoembryonic antigen-related cell adhesion molecule 5 | | X | | | | 1048 | Hs.220529 | CEA; CEACAM5; CD66e; carcinoembryonic antigen-related cell adhesion molecule 5 |
| S0237 | podocalyxin-like protein 1 | | X | | | | 5420 | Hs.16426 | PCLP; PODXL; PODOCALYXIN-LIKE PROTEIN |
| S0241 | glycyl-tRNA synthetase | X | | X | | X | 2617 | Hs.293885 | |
| S0251 | LBP protein 32 | | | | | X | 29841 | Hs.321264 | LBP-32; LBP protein 32 |
| S0253 | Putative Integral Membrane Transporter (LC27) | X | X | | | | 55353 | Hs.296398 | LAPTM4beta; LC27; putative integral membrane transporter; lysosomal-associated transmembrane protein 4 beta |
| S0255 | Cyclin E2 | | X | X | X | X | 9134 | Hs.408658 | CYCE2; CCNE2; G1/S-SPECIFIC CYCLIN E2 |
| S0260 | KIAA0253 | | X | X | X | | 23385 | Hs.4788 | KIAA0253; nicastrin; NCSTN |
| S0265 | FXYD domain-containing ion transport regulator 3 | | X | | | X | 5349 | Hs.301350 | MAT-8; MAT8; PLML; FXYD3; phospholemman-like protein; MAMMARY TUMOR, 8-KD; FXYD domain-containing ion transport regulator 3; FXYD domain containing ion transport regulator 3; FXYD domain containing ion transport regulator 3 isoform 2 precursor; FXYD domai |
| S0267 | Immunoglobulin Superfamily, Member 3 | | X | | | | 3321 | Hs.81234 | V8; IGSF3; immunoglobin superfamily, member 3; immunoglobulin superfamily, member 3 |
| S0270 | STAM2 | | X | | | | 10254 | Hs.17200 | STAM2; DKFZp564C047; Hbp; hypothetical protein; SIGNAL-TRANSDUCING ADAPTOR MOLECULE 2; STAM-like protein containing SH3 and ITAM domains 2; signal transducing adaptor molecule (SH3 domain and ITAM motif) 2 |
| S0273 | Dickkopf Homolog 1 | | X | | | | 22943 | Hs.40499 | DKK1; DKK-1; SK; dickkopf-1 like; dickkopf (*Xenopus laevis*) homolog 1; dickkopf homolog 1 (*Xenopus laevis*); DICKKOPF, *XENOPUS*, HOMOLOG OF, 1 |
| S0280 | Putative Anion Transporter 1 | X | | | | | 65010 | Hs.298476 | SLC26A6; DKFZP586E1422; solute carrier family 26, member 6 |
| S0286 | Wnt Inhibitory Factor 1 | | X | | | | 11197 | Hs.284122 | WIF1; WIF-1; Wnt inhibitory factor-1; WNT INHIBITORY FACTOR 1 |
| S0288 | PRAME | | X | | | | 23532 | Hs.30743 | MAPE; PRAME; OPA-INTERACTING PROTEIN 4; Opa-interacting protein OIP4; preferentially expressed antigen in melanoma; melanoma antigen preferentially expressed in tumors |
| S0295 | Prostaglandin E Synthase | | X | | | | 9536 | Hs.146688 | PGES; TP53I12; MGST1L1; PP1294; PP102; PTGES; MGC10317; PIG12; MGST1-L1; MGST-IV; MGST1-like 1; p53-INDUCED GENE 12; prostaglandin E synthase; p53-induced apoptosis protein 12; prostaglandin E synthase isoform 2; prostaglandin E synthase isoform 1; micros |
| S0296 | Solute Carrier Family 7, member 5/LAT1 protein | X | X | X | | X | 8140 | Hs.184601 | SLC7A5; MPE16; D16S469E; E16; 4F2LC; CD98; HLAT1; LAT1; CD98LC; 4F2 LC; 4F2 light chain; CD98 LIGHT CHAIN; INTEGRAL MEMBRANE PROTEIN E16; L-TYPE AMINO ACID TRANSPORTER 1; Solute carrier family 7, member 5; LARGE NEUTRAL AMINO ACIDS TRANSPORTER SMALL SUBUN |
| S0296P1 | Solute Carrier Family 7, member 5/LAT1 protein | | X | | X | | 8140 | Hs.184601 | SLC7A5; MPE16; D16S469E; E16; 4F2LC; CD98; HLAT1; LAT1; CD98LC; 4F2 LC; 4F2 light chain; CD98 LIGHT CHAIN; INTEGRAL MEMBRANE PROTEIN E16; L-TYPE AMINO ACID TRANSPORTER 1; Solute carrier family 7, member 5; LARGE NEUTRAL AMINO ACIDS TRANSPORTER SMALL SUBUN |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0297 | v-maf musculoaponeurotic fibrosarcoma (avian) oncogene family, protein K or NF-E2p18" | | | X | | | 7975 | Hs.131953 | FLJ32205; NFE2U; MAFK; NFE2, 18-KD SUBUNIT; nuclear factor erythroid-2, ubiquitous (p18); NUCLEAR FACTOR ERYTHROID 2, UBIQUITOUS SUBUNIT; v-maf musculoaponeurotic fibrosarcoma oncogene homolog K (avian); v-maf avian musculoaponeurotic fibrosarcoma oncogen |
| S0301 | CEGP1 | X | | | | | 57758 | Hs.222399 | SCUBE2; signal peptide, CUB domain, EGF-like 2 |
| S0303 | GABRE gamma-aminobutyric acid (GABA) A receptor, epsilon | | X | X | X | X | 2564 | Hs.22785 | GABRE; GABA(A) RECEPTOR; GABA-A RECEPTOR, EPSILON POLYPEPTIDE; GAMMA-AMINOBUTYRIC ACID RECEPTOR, EPSILON; GAMMA-AMINOBUTYRIC-ACID RECEPTOR EPSILON SUBUNIT PRECURSOR; gamma-aminobutyric acid (GABA) A receptor, epsilon, isoform 3; gamma-aminobutyric acid (G |
| S0305 | S100 calcium-binding protein A10 | | X | X | | X | 6281 | Hs.400250 | ANX2L; p10; GP11; S100A10; 42C; ANX2LG; CAL1L; P11; CLP11; Ca[1]; P10 PROTEIN; CALPACTIN I LIGHT CHAIN; CALPACTIN I, p11 SUBUNIT; CALPACTIN I, LIGHT CHAIN; CELLULAR LIGAND OF ANNEXIN II; S100 calcium-binding protein A10 (annexin II ligand, calpactin I, li |
| S0311 | v-myb avian myeloblastosis viral oncogene homolog-like 2 | X | | X | | X | 4605 | Hs.179718 | MYBL2; MGC15600; MYB-RELATED GENE BMYB; MYB-related protein B; v-myb myeloblastosis viral oncogene homolog (avian)-like 2; V-MYB AVIAN MYELOBLASTOSIS VIRAL ONCOGENE HOMOLOG-LIKE 2 |
| S0312 | nucleoside phosphorylase | X | | | | | 4860 | Hs.75514 | PNP; NP; EC 2.4.2.1; INOSINE PHOSPHORYLASE; PURINE-NUCLEOSIDE:ORTHOPHOSPHATE RIBOSYLTRANSFERASE; purine nucleoside phosphorylase; PNP NUCLEOSIDE PHOSPHORYLASE DEFICIENCY; ATAXIA WITH DEFICIENT CELLULAR IMMUNITY |
| S0314 | aldo-keto reductase family 1, member C4 | | | X | | X | 22948 | Hs.1600 | KIAA0098; CCT5; chaperonin containing TCP1, subunit 5 (epsilon) |
| S0315 | Non-metastatic cells 1, protein (NM23A) | X | X | X | | X | 4830 | Hs.118638 | NM23H1; NDPKA; NM23; NM23-H1; NME1; NDK A; EC 2.7.4.6; NUCLEOSIDE DIPHOSPHATE KINASE-A; NDP KINASE A; METASTASIS INHIBITION FACTOR NM23; NUCLEOSIDE DIPHOSPHATE KINASE A; non-metastatic cells 1 protein; TUMOR METASTATIC PROCESS-ASSOCIATED PROTEIN; NONMETAS |
| S0316 | Squalene epoxidase | X | X | X | | | 6713 | Hs.71465 | SQLE; SE; ERG1; EC 1.14.99.7; squalene epoxidase; squalene monooxygenase |
| S0319 | Pregnancy-induced growth inhibitor | | | X | | | 29948 | Hs.31773 | OKL38; pregnancy-induced growth inhibitor |
| S0326 | Putative 4TM Mal-like protein | X | | X | | X | 114569 | Hs.76550 | MAL2; MAL proteolipid protein 2; mal, T-cell differentiation protein 2 |

APPENDIX A-continued

| AGI ID | GENE NAME | BREAST PANEL? | | LUNG PANEL? | | COLON PANEL? | NCBI LocusLink ID | UniGene ID | ALIASES |
|---|---|---|---|---|---|---|---|---|---|
| | | Russ. | HH | Russ. | HH | Russ. | | | |
| S0330 | aldo-keto reductase family 1, member C1/C2 | | | X | X | X | 1645 | Hs.306098 | DDH1; 2-ALPHA-HSD; MBAB; 20-ALPHA-HSD; H-37; DD1; DD2; HBAB; AKR1C1; HAKRC; DDH; EC 1.3.1.20; 20 ALPHA-HYDROXYSTEROID DEHYDROGENASE; ALDO-KETO REDUCTASE C; DIHYDRODIOL DEHYDROGENASE 2; DIHYDRODIOL DEHYDROGENASE, TYPE I; CHLORDECONE REDUCTASE HOMOLOG HAKRC |
| S0330x1 | aldo-keto reductase family 1, member C1/C2 | | | X | X | | 1645 | Hs.306098 | DDH1; 2-ALPHA-HSD; MBAB; 20-ALPHA-HSD; H-37; DD1; DD2; HBAB; AKR1C1; HAKRC; DDH; EC 1.3.1.20; 20 ALPHA-HYDROXYSTEROID DEHYDROGENASE; ALDO-KETO REDUCTASE C; DIHYDRODIOL DEHYDROGENASE 2; DIHYDRODIOL DEHYDROGENASE, TYPE I; CHLORDECONE REDUCTASE HOMOLOG HAKRC |
| S0331 | aldo-keto reductase family 1, member C3 | | | X | X | | 8644 | Hs.78183 | HA1753; DD3; PGFS; HAKRB; KIAA0119; 3ALPHA-HSD; DDH1; AKR1C3; EC 1.3.1.20; 3-ALPHA-HYDROXYSTEROID DEHYDROGENASE; PROBABLE TRANS-1,2-DIHYDROBENZENE-1,2-DIOL DEHYDROGENASE; ALDO-KETO REDUCTASE B; DIHYDRODIOL DEHYDROGENASE 3; PROSTAGLANDIN F SYNTHASE; 3-@ALP |
| S0331x1 | aldo-keto reductase family 1, member C3 | | | X | X | | 8644 | Hs.78183 | HA1753; DD3; PGFS; HAKRB; KIAA0119; 3ALPHA-HSD; DDH1; AKR1C3; EC 1.3.1.20; 3-ALPHA-HYDROXYSTEROID DEHYDROGENASE; PROBABLE TRANS-1,2-DIHYDROBENZENE-1,2-DIOL DEHYDROGENASE; ALDO-KETO REDUCTASE B; DIHYDRODIOL DEHYDROGENASE 3; PROSTAGLANDIN F SYNTHASE; 3-@ALP |
| S0332 | aldo-keto reductase family 1, member C4 | | | X | X | | 1645 | Hs.306098 | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol |
| S0332x1 | aldo-keto reductase family 1, member C4 | | | X | X | | 1645 | Hs.306098 | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol |
| S0336 | Putative ParB-like nuclease domain containing protein | | | X | | | 140809 | Hs.135056 | |
| S0342 | Putative glucose transporter-like protein | X | X | X | | X | 154091 | Hs.26691 | GLUT8; GLUT12 |
| S0343 | Putative glucose transporter-like protein | X | X | X | | | 154091 | Hs.26691 | GLUT8; GLUT12 |
| S0374 | chloride intracellular channel 5 (CLIC5), | X | | X | | X | 53405 | Hs.283021 | CLIC; chloride intracellular channel 5 |
| S0380 | hypothetical protein (AX119005 Sequence 169 from Patent WO0129221) | | | X | | | | Hs.59509 | |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0384 | FERM, RhoGEF (ARHGEF) and pleckstrin domain protein 1 (chondrocyte-derived) (FARP1) | | | | | X | 10160 | Hs.183738 | CDEP; FARP1; chondrocyte-derived ezrin-like protein; CHRONDROCYTE-DERIVED EZRIN-LIKE PROTEIN; FERM, RhoGEF, and pleckstrin domain protein 1; FERM, ARHGEF, AND PLECKSTRIN DOMAIN-CONTAINING PROTEIN 1; FERM, RhoGEF (ARHGEF) and pleckstrin domain protein 1 (c |
| S0388 | zinc finger transcription factor TRPS1 (trichorhinophalangeal syndrome I gene) | X | | | | | 7227 | Hs.26102 | TRPS1; TRICHORHINOPHALANGEAL SYNDROME GENE; trichorhinophalangeal syndrome I gene; ZINC FINGER TRANSCRIPTION FACTOR TRPS1 |
| S0398 | FAT tumor suppressor (*Drosophila*) homolog (FAT) | | X | X | X | | 2195 | Hs.166994 | ME5; CDHF7; FAT; cadherin ME5; FAT PROTEIN HOMOLOG; FAT tumor suppressor precursor; FAT tumor suppressor (*Drosophila*) homolog; cadherin-related tumor suppressor homolog precursor; cadherin family member 7 precursor; homolog of *Drosophila* Fat protein precu |
| S0401 | granulin (GRN) | | | X | | X | 2896 | Hs.180577 | ACROGRANIN; PROEPITHELIN; PROGRANULIN; PEPI; PCDGF; granulin; GRN; EPITHELIN PRECURSOR |
| S0404 | N-myc downstream regulated (NDRG1) | X | X | X | X | X | 10397 | Hs.75789 | NDR1; DRG1; RTP; NDRG1; RIT42; CAP43; NDRG1 PROTEIN; DIFFERENTIATION-RELATED GENE 1 PROTEIN; NICKEL-SPECIFIC INDUCTION PROTEIN CAP43; NMYC DOWNSTREAM-REGULATED GENE 1; REDUCING AGENTS AND TUNICAMYCIN-RESPONSIVE PROTEIN; N-MYC DOWNSTREAM REGULATED GENE 1 P |
| S0411 | fatty acid binding protein 5 (psoriasis-associated)(FABP5) | | | X | | | 2171 | Hs.380942 | PAFABP; EFABP; E-FABP; FABP5; PA-FABP; FATTY ACID-BINDING PROTEIN, EPIDERMAL; FATTY ACID-BINDING PROTEIN 5; FATTY ACID-BINDING PROTEIN, PSORIASIS-ASSOCIATED; fatty acid binding protein 5 (psoriasis-associated) |
| S0413 | cyclin-dependent kinase inhibitor 1C (p57, Kip2)(CDKN1C) | | | X | | | 1028 | Hs.106070 | WBS; p57(KIP2); BWCR; CDKN1C; BWS; Beckwith-Wiedemann syndrome; cyclin-dependent kinase inhibitor 1C (p57, Kip2) |
| S0414 | alpha-methylacyl-CoA racemase(AMACR) | | | | | X | 23600 | Hs.128749 | AMACR; 5.1.99.4; ALPHA-METHYLACYL-CoA RACEMASE; AMACR DEFICIENCY; AMACR ALPHA-METHYLACYL-CoA RACEMASE DEFICIENCY; alpha-methylacyl-CoA racemase isoform 1; alpha-methylacyl-CoA racemase isoform 2 |
| S0415 | gamma-aminobutyric acid (GABA) A receptor, beta 3(GABRB3) | | X | X | | | 2562 | Hs.1440 | MGC9051; GABRB3; GABA-A RECEPTOR, BETA-3 POLYPEPTIDE; GAMMA-AMINOBUTYRIC ACID RECEPTOR, BETA-3; gamma-aminobutyric acid (GABA) A receptor, beta 3; gamma-aminobutyric acid (GABA) A receptor, beta 3 isoform 2 precursor; gamma-aminobutyric acid (GABA) A rece |

APPENDIX A-continued

| AGI ID | GENE NAME | BREAST PANEL? Russ. | HH | LUNG PANEL? Russ. | HH | COLON PANEL? Russ. | NCBI LocusLink ID | UniGene ID | ALIASES |
|---|---|---|---|---|---|---|---|---|---|
| S0417 | KIAA0872 protein (KIAA0872) | X | X | | | | 22879 | Hs.436089 | KIAA0872 protein |
| S0425 | tumor necrosis factor receptor superfamily, member 21(TNFRSF21) | | | | | X | 27242 | Hs.159651 | TNFRSF21; DR6; BM-018; TNFR-related death receptor 6; tumor necrosis factor receptor superfamily, member 21; tumor necrosis factor receptor superfamily, member 21 precursor |
| S0429 | KIAA1380 (thyroid hormone receptor interactor 8)(TRIP8) | | | | | X | 221037 | Hs.381298 | JMJD1C; TRIP8; jumonji domain containing 1C; THYROID HORMONE RECEPTOR INTERACTOR 8 |
| S0432 | BSTP5 | X | | X | X | X | | Hs.19322 | |
| S0440 | cell division cycle 25B (cdc25b) | X | X | | | | 994 | Hs.153752 | CDC25HU2; EC 3.1.3.48; M-PHASE INDUCER PHOSPHATASE 2; DUAL SPECIFICITY PHOSPHATASE CDC25B; cell division cycle 25B, isoform 4; cell division cycle 25B, isoform 1; cell division cycle 25B, isoform 2; cell division cycle 25B, isoform 3 |
| S0445 | laminin, beta 1 (lamb1) | | | X | | | 3912 | Hs.82124 | LAMB1; LAMININ, BETA-1; CUTIS LAXA-MARFANOID SYNDROME; laminin, beta 1; laminin, beta 1 precursor; LAMB1 NEONATAL CUTIS LAXA WITH MARFANOID PHENOTYPE |
| S0447 | papillary renal cell carcinoma (translocation-associated) (prcc) | X | | | | | 5546 | Hs.9629 | TPRC; MGC17178; MGC4723; PRCC; proline-rich protein PRCC; RCCP1 PRCC/TFE3 FUSION GENE; papillary renal cell carcinoma (translocation-associated); RENAL CELL CARCINOMA, PAPILLARY, 1 GENE; papillary renal cell carcinoma translocation-associated gene product |
| S0455 | tumor necrosis factor (ligand) superfamily, member 10 (TNFSF10) | | | | | X | 8743 | Hs.83429 | APO2L; TL2; Apo-2L; TNFSF10; Apo-2 ligand; APO2 LIGAND; TNF-RELATED APOPTOSIS-INDUCING LIGAND; TNF-related apoptosis inducing ligand TRAIL; tumor necrosis factor (ligand) superfamily, member 10; TUMOR NECROSIS FACTOR LIGAND SUPERFAMILY, MEMBER 10 |
| S0459 | titin | X | X | | | | 7273 | Hs.434384 | titin; CMH9; TTN; TTN CARDIOMYOPATHY, FAMILIAL HYPERTROPHIC, 9 |
| S0469 | DNA fragmentation factor, 45 kD, alpha polypeptide | | | X | | | 1676 | Hs.105658 | DFF45; DFF1; DFFA; ICAD; DFF-45; INHIBITOR OF CASPASE-ACTIVATED DNase; DNA FRAGMENTATION FACTOR, 45-KD, ALPHA SUBUNIT; DNA fragmentation factor, 45 kDa, alpha polypeptide; DNA fragmentation factor, 45 kD, alpha subunit; DNA fragmentation factor, 45 kD, alp |
| S0494 | Caspase 2 | X | | | | | 835 | Hs.108131 | CASP-2; ICH-1L/1S; CASP2; ICH1; NEDD2; CASPASE-2 PRECURSOR; ICH-1 protease; EC 3.4.22.—; NEDD2 apoptosis regulatory gene; caspase 2, isoform 3; caspase 2, isoform 4; caspase 2, isoform 1 preproprotein; caspase 2, isoform 2 precursor; NEURAL PRECURSOR CELL |
| S0501 | G1 to S phase transition 1 (GSPT1) | X | | X | | X | 2935 | Hs.2707 | GSPT1; eRF3a; ETF3A; GST1, YEAST, HOMOLOG OF; PEPTIDE CHAIN RELEASE FACTOR 3A; G1-TO S-PHASE TRANSITION 1; G1 to S phase transition 1 |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0502 | GCN5 general control of amino-acid synthesis 5-like 2 (yeast) (GCN5L2) | X | | X | | X | 2648 | Hs.101067 | hGCN5; GCN5; GCN5L2; HSGCN5; EC 2.3.1.—; HISTONE ACETYLTRANSFERASE GCN5; GENERAL CONTROL OF AMINO ACID SYNTHESIS PROTEIN 5-LIKE 2; GCN5 (general control of amino-acid synthesis, yeast, homolog)-like 2; General control of amino acid synthesis, yeast, homol |
| S0507 | Guanylate-binding protein (FLJ23293) | | | X | | | 64225 | Hs.27099 | ARL6IP2; ADP-ribosylation factor-like 6 interacting protein 2 |
| S0511 | HSPC037 protein | X | | | | | 51659 | Hs.433180 | Pfs2; DNA replication complex GINS protein PSF2 |
| S0524 | Hypothetical protein (FLJ20093) | X | | | | | 55608 | Hs.172572 | ANKRD10; ankyrin repeat domain 10 |
| S0527 | Hypothetical protein (KIAA0176) | | | | | X | N/A | Hs.4935 | KCTD2; potassium channel tetramerisation domain containing 2 |
| S0528 | Hypothetical protein (KIAA0856) | X | | X | | | 23312 | Hs.13264 | RC3; KIAA0856; rabconnectin-3 |
| S0544 | RhoGEF containing hypothetical protein (FLJ14642) | X | | | | | 84904 | Hs.245342 | hypothetical protein FLJ14642 |
| S0545 | RNA methyltransferase (HpaII tiny fragments locus 9C) | X | X | | X | | 27037 | Hs.63609 | D22S1733E; HTF9C; HpaII tiny fragments locus 9C; HpaII tiny fragments locus 9C |
| S0546 | Serine rich hypothetical protein | X | | | | | 157313 | Hs.373547 | CDCA2; cell division cycle associated 2 |
| S0553 | Similar to mitotic phosphoprotein 44 [*Xenopus laevis*] | | | X | | X | | Hs.180591 | |
| S0557 | SMC4 (structural maintenance of chromosomes 4, yeast)-like 1; SMC4L1; CAP-C | | | | | X | 10051 | Hs.50758 | CAP-C; SMC4L1; CAPC; HCAP-C; chromosome-associated polypeptide C; SMC4 (structural maintenance of chromosomes 4, yeast)-like 1; structural maintenance of chromosomes (SMC) family member, chromosome-associated protein C |
| S0564 | phosphatidylserine synthase 1 | X | X | X | | X | 9791 | Hs.77329 | KIAA0024; PSSA; PTDSS1; EC 2.7.8.—; phosphatidylserine synthase 1; PHOSPHATIDYLSERINE SYNTHASE I (SERINE-EXCHANGE ENZYME I) (EC 2.7.8.—) |
| S0565 | polo (*Drosophia*)-like kinase | X | X | | | | 5347 | Hs.433619 | PLK1; PLK; PLK-1; STPK13; POLO-LIKE KINASE; EC 2.7.1.—; polo (*Drosophia*)-like kinase; SERINE/THREONINE-PROTEIN KINASE PLK; SERINE-THREONINE PROTEIN KINASE 13; SERINE THREONINE PROTEIN KINASE 13 |
| S0567 | Pirin | X | | | | X | 8544 | Hs.424966 | Pirin; PIR |
| S0578 | ATP-binding cassette, sub-family A (ABC1), member 3 (ABCA3) | | | X | | | 21 | Hs.26630 | ABCA3; ABC3; LBM180; ABC-C; EST111653; ABC transporter 3; ATP-binding cassette 3; ATP-BINDING CASSETTE TRANSPORTER 3; ATP-BINDING CASSETTE, SUBFAMILY A, MEMBER 3; ATP-binding cassette, sub-family A member 3; ATP-binding cassette, sub-family A (ABC1), memb |
| S0579 | ATP-binding cassette, sub-family A (ABC1), member 7 (ABCA7) | | | X | X | | 10347 | Hs.134514 | ABCX; ABCA7; ABCA-SSN; autoantigen SS-N; macrophage ABC transporter; ATP-BINDING CASSETTE, SUBFAMILY A, MEMBER 7; ATP-binding cassette, sub-family A (ABC1), member 7; ATP-binding cassette, sub-family A, member 7, isoform a; ATP-binding cassette, sub-famil |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0581 | ATP-binding cassette, sub-family B (MDR/TAP), member 7 (ABCB7) | | X | X | | X | 22 | Hs.125856 | ABCB7; Atm1p; ASAT; ABC7; EST140535; ABC TRANSPORTER 7; ATP-binding cassette 7; ATP-BINDING CASSETTE TRANSPORTER 7; Anemia, sideroblastic, with spinocerebellar ataxia; ATP-BINDING CASSETTE, SUBFAMILY B, MEMBER 7; ATP-binding cassette, sub-family B, member |
| S0585 | ATP-binding cassette, sub-family C (CFTR/MRP), member 12 (ABCC12) | | | X | | X | 94160 | Hs.343663 | MRP9; ABCC12; ATP-binding cassette, sub-family C, member 12; ATP-binding cassette, sub-family C (CFTR/MRP), member 12 |
| S0586 | ATP-binding cassette, sub-family G (WHITE), member 2 (ABCG2) | | | X | X | | 9429 | Hs.194720 | ABC15; MXR1; ABCP; EST157481; MXR; ABCG2; ABC1; BCRP; mitoxantrone resistance protein; breast cancer resistance protein; placenta specific MDR protein; ATP-BINDING CASSETTE TRANSPORTER, PLACENTA-SPECIFIC; ATP-BINDING CASSETTE, SUBFAMILY G, MEMBER 2; ATP-b |
| S0593 | solute carrier family 21 (organic anion transporter), member 8 (SLC21A8) | X | X | X | | X | 28234 | Hs.274981 | SLC21A8; OATP8; ORGANIC ANION TRANSPORTER 8; SOLUTE CARRIER FAMILY 21, MEMBER 8; solute carrier family 21 (organic anion transporter), member 8 |
| S0597 | solute carrier family 22 (organic anion transporter), member 6 (SLC22A6) | X | | | | | 9356 | Hs.23965 | ROAT1; MGC45260; HOAT1; PAHT; SLC22A6; PAH TRANSPORTER; para-aminohippurate transporter; renal organic anion transporter 1; solute carrier family 22 member 6 isoform b; solute carrier family 22 member 6 isoform c; solute carrier family 22 member 6 isoform |
| S0604 | solute carrier family 35 (UDP-galactose transporter), member 2 (SLC35A2) | X | | X | | X | 7355 | Hs.21899 | UGT2; UGTL; UGAT; SLC35A2; UGT1; UDP-galactose translocator; UDP-GALACTOSE TRANSPORTER, ISOFORM 2; UGALT UDP-GALACTOSE TRANSPORTER, ISOFORM 1; solute carrier family 35 (UDP-galactose transporter), member A2; solute carrier family 35 (UDP-galactose transpo |
| S0607 | cdc25b isoforms 1,3 | | | | | X | 994 | Hs.153752 | CDC25HU2; EC 3.1.3.48; M-PHASE INDUCER PHOSPHATASE 2; DUAL SPECIFICITY PHOSPHATASE CDC25B; cell division cycle 25B, isoform 4; cell division cycle 25B, isoform 1; cell division cycle 25B, isoform 2; cell division cycle 25B, isoform 3 |
| S0609 | SCD stearoyl-CoA desaturase delta-9-desaturase | | | X | | | 6319 | Hs.119597 | SCD; DELTA(9)-DESATURASE; ACYL-COA DESATURASE; EC 1.14.99.5; stearoyl-CoA desaturase (delta-9-desaturase); FATTY ACID DESATURASE |
| S0611 | MAPK12 mitogen-activated protein kinase 12 | | | X | | X | 6300 | Hs.55039 | SAPK3; p38gamma; SAPK-3; ERK6; MAPK12; p38-GAMMA; PRKM12; ERK-6; ERK3; ERK5; EC 2.7.1.—; STRESS-ACTIVATED PROTEIN KINASE-3; mitogen-activated protein kinase 3; EXTRACELLULAR SIGNAL-REGULATED KINASE 6; MAP KINASE P38 GAMMA; stress-activated protein kinase |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0612 | NFKB2 nuclear factor of kappa light 2 (p49/p100) | | | X | | X | 4791 | Hs.73090 | LYT-10; LYT10; NFKB2; ONCOGENE LYT 10; TRANSCRIPTION FACTOR NFKB2; NFKB, p52/p100 SUBUNIT; LYMPHOCYTE TRANSLOCATION CHROMOSOME 10; NUCLEAR FACTOR KAPPA-B, SUBUNIT 2; Nuclear factor of kappa light chain gene enhancer in B-cells 2; nuclear factor of kappa l |
| S0613 | TNFRSF5: tumor necrosis factor receptor superfamily, member 5 (CD40) | | | X | | X | 958 | Hs.25648 | Bp50; TNFRSF5; MGC9013; CDW40; CD40 antigen; CD40L receptor; B CELL-ASSOCIATED MOLECULE CD40; CD40 type II isoform; B cell surface antigen CD40; nerve growth factor receptor-related B-lymphocyte activation molecule; tumor necrosis factor receptor superfam |
| S0614 | EBI3 Epstein-Barr virus induced gene 3 | | | X | X | X | 10148 | Hs.185705 | EBI3; EPSTEIN-BARR VIRUS-INDUCED GENE 3; Epstein-Barr virus induced gene 3 precursor |
| S0616 | ZNF339: zinc finger protein 339 | | | X | | | 58495 | Hs.71935 | ZNF339; zinc finger protein 339 |
| S0617 | DAB2IP: DAB2 interacting protein | | X | | | | 153090 | Hs.238465 | DAB2IP; DAB2 interacting protein |
| S0618 | PPFIA1: protein tyrosine phosphatase, receptor type, f polypeptide (PTPRF), interacting protein (liprin), alpha 1 | | | | | X | 8500 | Hs.183648 | MGC26800; LIP1; PPFIA1; LIP.1; LAR-interacting protein 1; PTPRF interacting protein alpha 1 isoform a; PTPRF interacting protein alpha 1 isoform b; protein tyrosine phosphatase, receptor type, f polypeptide (PTPRF), interacting protein (liprin), alpha 1 |
| S0631 | hypothetical protein CAB66760 | | | | | X | 56963 | Hs.271277 | RGMA; REPULSIVE GUIDANCE MOLECULE; RGM domain family, member A |
| S0633 | novel hypothetical protein | | X | | | X | 144347 | Hs.432901 | LOC144347; hypothetical protein LOC144347 |
| S0645 | frizzled homolog 7 FZD7 | | | X | | | 8324 | Hs.173859 | FzE3; FZD7; frizzled 7; frizzled homolog 7 (Drosophila); Frizzled, drosophila, homolog of, 7 |
| S0646 | SLC3A2: solute carrier family 3, member 2 | | | X | X | | 6520 | Hs.79748 | MDU1; 4T2HC; SLC3A2; NACAE; 4F2HC; 4F2 HEAVY CHAIN; CD98 HEAVY CHAIN; CD98 MONOCLONAL ANTIBODY 44D7; ANTIGEN DEFINED BY MONOCLONAL ANTIBODY 4F2, HEAVY CHAIN; antigen identified by monoclonal antibodies 4F2, TRA1.10, TROP4, and T43; SOLUTE CARRIER FAMILY 3 |
| S0651 | PLA2R1 phospholipase A2 receptor 1 | | | | | X | 22925 | Hs.171945 | PLA2IR; PLA2-R; PLA2R1; PLA2G1R; PHOSPHOLIPASE A2 RECEPTOR, 180-KD; phospholipase A2 receptor 1, 180 kDa |
| S0654 | KIAA0182 protein (KIAA0182) | | X | | | | 23199 | Hs.222171 | KIAA0182; KIAA0182 protein |
| S0659 | thymidine kinase 2, mitochondrial | | X | | | | 7084 | Hs.274701 | TK2; THYMIDINE KINASE, MITOCHONDRIAL; thymidine kinase 2, mitochondrial |
| S0663 | hypothetical protein FLJ12799 (FLJ12799) | | X | X | | X | 64430 | Hs.413671 | FLJ12799; hypothetical protein FLJ12799 |
| S0665 | KIAA1007 protein (KIAA1007) | | X | X | | X | 23019 | Hs.279949 | KIAA1007; KIAA1007 protein; adrenal gland protein AD-005; KIAA1007 protein isoform a; KIAA1007 protein isoform b |
| S0670 | DKFZP566O1646 protein (DC8) | | X | | | | 25936 | Hs.24427 | DC8; DKFZP566O1646 protein |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S0673 | ART-4 protein (ART-4) | | X | | | | 28987 | Hs.3566 | ART-4; NOB1P; adenocarcinoma antigen recognized by T lymphocytes 4; likely ortholog of mouse nin one binding protein |
| S0676 | guanine nucleotide binding protein (G protein) alpha 12 (GNA12) | | X | | | | 2768 | Hs.182874 | RMP; NNX3; GNA12; G alpha 12; Guanine nucleotide-binding protein, alpha-12 subunit; guanine nucleotide binding protein (G protein) alpha 12 |
| S0677 | GrpE-like protein cochaperone (HMGE) | | X | | | | 80273 | Hs.151903 | HMGE; GrpE-like protein cochaperone; HUMAN MITOCHONDRIAL GrpE PROTEIN; GrpE, *E. COLI*, HOMOLOG OF |
| S0684 | FLJ34922 | | X | | | | 91607 | Hs.235709 | |
| S0687 | hypothetical protein FLJ20457 | | X | | | | 54942 | Hs.29276 | FLJ20457; hypothetical protein FLJ20457 |
| S0691 | solute carrier family 7, (cationic amino acid transporter, y+ system) member 11 | | | | X | | 23657 | Hs.6682 | CCBR1; SLC7A11; xCT; cystine/glutamate transporter; SYSTEM Xc(—) TRANSPORTER-RELATED PROTEIN; SOLUTE CARRIER FAMILY 7, MEMBER 11; solute carrier family 7, (cationic amino acid transporter, y+ system) member 11 |
| S0695 | Integrin, beta 4 | | X | | | | 3691 | Hs.85266 | GP150; ITGB4; CD104 antigen; INTEGRIN, BETA-4; Integrin beta-4 precursor; integrin, beta 4 |
| S0702 | Solute Carrier Family 7, member 5/LAT1 protein | | X | | X | | 8140 | Hs.184601 | SLC7A5; MPE16; D16S469E; E16; 4F2LC; LAT1; CD98LC; 4F2 LC; 4F2 light chain; CD98 LIGHT CHAIN; INTEGRAL MEMBRANE PROTEIN E16; L-TYPE AMINO ACID TRANSPORTER 1; Solute carrier family 7, member 5; LARGE NEUTRAL AMINO ACIDS TRANSPORTER SMALL SUBUN |
| S5002 | cytokeratin 14 | X | | X | | X | 3861 | Hs.355214 | CK; KRT14; K14; EBS4; EBS3; cytokeratin 14; CK 14; KERATIN, TYPE I CYTOSKELETAL 14; keratin 14 (epidermolysis bullosa simplex, Dowling-Meara, Koebner) |
| S5003 | cytokeratin 17 | X | | | | | 3872 | Hs.514738 | PCHC1; PC; PC2; 39.1; KRT17; K17; CYTOKERATIN 17; VERSION 1; CK 17; KERATIN, TYPE I CYTOSKELETAL 17 |
| S5004 | cytokeratin 18 | X | | | | | 3875 | Hs.406013 | K18; CYK18; KRT18; CYTOKERATIN 18; CK 18; KERATIN, TYPE I CYTOSKELETAL 18 |
| S5005 | CAM5.2 (cytokeratin 8/18) | X | | X | | X | 3875 | Hs.65114 | K18; CYK18; KRT18; CYTOKERATIN 18; CK 18; KERATIN, TYPE I CYTOSKELETAL 18 |
| S5012 | EpCAM (Ab-1), mono | X | | X | | X | 4072 | Hs.692 | TROP1; LY74; Ep-CAM; GA733-2; EGP40; MK-1; CO17-1A; EPCAM; M4S1; KSA; TACSTD1; EGP; MK-1 antigen; EPITHELIAL CELLULAR ADHESION MOLECULE; GASTROINTESTINAL TUMOR-ASSOCIATED ANTIGEN 2, 35-KD GLYCOPROTEIN; tumor-associated calcium signal transducer 1 precurso |
| S5014 | Estrogen Receptor Beta (Ab-2), mono | X | | | | | 2100 | Hs.103504 | ER-BETA; ESR-BETA; ESR2; Erb; ESRB; NR3A2; ESTROGEN RECEPTOR, BETA; estrogen receptor 2 (ER beta) |
| S5038 | milk fat globule protein (C-Mu1) | X | | X | | X | 4582 | Hs.89603 | PEMT; MUC1; episialin; EMA; PUM; H23AG; CD227; PEM; CARCINOMA-ASSOCIATED MUCIN; H23 antigen; TUMOR-ASSOCIATED MUCIN; DF3 antigen; peanut-reactive urinary mucin; mucin 1, transmembrane; polymorphic epithelial mucin; MUCIN 1, URINARY; MUCIN, TUMOR-ASSOCIATE |

APPENDIX A-continued

| AGI ID | GENE NAME | BREAST PANEL? Russ. | HH | LUNG PANEL? Russ. | HH | COLON PANEL? Russ. | NCBI LocusLink ID | UniGene ID | ALIASES |
|---|---|---|---|---|---|---|---|---|---|
| S5044 | CD 71 MAB-3 | X | | X | | X | 7037 | Hs.77356 | P90; TR; TFRC; TFR; CD71; T9; TRFR; ANTIGEN CD71; TRANSFERRIN RECEPTOR PROTEIN; transferrin receptor (p90, CD71) |
| S5045 | c-ErbB2/Her-2 | X | | | | X | 2064 | Hs.323910 | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL |
| S5047 | LRP/MVP MAB-2 | X | | X | | X | 9961 | Hs.80680 | MVP; LRP; VAULT1; LUNG RESISTANCE-RELATED PROTEIN; MAJOR VAULT PROTEIN, RAT, HOMOLOG OF |
| S5064 | TP63 | | | X | | | 8626 | Hs.137569 | LMS; TP73L; KET; SHFM4; p73H; EEC3; TP63; p51; TUMOR PROTEIN p63; TUMOR PROTEIN p73-LIKE; p53-RELATED PROTEIN p63; tumor protein 63 kDa with strong homology to p53 |
| S5065 | estrogen receptor 1 | X | | | | | 2099 | Hs.1657 | ER; NR3A1; ESR1; Era; ESR; ER-ALPHA; ESRA; ESTRADIOL RECEPTOR; ESTROGEN RECEPTOR, ALPHA; estrogen receptor 1 (alpha) |
| S5066 | c-ErbB2/Her-2 | X | | | | X | 2064 | Hs.446352 | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL |
| S5067 | Cathepsin D | X | | X | | X | 1509 | Hs.343475 | CTSD; MGC2311; CPSD; EC 3.4.23.5; cathepsin D preproprotein; Cathepsin D precursor; cathepsin D (lysosomal aspartyl protease); |
| S5069 | CA 125 | | | X | | | 94025 | Hs.432676 | |
| S5070 | CA 15-3 | X | | X | | X | N/A | N/A | |
| S5071 | CA 19-9 | X | | X | | X | N/A | N/A | |
| S5072 | c-myc | | | X | | X | 4609 | Hs.79070 | c-Myc; MYC; ONCOGENE MYC; Myc proto-oncogene protein; PROTOONCOGENE HOMOLOGOUS TO MYELOCYTOMATOSIS VIRUS; v-myc myelocytomatosis viral oncogene homolog (avian); v-myc avian myelocytomatosis viral oncogene homolog; Avian myelocytomatosis viral (v-myc) onco |
| S5073 | e-cadherin | X | | X | | X | 999 | Hs.194657 | CDH1; Cadherin-1; Arc-1; ECAD; CDHE; Uvomorulin; LCAM; Epithelial-cadherin precursor; cell-CAM 120/80; CADHERIN, EPITHELIAL; calcium-dependent adhesion protein, epithelial; cadherin 1, E-cadherin (epithelial); cadherin 1, type 1 preproprotein; cadherin 1, |
| S5074 | gst-pi | | | X | | X | 2950 | Hs.226795 | GSTP1; DFN7; GSTP1-1; GST3; GSTPP; GST class-pi; glutathione transferase; EC 2.5.1.18; glutathione S-transferase pi; GST, CLASS PI; deafness, X-linked 7; GLUTATHIONE S-TRANSFERASE 3; GLUTATHIONE S-TRANSFERASE, PI; FAEES3 GLUTATHIONE S-TRANSFERASE PI PSEUD |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S5075 | p53 | | | X | | X | 7157 | Hs.1846 | p53; TP53; TRP53; PHOSPHOPROTEIN P53; TRANSFORMATION-RELATED PROTEIN 53; TUMOR SUPPRESSOR P53; CELLULAR TUMOR ANTIGEN P53; tumor protein p53 (Li-Fraumeni syndrome) |
| S5076 | progesterone receptor | X | | | | X | 5241 | Hs.2905 | NR3C3; PR; PGR; PROGESTERONE RESISTANCE; PSEUDOCORPUS LUTEUM INSUFFICIENCY PROGESTERONE RECEPTOR |
| S5077 | ps2 MAB-1 | X | | | | | 7031 | Hs.350470 | |
| S5079 | NSE | X | | X | | X | 2026 | Hs.511915 | NSE; ENO2; 2-phospho-D-glycerate hydro-lyase; ENOLASE, GAMMA; neurone-specific enolase; ENOLASE, NEURON-SPECIFIC; 2-phospho-D-glycerate hydrolyase; EC 4.2.1.11; Neural enolase; enolase-2, gamma, neuronal; neuron specific gamma enolase; enolase 2, (gamma, |
| S5080 | bcl-2 | | | X | | | 596 | Hs.79241 | BCL2; FOLLICULAR LYMPHOMA; APOPTOSIS REGULATOR BCL-2; B-cell CLL/lymphoma 2; B-cell lymphoma protein 2 alpha; B-cell lymphoma protein 2 beta; ONCOGENE B-CELL LEUKEMIA 2 LEUKEMIA, CHRONIC LYMPHATIC, TYPE 2 |
| S5081 | RB | | | X | | X | 5925 | Hs.75770 | p105-Rb; PP110; Retinoblastoma-1; RB; RB1; RETINOBLASTOMA-ASSOCIATED PROTEIN; RB OSTEOSARCOMA, RETINOBLASTOMA-RELATED; retinoblastoma 1 (including osteosarcoma) |
| S5082 | Synaptophysin | | | X | | X | 6855 | Hs.75667 | SYP; Synaptophysin; Major synaptic vesicle protein P38 |
| S5083 | bax | | | | | X | 581 | Hs.159428 | BAX; BCL2-associated X protein; APOPTOSIS REGULATOR BAX, MEMBRANE ISOFORM ALPHA |
| S6001 | estrogen receptor | | X | | | | 2099 | Hs.1657 | ER; NR3A1; ESR1; Era; ESR; ER-ALPHA; ESRA; ESTRADIOL RECEPTOR; ESTROGEN RECEPTOR, ALPHA; estrogen receptor 1 (alpha) |
| S6002 | progesterone receptor | | X | | | | 5241 | Hs.2905 | NR3C3; PR; PGR; PROGESTERONE RESISTANCE; PSEUDOCORPUS LUTEUM INSUFFICIENCY PROGESTERONE RECEPTOR |
| S6003 | c-ErbB2/Her-2 | | X | | | | 2064 | Hs.323910 | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL |
| S6004 | bcl-2 | | | | X | | 596 | Hs.79241 | BCL2; FOLLICULAR LYMPHOMA; APOPTOSIS REGULATOR BCL-2; B-cell CLL/lymphoma 2; B-cell lymphoma protein 2 alpha; B-cell lymphoma protein 2 beta; ONCOGENE B-CELL LEUKEMIA 2 LEUKEMIA, CHRONIC LYMPHATIC, TYPE 2 |

APPENDIX A-continued

| AGI ID | GENE NAME | BREAST PANEL? Russ. | BREAST PANEL? HH | LUNG PANEL? Russ. | LUNG PANEL? HH | COLON PANEL? Russ. | NCBI LocusLink ID | UniGene ID | ALIASES |
|---|---|---|---|---|---|---|---|---|---|
| S6005 | cytokeratin 5/6 | | X | | X | | 3852 | Hs.433845 | KRT5; EBS2; Keratin-5; K5; CYTOKERATIN 5; CK 5; 58 KDA CYTOKERATIN; KERATIN, TYPE II CYTOSKELETAL 5; keratin 5 (epidermolysis bullosa simplex, Dowling-Meara/Kobner/Weber-Cockayne types) |
| S6006 | p53 | | X | | X | | 7157 | Hs.1846 | p53; TP53; TRP53; PHOSPHOPROTEIN P53; TRANSFORMATION-RELATED PROTEIN 53; TUMOR SUPPRESSOR P53; CELLULAR TUMOR ANTIGEN P53; tumor protein p53 (Li-Fraumeni syndrome) |
| S6007 | ki67 | | X | | X | | 4288 | Hs.80976 | ki67; MKI67 |
| S6008 | EGFR 1 | | X | | X | | 1956 | Hs.77432 | S7; EGFR; 2.7.1.112; ERBB; ONCOGENE ERBB; ERBB1 SPECIES ANTIGEN 7; V-ERB-B AVIAN ERYTHROBLASTIC LEUKEMIA VIRAL ONCOGENE HOMOLOG; epidermal growth factor receptor (avian erythroblastic leukemia viral (v-erb-b) oncogene homolog) |
| S6011 | NSE | | | | X | | 2026 | Hs.146580 | NSE; ENO2; 2-phospho-D-glycerate hydro-lyase; ENOLASE, GAMMA; neurone-specific enolase; ENOLASE, NEURON-SPECIFIC; 2-phospho-D-glycerate hydrolyase; EC 4.2.1.11; Neural enolase; enolase-2, gamma, neuronal; neuron specific gamma enolase; enolase 2, (gamma, benign chorea; chorea, hereditary benign; NK-2 (*Drosophila*) homolog A (thyroid nuclear factor); Thyroid transcription factor 1 (NK-2, *Drosophila*, homolog of, A); BCH; BHC; TEBP; TTF1; NKX2A; TTF-1; NKX2.1 |
| S6012 | Thyroid Transcription Factor-1 | | | | X | | 7080 | Hs.94367 | |
| S6013 | c-ErbB2/Her-2 | | | | X | | 2064 | Hs.323910 | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL |

| | Antibody Generation | | | | IHC Images (Appendix B) | | |
|---|---|---|---|---|---|---|---|
| | Peptide 1 | Peptide 2 | Peptide 3 | | | | |
| AGI ID | (SEQ ID NO:) | (SEQ ID NO:) | (SEQ ID NO:) | TITER | Breast IHC | Lung IHC | Colon IHC |
| S0011 | DYISKSKEDVK LK (1) | EKRTNGLRRTPKQVD (2) | TEESINDEDIYKGL PDLIDE (3) | 1:90-1:100 | | | |
| S0018 | SKTINPQVSKT EYKELLQE (4) | DDNATTNAIDELKEC (5) | NQTDETLSNVEVF MQ (6) | 1:300 | | | |
| S0020 | SSDDGIRPLP EYSTEKHKK (7) | NKTKKKKSSRLPPEK (8) | DGKSKDKPPKRKK ADTE (9) | 1:100 | | | |
| S0021 | KNKEPLTKKG ETKTAERD (10) | KLTCTDLDSSPRSFRYS (11) | EVDYENPSNLAAG NKYT (12) | 1:200-1:2500 | 2_25_2_5_66_21_58 | | |
| S0022 | KTLQVFNPLR FSRENSEKIH (13) | QHFAIIECKVAVALT (14) | RKFLAPDHSRPPQ PVRQ (15) | 1:50-1:500 | 1_25_12_6_67_22_73 | 1_26_5_2_72_22_24 | 1_32_14_2_89_22_15 |
| S0024 | VLPLKNILDEIK KPKN (16) | YELCREVRRRMVQG KT (17) | MAKSAEVKLAIFG RAGVGK (18) | 1:900-1:1000 | | | |
| S0032 | KNTEISFKLGV EFDE (19) | HLQKWDGQETTLVRE (20) | TKPTTIIEKNGDILT LKTH (21) | 1:225 | | | |
| S0036 | LQQMAAKDR GTTKEVEEVS (22) | KRKISFASIEISSDNVDY SD (23) | DGNDVEFTWLRG NDSVRGLEH (24) | 1:250-1:500 | | | |
| S0037 | QRQQIAKSFK AQFGKDLTE (25) | REIMKAYEEDYGSSLEE DIQ (26) | EEYEKIANKSIEDSI KSE (27) | 1:30-1:40 | | | |
| S0039 | EGGSLVPAAR QQHCTQVRS RR (28) | RKAGKSKKSFSRKEAE (29) | KTHEKYGWVTPPV SDG (30) | 1:50-1:30000 | 3_18_4_3_108_39_26 | 3_26_6_4_67_39_51 | |
| S0040 | MDLEGDRNG GAKKKN (31) | NLEDLMSNITNRSDIND TG (32) | RGSQAQDRKLSTK EA (33) | 1:200-1:400 | 3_18_4_6_63_40_63 | 2_26_5_129_40_59 | 1_32_6_3_105_40_34 |
| S0041 | MDLEAAKNGT AWRPTSAE (34) | NFSFPVNFSLSLLNPGK (35) | KNSQMCQKSLDV ETDG (36) | 1:60-1:300 | 2_18_7_4_102_41_54 | | |

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0042 | MALRGFCSAD GSD (37) | KNWKKECAKTRKQPVK (38) | DSIERRPVKDGGG TNS (39) | 1:40-1:500 | 1_18_11_3_65_42_33 | 2_26_3_5_176_42_59 | 4_32_8_6_170_42_77 |
| S0043 | MLEKFCNSTF WNSSFLDSPE (40) | SILCGTFQFQTLIRT (41) | ENNESSNNPSSIA S (42) | 1:50-1:333 | 1_18_11_3_66_43_33 | 3_26_12_8_177_43_101 | 4_32_8_6_171_43_77 |
| S0044 | QEVKPNPLQD ANICSR (43) | DEISQRNRQLPSDGKK (44) | VQDFTAFWDKASE TPTLQ (45) | 1:20-1:100 | 2_18_7_10_67_44_144 | 2_26_8_3_169_44_36 | 4_32_8_6_167_44_77 |
| S0045 | MDALCGSGEL GSKFWDSN (46) | RKQEKQTARHKASAA (47) | DPQSVERKTISPG (48) | 1:2000 | | | |
| S0046 | MKDIDIGKEYII PSPGYRS (49) | RDREDSKFRRTRPLEC QD (50) | SKHESSDVNCRRL ER (51) | 1:100-1:300 | 1_18_5_5_68_46_49 | 1_26_14_8_134_46_99 | 4_32_8_6_120_46_77 |
| S0047 | MAAPAEPCAG QGVWNQTEP E (52) | DPGVVDSSSSGSAAGK D (53) | HTLVAENAMNAEK (54) | 1:50 | 3_25_5_3_118_47_33 | 3_26_10_4_173_47_47 | 4_32_8_6_169_47_77 |
| S0048 | QEVLSKIQHG HTIIS (55) | TNSSLNQNMTNGTR (56) | MSDSVILRSIKKFG EEND (57) | 1:600 | | | |
| S0049 | GADDPSSVTA EEIQR (58) | NAVASPEFPPRPRNT (59) | KPNGIYRKLMNKQ SFISA (60) | 1:10-1:25 | 2_18_3_8_71_49_118 | | |
| S0050 | MASSRCPAPR GCR (61) | QGGSGNPVRR (62) | EFVGDGIYNNTMG HVHS (63) | 1:80 | 3_18_11_7_103_50_77 | | |
| S0052 | MPLAFCGSEN HSAAYR (64) | DHLGKENDVFQPKTQF LG (65) | EIREEQCAPHEPT PQG (66) | 1:25-1:150 | 1_18_2_8_74_52_87 | | |
| S0053 | MSLSFCGNNI SS (67) | QRVNETQNGTNNTTGI SE (68) | DEIGDDSWRTGES SLPFES (69) | 1:25-1:50 | 3_18_3_7_75_53_69 | | |
| S0055 | MVKVTFNSAL AQKEAKDEP K (70) | QTIEENIKIFEEEVE (71) | HDKETYKLQRRET IKGIQKRE (72) | 1:450-1:500 | | | |
| S0057 | HKKETESDQD DEIEKTDRRQ (73) | EGFKVKTKKEIRHVEKK SHS (74) | MAHAASQLKKNR DLEINAEE (75) | 1:750 | | | |
| S0058 | ERALAAAQRC HKKVMKER (76) | TAGMKDLLSVFQAYQ (77) | DPPRTVLQAPKEW VCL (78) | 1:20 | | | |

-continued

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0059 | MEAADASRSN GSSPEARDAR (79) | ELHLKPHLEGAAFRDH Q (80) | EGEGLGQSLGNFK DDLLN (81) | 1:50-1:3000 | 2_18_2_5_41_59_62 | 2_26_13_1_128_59_13 | 4_32_8_6_166_59_77 |
| S0059P2 | ELHLKPHLEG AAFRDHQ (82) | N/A | N/A | 1:90 | | | |
| S0063 | GSERGAGR GSSGGREE (83) | KIWSLAETATSPDNPRR S (84) | KKLLKTAFQPVPR RPQNHLD (85) | 1:200-1:1200 | | | |
| S0068 | RRSSTTHVKQ AINKMLTKISS (86) | N/A | N/A | 1:500-1:40000 | | | |
| S0070 | MRRKNTCQNF MEYFCISLAF (87) | NETILYFPFSSHSSYTV RSKK (88) | KVQIPAYIEMNIPL VILCQ (89) | 1:10-1:100 | | | |
| S0072 | MLTELEKALN SIIDVYHK (90) | RDDLKKLLETECPQYIR KKGAD (91) | KMGVAAHKKSHE ESHKE (92) | 1:6500-1:10000 | | | |
| S0073 | PESRKDPSGA SNPSADS (93) | HGLAPHESQLHLKGD (94) | EQQHKLDFKAYEQ ALQYS (95) | 1:100-1:2700 | | | |
| S0073P2 | PESRKDPSGA SNPSADS (96) | HGLAPHESQLHLKGD (97) | EQQHKLDFKAYEQ ALQYS (98) | 1:50-1:450 | | | |
| S0074 | EEYVGLSANQ CAVPAKDRVD (99) | RVDCGYPHVTPKECN (100) | VPWCFKPLQEAEC TF (101) | 1:2500-1:30000 | 1_25_8_4_98_74_49 | 2_26_4_3_68_74_32 | |
| S0074P3 | VPWCFKPLQE AECTF (102) | N/A | N/A | 1:810 | | | |
| S0076x1 | KKEPVTTRQV RTIVEE (103) | QDGKVISSREQVHQTT R (104) | SSSIKGSSGLGGG SS (105) | 1:200 | | | |
| S0079 | DHNHAASGKN KRKALCPDHD (106) | EEPAMEMKRGPLFSHL SSQNI (107) | QRYSREELKDAGV ATL (108) | 1:400-1:800 | | | |
| S0081 | MDIEAYLERIG YKKSRNKLDL E (109) | QMWQPLELISGKDQPQ VPCVFR (110) | FNISLQRKLVPKH GDRFFTI (111) | 1:10-1:60 | 1_18_5_5_55_81_49 | | |

-continued

| AGI ID | Antibody Generation Peptide 1 (SEQ ID NO:) | Peptide 2 (SEQ ID NO:) | Peptide 3 (SEQ ID NO:) | TITER | IHC Images (Appendix B) Breast IHC | Lung IHC | Colon IHC |
|---|---|---|---|---|---|---|---|
| S0086 | QPPPLCQWG RHQPSWKPL MN (112) | EKTHGLVVENQELRQR LGMD (113) | RQRLTHLSPEKA LRRKLKNR (114) | 1:180-1:400 | | | |
| S0096 | REHMQAVTRN YITHPR (115) | KKSKAVLDYHDDN (116) | DEFYSREGRLQDL APDTAL (117) | 1:100-1:800 | | | |
| S0110 | RYAPDFARDK DQRSLDID (118) | SVFYQYLEQSKYRVMN KDQ (119) | EDGAWPVLLDEFV EWQKVRQTS (120) | 1:500-1:2500 | 1_25_14_7_92_110_98 | | 4_32_8_6_207_110_77 |
| S0117 | SFKSPQVVLK EEEEKNEKR (121) | RKKQQEAQGEKASRYI E (122) | EDIGITVDTVLILEE KEQTN (123) | 1:200 | | | |
| S0119 | DFRCEEGQEE GGCLPRPQ (124) | DGTSFAEEVEKPTKCG CALCA (125) | KAFRGATDLKNLR LDKNQ (126) | 1:900 | | | |
| S0132 | MNLLDPFMKM TDEQEKGLS (127) | NTFPKGEPDLKKESEE DK (128) | KNGQAEAEEATEQ THISPN (129) | 1:100-1:500 | 4_25_6_1_95_132_6 | 1_26_4_8_127_132_109 | |
| S0137 | QASSLRLEPG RANDGDWH (130) | ELKGFAERLQRNESGL DSGR (131) | RSGKSQPSYIPFLL REE (132) | 1:2000-1:5000 | 4_25_14_3_51_137_42 | 1_26_3_1_65_137_3 | 1_32_5_3_80_137_33 |
| S0139 | RRSDYAKVAK IFYNLSIQSFD D (133) | KNFTMNEKLKKFFNVLT TN (134) | EFFVNEARKNNHH FKSESEE (135) | 1:2500-1:30000 | | | |
| S0140 | KNTQAAEALV KLYETKLCE (136) | QENQPENSKTLATQLN Q (137) | KQMEKDLAFQKQ VAEKQLK (138) | 1:250-1:20000 | 2_25_5_5_70_140_61 | | |
| S0140P1 | KNTQAAEALV KLYETKLCE (136) | N/A | N/A | 1:270 | | | |
| S0143 | EFVEQLRKEG VFAKEVR (139) | DRHPQALEAAQAELQQ HD (140) | REVRQLTLRKLQE LSSKADE (141) | 1:5000-1:30000 | 2_25_12_8_64_143_101 | | |
| S0143P3 | EFVEQLRKEG VFAKEVR (139) | DRHPQALEAAQAELQQ HD (140) | REVRQLTLRKLQE LSSKADE (141) | 1:300-1:630 | | | |

| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
|---|---|---|---|---|---|---|---|
| S0144 | AYIREGHEKQ ADIMIFFAE (142) | DEASLEPGYPKHIKELG R (143) | RGSFMGSDEVFTY FYK (144) | 1:500-1:20000 | 2_25_13_7_54_144_97 | 2_26_12_7_208_144_96 | |
| S0149 | RQEHCMSEHF KNRPACLGAR (145) | QGHKWGESPSQGTQA GAGK (146) | RACGKRVSEGDR NGSGGGKWG (147) | 1:400-1:20000 | | | |
| S0156 | MVEAFCATWK LTNSQN (148) | QVGNVTKPTVIISQE (149) | KVVIRTLSTPKNTE (150) | 1:100-1:20000 | | | |
| S0158 | RAVFREAEVT LEAGGAEQE (151) | QEPALFSTDNDDFTVR N (152) | QKYEAHVPENAVG HE (153) | 1:150-1:500 | 1_18_9_10_8_158_102 | 1_26_3_8_69_158_110 | 1_32_2_1_94_158_2 |
| S0165 | KKIIEKMLNSD KSN (154) | N/A | N/A | 1:100-1:500 | | | |
| S0171 | GKPGNQNSK NEPPKKRERE R (155) | QAEAPLVPLSRQNK (156) | NCFLTERKAQPDE (157) | 1:22500-1:30000 | | | |
| S0193 | KQVDLENVWL DFIRE (158) | EFDTVDLSAVDVHPN (159) | NKEVYHEKDIKVFF DKAK (160) | 1:20000 | | | |
| S0211 | KRGIEERIQEE SGFLIE (161) | DRVIGKNRQPKFEDRT K (162) | NPQHFLDDKGQFK KSD (163) | 1:500-1:2500 | | | |
| S0218 | RHCILGEWLPI LIMAVFN (164) | KQRELAGNTMTVSYMS (165) | RNAHGSCLHASTA NGSILAGL (166) | 1:20-1:50 | 4_25_8_5_73_218_64 | | |
| S0221 | ELMEKEVEPE GSKRTD (167) | KARSFCKTHARLFKK (168) | KNKRLSGMEEWIE GEK (169) | 1:500-1:1200 | | | |
| S0223 | EGSTDLPLAP ESRVDPE (170) | KVAQQQRHLEKQHLR (171) | DHKHLDHEVAKPA RRKRLPE (172) | 1:30-1:10000 | | | 1_32_8_3_135_223_36 |
| S0235 | KLTIESTPPNV AEGKEC (173) | KSDLVNEEATGQFRVY PELPK (174) | KPVEDKDAVAFTC EPEAQ (175) | 1:500-1:4500 | | | |
| S0237 | DEKLISLICRA VKATFNPAQD K (176) | KDKWDELKEAGVSDM KLGD (177) | DSWIVPLDNLTKD DLDEEDTHL (178) | 1:1000 | | | |

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0241 | RKRVLEAKEL ALQPKDDIVD (179) | RHGVSHKVDDSGSIG RRYAR (180) | EARYPLFEGQETG KKETIEE (181) | 1:500-1:7500 | | 1_26_7_3_133_241_35 | 4_32_8_168_241_77 |
| S0251 | EALYPQRRSY TSEDEAWK (182) | DYYKVPRERRSSTAKP EVE (183) | DKYDVPHDKIGKIF KKCKK (184) | 1:5400 | | | 2_32_5_6_134_251_80 |
| S0253 | DPDQYNFSSS ELGGDFEFMD D (185) | EYIRQLPPNFPYRDD (186) | DTTVLLPPYDDAT VNGAAKE (187) | 1:500-1:2000 | | | |
| S0255 | RREEVTKKHQ YEIR (188) | KESRVVHDKHFEVLHS DLE (189) | DFFDRFMLTQKDI NK (190) | 1:1000-1:2000 | | | |
| S0260 | ESKHFTRDLM EKLKGRTSR (191) | ETDRLPRCVRSTARLA R (192) | ESRWKDIRARIFLI ASKELE (193) | 1:3600-1:5400 | | | |
| S0265 | SEWRSSGEQ AGR (194) | KCKCKFGQKSGHHPG E (195) | KVTLGLLVFLAGFP VLDANDLED (196) | 1:400 | | | |
| S0267 | KVAKESDSVF VLKIYHLRQED (197) | EREKTVTGEFIDKESKR PK (198) | KRAEDTAGQTALT VMRPD (199) | 1:200-1:250 | | 2_26_9_1_205_267_9 | |
| S0270 | KVARKVRALY DFEAVEDNE (200) | ETEVAAVDKLNVIDDDV E (201) | EIKKSEPEPVYIDE DKMDR (202) | 1:1000-1:9000 | | 2_26_8_3_200_270_36 | |
| S0273 | DEECGTDEYC ASPTRGGD (203) | RGEIEETITESFGNDHS TLD (204) | N/A | 1:400-1:500 | | | |
| S0280 | MDLRRRDYH MERPLLNQEH LEE (205) | DTDIYRDVAEYSEAKE (206) | EFYSDALKQRCGV DVDFLISQKKK (207) | 1:1800-1:2400 | 2_25_6_1_108_280_6 | | |
| S0286 | DAHQARVLIG FEEDILIVSE EK (208) | ERRICECPDGFHGPHC (209) | N/A | 1:90 | | | |
| S0288 | DIKMILKMVQL DSIEDLE (210) | KRKVDGLSTEAEQPFIP KVKRKK (211) | KEGACDELFSYLIE VE (212) | 1:1200 | | | |
| S0295 | RLRKKAFANP EDALR (213) | RSDPDVERCLRAHRND (214) | RVAHTVAYLGKLR APIR (215) | 1:100-1:2400 | | | |

-continued

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0296 | KRRALAAPAA EEKEEAR (216) | EAREKMLAAKSADGSA PAGE (217) | MIWLRHRKPELER PIK (218) | 1:300-1:5000 | 1_25_8_4_56_296_49 | 3_26_13_6_54_296_72 | 4_32_8_6_90_296_77 |
| S0296P1 | KRRALAAPAA EEKEEAR (216) | EAREKMLAAKSADGSA PAGE (217) | MIWLRHRKPELER PIK (218) | 1:225-1:1350 | | | |
| S0297 | KPNKALKVKK EAGE (219) | KRVTQKEELERQRVEL QQEVEK (220) | RLELDLALRSKYE (221) | 1:333-1:800 | | | |
| S0301 | KMHTDGRSCL EREDTVLEVT E (222) | KKGFKLLTDEKSCQDV DE (223) | KRTEKRLRLRKAIRTL RKAVHRE (224) | 1:3500-1:5400 | | | |
| S0303 | RVEGPQTESK NEASSRD (225) | EETKSTETETGSRVGKL PE (226) | N/A | 1:300 | | | |
| S0305 | DKGYLTKEDL RVLMEKE (227) | KDPLAVDKIMKDLDQC RDGK (228) | N/A | 1:8300-1:10000 | | | |
| S0311 | EEDLKEVLRS EAGIELIIEDDI R (229) | MSRRTRCEDLDELHYQ DTDSD (230) | RRSPIKKVRKSLAL DIVDED (231) | 1:750-1:5000 | | | |
| S0312 | EDYKNTAEWL LSHTKHR (232) | DERFGDRFPAMSDAYD RTMRQR (233) | KVIMDYESLEKAN HEE (234) | 1:1000-1:3600 | | | |
| S0314 | DQDRKSRLM GLEALKSHIMA AK (235) | KGVIVDKDFSHPQMPK KVED (236) | RMILKIDDIRKPGE SEE (237) | 1:6000-1:30000 | | | |
| S0315 | RLQPEFKPKQ LEGTMANCER (238) | KFMQASEDLLKEHYVD LKDR (239) | DSVESAEKEIGLW FHPEELVD (240) | 1:9000-1:18000 | 1_18_2_4_16_315_43 | 2_26_8_3_206_315_36 | |
| S0316 | KSPPESENKE QLEARRRR (241) | RDGRKVTVIERDLKEPD R (242) | DHLKEPFLEATDN SHLR (243) | 1:1000-1:10000 | 1_25_12_1_85_316_12 | 2_26_3_3_75_316_31 | |
| S0319 | DLEVKDWMQ KKRRGLRNSR (244) | EYHKVHQMMREQSILS PSPYEGYR (245) | RHQLLCFKEDCQA VFQDLEGVEK (246) | 1:900 | | 2_26_6_6_203_319_79 | |

-continued

| | Antibody Generation | | | | IHC Images (Appendix B) | | |
|---|---|---|---|---|---|---|---|
| | Peptide 1 | Peptide 2 | Peptide 3 | | | | |
| AGI ID | (SEQ ID NO:) | (SEQ ID NO:) | (SEQ ID NO:) | TITER | Breast IHC | Lung IHC | Colon IHC |
| S0326 | GPDILRTYSGA FVCLE (247) | CSLGLALRRWRP (248) | N/A | 1:120-1:1200 | 2_25_8_1_42_326_8 | | 3_32_12_4_115_326_45 |
| S0330 | RYLTLDIFAGP PNYPFSDEY (249) | N/A | N/A | 1:2500-1:75000 | | 4_27_11_1_140_330_11 | 3_32_7_2_78_330_22 |
| S0330x1 | RYLTLDIFAGP PNYPFSDEY (249) | N/A | N/A | 1:600 | | | |
| S0331 | HYFNSDSFAS HPNYPYSDEY (250) | N/A | N/A | 1:300-1:320 | | 2_26_5_5_59_331_29 | |
| S0331x1 | HYFNSDSFAS HPNYPYSDEY (250) | N/A | N/A | 1:150 | | | |
| S0332 | RYVVMDFLMD HPDYPFSDEY (251) | N/A | N/A | 1:400 | | 2_26_5_5_60_332_61 | |
| S0332x1 | RYVVMDFLMD HPDYPFSDEY (251) | N/A | N/A | 1:100-1:150 | | | |
| S0336 | DPAKVQSLVD TIREDPD (252) | RETIPAKLVQSTLSDLR (253) | N/A | 1:1600 | | | |
| S0342 | SDTTEELTVIK SSLKDE (254) | N/A | N/A | 1:400-1:1250 | 3_25_12_8_111_342_101 | 3_26_8_3_132_342_36 | |
| S0343 | HSRSSLMPLR NDVDKR (255) | N/A | N/A | 1:50-1:125 | 2_18_13_6_30_343_78 | | |
| S0374 | DANTCGEDKG SRRKFLDGDE (256) | N/A | N/A | 1:5000-1:9000 | 2_25_2_4_109_374_55 | | |
| S0380 | QLEEMTELES PKCKRQENEQ (257) | N/A | N/A | 1:2000-1:9000 | | 2_26_8_7_195_380_92 | |
| S0384 | QADGAASAPT EEEEEVVKDR (258) | N/A | N/A | 1:100 | | | |

-continued

| | Antibody Generation | | | | IHC Images (Appendix B) | | |
|---|---|---|---|---|---|---|---|
| | Peptide 1 | Peptide 2 | Peptide 3 | | | | |
| AGI ID | (SEQ ID NO:) | (SEQ ID NO:) | (SEQ ID NO:) | TITER | Breast IHC | Lung IHC | Colon IHC |
| S0388 | SGDSLETKED QKMSPKATEE (259) | N/A | N/A | 1:600 | | | |
| S0398 | KIRLPEREKPD RERNARREP (260) | N/A | N/A | 1:200 | | | |
| S0401 | RGTKCLRREA PRWDAPLRDP (261) | N/A | N/A | 1:600-1:2000 | | | |
| S0404 | GTRSRSHTSE GTRSRSHTSE (262) | N/A | N/A | 1:100-1:900 | 4_18_8_4_9_404_53 | 2_26_5_5_66_404_61 | 4_32_8_6_91_404_77 |
| S0411 | EETTADGRKT QTVCNFTD (263) | N/A | N/A | 1:1800 | | | |
| S0413 | AKRKRSAPEK SSGDVP (264) | N/A | N/A | 1:2700 | | | |
| S0414 | RVDRPGSRYD VSRLGRGKRS (265) | N/A | N/A | 1:100 | | | |
| S0415 | ETVDKLLKGY DIRLRPD (266) | N/A | N/A | 1:600-1:1800 | | | |
| S0417 | APGGAEDLED TQFPSERARE (267) | N/A | N/A | 1:9000 | | | |
| S0425 | RKSSRTLKKG PRQDPSAIVE (268) | N/A | N/A | 1:9000 | | | |
| S0429 | GSESGDSDES ESKSEQRTKR (269) | N/A | N/A | 1:1200 | | | |
| S0432 | EADSGDARRL PRARGERRR H (270) | N/A | N/A | 1:90-1:100 | 2_25_11_6_50_432_74 | 4_26_1_3_209_432_29 | 2_32_7_1_209_432_7 |

-continued

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0440 | RLERPQDRDT PVQMKRRRS (271) | N/A | N/A | 1:350-1:1200 | 1_18_11_6_249_440_56 | | |
| S0445 | DRVEDVMME RESQFKEKQE (272) | N/A | N/A | 1:600 | | | |
| S0447 | DEAFKRLQGK RNRGREE (273) | N/A | N/A | 1:6000 | | | |
| S0455 | RFQEEIKENTK NDKQ (274) | N/A | N/A | 1:900 | | | |
| S0459 | KRDKEGVRW TKCNKKTLTD (275) | N/A | N/A | 1:2700-1:8100 | | | |
| S0469 | KEGSLLSKQE ESKAAFGEE (276) | N/A | N/A | 1:600 | | | |
| S0494 | ESDAGKEKLP KMRLPTRSD (277) | N/A | N/A | 1:2000 | | | |
| S0501 | ERDKGKTVEV GRAYFETEK (278) | N/A | N/A | 1:15000 | | | |
| S0502 | EKFRVEKDKL VPEKR (279) | N/A | N/A | 1:9000 | | | |
| S0507 | ENYEDDDLVN SDEVMKKP (280) | N/A | N/A | 1:9000 | | | |
| S0511 | PKADEIRTLVK DMWDTR (281) | N/A | N/A | 1:2000 | | | |
| S0524 | RKRCLEDSED FGVKKARTE (282) | N/A | N/A | 1:4500 | | | |

-continued

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0527 | EPKSFLCRLC CQEDPELDS (283) | N/A | N/A | 1:1500 | | | |
| S0528 | EEYDRESKSS DDVDYRGS (284) | N/A | N/A | 1:350-1:1200 | | | |
| S0544 | EQRARWERK RACTARE (285) | N/A | N/A | 1:40 | | | |
| S0545 | ERKQLECEQV LQKLAKE (286) | N/A | N/A | 1:900-1:5400 | | | |
| S0546 | RNSETKVRRS TRLQKDLEN (287) | N/A | N/A | 1:1200 | | | |
| S0553 | SDYQVISDRQ TPKKDE (288) | N/A | N/A | 1:5400 | | | |
| S0557 | DIEGKLPQTE QELKE (289) | N/A | N/A | 1:200 | | | |
| S0564 | DDVNYKMHFR MINEQQVED (290) | N/A | N/A | 1:1000-1:8000 | 3_25_5_3_45_564_33 | | |
| S0565 | ENPLPERPRE KEEPVVR (291) | N/A | N/A | 1:10-1:100 | 2_18_15_5_99_565_75 | | |
| S0567 | REQSEGVGA RVRRSIGRPE (292) | N/A | N/A | 1:240 | | | |
| S0578 | PRAVAGKEEE DSDPEKALR (293) | N/A | | 1:1500 | | | |
| S0579 | EKADTDMEGS VDTRQEK (294) | N/A | N/A | 1:400 | | | |

-continued

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0581 | RVQNHDNPK WEAKKENISK (295) | N/A | N/A | 1:4000-1:10000 | | | |
| S0585 | RSPPAKGATG PEEQSDSLK (296) | N/A | N/A | 1:500 | | | |
| S0586 | REEDFKATEII EPSKQDKP (297) | N/A | N/A | 1:333-1:400 | | | |
| S0593 | DKTCMKWST NSCGAQ (298) | N/A | N/A | 1:500-1:2400 | | | |
| S0597 | DANLSKNGGL EVWL (299) | N/A | N/A | 1:3000 | | | |
| S0604 | EPFLPKLLTK (300) | N/A | N/A | 1:2400 | | | |
| S0607 | RKSEAGSGAA SSSGEDKEN (301) | N/A | N/A | 1:1800 | | | |
| S0609 | DDIYDPTYKD KEGPSPKVE (302) | N/A | N/A | 1:2000-1:5000 | | | |
| S0611 | QSDEAKNNM KGLPELEKKD (303) | N/A | N/A | 1:100 | | | |
| S0612 | SRPQGLTEAE QRELEQEAK (304) | N/A | N/A | 1:4500 | | | |
| S0613 | RVQQKGTSET DTIC (305) | N/A | N/A | 1:250-1:270 | | | |
| S0614 | VRLSPLAERQ LQVQWE (306) | N/A | N/A | 1:1200-1:3000 | | | |
| S0616 | RRSLGVSVRS WDELPDEKR (307) | N/A | N/A | 1:2500 | | | |

-continued

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0617 | DEGLGPDPPH RDRLRSK (308) | N/A | N/A | 1:600 | | | |
| S0618 | SGKRSSDGSL SHEEDLAK (309) | N/A | N/A | 1:150 | | | |
| S0631 | SQERSDSPEI CHYEKSFHK (310) | N/A | N/A | 1:600 | | | |
| S0633 | KVNPEPTHEIR CNSEVK (311) | N/A | N/A | 1:100-1:200 | | | |
| S0645 | SDGRGRPAFP FSCPRQ (312) | N/A | N/A | 1:900 | | | |
| S0646 | GSKEDFDSLL QSAKK (313) | N/A | N/A | 1:3600-1:5400 | | | |
| S0651 | QKEEKTWHEA LRSCQADN (314) | N/A | N/A | 1:3600 | | | |
| S0654 | EKAEEGPRKR EPAPLDK (315) | N/A | N/A | 1:400 | | | |
| S0659 | EQNRDRILTPE NRK (316) | | | 1:300 | | | |
| S0663 | RDWVIGLVSD EKWK (317) | N/A | | 1:900 | | | |
| S0665 | DSYLKTRSPV TFLSDLR (318) | | | 1:1500-1:3000 | | | |
| S0670 | KCRGETVAKE ISEAMKS (319) | N/A | | 1:900 | | | |
| S0673 | KPPQETEKGH SACEPEN (320) | | | 1:50 | | | |

-continued

| | Antibody Generation | | | | IHC Images (Appendix B) | | |
|---|---|---|---|---|---|---|---|
| AGI ID | Peptide 1 (SEQ ID NO:) | Peptide 2 (SEQ ID NO:) | Peptide 3 (SEQ ID NO:) | TITER | Breast IHC | Lung IHC | Colon IHC |
| S0676 | ERRAGSGAR DAERE (321) | N/A | N/A | 1:1200 | | | |
| S0677 | SEQKADPPAT EKTLLE (322) | N/A | N/A | 1:500-1:1000 | | | |
| S0684 | EAEWSQGVQ GTLRIKKYLT (323) | N/A | N/A | 1:8100 | | | |
| S0687 | EESKSITEGLL TQKQYE (324) | | | 1:1260 | | | |
| S0691 | QNFKDAFSGR DSSITR (325) | N/A | N/A | 1:1575-1:2000 | | | |
| S0695 | TEDVDEFRNK LQGER (326) | N/A | N/A | 1:4050 | | | |
| S0702 | KGDVSNLDPN FSFEGTKLDV (327) | N/A | N/A | 1:133650-1:178200 | | | |

APPENDIX C

| BREAST PROGNOSIS (HH COHORT) | | | All Log rank | | ER Pos Log rank | | ER Pos/ Node Neg Log rank | | ER neg Log rank | |
|---|---|---|---|---|---|---|---|---|---|---|
| AGI ID | Dilution (1:X) | Scoring method | P value | Hazard ratio | P value | Hazard ratio | P value | Hazard ratio | P value | Hazard ratio |
| s0021 | 500 | 3 | 0.0001 | 2.8378 | 0.0014 | 3.6147 | 0.0003 | 4.9455 | 0.0588 | 2.0089 |
| s0022 | 100 | 2 | >0.10 | 0.9363 | >0.10 | 0.6376 | >0.10 | 0.8219 | >0.10 | 1.4664 |
| s0039 | 100 | 1 | >0.10 | 1.1066 | 0.0625 | 1.1982 | 0.0551 | 1.2810 | >0.10 | 1.0798 |
| s0040 | 200 | 3 | 0.0389 | 1.7357 | >0.10 | 1.2649 | 0.0983 | 2.2353 | 0.0449 | 2.0825 |
| s0059 | 300 | 3 | 0.0469 | 1.9686 | 0.0468 | 3.7769 | 0.0099 | 5.4146 | >0.10 | 1.3547 |
| s0063 | 300 | 2 | 0.0037 | 1.7351 | 0.0418 | 1.6450 | >0.10 | 1.5656 | >0.10 | 1.5060 |
| s0068 | 700 | 2 | 0.0218 | 0.6445 | >0.10 | 0.8501 | >0.10 | 0.7793 | 0.0982 | 0.5632 |
| s0072 | 6500 | 2 | 0.0627 | 1.4824 | 0.0069 | 2.2083 | >0.10 | 1.0843 | >0.10 | 0.7685 |
| s0073P2 | 450 | 2 | 0.0023 | 0.5703 | >0.10 | 0.7329 | >0.10 | 0.6297 | 0.0987 | 0.4909 |
| s0076x1 | 200 | 2 | 0.0807 | 1.2392 | >0.10 | 0.6988 | >0.10 | 0.9070 | >0.10 | 1.1187 |
| s0079I | 400 | 2 | 0.0007 | 1.9503 | 0.0002 | 2.5357 | >0.10 | 1.3644 | >0.10 | 1.1705 |
| s0081 | 60 | 2 | 0.0026 | 0.5093 | 0.0384 | 0.5774 | >0.10 | 0.8913 | >0.10 | 0.5235 |
| s0137 | 2500 | 2 | 0.0322 | 1.4856 | 0.0745 | 1.5241 | 0.0872 | 1.8527 | >0.10 | 1.2568 |
| s0143P3 | 630 | 1 | 0.0932 | 1.0806 | 0.0342 | 1.1450 | >0.10 | 1.1183 | >0.10 | 1.0291 |
| s0143P3 | 630 | 3 | 0.0294 | 1.7362 | 0.0103 | 2.1681 | >0.10 | 1.7919 | >0.10 | 1.2595 |
| s0235 | 4500 | 2 | 0.0174 | 1.6960 | 0.0284 | 1.8866 | >0.10 | 1.4827 | >0.10 | 1.4227 |
| s0237 | 1000 | 3 | >0.10 | 1.3805 | >0.10 | 1.9314 | 0.0431 | 3.2504 | >0.10 | 0.9726 |
| s0255n | 1000 | 2 | >0.10 | 0.7361 | 0.0933 | 0.6593 | >0.10 | 0.6550 | >0.10 | 0.9813 |
| s0260 | 5400 | 2 | >0.10 | 1.0896 | 0.0695 | 0.2945 | >0.10 | 0.6016 | >0.10 | 1.2113 |
| s0296P1 | 225 | 2 | 0.0038 | 1.7491 | 0.0002 | 2.5560 | 0.0466 | 2.3419 | >0.10 | 0.8519 |
| s0303 | 300 | 2 | 0.0860 | 1.4072 | >0.10 | 1.1960 | >0.10 | 1.5662 | >0.10 | 1.3788 |
| s0305 | 8332 | 2 | 0.0809 | 1.2267 | >0.10 | 1.1590 | >0.10 | 0.9719 | >0.10 | 1.2343 |
| s0330x1 | 600 | 2 | >0.10 | 0.9730 | 0.0134 | 3.3569 | 0.0632 | 5.4988 | 0.0555 | 0.0021 |
| s0343 | 125 | 2 | >0.10 | 0.7487 | 0.0795 | 0.6256 | >0.10 | 0.5594 | >0.10 | 1.1414 |
| s0398 | 200 | 2 | 0.0125 | 0.4725 | >0.10 | 0.6070 | >0.10 | 0.8846 | 0.0725 | 0.1956 |
| s0398 | 200 | 3 | 0.0551 | 0.3428 | 0.0790 | 0.3049 | >0.10 | 0.4646 | >0.10 | 0.6364 |
| s0404 | 150 | 1 | 0.0321 | 1.1427 | >0.10 | 1.1160 | >0.10 | 1.1811 | >0.10 | 1.0783 |
| s0404 | 150 | 3 | 0.0087 | 1.8696 | >0.10 | 1.7755 | 0.0727 | 2.3524 | >0.10 | 1.4714 |
| s0459 | 2700 | 2 | >0.10 | 1.3287 | >0.10 | 1.4538 | >0.10 | 1.2304 | >0.10 | 0.9768 |
| s0545 | 900 | 2 | 0.0000 | 2.2547 | 0.0048 | 2.1037 | >0.10 | 1.7913 | 0.0300 | 2.0266 |
| s0654 | 400 | 3 | 0.0050 | 2.8738 | >0.10 | 1.5890 | >0.10 | 1.2356 | 0.0119 | 3.1822 |
| s0670 | 900 | 2 | >0.10 | 0.7709 | 0.0715 | 0.5411 | 0.0652 | 0.2800 | >0.10 | 0.9506 |
| s0676 | 1200 | 1 | 0.0088 | 1.1968 | >0.10 | 1.0888 | >0.10 | 1.2110 | 0.0130 | 1.2678 |
| s0677 | 500 | 2 | 0.0041 | 1.7183 | 0.0289 | 1.7290 | >0.10 | 1.1095 | >0.10 | 1.3276 |
| s0691NM | 1575 | 2 | 0.0280 | 1.8399 | >0.10 | 1.0211 | >0.10 | 1.6936 | 0.0761 | 1.8725 |
| s0702 | 178200 | 2 | 0.0005 | 1.9066 | 0.0000 | 2.8624 | 0.0120 | 2.6656 | >0.10 | 0.9739 |
| s6001 | na | 1 | 0.0292 | 0.8715 | na | na | na | na | na | na |
| s6002 | na | 1 | 0.0027 | 0.8341 | 0.0214 | 0.8319 | >0.10 | 0.8850 | >0.10 | 0.9325 |
| s6003 | na | 3 | 0.0176 | 1.9477 | 0.0051 | 3.1766 | >0.10 | 1.3355 | >0.10 | 1.2017 |
| s6006 | na | 2 | 0.0194 | 1.5374 | 0.0958 | 1.5021 | 0.0135 | 2.3697 | >0.10 | 1.2597 |
| s6007 | na | 1 | 0.0756 | 1.1144 | 0.0107 | 1.2055 | >0.10 | 1.0747 | 0.0342 | 0.9164 |

APPENDIX D

| LUNG PROGNOSIS (HH COHORT) | | | All Log rank | | Chi square P value | Adenocarcinoma Log rank | | Chi square P value | Squamous cell Log rank | | Chi square P value |
|---|---|---|---|---|---|---|---|---|---|---|---|
| AGI ID | Dilution (1:X) | Scoring method | P value | Hazard ratio | | P value | Hazard ratio | | P value | Hazard ratio | |
| s0021 | 1500 | 3 | 0.1288 | 1.8320 | 0.0240 | 0.2188 | 1.6167 | 0.0860 | 0.0005 | 0.0657 | 0.0100 |
| s0022 | 250 | 2 | 0.0116 | 0.3747 | 0.1000 | >0.10 | nd | >0.10 | >0.10 | nd | >0.10 |
| s0039 | 400 | 2 | 0.3532 | 1.5469 | 0.0080 | >0.10 | nd | >0.10 | >0.10 | nd | >0.10 |
| s0046 | 300 | 2 | 0.0145 | 0.5165 | 0.0270 | >0.10 | nd | >0.10 | 0.0529 | 0.3302 | 0.0850 |
| s0063 | 1200 | 2 | >0.10 | nd | >0.10 | 0.0831 | 1.8631 | 0.0550 | >0.10 | nd | >0.10 |
| s0072 | 6500 | 2 | 0.2633 | 1.3570 | 0.0680 | >0.10 | nd | >0.10 | >0.10 | nd | >0.10 |
| s0073P2 | 50 | 2 | 0.0935 | 0.4640 | 0.0430 | >0.10 | nd | >0.10 | >0.10 | nd | >0.10 |
| s0074P3 | 810 | 3 | 0.0723 | 0.0022 | 0.0530 | >0.10 | nd | >0.10 | >0.10 | nd | >0.10 |
| s0137 | 5000 | 2 | 0.0610 | 1.6429 | 0.1010 | 0.2271 | 1.5312 | 0.0660 | >0.10 | nd | >0.10 |
| s0143P3 | 300 | 3 | >0.10 | nd | >0.10 | 0.0008 | 4.5211 | 0.0270 | >0.10 | nd | >0.10 |
| s0296P1 | 1350 | 2 | 0.0783 | 1.6148 | 0.0460 | 0.0237 | 2.1849 | 0.0180 | 0.1042 | 0.3968 | 0.0840 |
| s0303 | 300 | 2 | >0.10 | nd | >0.10 | 0.0469 | 2.0494 | 0.5360 | >0.10 | nd | >0.10 |
| s0330 | 15000 | 3 | >0.10 | nd | >0.10 | >0.10 | nd | >0.10 | 0.0124 | 0.2278 | 0.0460 |
| s0330 | 45000 | 3 | 0.0880 | 0.5248 | 0.0440 | >0.10 | nd | >0.10 | 0.0188 | 0.1270 | 0.0130 |
| s0330x1 | 600 | 3 | >0.10 | nd | >0.10 | >0.10 | nd | >0.10 | 0.0455 | 0.1631 | 0.0080 |
| s0331 | 300 | 3 | 0.2157 | 0.6603 | 0.0850 | >0.10 | nd | >0.10 | 0.0404 | 0.2350 | 0.0050 |
| s0331x1 | 300 | 3 | >0.10 | nd | >0.10 | >0.10 | nd | >0.10 | 0.0705 | 0.2744 | 0.0360 |
| s0332 | 400 | 3 | 0.1496 | 0.5639 | 0.0680 | >0.10 | nd | >0.10 | 0.0621 | 0.1785 | 0.0160 |
| s0332x1 | 150 | 2 | >0.10 | nd | >0.10 | >0.10 | nd | >0.10 | 0.0321 | 0.1466 | 0.1290 |

APPENDIX D-continued

| LUNG PROGNOSIS (HH COHORT) | | | All Log rank | | Chi square | Adenocarcinoma Log rank | | Chi square | Squamous cell Log rank | | Chi square |
|---|---|---|---|---|---|---|---|---|---|---|---|
| AGI ID | Dilution (1:X) | Scoring method | P value | Hazard ratio | P value | P value | Hazard ratio | P value | P value | Hazard ratio | P value |
| s0398 | 200 | 2 | 0.1253 | 0.5775 | 0.0870 | >0.10 | nd | >0.10 | 0.3348 | 0.6094 | 0.0640 |
| s0404 | 900 | 3 | 0.1273 | 1.7817 | 0.0420 | >0.10 | nd | >0.10 | >0.10 | nd | >0.10 |
| s0545 | 2700 | 2 | 0.1246 | 1.8432 | 0.0150 | 0.0191 | 3.2839 | 0.0180 | >0.10 | nd | >0.10 |
| s0586 | 400 | 2 | 0.0204 | 0.4659 | 0.4380 | 0.1322 | 0.2457 | 0.0960 | >0.10 | nd | >0.10 |
| s0691 | 1575 | 3 | >0.10 | nd | >0.10 | >0.10 | nd | >0.10 | 0.0608 | 3.1820 | 0.0420 |
| s0702 | 178200 | 1 | >0.10 | nd | >0.10 | >0.10 | nd | >0.10 | 0.0463 | 0.6944 | 0.5360 |
| s6006 | 1 | 2 | >0.10 | nd | >0.10 | 0.1259 | 1.7720 | 0.0550 | >0.10 | nd | >0.10 |
| s6007 | 1 | 2 | >0.10 | nd | >0.10 | 0.0316 | 3.4266 | 0.0110 | >0.10 | nd | >0.10 |
| s6008 | 1 | 2 | >0.10 | nd | >0.10 | >0.10 | nd | >0.10 | 0.2388 | 1312.0118 | 0.0230 |
| s6013 | 1 | 2 | >0.10 | nd | >0.10 | 0.0154 | 2.5755 | 0.0540 | >0.10 | nd | >0.10 |
| s0614 | 3000 | 2 | 0.0930 | 1.5785 | 0.0860 | >0.10 | nd | >0.10 | >0.10 | nd | >0.10 |

APPENDIX E

| BREAST PROGNOSIS (HH COHORT) | | | All Log rank | | ER Pos Log rank | | ER Pos/ Node Neg Log rank | | ER neg Log rank | |
|---|---|---|---|---|---|---|---|---|---|---|
| AGI ID | Dilution (1:X) | Scoring method | P value | Hazard ratio | P value | Hazard ratio | P value | Hazard ratio | P value | Hazard ratio |
| s0022 | 100 | 2 | >0.10 | 0.8660 | 0.0633 | 0.5679 | >0.10 | 0.8810 | >0.10 | 1.3696 |
| s0053 | 30 | 2 | 0.0496 | 0.6276 | >0.10 | 0.7265 | >0.10 | 1.0372 | >0.10 | 0.5002 |
| s0059P2 | 90 | 2 | 0.0088 | 1.9934 | >0.10 | 1.7964 | >0.10 | 1.8087 | >0.10 | 1.4654 |
| s0063 | 300 | 2 | 0.0031 | 1.7208 | 0.0955 | 1.5202 | >0.10 | 1.5656 | >0.10 | 1.7249 |
| s0063 | 600 | 2 | 0.0006 | 1.9517 | 0.0154 | 2.0148 | 0.0660 | 2.4507 | >0.10 | 1.4408 |
| s0068 | 700 | 2 | 0.0312 | 0.6537 | >0.10 | 0.8644 | >0.10 | 0.7793 | 0.0936 | 0.5597 |
| s0072 | 6500 | 2 | >0.10 | 1.4087 | 0.0307 | 2.0193 | >0.10 | 1.3344 | >0.10 | 0.7426 |
| s0073p2 | 450 | 2 | 0.0060 | 0.6051 | >0.10 | 0.8755 | >0.10 | 1.0495 | >0.10 | 0.4614 |
| s0076x1 | 200 | 2 | 0.0471 | 1.6431 | >0.10 | 0.5060 | >0.10 | 0.8227 | >0.10 | 1.3384 |
| s0079 | 400 | 2 | 0.0006 | 1.8382 | 0.0050 | 2.0469 | >0.10 | 1.0820 | >0.10 | 1.2420 |
| s0081 | 60 | 2 | 0.0006 | 0.5518 | 0.0621 | 0.6335 | >0.10 | 0.7897 | >0.10 | 0.4758 |
| s0140 | 500 | 2 | 0.0146 | 1.7628 | >0.10 | 1.7553 | >0.10 | 0.6881 | >0.10 | 1.3817 |
| s0235 | 4500 | 2 | 0.0002 | 1.9769 | 0.0017 | 2.1999 | >0.10 | 1.5655 | >0.10 | 1.5469 |
| s0253 | 2000 | 2 | 0.0579 | 1.5740 | >0.10 | 1.5128 | 0.0784 | 2.1386 | >0.10 | 1.4763 |
| s0253 | 500 | 2 | >0.10 | 1.1127 | >0.10 | 0.7030 | >0.10 | 0.8017 | 0.0377 | 2.1389 |
| s0255 | 1000 | 2 | 0.0610 | 0.6995 | 0.0603 | 0.6193 | >0.10 | 0.6550 | >0.10 | 0.8992 |
| s0296P1 | 225 | 1 | 0.0028 | 1.1896 | 0.0001 | 1.3344 | 0.0008 | 1.3554 | >0.10 | 0.9879 |
| s0296P1 | 225 | 2 | 0.0052 | 1.7183 | 0.0014 | 2.3378 | 0.0466 | 2.3419 | >0.10 | 0.8994 |
| s0305 | 8332 | 2 | 0.0945 | 1.5030 | >0.10 | 1.2945 | >0.10 | 0.9447 | >0.10 | 1.4199 |
| s0330x1 | 600 | 2 | >0.10 | 0.7456 | 0.0945 | 2.6186 | 0.0632 | 5.4988 | 0.0525 | 0.0021 |
| s0404 | 150 | 2 | 0.0265 | 1.6475 | >0.10 | 1.3534 | >0.10 | 1.8109 | >0.10 | 1.4264 |
| s0404 | 150 | 3 | 0.0027 | 2.0719 | 0.0706 | 1.8942 | 0.0623 | 2.4347 | >0.10 | 1.6912 |
| s0440 | 1200 | 2 | 0.0581 | 0.6270 | >0.10 | 0.8110 | >0.10 | 0.6788 | >0.10 | 0.2904 |
| s0545 | 2700 | 2 | 0.0000 | 2.4278 | >0.10 | 1.7002 | >0.10 | 0.7788 | 0.0024 | 2.4284 |
| s0545 | 900 | 2 | 0.0000 | 2.2447 | 0.0055 | 2.1160 | >0.10 | 1.7913 | 0.0412 | 1.9465 |
| s0654 | 400 | 2 | >0.10 | 0.8150 | 0.0676 | 0.4627 | >0.10 | 0.6037 | >0.10 | 1.7718 |
| s0670 | 900 | 2 | >0.10 | 0.7040 | 0.0258 | 0.4379 | 0.0652 | 0.2800 | >0.10 | 0.8549 |
| s0676 | 1200 | 1 | 0.0113 | 1.1614 | >0.10 | 1.0623 | >0.10 | 1.2110 | 0.0212 | 1.2442 |
| s0676 | 1200 | 2 | 0.0392 | 1.5231 | >0.10 | 1.2602 | >0.10 | 1.9314 | 0.0875 | 1.8335 |
| s0677 | 1000 | 1 | 0.0017 | 1.1649 | 0.0076 | 1.2173 | >0.10 | 1.0408 | >0.10 | 1.0892 |
| s0677 | 1000 | 2 | 0.0123 | 1.5683 | 0.0148 | 1.8170 | >0.10 | 1.0567 | >0.10 | 1.2487 |
| s0687 | 1260 | 2 | 0.0830 | 0.6973 | 0.0519 | 0.5427 | >0.10 | 1.1017 | >0.10 | 0.8919 |
| s0691 | 1575 | 1 | 0.0001 | 1.2824 | >0.10 | 1.0463 | >0.10 | 1.1225 | 0.0058 | 1.2902 |
| s0691 | 1575 | 2 | 0.0020 | 2.1106 | >0.10 | 1.1418 | >0.10 | 1.6936 | 0.0217 | 2.1925 |
| s0695 | 2700 | 2 | 0.0459 | 1.4465 | >0.10 | 1.0295 | >0.10 | 0.9663 | >0.10 | 1.2102 |
| s0702 | 178200 | 2 | 0.0001 | 2.0291 | 0.0000 | 3.1207 | 0.0010 | 3.3919 | >0.10 | 1.0431 |
| s6001 | na | 2 | 0.0009 | 0.5721 | >0.10 | 1.0000 | >0.10 | 1.0000 | >0.10 | 1.0000 |
| s6002 | na | 2 | 0.0004 | 0.5236 | 0.0083 | 0.5255 | >0.10 | 0.6236 | >0.10 | 0.9192 |
| s6006 | na | 1 | 0.0413 | 1.1246 | 0.0591 | 1.1129 | 0.0334 | 1.3081 | >0.10 | 1.0566 |
| s6006 | na | 2 | 0.0399 | 1.4388 | >0.10 | 1.3185 | 0.0095 | 2.4996 | >0.10 | 1.2815 |
| s6007 | na | 1 | >0.10 | 1.1140 | 0.0086 | 1.1848 | >0.10 | 1.0585 | 0.0284 | 0.9403 |
| s6007 | na | 2 | 0.0358 | 1.4803 | 0.0537 | 1.6016 | >0.10 | 1.0875 | >0.10 | 0.9724 |
| s6007 | na | 3 | >0.10 | 1.1979 | 0.0032 | 2.4860 | >0.10 | 2.1836 | 0.0232 | 0.4636 |

APPENDIX F

| | | | HH 5 yr recurrence | | UAB 5 yr survival | | |
|---|---|---|---|---|---|---|---|
| LUNG PROGNOSIS (HH & UAB COHORTS) | | | | | | | |
| AGI ID | Dilution (1:X) | Scoring method | P value | Hazard ratio | P value | Hazard ratio | |
| s0073P2 | 50 | 2 | 0.129 | 0.497 | 0.192 | 0.660 | All |
| s0074P3 | 810 | 3 | 0.091 | 0.002 | 0.096 | 0.002 | |
| s0586 | 400 | 2 | 0.007 | 0.385 | 0.148 | 0.619 | |
| s6007 | 1 | 2 | 0.081 | 2.420 | 0.112 | 2.099 | |
| s0074P3 | 810 | 3 | 0.166 | 0.002 | 0.076 | 0.002 | Adenocarcinoma |
| s0143P3 | 300 | 3 | 0.001 | 4.521 | 0.023 | 4.450 | |
| s0296P1 | 1350 | 2 | 0.024 | 2.185 | 0.021 | 2.214 | |
| s0303 | 300 | 2 | 0.047 | 2.049 | 0.007 | 3.358 | |
| s6006 | 1 | 2 | 0.126 | 1.772 | 0.164 | 1.650 | |
| s6007 | 1 | 2 | 0.032 | 3.427 | 0.033 | 2.734 | |

We claim:

1. A kit comprising a prognostic panel of antibodies that includes:
 a first antibody that binds to SLC7A5;
 a second antibody that binds to HTF9C;
 a third antibody that binds to p53;
 a fourth antibody that binds to NDRG1; and
 a fifth antibody that binds to CEACAM5,
wherein the total number of antibodies included in the kit does not exceed 10.

2. The kit of claim 1, wherein the kit is for prognosis of a breast cancer patient.

3. The kit of claim 2, wherein the breast cancer is estrogen receptor positive (ER+).

4. The kit of claim 3, wherein the breast cancer is node negative (Node –).

5. The kit of claim 2, wherein across a population of breast cancer patients, a higher level of binding of each of the antibodies correlates with a higher likelihood that the patient will die from breast cancer or have a recurrence.

6. A kit consisting essentially of a prognostic panel of antibodies, the prognostic panel of antibodies including:
 a first antibody that binds to SLC7A5;
 a second antibody that binds to HTF9C;
 a third antibody that binds to p53;
 a fourth antibody that binds to NDRG1; and
 a fifth antibody that binds to CEACAM5,
wherein the total number of antibodies included in the kit does not exceed 10.

7. The kit of claim 6, wherein the kit is for prognosis of a breast cancer patient.

8. The kit of claim 7, wherein the breast cancer is estrogen receptor positive (ER+).

9. The kit of claim 8, wherein the breast cancer is node negative (Node–).

10. The kit of claim 7, wherein across a population of breast cancer patients, a higher level of binding of each of the antibodies correlates with a higher likelihood that the patient will die from breast cancer or have a recurrence.

11. A kit comprising a prognostic panel of antibodies, the prognostic panel of antibodies consisting of:
 a first antibody that binds to SLC7A5;
 a second antibody that binds to HTF9C;
 a third antibody that binds to p53;
 a fourth antibody that binds to NDRG1; and
 a fifth antibody that binds to CEACAM5,
wherein the total number of antibodies included in the kit does not exceed 5.

12. The kit of claim 11, wherein the kit is for prognosis of a breast cancer patient.

13. The kit of claim 12, wherein the breast cancer is estrogen receptor positive (ER+).

14. The kit of claim 13, wherein the breast cancer is node negative (Node–).

15. The kit of claim 12, wherein across a population of breast cancer patients, a higher level of binding of each of the antibodies correlates with a higher likelihood that the patient will die from breast cancer or have a recurrence.

* * * * *